United States Patent
Murriel et al.

(10) Patent No.: US 11,046,760 B2
(45) Date of Patent: Jun. 29, 2021

(54) COMBINATION THERAPY FOR TREATMENT OF DISEASE

(71) Applicant: OncoMed Pharmaceuticals, Inc., Redwood City, CA (US)

(72) Inventors: Christopher Lamond Murriel, San Francisco, CA (US); Timothy Charles Hoey, Hillsborough, CA (US); Austin L. Gurney, San Francisco, CA (US); Julie Michelle Roda, Foster City, CA (US); Minu K. Srivastava, Sunnyvale, CA (US); Inkyung Park, Palo Alto, CA (US); Jakob Dupont, Hillsborough, CA (US)

(73) Assignee: ONCOMED PHARMACEUTICALS, INC., Redwood City, CA (US)

( * ) Notice: Subject to any disclaimer, the term of this patent is extended or adjusted under 35 U.S.C. 154(b) by 234 days.

(21) Appl. No.: 15/889,532

(22) Filed: Feb. 6, 2018

(65) Prior Publication Data
US 2018/0273618 A1    Sep. 27, 2018

Related U.S. Application Data

(63) Continuation of application No. 14/928,271, filed on Oct. 30, 2015, now abandoned.

(60) Provisional application No. 62/242,567, filed on Oct. 16, 2015, provisional application No. 62/192,133, filed on Jul. 14, 2015, provisional application No. 62/127,172, filed on Mar. 2, 2015, provisional application No. 62/073,634, filed on Oct. 31, 2014.

(51) Int. Cl.
| | |
|---|---|
| *A61K 39/395* | (2006.01) |
| *C12N 15/11* | (2006.01) |
| *C12N 15/113* | (2010.01) |
| *C07K 16/28* | (2006.01) |
| *A61K 31/282* | (2006.01) |
| *A61K 31/519* | (2006.01) |
| *C07K 14/475* | (2006.01) |
| *C07K 16/22* | (2006.01) |
| *A61K 39/00* | (2006.01) |

(52) U.S. Cl.
CPC ............ *C07K 16/28* (2013.01); *A61K 31/282* (2013.01); *A61K 31/519* (2013.01); *A61K 39/3955* (2013.01); *A61K 39/39558* (2013.01); *C07K 16/2803* (2013.01); *C07K 16/2827* (2013.01); *C12N 15/113* (2013.01); *C12N 15/1136* (2013.01); *A61K 2039/505* (2013.01); *A61K 2039/507* (2013.01); *A61K 2039/572* (2013.01); *C07K 14/475* (2013.01); *C07K 16/22* (2013.01); *C07K 2317/24* (2013.01); *C07K 2317/31* (2013.01); *C07K 2317/56* (2013.01); *C07K 2317/565* (2013.01); *C07K 2317/76* (2013.01); *C12N 15/11* (2013.01)

(58) Field of Classification Search
CPC .......... C07K 2317/76; C07K 2317/565; C07K 16/2863; C07K 16/22; C07K 16/28; C07K 16/00; C07K 2316/96; C07K 16/24; C07K 14/47; C07K 14/435; C07K 14/70596; A61K 39/3955; A61K 2039/505; A61K 38/00; A61K 39/39558; A61K 38/177; A61K 39/395; A61K 38/16; A61K 38/18; A61K 38/19
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,816,567 A | 3/1989 | Cabilly et al. |
| 5,013,556 A | 5/1991 | Woodle et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |

(Continued)

FOREIGN PATENT DOCUMENTS

| | | |
|---|---|---|
| CA | 2789446 A1 | 8/2011 |
| EP | 0861894 A1 | 9/1998 |

(Continued)

OTHER PUBLICATIONS

Bassil et al. Notch ligand delta-like 4 blockade alleviates experimental autoimmune encephalomyelitis by promoting regulatory T cell development. J Immunol 187: 2322-2328, 2011.*

(Continued)

*Primary Examiner* — Bridget E Bunner
(74) *Attorney, Agent, or Firm* — Sterne, Kessler, Goldstein & Fox P.L.L.C.

(57) ABSTRACT

The present invention provides methods comprising combination therapy for modulating immune responses, for inhibiting tumor growth, and/or for treating cancer. In particular, the present invention provides Notch pathway inhibitors in combination with immunotherapeutic agents for the treatment of cancer and other diseases.

19 Claims, 25 Drawing Sheets
Specification includes a Sequence Listing.

(56) References Cited

U.S. PATENT DOCUMENTS

| | | |
|---|---|---|
| 5,750,373 A | 5/1998 | Garrard et al. |
| 5,840,299 A | 11/1998 | Bendig et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim |
| 6,664,098 B1 | 12/2003 | Sakano |
| 6,676,941 B2 | 1/2004 | Thorpe et al. |
| 6,689,744 B2 | 2/2004 | Gao et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horovvicz David et al. |
| 7,183,076 B2 | 2/2007 | Arathoon et al. |
| 7,227,004 B2 | 6/2007 | Kim |
| 7,354,581 B2 | 4/2008 | Cedarbaum et al. |
| 7,449,182 B2 | 11/2008 | Cedarbaum et al. |
| 7,482,005 B2 | 1/2009 | Kim et al. |
| 7,488,806 B2 | 2/2009 | Papadopoulos et al. |
| 7,531,172 B2 | 5/2009 | Stahl et al. |
| 7,534,868 B1 | 5/2009 | Papadopoulos et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,803,377 B2 | 9/2010 | Yan et al. |
| 7,897,725 B2 | 3/2011 | McCarthy et al. |
| 7,906,116 B2 | 3/2011 | Gill et al. |
| 7,910,098 B2 | 3/2011 | Fuh et al. |
| 7,919,593 B2 | 4/2011 | Papadopoulos et al. |
| 7,951,917 B1 | 5/2011 | Arathoon et al. |
| 8,048,418 B2 | 11/2011 | Noguera-Troise et al. |
| 8,133,857 B2 | 3/2012 | Aikawa |
| 8,192,738 B2 | 6/2012 | Bedian et al. |
| 8,216,571 B2 | 7/2012 | Ramachandra et al. |
| 8,404,233 B2 | 3/2013 | Sunamura et al. |
| 8,518,887 B2 | 8/2013 | Noguera-Troise et al. |
| 8,557,965 B2 | 10/2013 | Saunders et al. |
| 8,685,401 B2 | 4/2014 | Harris et al. |
| 8,765,125 B2 | 7/2014 | Skokos |
| 8,840,886 B2 | 9/2014 | Noguera-Troise et al. |
| 8,858,941 B2 | 10/2014 | Gurney et al. |
| 8,883,145 B2 | 11/2014 | Stagg et al. |
| 8,889,131 B2 | 11/2014 | Aikawa et al. |
| 8,889,133 B2 | 11/2014 | Skokos |
| 9,029,508 B2 | 5/2015 | Ghayur et al. |
| 9,115,195 B2 | 8/2015 | Chen et al. |
| 9,132,190 B2 | 9/2015 | Benatuil et al. |
| 9,228,020 B2 | 1/2016 | Gurney |
| 9,309,311 B2 | 4/2016 | Gurney et al. |
| 9,376,488 B2 | 6/2016 | Gurney et al. |
| 9,376,497 B2 | 6/2016 | Gurney et al. |
| 9,403,904 B2 | 8/2016 | Smider et al. |
| 9,469,689 B2 | 10/2016 | Chen et al. |
| 9,511,139 B2 | 12/2016 | Stagg et al. |
| 9,574,009 B2 | 2/2017 | Gurney et al. |
| 9,599,620 B2 | 3/2017 | Benner et al. |
| 2002/0028488 A1 | 3/2002 | Singh et al. |
| 2002/0032315 A1 | 3/2002 | Baca et al. |
| 2003/0175877 A1 | 9/2003 | Baker et al. |
| 2003/0180784 A1 | 9/2003 | McCarthy et al. |
| 2004/0123343 A1 | 6/2004 | La et al. |
| 2004/0133357 A1 | 7/2004 | Zhong et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0261477 A1 | 11/2005 | Champion et al. |
| 2005/0276808 A1 | 12/2005 | Cedarbaum |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0082846 A1 | 4/2007 | Ish-Horowicz et al. |
| 2007/0098712 A1 | 5/2007 | Arathoon et al. |
| 2007/0141065 A1 | 6/2007 | Fuh et al. |
| 2007/0154391 A1 | 7/2007 | Kim et al. |
| 2007/0178552 A1 | 8/2007 | Arathoon et al. |
| 2007/0190573 A1 | 8/2007 | Hess et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0064049 A1 | 3/2008 | Clarke et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0178305 A1 | 7/2008 | Clarke et al. |
| 2008/0181893 A1 | 7/2008 | Lobov et al. |
| 2008/0181899 A1 | 7/2008 | Papadopoulos et al. |
| 2008/0220495 A1 | 9/2008 | McCarthy et al. |
| 2009/0004205 A1 | 1/2009 | Clarke et al. |
| 2009/0017035 A1 | 1/2009 | Papadopoulos et al. |
| 2009/0023591 A1 | 1/2009 | Spanuth |
| 2009/0035308 A1 | 2/2009 | Gill et al. |
| 2009/0142354 A1 | 6/2009 | Papadopoulos et al. |
| 2009/0217401 A1 | 8/2009 | Korman et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy et al. |
| 2010/0015133 A1 | 1/2010 | Igawa et al. |
| 2010/0076178 A1 | 3/2010 | Ghayur et al. |
| 2010/0086544 A1 | 4/2010 | Mass et al. |
| 2010/0119526 A1 | 5/2010 | Hellstroem |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0091372 A1 | 4/2011 | Ghayur et al. |
| 2011/0113865 A1 | 5/2011 | Hess et al. |
| 2011/0117079 A1 | 5/2011 | Benatuil et al. |
| 2011/0123532 A1 | 5/2011 | Gurney et al. |
| 2011/0165162 A1 | 7/2011 | Hoey et al. |
| 2011/0172398 A1 | 7/2011 | Borges et al. |
| 2011/0217237 A1 | 9/2011 | Chen et al. |
| 2011/0306044 A1 | 12/2011 | McCarthy et al. |
| 2012/0070438 A1 | 3/2012 | Hoey et al. |
| 2012/0116057 A1 | 5/2012 | Kannan et al. |
| 2012/0245151 A1 | 9/2012 | Gavai et al. |
| 2012/0263721 A1 | 10/2012 | Stagg et al. |
| 2012/0288496 A1 | 11/2012 | Gurney et al. |
| 2013/0131076 A1 | 5/2013 | Fernandez et al. |
| 2013/0164295 A1 | 6/2013 | Gurney et al. |
| 2013/0253172 A1 | 9/2013 | Gurney et al. |
| 2013/0309250 A1 | 11/2013 | Cogswell et al. |
| 2013/0323248 A1 | 12/2013 | Gros et al. |
| 2013/0323260 A1 | 12/2013 | Walsh et al. |

(56) References Cited

U.S. PATENT DOCUMENTS

| | | |
|---|---|---|
| 2013/0323265 A1 | 12/2013 | Stagg et al. |
| 2014/0017244 A1 | 1/2014 | Duerr et al. |
| 2014/0093499 A1 | 4/2014 | Gschwind et al. |
| 2014/0134169 A1 | 5/2014 | Kuhnert et al. |
| 2014/0206853 A1 | 7/2014 | Foltz et al. |
| 2014/0220001 A1 | 8/2014 | Benner et al. |
| 2014/0227252 A1 | 8/2014 | Benner et al. |
| 2014/0348835 A1 | 11/2014 | Gu et al. |
| 2015/0005475 A1 | 1/2015 | Kucia et al. |
| 2015/0098949 A1 | 4/2015 | Gurney et al. |
| 2015/0118232 A1 | 4/2015 | Stagg et al. |
| 2015/0183856 A1 | 7/2015 | Kim et al. |
| 2016/0068596 A1 | 3/2016 | De Sauvage et al. |
| 2016/0176962 A1 | 6/2016 | Murriel et al. |

FOREIGN PATENT DOCUMENTS

| | | | |
|---|---|---|---|
| EP | 1004669 A1 | 5/2000 | |
| EP | 1179541 B1 | 5/2000 | |
| EP | 0662827 B1 | 4/2002 | |
| EP | 0979281 B1 | 7/2005 | |
| EP | 1615036 A1 | 1/2006 | |
| EP | 0972041 B1 | 10/2006 | |
| EP | 1810979 A1 | 7/2007 | |
| EP | 1870459 A1 | 12/2007 | |
| EP | 0662827 A1 | 8/2011 | |
| EP | 2488204 A1 | 8/2012 | |
| GB | 2449354 A | 11/2008 | |
| JP | 2011505135 A | 12/1998 | |
| JP | 2005511754 A | 11/2008 | |
| WO | WO-9219734 A1 | 11/1992 | |
| WO | WO-9407474 A1 | 4/1994 | |
| WO | WO-9701571 A1 | 4/1994 | |
| WO | WO-9845331 A2 | 10/1998 | |
| WO | WO-9845434 A1 | 10/1998 | |
| WO | WO-9851799 A1 | 11/1998 | |
| WO | WO-9857621 A1 | 12/1998 | |
| WO | WO-0006726 A2 | 2/2000 | |
| WO | WO-0140466 A2 | 6/2001 | |
| WO | WO-2012447 A2 | 2/2002 | |
| WO | WO-03041735 A2 | 2/2003 | |
| WO | WO-03050502 A2 | 6/2003 | |
| WO | WO-2004110490 A2 | 12/2004 | |
| WO | WO-2006027693 A2 | 3/2006 | |
| WO | WO-2006028936 A2 | 3/2006 | |
| WO | WO-2006033386 A1 | 3/2006 | |
| WO | WO-2006052128 A1 | 5/2006 | |
| WO | WO-2006106905 A1 | 10/2006 | |
| WO | WO-2007028110 A2 | 3/2007 | |
| WO | WO-2007070671 A2 | 3/2007 | |
| WO | WO-2007143689 A2 | 12/2007 | |
| WO | WO-2007145840 A2 | 12/2007 | |
| WO | WO-2007147901 A1 | 12/2007 | |
| WO | WO-2008042236 A2 | 4/2008 | |
| WO | WO-2008060705 A2 | 4/2008 | |
| WO | WO-2008070042 A2 | 6/2008 | |
| WO | WO-2008076379 A2 | 6/2008 | |
| WO | WO-2008079326 A2 | 7/2008 | |
| WO | WO-2008091222 A1 | 7/2008 | |
| WO | WO-2008139202 A1 | 11/2008 | |
| WO | WO-2009073160 A1 | 6/2009 | |
| WO | WO-2009075565 A1 | 6/2009 | |
| WO | WO-2009080251 A1 | 7/2009 | |
| WO | WO-2009085209 A2 | 7/2009 | |
| WO | WO-2009089004 A1 | 7/2009 | |
| WO | WO-2009134776 A2 | 11/2009 | |
| WO | WO2010/005567 A2 | 1/2010 | |
| WO | WO-2010010153 A1 | 1/2010 | |
| WO | WO-2010054010 A1 | 5/2010 | |
| WO | WO-2010124009 A2 | 10/2010 | |
| WO | WO-2010129304 A2 | 10/2010 | |
| WO | WO-2011039370 A1 | 4/2011 | |
| WO | WO-2011047383 A1 | 4/2011 | |
| WO | WO-2011047442 A1 | 4/2011 | |
| WO | WO-2011068840 A1 | 6/2011 | |
| WO | WO-2011100566 A2 | 6/2011 | |
| WO | WO-2011109298 A2 | 9/2011 | |
| WO | WO-2012068098 A1 | 9/2011 | |
| WO | WO-2013044215 A1 | 3/2013 | |
| WO | WO2013/173542 A1 | 11/2013 | |
| WO | WO-2014049100 A1 | 4/2014 | |
| WO | WO-2015130751 A1 | 9/2015 | |

OTHER PUBLICATIONS

Currie et al. Dual control of antitumor CD8 T cells through the programmed death-1/programmed death-ligand 1 pathway and immunosuppressive CD4T cells: regulation and counterregulation. J Immunol 183: 7898-7908, 2009.*

He et al. EFfectof DLL4 siRNA on proliferation, migration, and tube formation of choroid-retinal endothelial cells under hypoxic conditions. Chin Med J 124(1): 118-126, 2011.*

Hu et al. Biological roles of the delta family Notch ligand Dll4 in tumor and endothelial cells in ovarian cancer. Cancer Res 71(18): 6030-6039,2011.*

Mukherjee et al. Regulation of T cell activation by Notch ligand, DLL4, promotes IL-17 production and Rorc activation. J Immunol 182:7381-7388,2009.*

Parry et al. CTLA-1 and PD-1 receptors inhibit T-cell activation by dinstinct mechanisms. Mol Cell Biol 25(21): 9543-9553, 2005.*

Rutz et al. Notch ligands Delta-like 1, Delta-like 4 and Jagged 1 differentially regulate activation of peripheral T helper cells. Eur J Immunol 35: 2443-2451,2005.*

Tran et al. Blockade of individual Notch ligands and receptors controls graft-versus-host disease. J Clin Invest 123(4): 1590-1604, 2013.*

Al-Hajj, M., et al., "Prospective Identification of Tumorigenic Breast Cancer Cells," Proceedings of the National Academy of Sciences 100(7):3983-3988, The National Academy of Sciences, United States (2003).

Allenspach, E.J., et al., "Notch Signaling in Cancer," Cancer Biology Therapy 1(5):466-476, Informa UK Limited, United Kingdom (2002).

Amado, R.G., et al., "Wild-Type KRAS is Required for Panitumurnab Efficacy in Patients with Metastatic Colorectal Cancer," Journal of Clinical Oncology 26(10):1626-1634, American Society of Clinical Oncology, United States (2008).

Artavanis-Tsakonas, S., et al., "Notch Signaling: Cell Fate Control and Signal Integration in Development," Science 284(5415):770-776, American Association for the Advancement of Science, United States (1999).

Axelson, H., "Notch Signaling and Cancer: Emerging Complexity," Seminars in Cancer Biology 14(5):317-319, Academic Press, England (2004).

Barbas, C.F. 3RD., et al., "In vitro evolution of a neutralizing human antibody to human immunodeficiency virus type 1 to enhance affinity and broaden strain cross-reactivity," Proceedings of the National Academy of Sciences 91(9):3809-3813, National Academy of Sciences, United States (1994).

Beachy, P.A., et al., "Tissue Repair and Stern Cell Renewal in Carcinogenesis," Nature 432(7015):324-331, Nature Publishing Group, England (2004).

Bellavia, D., et al,, "Constitutive Activation of NF-κB and T-cell Leukemia/lymphoma in Notch3 Transgenic Mice," The EMBO Journal 19(13):3337-3348, European Molecular Biology Organization, Germany (2000).

Benvenuti, S., et al., "Oncogenic activation of the RAS/RAF signaling pathway impairs the response of metastatic colorectal cancers to anti-epidermal growth factor receptor antibody therapies," Cancer Research 67(6):2643-2648, American Association for Cancer Research, United States (2007).

Besseyrias, V., et al., "Hierarchy of Notch-Delta interactions promoting T cell lineage commitment and maturation," The Journal of Experimental Medicine 204(2):331-343, The Rockefeller University Press, United States (2007).

Beviglia, L., et al., "Anti-DLL4 reduces tumor growth and tumorigenicity in B-RAF V600E melanomas including those with acquired

(56) References Cited

OTHER PUBLICATIONS resistance to B-RAF inhibitors," AACR 103rd Annual Meeting 2012, Mar. 31-Apr. 4, Abstract LB-196, 1 page (2012).
Beviglia, L., et al., "Anti-DLL4 Treatment Inhibits Melanoma Tumor Growth, Recurrence, Metastases and Reduces Frequency of Cancer Stem Cells in a Clinically Relevant Tumor Model in NOD/SCID Mice," Cancer Research 71(8 Suppl.):Abstract 2834, AACR 102nd Annual Meeting 2011, Apr. 2-6, 2011.
Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).
Bloom, J.W., et al., "Intrachain disulfide bond in the core hinge region of human IgG4," Protein Science 6(2):407-415, John Wiley & Sons, Inc., United States (1997).
Boerner, P., et al., "Production of Antigen-specific Human Monoclonal Antibodies from in Vitro-primed Human Splenocytes," Journal of Immunology 147(1):86-95, The American Association of immunologists, United States (1991).
Bonnet, D. and Dick, J.E., "Human acute myeloid leukemia is organized as a hierarchy that originates from a primitive hematopoietic cell," Nature Medicine 3(7):730-737, Nature Publishing Company, United States (1997).
Bray, S.J., "Notch signalling: a simple pathway becomes complex," Nature Reviews Molecular Cell Biology 7(9):678-689, Nature Publishing Group, United States (2006).
Brennan, K. and Brown, A.M., "Is there a Role for Notch Signalling in Human Breast Cancer?," Breast Cancer Research 5(2):69-75, BioMed Central Ltd., United Kingdom (2003).
Brennan, M., et al., "Preparation of Bispecific Antibodies by Chemical Recombination of Monoclonal Immunoglobulin G1 Fragments," Science 229(4708):81-83, American Association for the Advancement of Science, United States (1985).
Brorson, K., et al., "Mutational Analysis of Avidity and Fine Specificity of Anti-Levan Antibodies," Journal of Immunology 163(12):6694-6701, American Association of Immunologists, United States (1999).
Brummell, D.A., et al., "Probing the Combining Site of an Anti-Carbohydrate Antibody by Saturation-Mutagenesis: Role of the Heavy-Chain CDR3 Residues," Biochemistry 32(4)1180-1187, American Chemical Society, United States (1993).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology 111(5Pt1):2129-2138, The Rockefeller University Press, United States (1990).
Burks, E.A., et al., "In vitro Scanning Saturation Mutagenesis of an Antibody Binding Pocket," Proceedings of the National Academy of Sciences of the United States of America 94(2):412-417, National Academy of Sciences, United States (1997).
Callahan, R. And Raafat, A., "Notch Signaling in Mammary Gland Tumorigenesis," Journal of Mammary Gland Biology and Neoplasia 6(1):23-36, Kluwer Academic/Plenum Publishers, United States (2001).
Carter, P., "Improving the efficacy of antibody-based cancer therapies," Nature Reviews Cancer 1(2):118-129, Nature Publishing Group, United States (2001).
Chartier, C., et al., "The Hippo Signaling Pathway Mediates BMP Inhibition of Cancer Stem Cells," 2015 AACR Annual meeting, Apr. 18-22, Abstract 2322, 1 page (2015).
Chau, I. and Cunningham, D., "Treatment in advanced colorectal cancer: what, when and how?," British Journal of Cancer 100(11)1 704-1719, Nature Publishing Group, United States (2009).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).

Chi, A.S., et al., "Angiogenesis as a Therapeutic Target in Malignant Gliomas," Oncologist 14(6):621-636, AlphaMed Press, United States (2009).
Chothia, C. and Lesk, A.M., "Canonical structures for the hypervariable regions of immunoglobulins," Journal of Molecular Biology 196(4):901-917, Elsevier Science, United States (1987).
Chothia, C., et al., "Domain association in immunoglobulin molecules. The packing of variable domains," Journal of Molecular Biology 186(3):651-663, Elsevier Science, England (1985).
Chowdhury, P.S. and Pastan, I., "Improving Antibody Affinity by Mimicking Somatic Hypermutation in vitro," Nature Biotechnology 17(6):568-572, Nature Publishing Group, United States (1999).
Clarke, M.F., et al,, "Cancer stem cells—perspectives on current status and future directions: AACR Workshop on cancer stem cells," Cancer Research 66(19):9339-9344, American Association for Cancer Research, United States (2006).
Claxton, S. and Fruttiger. M., "Periodic Delta-like 4 expression in developing retinal arteries," Gene Expression Pattern 5:123-127, Elsevier B.V., Netherlands (2004).
Cole, S.P.C., et al., "The EBV-Hybridoma Technique and Its Application to Human Lung Cancer," Monoclonal Antibodies and Cancer Therapy, 77-96, Proceedings of the Roche-UCLA Symposium, United States (1985).
Colman, P.M., "Effects of Amino Acid Sequence Changes on Antibody-Antigen Interactions," Research in Immunology 145(1);33-36, Elsevier, France (1994).
Zagouras, P., et al., "Alterations in Notch Signaling in Neoplastic Lesions of the Human Cervix," Proceedings of the National Academy of Sciences 92(14):6414-6418, National Academy of Sciences, United States (1995).
Cubillo, A., et al., "A Ph1b Study of Demcizumab (DEM, anti-DLL4) with Gemcitabine (GEM) in Patients with 1st Line Locally Advanced or Metastatic Pancreatic Cancer," AACR-NCI-EORTC International Conference on Molecular Targets and Cancer Therapeutics, Oct. 19-23, 2013, Poster (2013), 8 pages.
Cubillo, A., et al., "A Phase lb study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).
Dalerba, P., et al., "Phenotypic characterization of human colorectal cancer stem cells," Proceedings of the National Academy of Sciences 104(24):10158-10163, National Academy of Sciences, United States (2007).
Dando, J.S., et al., "Notch/Delta4 interaction in human embryonic liver CD34+ CD38- cells: positive influence on BFU-E production and LTC-IC potential maintenance," Stem Cells 23(4):550-560, John Wiley & Sons, Inc., United States (2005).
Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).
Deonarain, M.P., et al., "Antibodies Targeting Cancer Stem Cells: A New Paradigm in Immunotherapy?," mAbs 1(1):12-25,Taylor & Francis, United States (2009).
Dixit, R., "Cardiovascular Safety of Biologics: Challenges and Opportunities," Medimmune, Safety Pharmacology Society, Annular Meeting Speakers Presentations (Oct. 3, 2012).
Dontu, G., et al., "Role of Notch Signaling in Cell-Fate Determination of Human Mammary Stem/progenitor Cells," Breast Cancer Research 6(6):R605-R615, BioMed Central, England (2004).
Dorsch, M., et al., "Ectopic expression of Delta4 impairs hematopoietic development and leads to lymphoproliferative disease," Blood 100(6):2046-2055, American Society of Hematology, United States (2002).
Dreher, M.L., et al., "Colony assays for antibody fragments expressed in bacteria," Journal of Immunological Methods 139(2):197-205, Elsevier Science, United States (1991).
Duarte, A., et al., "Dosage-sensitive requirement for mouse Dll4 in artery development," Genes & Development 18(20):2474-2478, Cold Spring Harbor Laboratory Press, United States (2004).

(56) References Cited

OTHER PUBLICATIONS

Dupont, J. "Anti-Angiogenic Agents and Cardiovascular Effects: Implications for Clinical Development in Cancer," presentation given in Barcelona, Spain on Nov. 4, 2011, 16 pages.

Dupont, J., et al., "A Phase 1b Study of Anti-DLL4 (Delta-Like Ligand 4) Antibody Demcizumab (DEM) with Pemetrexed (PEM) and Carboplatin (CARBO) in Patients with 1st-Line Non-Squamous NSCLC," 2015 European Lung Cancer Conference (ELCC), Geneva, Switzerland, Apr. 15-18, Abstract 114, 2 pages (2015).

Ellisen, L.W., et al., "TAN-1, the Human Homolog of the *Drosophila* Notch Gene, Is Broken by Chromosomal Translocations in T Lymphoblastic Neoplasms," Cell 66(4):649-661, Elsevier Science, United States (1991).

Engin,F., et al., "Dimorphic effects of Notch signaling in bone homeostasis," Nature Medicine 14(3):299-305, Nature Publishing Group, United States (2008).

English language translation of Oishi, H., et al., "Novel therapeutic strategy for pancreatic cancer targeting Notch signaling pathway," Proceedings of the Japanese Cancer Association 65:311-312, Japan (2006).

English language translation of "Tumor-angiogenesis suppression therapy targeting the Notch signaling pathway," Suizo (Pancreas) 21(3):249, Japan (2006).

Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).

European Search Report for EP Application No. EP10824244.7, Munich, Germany, dated Feb. 18, 2013, 6 pages.

Farnie, G. and Clarke, R.B., "Mammary stem cells and breast cancer—role of Notch signalling," Stem Cell Reviews and Reports 3(2):169-175, Humana Press, United States (2007).

Farnie, G., et al., "Novel cell culture technique for primary ductal carcinoma in situ: role of Notch and epidermal growth factor receptor signaling pathways," Journal of the National Cancer Institute 99(8):616-627, Oxford University Press, United Kingdom (2007).

Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2011).

Fleming, R.J., et al., "The NOTCH receptor and its ligands," Trends in Cell Biology 7(11):437-441, Elsevier Science Ltd., The Netherlands (1997).

Fre, S., et al., "Notch Signals Control the Fate of Immature Progenitor Cells in the Intestine," Nature 435(7044):964-968, Nature Publishing Group, United States (2005).

Fung, E., et al., "Delta-like 4 induces notch signaling in macrophages: implications for inflammation," Circulation 115(23):2948-2956, American Heart Association, Inc., United States (2007).

Gagnon, M.L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).

Gale, N.W., et al., "Haploinsufficiency of Delta-like 4 Ligand Results in Embryonic Lethality due to Major Defects in arterial and Vascular Development," Proceedings of the National Academy of Sciences 101(45):15949-15954, National Academy of Sciences, United States (2004).

Gallahan, D., et al., "A new common integration region (int-3) for mouse mammary tumor virus on mouse chromosome 17," Journal of Virology 61(1)218-220, American Society for Microbiology, United States (1987).

Gallahan, D., et al., "Expression of a Truncated Int3 Gene in Developing Secretory Mammary Epithelium Specifically Retards Lobular Differentiation Resulting in Tumorigenesis," Cancer Research 56(8):1775-1785, American Association for Cancer Research, United States (1996).

Garber, K., "Notch emerges as new cancer drug target," Journal of the National Cancer Institute 99(17):1284-1285, Oxford University Press, United States (2007).

Gracian, A.C., et al., "A phase 1b study of the anticancer stem cell agent demcizumab (DEM) and gemcitabine (GEM) with or without paclitaxel protein bound particles (nab-paclitaxel) in patients with pancreatic cancer," 2014 Gastrointestinal Cancers Symposium, Abstract 279, 2 pages (2014).

Gray-Schopfer, V.C., et al., "The Role of B-RAF in Melanoma," Cancer Metastasis Reviews 24(1):165-183, Springer Science + Business Media, Inc., Netherlands (2005).

Gridley, T., "Notch Signaling During Vascular Development," Proceedings of the National Academy of Sciences 98(10):5377-5378, National Academy of Sciences, United States (2001).

Gridley, T. "Notch signaling in vascular development and physiology," Development 134(15):2709-2718, (2007).

Gronberg, B.H., et al., "Phase III Study by the Norwegian Lung Cancer Study Group: Pemetrexed Plus Carboplatin Compared with Gemcitabine Plus Carboplatin as First-line Chemotherapy in Advanced Non-small-cell Lung Cancer," Journal of Clinical Oncology 27(19):3217-3224, American Society of Clinical Oncology, United States (2009).

Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (1994).

Gurney, A. and Hoey, T., "Anti-DLL4, a Cancer Therapeutic with Multiple Mechanisms of Action," Vascular Cell 3, 4 pages, BioMed Central, United States (2011).

Hainaud, P., et al., "The role of the vascular endothelial growth factor-Delta-like 4 ligand/Notch4-ephrin B2 cascade in tumor vessel remodeling and endothelial cell functions," Cancer Research 66(17):8501-8510, American Association for Cancer Research, United States (2006).

Hallahan, A.R., et al., "The SmoA1 Mouse Model Reveals that Notch Signaling is Critical for the Growth and Survival of Sonic Hedgehog-Induced Medulloblastomas," Cancer Research 64(21):7794-7800, American Association for Cancer Research, United States (2004).

Han, W., et al., "A soluble form of human Delta-like-1 inhibits differentiation of hematopoietic progenitor cells," Blood 95(5):1616-1625, The American Society of Hematology, United States (2000).

Harlow, E. and Lane, D., eds., "Immunoassays," in Antibodies: A Laboratory Manual, 14:553-612, Cold Spring Harbor Laboratory, United States (1988).

Harper, J.A., et al., "Notch Signaling in Development and Disease," Clinical Genetics 64(6):461-472, Blackwell Publishing, United States (2003).

Harrington, L.S., et al., "Regulation of multiple angiogenic pathways by Dll4 and Notch in human umbilical vein endothelial cells," Microvascular Research 75(2):144-154, Elsevier Science, United States (2008).

Harris, W.J., "Production of Humanized Monoclonal Antibodies for in vivo Imaging and Therapy," Biochemical Society Transactions 23(4):1035-1038, Portland Press on the Behalf of the Biochemical Society, England (1995).

Hawkins, R.E., et al., "Selection of phage antibodies by binding affinity. Mimicking affinity maturation," Journal of Molecular Biology 226(3):889-896, Elsevier Science, United States (1992).

Hellström, M., et al., "Dll4 signalling through Notch1 regulates formation of tip cells during angiogenesis," Nature 445(7129)776-780, Nature Publishing Group, United States (2007).

Henning, K., et al., "mNotch1 signaling and erythropoietin cooperate in erythroid differentiation of multipotent progenitor cells and upregulate beta-globin," Experimental Hematology 35(9):1321-1332, Elsevier Science, United States (2007).

Hermentin, P. and Seiler, F.R., "Investigations with Monoclonal Antibody Drug (Anthracycline) Conjugates," Behring Institute Research Communications 82:197-215, Behringwerke Ag, Germany (1988).

Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Can-

(56) References Cited

OTHER PUBLICATIONS cer," European Society for Medical Oncology 2014 Congress, Sep. 17 and Sep. 28, Poster 616PD, 1 page (2014).

Hidalgo, M., et al., "A Phase 1b Study of the Anti-Cancer Stem Cell Agent Demcizumab (DEM, Anti-DLL4) and Gemcitabine (GEM) with or without Paclitaxel Protein Bound Particles (Nab-Paclitaxel) in pts with Pancreatic Cancer," 2015 ASCO Annual Meeting, Abstract 4118, 3 pages (2015),.

Hidalgo, M., et al., "Pre-Clinical and Clinical Activity of Anti-DLL4 (Demcizumab) in Combination with Gemcitabine Plus nab-Paclitaxel in Pancreatic Cancer," 26th EORTC-NCI-AACR Symposium on Molecular Targets and Cancer Therapeutics Preclinical Models Poster Session, Abstract 166, 2 pages (Nov. 2014).

Hoey, T., et al., "DLL4 blockade inhibits tumor growth and reduces tumor-initiating cell frequency,"Cell Stem Cell 5(2):168-177, Elsevier Science, United States (2009).

Hofmann, J.J. and Iruela-Arispe, M.L., "Notch signaling in blood vessels: who is talking to whom about what?," Circulation Research 100(11):1556-1568, American Heart Association, Inc., United States (2007).

Holash, J., et al., "Inhibitors of growth factor receptors, signaling pathways and angiogenesis as therapeutic molecular agents," Cancer Metastasis Rev 25:243-252, Dordrecht, Netherlands (2006).

Holash, J. et al., "VEGF-Trap: A VEGF Blocker with Potent Antitumor Effects," Proceedings of the National Academy of Sciences USA 99(17):11393-11398, National Academy of Sciences, United States (2002).

Holm, P., et al., "Functional Mapping and Single Chain Construction of the Anti-Cytokeratin 8 Monoclonal Antibody TS1," Molecular Immunology 44(6):1075-1084, Pergamon Press, England (2007).

Hoogenboom, H.R. and Winter, G., "By-Passing Immunisation. Human Antibodies from Synthetic Repertoires of Germline VH Gene Segments Rearranged in vitro," Journal of Molecular Biology 227(2):381-388, Elsevier, England (1992).

Hope, K.J., et al., "Acute myeloid leukemia originates from a hierarchy of leukemic stem cell classes that differ in selfrenewal capacity," Nature Immunology 5(7):738-743, Nature Publishing Group, United States (2004).

Hopfer, O., et al., "The Notch Pathway in Ovarian Carcinomas and Adenomas," British Journal of Cancer 93(6):709-718, Nature Publishing Group on behalf of Cancer Research UK, England (2005).

Humphreys, D.P., et al., "Formation of dimeric Fabs in *Escherichia coli*: effect of hinge size and isotype, presence of interchain disulphide bond, Fab' expression levels, tail piece sequences and growth conditions," Journal of Immunological Methods 209(2):193-202, Elsevier Science, Netherlands (1997).

Hurle, M.R. and Gross, M., "Protein engineering techniques for antibody humanization," Current Opinion in Biotechnology 5(4):428-433, (1994).

Hurwitz, H.I., et al., "Phase I Trial of Pazopanib in Patients with Advanced Cancer," Clinical Cancer Research 15(12):4220-4227, American Association for Cancer Research, United States (2009).

Hwang, K.J., et al. "Hepatic uptake and degradation of unilamellar sphingomyelin/cholesterol liposomes: a kinetic study," Proceedings of the National Academy of Sciences 77(7):4030-4034, National Academy of Sciences, United States (1980).

International Preliminary Report on Patentability and Written Opinion for International Application No. PCT/US2010/53064, International Searching Authority, dated Feb. 14, 2011, 7 pages.

International Preliminary Report on Patentability for International Application No. PCT/US2013/065015, The international Bureau of WIPO, Switzerland, dated Apr. 22, 2014, 17 pages.

International Search Report for International Application No. PCT/US2010/53064, dated Feb. 14, 2011, 3 Pages.

International Search Report for International Patent Application No. PCT/US11/60773, International Searching Authority, Alexandria, Virginia, United States, dated Mar. 26, 2012, 3 pages.

International Search Report for International Patent Application No. PCT/U52007/020889, United States Patent and Trademark Office, United States, dated Apr. 9, 2008, 5 pages.

International Search Report with the Written Opinion of the International Searching Authority for International application No. PCT/US10/32625, United States Patent and Trademark Office, United States, dated Dec. 17, 2010, 11 pages.

International Search Report with the Written Opinion of the International Searching Authority for International application No. PCT/US12/56886, United States Patent and Trademark Office, United States, dated Feb. 28, 2013, 8 pages.

International Search Report with Written Opinion for International Application No. PCT/US2010/58511, International Searching Authority, United States, dated Mar. 3, 2011, 9 pages.

Ishiko, E., et al., "Notch signals inhibit the development of erythroid/megakaryocytic cells by suppressing GATA-1 activity through the induction of HES1," The Journal of Biological Chemistry 280(6):4929-4939, American Society for Biochemistry and Molecular Biology, United States (2005).

Iso, T., et al., "Notch Signaling in Vascular Development," Arteriosclerosis, Thrombosis, and Vascular Biology 23(4):543-553, American Heart Association, Inc., United States (2003).

Izzedine, H., et al., "Management of Hypertension in Angiogenesis Inhibitor-Treated Patients," Annals of Oncology 20(5):807-815, Oxford University Press, England (2009).

Jackson, J.R., et al., "In vitro antibody maturation. Improvement of a high affinity, neutralizing antibody against IL-1 beta," The Journal of Immunology 154(7):3310-3319, The American Association of Immunologists, Inc., United States (1995).

Janeway, Jr., et al., "Immunobiology, The Immune System in Health and Disease," Edition 4:579-581, Current Biology Publications (1999).

Jang, Y.J., et al., "The Structural Basis for DNA Binding by an Anti-DNA Autoantibody," Molecular Immunology 35(18):1207-1217, Pergamon Press, England (1998).

Jarriault, S., et al., "Signalling Downstream of Activated Mammalian Notch," Nature 377(6547):355-358, Nature Publishing Group, United States (1995).

Jeffries, S. and Capobianco, A.J., "Neoplastic transformation by Notch requires nuclear localization," Molecular and Cellular Biology 20(11):3928-3941, American Society for Microbiology, United States (2000).

Jhappan, C., et al., "Expression of an Activated Notch-Related int-3 Transgene Interferes with Cell Differentiation and Induces Neoplastic Transformation in Mammary and Salivary Glands," Genes & Development 6(3):345-355, Cold Spring Harbor Laboratory Press, United States (1992).

Jimeno, A., et al., "Phase 1 study of REGN421 (R)/SAR153192, a fully-human delta-like ligand 4 (Dll4) monoclonal antibody (mAb), in patients with advanced solid tumors," ASCO University 2013 ASCO Annual Meeting accessed at http://meetinglibrary.asco.org/content/113836-132, 2 pages.

Jones, P.T., et al., "Replacing the Complementarity-Determining Regions in a Human Antibody with those from a Mouse," Nature 321(6069):522-525, Nature Publishing Group, England (1986).

Kim, E.S., et al., "Potent VEGF blockade causes regression of coopted vessels in a model of neuroblastoma," Proceedings of the National Academy of Sciences 99(17):11399-11404, National Academy of Sciences, United States (2002).

Kingsman, A.J., et al., "Replication in Saccharomyces Cerevisiae of Plasmid pBR313 Carrying DNA from the Yeast Trpl Region," Gene 7(2):141-152, Elsevier/North-Holland Biomedical Press, Netherlands (1979).

Kobayashi, H., et al., "Tryptophan H33 Plays an Important Role in Pyrimidine (6-4) Pyrirrnidone Photoproduct Binding by a High-Affinity Antibody," Protein Engineering Design and Selection 12(10):879-884, Oxford University Press, United States (1999).

Kopper, L. And Hajdu, M., "Tumor Stem Cells," Pathology and Oncology Research 10(2):69-73, Aranyl Lajos Foundation, Hungary (2004).

Kostelny, S.A., et al., "Formation of a Bispecific Antibody by the Use of Leucine Zippers," The Journal of Immunology 148(5):1547-1553, American Association of Immunologists, United States (1992).

(56) References Cited

OTHER PUBLICATIONS

Krebs, L.T., et al., "Haploinsufficient Lethality and Formation of Arteriovenous Malformations in Notch Pathway Mutants," Genes & Development 18(20):2469-2473, Cold Spring Harbor Laboratory Press, United States (2004).
Krebs, L.T., et al., "Notch Signaling is Essential for Vascular Morphogenesis in Mice," Genes & Development 14(11):1343-1352, Cold Spring Harbor Laboratory Press, United States (2000).
Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).
Lapidot, T., et al., "A Cell Initiating Human Acute Myeloid Leukaemia After Transplantation Into SCID Mice," Nature 367(6464):645-648, Nature Publishing Group, United States (1994).
Lauret, E., et al., "Membrane-Bound Delta-4 Notch Ligand Reduces the Proliferative Activity of Primitive Human Hematopoietic CD34+ CD38low Cells while Maintaining their LTC-IC Potential," Leukemia 18(4):788-797, Nature Publishing Group, United States (2006).
Lazar, E., et al., "Transforming Growth Factor α: Mutation of Aspartic Acid 47 and Leucine 48 Results in Different Biological Activities," Molecular and Cellular Biology 8(3):1247-1252, American Society for Microbiology, United States (1988).
Lee, H.S., et al., "Generation and characterization of a novel single-gene-encoded single-chain immunoglobulin molecule with antigen binding activity and effector functions," Molecular Immunology 36(1):61-71, Elsevier Science Ltd., Netherlands (1999).
Leethanakul, C., et al., "Distinct Pattern of Expression of Differentiation and Growth-Related Genes in Squamous Cell Carcinomas of the Head and Neck Revealed by the Use of Laser Capture Microdissection and cDNA Arrays," Oncogene 19(28):3220-3224, Nature Publishing Group, United States (2000).
Lenihan, D.J., "How is cardiac toxicity defined and what impact does this have on cancer outcome or drug development," PowerPoint Presentation from the DIA Meeting, 42 slides (2011).
Leong, K.G. and Karsan, A., "Recent Insights into the Role of Notch Signaling in Tumorigenesis," Blood 107(6):2223-2233, The American Society of Hematology, United States (2006).
Li, J.L. and Harris A.L., "Notch Signaling from Tumor Cells: A New Mechanism of Angiogenesis," Cancer Cell 8(1):pp. 1-3. Cell Press, United States (2005).
Li, X., et al,, "Notch3 Signaling is Required for the Development of Pulmonary Arterial Hypertension," Nature Medicine 15(11):1289-1297, Nature Publishing Company, United States (2009).
Lievre, A., et al., "KRAS Mutation Status Is Predictive of Response to Cetuximab Therapy in Colorectal Cancer," Cancer Research 66(8):3992-3995, American Association for Cancer Research, United States (2006).
Limbourg, A., et al., "Notch ligand Delta-like 1 is essential for postnatal arteriogenesis," Circulation Research 100(3):363-371, American Heart Association, Inc., United States (2007).
Liu, S., et al., "Mammary stem cells, self-renewal pathways, and carcinogenesis," Breast Cancer Research 7(3):86-95, BioMed Central, England (2005).
Liu, Z.J., et al., "Inhibition of endothelial cell proliferation by Notch1 signaling is mediated by repressing MAPK and P14K/Akt pathways and requires MAML1," Federation of American Societies for Experimental Biology 20:E201-E210, American Society for Experimental Biology, United States (2006).
Liu, Z.J., et al., "Regulation of Notch1 and Dll4 by vascular endothelial growth factor in arterial endothelial cells: implications for modulating arteriogenesis and angiogenesis," Molecular and Cellular Biology 23(1):14-25, American Society for Microbiology, United States (2003).
Lobov, I.B., et al., "Delta-like ligand 4 (Dll4) is induced by VEGF as a negative regulator of angiogenic sprouting," Proceedings of the National Academy of Sciences 104(9):3219-3224, National Academy of Sciences, United States (2007).
Lu, K.V., and Bergers, G., "Mechanisms of evasive resistance to anti-VEGF therapy in glioblastoma," CNS Oncology 2(1):49-65, Future Medicine, Inc., United States (2013).
Luca, V.C., et al., "Structural basis for Notch1 engagement of Delta-like 4," Science, 347(6224):847-853, American Association for the Advancement of Science, United States (2015).
MacCallum, R.M., et al., "Antibody-Antigen Interactions: Contact Analysis and Binding Site Topography," Journal of Molecular Biology 262(5):732-745, Elsevier, England (1996).
Maeda, H., et al., "Construction of Reshaped Human Antibodies with HIV-Neutralizing Activity," Human Antibodies and Hybridomas 2(3):124-134, Butterworth-Heinemann, United Kingdom (1991).
Mailhos, C., et al., "Delta4, an Endothelial Specific Notch Ligand Expressed at Sites of Physiological and Tumor Angiogenesis," Differentiation 69:135-144, Elsevier, England (2001).
Marks, J.D., et al., "By-Passing Immunization: Building High Affinity Human Antibodies by Chain Shuffling," Biotechnology 10(7):779-783, Nature Publishing Company, United States (1992).
Marks, J.D., et al., "By-passing immunization. Human Antibodies from V-Gene Libraries Displayed on Phage," Journal of Molecular Biology 222(3):581-597, Academic Press Limited, United States (1991).
Mazella, J., et al., "Expression of Delta-like protein 4 in the human endometrium," Endocrinology 149(1):15-19, Association for the Study of Internal Secretions, United States (2008).
McKeage, M., et al., "A Phase 1b Study of Demcizumab plus Pemetrexed and Carboplatin in Patients with 1st line Non-Squamous Non-Small Cell Lung Cancer (NSCLC)," 24th EORTC-NCI-AACR Symposium on Molecular Targets and Cancer Therapeutics, Nov. 6-9, 2012, Poster (2012), 9 pages.
McKeage, M., et al., "A Phase 1b study of demcizumab (DEM, anti-DLL4) plus pemetrexed and carboplatin in patients with first line stage IIIb/IV non-squamous non-small cell lung cancer," Proceedings of the AACR-NCI-EORTC International Conference on Molecular Targets and Cancer Therapeutics, Oct. 19-23, 2013, Abstract A71, 2 pages (2013).
McKeage, M., et al., "Phase 1b Study of Demcizumab plus Pemetrexed and Carboplatin in Patients with 1st line Non-Small Cell Lung Cancer (NSCLC)," AACR-NCI-EORTC International Conference on Molecular Targets and Cancer Therapeutics, Oct. 19-23, 2013, Poster (2013), 8 pages.
McKeage, M.J., et al., "A phase 1b study of the anticancer stem cell agent demcizurnab (DEM), pemetrexed (PEM), and carboplatin (CARBO) in pts with first-line nonsquamous NSCLC," 2014 ASCO Annual Meeting, Abstract 2544, 2 pages (2014).
McKeage, M.J., et al., "A Phase 1b Study of the Anti-Cancer Stem Cell Agent Demcizumab (DEM), Pemetrexed (PEM) and Carboplatin (CARBO) in Patients with 1st Line Non-Squamous Non-Small Cell Lung Cancer (NSCLC)," 2015 ASCO Annual Meeting, Abstract 8045, 2 pages (2015).
Merchant, A.M., et al., "An Efficient Route to Human Bispecific IgG," Nature Biotechnology 16(7):677-681, Nature Publishing Group, United States (1998).
Miele, L. and Osborne, B., "Arbiter of Differentiation and Death: Notch Signaling Meets Apoptosis," Journal of Cellular Physiology 181(3):393-409, Wiley-Liss, Inc., United States (1999).
Miele, L., "Notch Signaling," Clinical Cancer Research 12:1074-1077, The American Association for Cancer Research, United States (2006 ).
Milano, J., et al., "Modulation of Notch Processing by D-Secretase Inhibitors Causes Intestinal Goblet Cell Metaplasia and Induction of Genes Known to Specify Gut Secretory Lineage Differentiation," Toxicological Sciences 82(1):341-358, Oxford University Press, United States (2004).
Milstein, C. and Cuello, A.C., "Hybrid Hybridomas and Their Use in Immunohistochemistry," Nature 305 (5934):537-540, Nature Publishing Group, England (1983).
Morimoto, K., and Inouye K., "Single-step purification of F(ab')2 mu fragments of mouse monoclonal antibodies (immunoglobulins G1) by hydrophobic interaction high-performance liquid chromatography using TSKgel Phenyl-5PW," Journal of Biochemical and Biophysical Methods 24(1-2):107-117, Elsevier/North-Holland Biomedical Press, Netherlands (1993).

(56) References Cited

OTHER PUBLICATIONS

Morrison, S.J., et al., "Hematopoietic Stem Cells: Challenges to Expectations," Current Opinion in Immunology 9(2):216-221, Elsevier Science, United States (1997).
Morrison, S.J., et al., "Regulatory Mechanisms in Stem Cell Biology," Cell 88(3):287-298, Elsevier Science, United States (1997).
Morrison, S.J., et al., "The Biology of Hematopoietic Stem Cells," Annual Review of Cell and Developmental Biology 11:35-71, Annual Reviews, United States (1995).
Morrison, S.J., et al., "Transient Notch activation initiates an irreversible switch from neurogenesis to gliogenesis by neural crest stem cells," Cell 101(5):499-510, Elsevier Science, United States (2000).
Morrison, S.L., et al., "Chimeric Human Antibody Molecules: Mouse Antigen-Binding Domains with Human Constant Region Domains," Proceedings of the National Academy of Sciences USA 81(21):6851-6855, National Academy of Sciences, United States (1984).
Nam, Y., et al., "Notch Signaling as a Therapeutic Target," Current Opinion in Chemical Biology 6(4):501-509, Elsevier Science, United States (2002).
NCT00744562, "A Phase 1 Dose Escalation Study of OMP-21M18 in Subjects With Solid Tumors," ClinicalTrials.gov archive, accessed at http://clinicaltrials.gov/archiveiNCT00744562/2008_10_06, accessed on Feb. 2, 2012, 4 pages.
NCT01189929, "A Phase 1b Study of Gemcitabine Plus OMP-21M18 as 1st-line Treatment in Subjects With Locally Advanced or Metastatic Pancreatic Cancer" as updated on Aug. 26, 2010, ClinicalTrials.gov archive, accessed at https://clinicaltrials.gov/archives/NCT01189929/2010_08_26, accessed on Apr. 20, 2015, 5 pages.
NCT01189929, "A Phase 1b Study of Gemcitabine Plus OMP-21M18 as 1st-line Treatment in Subjects With Locally Advanced or Metastatic Pancreatic Cancer" as updated on Dec. 15, 2011, ClinicalTrials.gov archive, accessed at https://clinicaltrials.gov/archives/NCT01189929/2011_12_15, accessed on Apr. 20, 2015, 5 pages.
NCT01189968, "A Phase 1b Study of Carboplatin and Pemetrexed Plus OMP-21M18 as 1st-line Treatment in Subjects with Non-Squamous Non-Small Cell Lung Cancer" as updated on Aug. 26, 2010, ClinicalTrials.gov archive, accessed at https://clinicaltrials.gov/archive/NCT01189968/2010_08_26, accessed on Apr. 20, 2015, 5 pages.
NCT01189968, "A Phase 1b Study of Carboplatin and Pemetrexed Plus OMP-21M18 in Subjects with Non-Squamous Non-Small Cell Lung Cancer" as updated on Dec. 15, 2011, ClinicalTrials.gov archive, accessed at https://clinicaltrials.gov/archive/NCT01189968/2011_12_15, accessed on Apr. 20, 2015, 5 pages.
NCT01189968, "A Phase 1b Study of Carboplatin and Pemetrexed Plus OMP-21M18 in Subjects With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.
Nickoloff, B.J., et al., "Notch Signaling as a Therapeutic Target in Cancer: a New Approach to the Development of Cell Fate Modifying Agents," Oncogene 22(42):6598-6608, Nature Publishing Group, England (2003).
Noguera, I., et al., "Delta-like ligand 4 (Dll4) is critical for tumor growth and angiogenesis," Proceedings of the Annual Meeting of American Association for Cancer Research 47:1342, American Association for Cancer Research, United States (2006).
Noguera, I., et al., "Expression of Delta-like 4 (Dll4) ligand in mouse tumor models," Proceedings of the Annual Meeting of the American Association for Cancer Research 46(Supp15):1104, American Association for Cancer Research, United States (2005).
Noguera-Troise, I., et al., "Blockade of Dll4 inhibits tumour growth by promoting nonproductive angiogenesis," Nature 444(7122):1032-1037, Nature Publishing Group, United States (2006).
Nohaile, M.J., et al., "Altering dimerization specificity by changes in surface electrostatics," Proceedings of the National Academy of Sciences 98(6):3109-3114, National Academy of Sciences, United States (2001).

Novotny, J. and Haber, E., "Structural invariants of antigen binding: comparison of immunoglobulin VL-VH and VL-VL domain dimers," Proceedings of the National Academy of Sciences 82(14):4592-4596, National Academy of Sciences, United States (1985).
Oishi, H.. et al., "Novel therapeutic strategy for pancreatic cancer targeting Notch signaling pathway," Proceedings of the Japanese Cancer Association 65:311-312, (2006).
OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.
OncoMed Pharmaceuticals Press Release, "OncoMed and Lilly Enter Clinical Supply Agreement to Evaluate the Combination of Demcizumab and Alimta(R) (pemetrexed for injection) in Lung Cancer," Apr. 2, 2015, 4 pages.
OncoMed Pharmaceuticals, Press Release, "OncoMed Announces Abstracts Accepted at the 2014 ASCO Annual Meeting," Apr. 23, 2014, 2 pages.
OncoMed Pharmaceuticals Press Release, "OncoMed Announces Abstracts Accepted for Presentation at the 2015 ASCO Annual Meeting," Apr. 21, 2015, 2 pages.
OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.
OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.
OncoMed Pharmaceuticals Press Release, "OncoMed Doses First Patient in Phase 1 Clinical Trial of Novel Anti-DLL4/VEGF Bispecific Antibody," Jan. 5, 2015, 2 pages.
OncoMed Pharmaceuticals Press Release, "OncoMed Highlights Immuno-Oncology Discoveries During 2015 Research & Development Day," Apr. 29, 2015, 3 pages.
OncoMed Pharmaceuticals Press Release, "OncoMed Initiates Dosing in Phase 2 Clinical Trial of Demcizumab for the Treatment of Non-Small Cell Lung Cancer," Feb. 4, 2015, 3 pages.
OncoMed Pharmaceuticals Press Release, "OncoMed Initiates Dosing in Randomized Phase 2 Clinical Trial of Demcizumab in Pancreatic Cancer Patients," Apr. 22, 2015, 3 pages.
OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.
OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.
OncoMed Pharmaceuticals, Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.
OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.

(56) References Cited

OTHER PUBLICATIONS

OncoMed Pharmaceuticals, Press Release, "OncoMed Pharmaceuticals Updates Phase 1b Data for Demcizumab With Pemetrexed and Carboplatin in Patients With First-Line Stage IIIb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.
OncoMed Pharmaceuticals Press Release, "OncoMed Presents Data From Phase 1b Trial of Demcizumab in Pancreatic Cancer at the 2015 ASCO Annual Meeting," Jun. 1, 2015, 3 pages.
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents Demcizumab Data From Phase 1b Clinical Trial in Non-Small Cell Lung Cancer Patients at the European Lung Cancer Conference," Apr. 16, 2015, 3 pages.
OncoMed Pharmaceuticals Press Release. "OncoMed Presents New Clinical and Biomarker Data From Its Tarextumab and Demcizumab Clinical Trials at the EORTC-NCI-AACR Symposium," Nov. 21, 2014, 3 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Presents Updated Demcizumab Data in Non-Small Cell Lung Cancer at the 2015 ASCO Annual Meeting," Jun. 1, 2015, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.
OncoMed Pharmaceuticals Press Release, "OncoMed to Present Clinical Data for Demcizumab at the European Lung Cancer Conference," Apr. 9, 2015, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.
OncoMed Pharmaceuticals Press Release, "OncoMed to Present New Data in Six Anti-Cancer Stem Cell Programs at AACR," Apr. 2, 2013, 2 pages.
Parks, A.L., et al., "Structure-function analysis of delta trafficking, receptor binding and signaling in *Drosophila*," Genetics 174(4):1947-1961, Genetics Society of America, United States (2006).
Parr, C., et al., "The Possible Correlation of Notch-1 and Notch-2 with Clinical Outcome and Tumour Clinicopathological Parameters in Human Breast Cancer," International Journal of Molecular Medicine 14(5):779-786, Spandidos Publications, Greece (2004).
Patel, N.S., et al., "Up-regulation of delta-like 4 ligand in human tumor vasculature and the role of basal expression in endothelial cell function," Cancer Research 65(19):8690-8697, American Association for Cancer Research, United States (2005).
Paul, W.E., "Immunogenicity and Antigen Structure," in *Fundamental Immunology*, Third Edition, pp. 242, Raven Press, United States (1993).
Pear, W.S. and Aster, J.C., "T Cell Acute Lymphoblastic Leukemia/Lymphoma: a Human Cancer Commonly Associated with Aberrant NOTCH1 Signaling," Current Opinion in Hematology 11(6):426-433, Lippincott Williams & Wilkins, United States (2004).
Pear, W.S., et al., "Exclusive development of T cell neoplasms in mice transplanted with bone marrow expressing activated Notch alleles," The Journal of Experimental Medicine 183(5):2283-2291, the Rockefeller University Press, United States (1996).
Phng, L.K., et al., "Nrarp coordinates endothelial Notch and Wnt signaling to control vessel density in angiogenesis," Developmental Cell 16(1):70-82, Elsevier Science, United States (2009).
Pisano, C., et al., "Undersulfated, low-molecular-weight glycol-split heparin as an antiangiogenic VEGF antagonist," Glycobiology 15(2)1C-6C, Oxford University Press, England (2005).
Politi, K., et al., "Notch in Mammary Gland Development and Breast Cancer," Seminars in Cancer Biology 14(5):341-347, Academic Press, United States (2004).
Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).
Presta, L.G,, et al., "Humanization of an antibody directed against IgE," The Journal of Immunology 151(5):2623-2632, The American Association of Immunologists, Inc., United States (1993).
Purow, B.W., et al., "Expression of Notch-1 and its Ligands, Delta-like-1 and Jagged-1, is Critical for Glioma Cell Survival and Proliferation," Cancer Research 65(6):2353-2363, American Association for Cancer Research, United States (2005).
Rae, F.K., et al., "Novel Association of a Diverse Range of Genes with Renal Cell Carcinoma as Identified by differential Display," International Journal of Cancer 88(5):726-732, John Wiley & Sons, Inc., United States (2000).
Rao, P.K., et al., "Isolation and characterization of the notch ligand delta4," Experimental Cell Research 260(2):379-386, Elsevier Science, United States (2000).
Rehman, A.O. and Wang, C-U, "Notch signaling in the regulation of tumor angiogenesis," Trends in Cell Biology 16(6):293-300, Elsevier Ltd., England (2006).
Reya, T., et al., "Stem Cells, Cancer, and Cancer Stem Cells," Nature 414(6859):105-111, Nature Publishing Group, England (2001).
Ridgway, J. et al,, "Inhibition of Dll4 signalling inhibits tumour growth by deregulating angiogenesis," Nature 444(7122):1083-1087, Nature Publishing Group, United States (2006).
Riechmann, L., et al., "Reshaping Human Antibodies for Therapy," Nature 332(6162):323-327, Nature Publishing Group, United States (1988).
Robey, E., et al., "An Activated form of Notch Influences the Choice between CD4 and CD8 T Cell Lineages," Cell 87(3):483-492, Elsevier Science, United States (1996).
Rudikoff, S., et al., "Single Amino Acid Substitution Altering Antigen-Binding Specificity," Proceedings of the National Academy of Sciences 79(6):1979-1983, The National Academy of Sciences, United States (1982).
Sainson, R.C. and Harris, A.L., "Anti-Dll4 therapy: can we block tumour growth by increasing angiogenesis?," 13(9):389-395, Elsevier Science, United States (2007).
Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).
Scehnet, J.S., et al., "Inhibition of Dll4-mediated signaling induces proliferation of immature vessels and results in poor tissue perfusion," Blood 109(11):4753-4760, American Society of Hematology, United Science (2007).
Schier, R., et al., "Identification of functional and structural amino-acid residues by parsimonious mutagenesis," Gene 169(2):147-155, Elsevier Science B.V., Netherlands (1996).
Schmidt, C., "Drug Makers Chase Cancer Stem Cells," Nature Biotechnology 26(4):366-367, Nature Publishing Group, United States (2008).
Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1): 217-225, The Rockefeller University Press, United States (1992).
Shawber, C.J., et al., "Notch Signaling in Primary Endothelial Cells," Annals of the New York Academy of Sciences 995:162-170, New York Academy of Sciences, United States (2003).

(56) References Cited

OTHER PUBLICATIONS

Sheets, M.D., et al., "Efficient Construction of a Large Nonimmune Phage Antibody Library: The Production of High-affinity Human Single-chain Antibodies to Protein Antigens," Proceedings of the National Academy of Sciences 95(11):6157-6162, The National Academy of Sciences, Unites States (1998).

Shields, J.M., et al., "Lack of Extracellular Signal-Regulated Kinase Mitogen-Activated Protein Kinase Signaling Shows a New Type of Melanoma," Cancer Research 67(4):1502-1512, American Association for Cancer Research, United States (2007).

Shutter, J. R., et al., "Dll4, a Novel Notch Ligand Expressed in Arterial Endothelium," Genes & Development 14(11):1313-1318, Cold Spring Harbor Laboratory Press, United States (2000).

Sica, D.A., "Angiogenesis Inhibitors and Hypertension," US Cardiovascular Disease 79-80, Touch Briefings, United States (2007).

Siekmann, A.F. and Lawson, N.D., "Notch signalling limits angiogenic cell behaviour in developing zebrafish arteries," Nature 445(7129):781-784, Nature Publishing Group, United States (2007).

Siena, S., et al., "Biomarkers predicting clinical outcome of epidermal growth factor receptor-targeted therapy in metastatic colorectal cancer," Journal of the National Cancer Institute 101(19):1308-1324, Oxford University Press, England (2009).

Sims, M.J., et al., "A humanized CD18 antibody can block function without cell destruction," The Journal of Immunology 151(4):2296-2308, The American Association of Immunologists, United States (1993).

Skolnick, "From Genes to Protein Structure and Function: Novel Applications of Computational Approaches in the Genomic Era," Trends in Biotechnology 18:34-39, Elsevier Science Publishers, London (2000).

Smith, D.C., et al., "A First-in-Human, Phase 1 Trial of the Anti-DLL4 Antibody (OMP- 21M18) Targeting Cancer Stem Cells (CSCs) in Patients with Advanced Solid Tumors," http://www.oncomed.com/news/pr/studylposterfinalNov10.pdf, accessed Feb. 2, 2012, 1 page.

Smith, D.C., et al., "A Phase I Dose Escalation and Expansion Study of the Anticancer Stem Cell Agent Demcizumab (Anti-DLL4) in Patients with Previously Treated Solid Tumors," Clinical Cancer Research 20(24):6295-6303, American Association for Cancer Research, United States (2014).

Smith, G.H., et al., "Constitutive Expression of a Truncated INT3 Gene in Mouse Mammary Epithelium Impairs Differentiation and Functional Development," Cell Growth & Differentiation 6(5):563-577, The American Association for Cancer Research, United States (1995).

Soriano J.V., et al., "Expression of an activated Notch4(int-3) oncoprotein disrupts morphogenesis and induces an invasive phenotype in mammary epithelial cells in vitro," International Journal of Cancer 86(5):652-659, John Wiley & Sons, United States (2000).

Srivastava, M., et al., "Dual Targeting of Delta-Like Ligand 4 (DLL4) and Programmed Death 1 (PD1) Inhibits Tumor Growth and Generates Enhanced Long-Term Immunological Memory," 2015 AACR Annual Meeting, Apr. 19, Abstract 255, 1 page (2015).

Stinchcomb, D.T., et al., "Isolation and Characterisation of a Yeast Chromosomal Replicator," Nature 282(5734):39-43, Nature Publishing Group, England (1979).

Sugimoto, A. et al., "Delta-4 Notch Ligand Promotes Erythroid Differentiation of Human Umbilical Cord Blood CD34+ Cells," Experimental Hematology 34(4):424-432, Elsevier Science Inc, Netherlands (2006).

Sullivan, D.C. and Bicknell, R., "New molecular pathways in angiogenesis," British Journal of Cancer 89:228-231, Cancer Research UK, United Kingdom (2003).

Supplementary European Search Report issued in the corresponding European Patent Application No. 07838966, European Patent Office, Munich, Germany, dated Apr. 6, 2010.

Suresh, M.R., et al., "Bispecific Monoclonal Antibodies from Hybrid Hybridomas," Methods in Enzymology 121:210-228, Academic Press Inc., United States (1986).

Suzuki, T., et al., "Imbalanced Expression of TAN-1 and Human Notch4 in Endometrial Cancers," International Journal of Oncology 17(6):1131-1139, Spandidos Publications, Greece (2000).

Takeda, T. and Kohno, M., "Brain Natriuretic Peptide in Hypertension," Hypertension Research 18(4):259-266, Nature Publishing Group, England (1995).

Tannock, I.F. and Hill R.P., "The Basic Science of Oncology," pp. 357-358, McGraw-Hill, United States (1998).

Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):3 pages, American Society of Hematology, United States (2003).

Tax, F.E., et al., "Sequence of C. elegans lag-2 Reveals a Cell-Signalling Domain Shared with Delta and Serrate of Drosophila," Nature 368(6467):150-154, The National Academy of Sciences, United States (1994).

Thelu, J., et al., "Notch Signalling is Linked to Epidermal Cell Differentiation Level in Basal Cell Carcinoma, Psoriasis and Wound Healing," BMC Dermatology 2(1):7, BioMed Central, England (2002).

Thurston, G., and Gale, N.W., "Vascular Endothelial Growth Factor and Other Signaling Pathways in Developmental and Pathologic Angiogenesis," International Journal of Hematology 80:7-20, The Japanese Society of Hematology, Japan (2004).

Thurston, G., et al., "The Delta paradox: DLL4 blockade leads to more tumour vessels but less tumour growth," Nature Reviews Cancer 7(5):327-331, Nature Publishing Group, United States (2007).

Ton, N.C. and Jayson, G.C., "Resistance to Anti-VEGF Agents," Current Pharmaceutical Design 10:51-64, Bentham Science Publishers Ltd., Netherlands (2004).

Traunecker, A., et al., "Bispecific single chain molecules (Janusins) target cytotoxic lymphocytes on HIV infected cells," The EMBO Journal 10(12):3655-3659, Oxford University Press, United Kingdom (1991).

Tutt, A., et al., "Trispecific F(ab')3 Derivatives that use Cooperative Signaling Via the TCR/CD3 Complex and CD2 to Activate and Redirect Resting Cytotoxic T Cells," The Journal of Immunology 147: 60-69, The American Association of immunologists, United States (1991).

Unknown Author., "Tumor angiogenesis suppression therapy targeting the Notch signaling pathway," Suizo (Pancreas) 21(3):249, (2006).

Urlaub, G. and Chasin, L.A., "Isolation of Chinese Hamster Cell Mutants Deficient in Dihydrofolate Reductase Activity," Proceedings of the National Academy of Sciences, USA77(7):4216-4220, National Academy of Sciences, United States (1980).

Uyttendaele, H., et al., "Notch4 and Wnt-1 Proteins Function to Regulate Branching Morphogenesis of Mammary Epithelial Cells in an Opposing Fashion," Developmental Biology 196(2):204-217, Elsevier Inc., Netherlands (1998).

Van Es, J.H., and Clevers, H., "Notch and Wnt Inhibitors as Potential New Drugs for Intestinal Neoplastic Disease," Trends in Molecular Medicine 11(11):496-502, Elsevier Inc., Netherlands (2005).

Van Limpt, V., et al., "SAGE Analysis of Neuroblastoma Reveals a High Expression of the Human Homologue of the Drosophila Delta Gene," Medical and Pediatric Oncology 35(6):554-558, Wiley-Liss, Inc., United States (2000).

Vaswani, S.K. and Hamilton, R.G., "Humanized antibodies as potential therapeutic drugs," Annals of Allergy, Asthma & Immunology 81(2):105-115, American College of Allergy, Asthma, & Immunology, United States (1998).

Vaughan, T.J., et al., "Human Antibodies with Sub-nanomolar Affinities Isolated from a Large non-Immunized Phage Display Library," Nature Biotechnology 14(3):309-314, Nature Publishing Co., United States (1996).

Verhoeyen, M., et al., "Reshaping Human Antibodies: Grafting an Antilysozyme Activity," Science 239(4847):1534-1536, American Association for the Advancement of Science, United States (1988).

Wang, J.C., et al., "Primitive human hematopoietic cells are enriched in cord blood compared with adult bone marrow or mobilized peripheral blood as measured by the quantitative in vivo SCID-

(56) References Cited

OTHER PUBLICATIONS repopulating cell assay," Blood 89(11):3919-3924, American Society of Hematology, United States (1997).
Ward, E.S., "Antibody engineering using *Escherichia coli* as host," Advances in Pharmacology 24:1-20, Academic Press, United States (1993).
Weijzen, S., et al., "Activation of Notch-1 Signaling Maintains the Neoplastic Phenotype in Human Ras-Transformed Cells," Nature Medicine 8(9):979-986, Nature Publishing Group, United States (2002).
Weng, A.P., et al., "Growth Suppression of Pre-T Acute Lymphoblastic Leukemia Cells by Inhibition of Notch Signaling," Molecular and Cellular Biology 23(2):655-664, American Society for Microbiology, United States (2003).
Weng, A.P., et al., "Activating Mutations of NOTCH1 in Human T Cell Acute Lymphoblastic Leukemia," Science 306(5694):269-271, American Association for the Advancement of Science, United States (2004).
Williams, C.K., et al., "Up-regulation of the Notch ligand Delta-like 4 inhibits VEGF-induced endothelial cell function," Blood 107(3):931-939, American Society of Hematology, United States (2006).
Wilson, A. and Radtke, F., "Multiple Functions of Notch Signaling in Self-Renewing Organs and Cancer," FEBS Letters 580(12):2860-2868, Elsevier Science, United States (2006).
Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).
Written Opinion of the International Searching Authority for International application No. PCT/US2007/020889, United States Patent and Trademark Office, United States, dated Apr. 9, 2008, 4 pages.
Written Opinion of the International Searching Authority for International Patent Application No. PCT/US11/60773, International Searching Authority, Alexandria, Virginia, United States, dated Mar. 26, 2012, 5 pages.
Wu, C., et al., "Simultaneous targeting of multiple disease mediators by a dual-variable-domain immunoglobulin," Nature Biotechnology 25(11):1290-1297, Nature Publishing Co., United States (2007).
Wu, H., et al,, "Humanization of a Murine Monoclonal Antibody by Simultaneous Optimization of Framework and CDR Residues," Journal of Molecular Biology 294(1):151-162, Elsevier, England (1999).
Xu, A., et al., "Regions of *Drosophila* Notch that Contribute to Ligand Binding and the Modulatory Influence of Fringe," The Journal of Biological Chemistry 280(34):30158-30165, American Society for Biochemistry and Molecular Biology, United States (2005).
Yan, M., et al., "Chronic DLL4 blockade induces vascular neoplasms," Nature 463(7282):E6-E7, Macmillan Publishers Limited, England (2010).
Yan, Wei., "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.
Yan, Wei, The Design and Engineering of Fc Heterodimers for the Production of Bispecific Antibodies and Other Heterodimer Fusion Proteins, Symposium Abstract, 20th Annual International Conference, Antibody Engineering, Antibody Engineering and Immunotherapeutics for the 21st Century, Dec. 6-10, 2009, San Diego, California.
Yan, Wei, "The Design and Engineering of Fc Heterodimers for the Production of Bispecific Antibodies," Symposium Abstract, Eleventh Annual Phage Display of Antibodies and Peptides, Approaches for 2nd Generation Biologics, Apr. 6-Apr. 7, 2009, Boston, Massachusetts.
Yan, X.Q., et al., "A novel Notch ligand, Dll4, induces T-cell leukemia/lymphoma when overexpressed in mice by retroviral-mediated gene transfer," Blood 98(13):3793-3799, American Society of Hematology, United States (2001).
Yelton, D.E., "Affinity maturation of the BR96 anti-carcinoma antibody by codon-based mutagenesis," The Journal of Immunology 155(4):1994-2004, The American Association of Immunologists, United States (1995).
Yen, W., et al., "Targeting Cancer Stem Cells and Vasculature by a Novel Anti-Delta-Like 4 Ligand (DLL4) Antibody for Treatment of Triple Negative Breast Cancer," Cancer Research 69(Suppl.)(24):788s-789s, Abstract 5071, American Association for Cancer Research, United Sates (2009).
Yen, W.C., at al., "Targeting Cancer Stem Cells and Vasculature by a Novel Anti-Dll4 Antibody Inhibits Pancreatic Tumor Growth and Delays Tumor Recurrence," Presented at the 100th Annual Meeting of the American Association for Cancer Research in Denver, Colorado on Apr. 18-22, (2009).
Yen. W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).
Yen, W.C., et al., "Anti-DLL4 has broad spectrum activity in pancreatic cancer dependent on targeting DLL4-Notch signaling in both tumor and vasculature cells," Clinical Cancer Research 18(19):5374-5386, American Association for Cancer Research, United States (2012).
Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).
Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).
Yen, W-C., et al., "The combination of gemcitabine/nab-paclitaxel and anti-DLL4 (derncizurnab) produces synergistic growth inhibition, delays tumor recurrence and reduces tumor initiating cells in pancreatic cancer," American Association for Cancer Research Annual Meeting 2014, Abstract 1898, 1 page (2014).
Yoneya, T., et al., "Molecular Cloning of Delta-4, A New Mouse and Human Notch Ligand," Journal of Biochemistry 129(1):27-34, Japanese Biochemical Society, Japan (2001).
Chen, C., et al., "Generation and Analysis of Random Point Mutations in an Antibody CDR2 Sequence: Many Mutated Antibodies Lose their Ability to Bind Antigen," The Journal of Experimental Medicine 176(3):855-866, Rockefeller University Press, United States (1992).
International Search Report for International Application No. PCT/US16/53316, ISA/US, Alexandria, Virginia, dated Feb. 21, 2017, 7 pages.
International Search Report for International Application No. PCT/US2015/024251, ISA/US, Alexandria, Virginia, United States, dated Jul. 16, 2015, 4 pages.
International Search Report with the Written Opinion of the International Searching Authority for International application No. PCT/US15/58327, United States Patent and Trademark Office, United States, dated May 19, 2016, 12 pages.
Janda, C.Y., "Structural Basis of Wnt Recognition by Frizzled," Science 337(6090):59-64, American Association for the Advancement of Science, United States (2012).
McAuliffe, S.M., et al., "Targeting Notch, a Key Pathway for Ovarian Cancer Stem Cells, Sensitizes Tumors to Platinum Therapy," Proceedings of the National Academy of Sciences USA 109(43):E2939-E2948, National Academy of Sciences, United States (2012) with Supporting Information.
Nimmagadda, S., et al., "Expression pattern of Dll4 during chick embryogenesis," Histochem Cell Biol 128(2)1 47-152, Springer-Verlag, Germany (2007).
Oie, E., et al., "Activation of Notch signaling in cardiomyocytes during post-infarction remodeling," Scandinavian Cardiovascular Journal 44(6):359-366, Informa Healthcare, England (2010).
Smith, D.C., et al., "A First-in-Human, Phase I Trial of the Anti-DLL4 Antibody (OMP-21M18) Targeting Cancer Stem Cells (CSC)

(56) References Cited

OTHER PUBLICATIONS in Patients with Advanced Solid Tumors," European Journal of Cancer Supplement 8(7):73, Abstract 222, 1 page (2010).

Vincke, C., and Muyldermans, S., "Introduction to Heavy Chain Antibodies and Derived Nanobodies," Methods in Molecular Biology 911:15-26, Springer Science + Business Media, Germany (2012).

Written Opinion for International Application No. PCT/US16/53316, ISA/US, Alexandria, Virginia; dated Feb. 21, 2017, 9 pages.

Written Opinion for International Application No. PCT/US2015/024251, ISA/US, Alexandria, Virginia, United States, dated Jul. 16, 2015, 7 pages.

Ostrand-Rosenberg, S. and Sinha, P., "Myeloid-Derived Suppressor Cells: Linking Inflammation and Cancer," Journal of Immunology 182(8):4499-4506, American Association of Immunologists, United States (2009).

Palma, G., et al., "Interleukin 18: Friend or foe in cancer," Biochimica et Biophysica Acta 1836(2):296-303, Elsevier B.V., Netherlands (2013).

Pardoll, D.M., "The Blockade of Immune Checkpoints in Cancer Immunotherapy," Nature Reviews Cancer 12(4):252-264, Nature Publishing Group, England (2012).

Siegel, R., et al., "Cancer Statistics, 2012," CA: A Cancer Journal for Clinicians 62(1):10-29, American Cancer Society, Inc., United States (2012).

Mochizuki, K., et al., "Delta-like Ligand 4 Identifies a Previously Uncharacterized Population of Inflammatory Dendritic Cells That Plays Important Roles in Eliciting Allogeneic T Cell Responses in Mice," in: The Journal of Immunology 190(7):3772-3782, American Association of Immunologists, Bethesda, MD (Apr. 2013).

Clackson, T., et al., "Making Antibody Fragments using Phage Display Libraries," Nature 352(6336):624-628, Nature Publishing Group, England (Aug. 1991).

Goding, J.W., "Production of Monoclonal Antibodies," in Monoclonal Antibodies: Principles and Practice, 2nd ed., pp. 59-103, Academic Press Inc., London (1986).

International Preliminary Report on Patentability for Application No. PCT/US2016/053316, International Searching Authority, dated Apr. 5, 2018, 11 pages.

Jemal, A., et al., "Cancer Statistics, 2003," CA—A Cancer Journal for Clinicians 53(1):05-26, American Cancer Society, United States (2003).

Kohler, G. and Milstein, C., "Continuous Cultures of Fused Cells Secreting Antibody of Predefined Specificity," Nature 256(5517):495-497, Macmillan Journals Ltd., England (Aug. 1975).

McCafferty, J., et al., "Phage Antibodies: Filamentous Phage Displaying Antibody Variable Domains," Nature 348(6301):552-554, Nature Publishing Group, London (Dec. 1990).

Yeh, E.T., "Cardiotoxicity Induced by Chemotherapy and Antibody Therapy," Annual Review of Medicine 57: 485-498, Annual Reviews, United States (2006).

Rizzo, P., et al., "Rational Targeting of Notch Signaling in Cancer," Oncogene 27(38):5124-5131, Nature Publishing Group, England (Sep. 2008).

International Preliminary Report on Patentability, including the Written Opinion of the International Searching Authority, for International Application No. PCT/US2016/049703, dated Mar. 6, 2018, 12 pages.

Office Action dated Apr. 13, 2017 in U.S. Appl. No. 14/928,271, inventors Murriel, Christopher L., et al., filed Oct. 30, 2015, 17 pages.

Office Action dated Nov. 6, 2017 in U.S. Appl. No. 14/928,271, inventors Murriel, Christopher L., et al., filed Oct. 30, 2015, 14 pages.

\* cited by examiner

COMBINATION THERAPY FOR TREATMENT OF DISEASE

CROSS-REFERENCE TO RELATED APPLICATIONS

This application is a continuation of U.S. application Ser. No. 14/928,271, filed Oct. 30, 2015, which claims the priority benefit of U.S. Provisional Application No. 62/073,634, filed Oct. 31, 2014, U.S. Provisional Application No. 62/127,172, filed Mar. 2, 2015, U.S. Provisional Application No. 62/192,133, filed Jul. 14, 2015, and U.S. Provisional Application No. 62/242,567, filed Oct. 16, 2015, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 2293_1340005_SeqListing_ST25.txt, Size: 64.4 kilobytes; and Date of Creation: Feb. 5, 2018) is herein incorporated by reference in its entirety.

FIELD OF THE INVENTION

The present invention provides methods comprising combination therapy for modulating immune responses and treating cancer and other diseases. In particular, the present invention provides Notch pathway inhibitors, including DLL4 antagonists and Notch receptor antagonists, in combination with at least one additional immunotherapeutic agent for the treatment of cancer.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Siegel et al., 2012, CA: *Cancer J. Clin.*, 62:10-29).

Signaling pathways connect extracellular signals to the nucleus leading to expression of genes that directly or indirectly control cell growth, differentiation, survival, and death. In a wide variety of cancers, signaling pathways are dysregulated and may be linked to tumor initiation and/or progression. Signaling pathways implicated in human oncogenesis include, but are not limited to, the Wnt pathway, the Ras-Raf-MEK-ERK or MAPK pathway, the PI3K-AKT pathway, the CDKN2A/CDK4 pathway, the Bcl-2/TP53 pathway, and the Notch pathway.

The Notch pathway is involved in multiple aspects of vascular development including proliferation, migration, smooth muscle differentiation, angiogenesis, and arterial-venous differentiation (Iso et al., 2003, *Arterioscler. Thromb. Vasc. Biol.*, 23:543). The Notch receptor ligand DLL4 (Delta-like ligand 4) is an important component of the Notch pathway and plays a role in angiogenesis. Heterozygous loss of DLL4 results in severe defects in arterial development and yolk sac vascularization, leading to embryonic lethality (Duarte et al., 2004, *Genes Dev.*, 18:2474-78; Gale et al., 2004, *PNAS*, 101:15949-54; Krebs et al., 2004, *Genes Dev.*, 18:2469-73). Furthermore, tumor cells and tumor vasculature often over-express DLL4, suggesting that DLL4 expression is an important player in tumor angiogenesis (Patel et al., 2005, *Cancer Res.*, 65:8690-97; Yan et al., 2001, *Blood*, 98:3793-99). Thus, blocking DLL4 signaling and/or Notch signaling has emerged as a promising path for the development of new anti-cancer therapies.

Blocking Notch pathway signaling, such as by an anti-DLL4 antibody, has been shown to reduce tumor growth by multiple different mechanisms (Ridgway et al., 2006, *Nature*, 444:1083-87; Noguera-Troise et al., *Nature*, 444: 1032-37; Hoey et al., 2009, *Cell Stem Cell*, 5:168-77). For example, DLL4 blocking antibodies have been reported to result in endothelial cell proliferation and the development of blood vessels, however, these blood vessels lack a functional lumen. This dysangiogenic effect has been reported to block tumor growth by promoting the development of non-functional blood vessels (Ridgway et al., 2006, *Nature*, 444:1083-87; Noguera-Troise et al., *Nature*, 444:1032-37; Scehnet et al., 2007, *Blood*, 109:4753-60). Additionally, DLL4 blocking antibodies have been shown to inhibit tumor growth by reducing the proliferation of tumor cells and reducing cancer stem cell frequency. Although the mechanism behind the reduction of cancer stem cells or CSCs is unknown, it is hypothesized that DLL4 is required for the self-renewal of CSCs and maintains these cells in an undifferentiated state (Hoey et al., 2009, *Cell Stem Cell*, 5:168-77).

Unlike therapeutic approaches that attempt to block the signaling of tumor angiogenic factors, blockade of DLL4 signaling by anti-human DLL4 antibodies can result in endothelial hypertrophy and the creation of non-functional microvessels. Consequently, even in the presence of tumor angiogenic factors, blockade of DLL4 signaling through administration of anti-human DLL4 antibodies can result in dysangiogenesis which inhibits the ability of the tumor to induce the functional blood vessel formation needed to support growth of the tumor.

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include methods to induce or enhance specific immune responses or to inhibit or reduce specific immune responses. The immune system is a highly complex system made up of a great number of cell types, including but not limited to, T-cells, B-cells, natural killer cells, antigen-presenting cells, dendritic cells, monocytes, granulocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases).

Generally, an immune response is initiated through antigen recognition by the T-cell receptor (TCR) and is regulated by a balance between stimulatory and inhibitory signals (i.e., immune checkpoints). Under normal conditions, immune checkpoints are necessary to maintain a balance between activating and inhibitory signals and to ensure the development of an effective immune response while safeguarding against the development of autoimmunity or damage to tissues when the immune system is responding to a foreign or pathogenic agent. An important immune checkpoint receptor is CTLA-4 which is expressed on T-cells and is highly expressed on regulatory T-cells (Tregs). CTLA-4 is considered to act as an inhibitory molecule or an immune response "brake" and primarily regulates the amplitude of T-cell activation. CTLA-4 counteracts the activity of the co-stimulatory receptor, CD28, which acts in concert with the TCR to activate T-cells. CTLA-4 and CD28 share identical ligands or counter-receptors, B7-1 (CD80) and B7-2 (CD86) and the balance of the immune response probably involves competition of CTLA-4 and CD28 for binding to the ligands. Another important immune checkpoint receptor is PD-1 which is expressed on T-cells after activation, is highly expressed on Tregs, and is expressed on other activated cells including B-cells and natural killer (NK) cells. Similar to CTLA-4, PD-1 is considered to act as an inhibitory molecule and a "brake" on the immune response. There are two ligands/counter-receptors for PD-1, PD-L1 (also known as B7-H1 and CD274) and PD-L2 (also known as B7-DC and CD273). (See, Pardoll, 2012, *Nature Reviews Cancer*, 12:252-264).

The concept of cancer immunosurveillance is based on the theory that the immune system can recognize tumor cells, mount an immune response, and suppress the development and/or progression of a tumor. However, it is clear that many cancerous cells have developed mechanisms to evade the immune system which can allow for uninhibited growth of tumors. Immune checkpoints can be dysregulated by tumors and may be manipulated by tumors to be used as an immune resistance mechanism. Cancer immunotherapy focuses on the development of agents that can activate and/or boost the immune system to achieve a more effective response to inhibiting tumor growth and/or killing tumor cells.

It is one of the objectives of the present invention to provide improved methods for cancer treatment, particularly methods using Notch pathway inhibitors in combination with immunotherapeutic agents.

BRIEF SUMMARY OF THE INVENTION

The present invention provides methods of treating diseases such as cancer, wherein the methods comprise administering to a subject in need thereof a Notch pathway inhibitor (e.g., a DLL4 antagonist or a Notch receptor antagonist) in combination with a second agent, wherein the second agent is an immunotherapeutic agent. Combination therapy with at least two therapeutic agents often uses agents that work by different mechanisms of action, and/or target different pathways and may result in additive or synergetic effects. Combination therapy may allow for a lower dose of each agent than used in monotherapy, thereby reducing toxic side effects and/or increasing the therapeutic index of the agent(s). Combination therapy may decrease the likelihood that resistance to an agent will develop. Combination therapy may allow one agent to sensitize tumor cells (including cancer stem cells) to enhanced activity by a second agent. Combination therapy comprising an immunotherapeutic agent may allow one agent to enhance the immune response to a tumor or tumor cells while the second agent may be effective at killing tumor cells more directly. In addition, the order and/or timing of the administration of each therapeutic agent may affect the overall efficacy of a drug combination.

The invention provides Notch pathway inhibitors, including but not limited to, Delta-like ligand 4 (DLL4) antagonists and Notch receptor antagonists. DLL4 antagonists include but are not limited to, antibodies and other polypeptides that bind DLL4, small molecules that bind DLL4, and soluble Notch proteins. "DLL4 antagonist" as used herein includes bispecific antibodies, heterodimeric bispecific molecules, homodimeric bispecific molecules, and/or bifunctional molecules comprising an anti-DLL4 antibody and an immunotherapeutic agent. Notch receptor antagonists include but are not limited to, antibodies and other polypeptides that bind Notch1, Notch2, Notch3, and/or Notch4, small molecules that bind Notch1, Notch2, Notch3, and/or Notch4, and soluble Notch ligands (DLL1, DLL3, DLL4, Jag1 and Jag2). "Notch receptor antagonist" as used herein includes bispecific antibodies, heterodimeric bispecific molecules, homodimeric bispecific molecules, and/or bifunctional molecules comprising an anti-Notch antibody and an immunotherapeutic agent.

The invention provides immunotherapeutic agents, including but not limited to, a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

Compositions comprising a Notch pathway inhibitor (e.g., a DLL4 antagonist or a Notch receptor antagonist) and/or at least one additional immunotherapeutic agent are provided. Pharmaceutical compositions comprising the Notch pathway inhibitors and/or the immunotherapeutic agents are provided.

As drug discovery and development advances, especially in the cancer field, the "one drug fits all" approach is shifting to a "personalized medicine" strategy. Personalized medicine strategies may include treatment regimens that are based upon biomarkers, including prognostic markers, pharmacodynamics markers, and predictive markers. In general, predictive biomarkers assess the likelihood that a tumor or cancer will be responsive to or sensitive to a specific therapeutic agent or a combination of agents, and may allow for the identification and/or the selection of patients most likely to benefit from the use of that agent or agents. The invention provides the use of PD-L1 as a predictive biomarker for responsiveness to treatment with a Notch pathway inhibitor in combination with an immunotherapeutic agent. Also provided are methods of using the predictive biomarker for identifying and/or selecting tumors and/or patients with cancer as likely to be responsive or non-responsive to treatment. Methods for treating patients that are predicted and/or identified to be responsive to treatment with a Notch pathway inhibitor in combination with an immunotherapeutic agent are also provided.

In one aspect, the invention provides methods of inhibiting tumor growth. In some embodiments, a method comprises contacting tumor cells with an effective amount of a Notch pathway inhibitor in combination with an effective amount of a second agent, wherein the second agent is an immunotherapeutic agent. The method may be in vivo or in vitro. In certain embodiments, the tumor is in a subject, and contacting tumor cells with the Notch pathway inhibitor and the immunotherapeutic agent comprises administering a therapeutically effective amount of each of the agents to the subject. In some embodiments, a method of inhibiting tumor growth comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting tumor growth comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent.

In another aspect, the invention provides a method of treating cancer. In some embodiments, a method of treating cancer comprises administering to a subject a therapeutically effective amount of a Notch pathway inhibitor in combination with a therapeutically effective amount of a second agent, wherein the second agent is an immunotherapeutic agent. In some embodiments, a method of treating cancer comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of treating cancer comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent.

In another aspect, the invention provides a method of. In some embodiments, a method of modulating the immune response comprises administering to a subject a therapeutically effective amount of a Notch pathway inhibitor in combination with a therapeutically effective amount of a second agent, wherein the second agent is an immunotherapeutic agent. In some embodiments, the immune response is an anti-tumor response. In some embodiments, the immune response is enhanced, increased, activated, and/or induced. In some embodiments, the modulation of the immune response comprises an increased Th1-type response. In some embodiments, the modulation of the immune response comprises a decreased Th2-type response. In some embodiments, the modulation of the immune response comprises an decreased Th17-type response.

In another aspect, the invention provides a method of inhibiting the activity of regulatory T-cells (Tregs). In some embodiments, a method of inhibiting the activity of Tregs comprises administering to a subject a therapeutically effective amount of a Notch pathway inhibitor in combination with a therapeutically effective amount of a second agent, wherein the second agent is an immunotherapeutic agent. In some embodiments, a method of inhibiting the activity of Tregs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the activity of Tregs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, the inhibition of Treg activity comprises inhibiting the suppression of immune responses. In some embodiments, the inhibition of Treg activity results in the inhibition of suppression of immune responses.

In another aspect, the invention provides a method of inhibiting the activity of myeloid-derived suppressor cells (MDSCs). In some embodiments, a method of inhibiting the activity of MDSCs comprises administering to a subject a therapeutically effective amount of a Notch pathway inhibitor in combination with a therapeutically effective amount of a second agent, wherein the second agent is an immunotherapeutic agent. In some embodiments, a method of inhibiting the activity of MDSCs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the activity of MDSCs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, the inhibition of MDSC activity comprises inhibiting the suppression of immune responses. In some embodiments, the inhibition of MDSC activity results in the inhibition of suppression of immune responses.

In another aspect, the invention provides a method of enhancing the antigen-specific memory response to a tumor. In some embodiments, a method of enhancing the antigen-specific memory response to a tumor comprises administering to a subject a therapeutically effective amount of a Notch pathway inhibitor in combination with a therapeutically effective amount of a second agent, wherein the second agent is an immunotherapeutic agent. In some embodiments, a method of enhancing the antigen-specific memory response to a tumor comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of enhancing the antigen-specific memory response to a tumor comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent.

In another aspect, the invention provides a method of activating or enhancing a persistent or long-term immune response to a tumor. In some embodiments, a method of activating or enhancing a persistent immune response to a tumor comprises administering to a subject a therapeutically effective amount of a Notch pathway inhibitor in combination with a therapeutically effective amount of a second agent, wherein the second agent is an immunotherapeutic agent. In some embodiments, a method of activating or enhancing a persistent immune response to a tumor comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of activating or enhancing a persistent immune response to a tumor comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent.

In another aspect, the invention provides a method of inducing a persistent or long-term immunity which inhibits tumor relapse or tumor regrowth. In some embodiments, a method of inducing a persistent immunity which inhibits tumor relapse or tumor regrowth comprises administering to a subject a therapeutically effective amount of a Notch pathway inhibitor in combination with a therapeutically effective amount of a second agent, wherein the second agent is an immunotherapeutic agent. In some embodiments, a method of inducing a persistent immunity which inhibits tumor relapse or tumor regrowth comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inducing a persistent immunity which inhibits tumor relapse or tumor regrowth comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent.

In another aspect, the invention provides a method to increase the efficacy of an immune checkpoint modulator. In some embodiments, a method to increase the efficacy of an immune checkpoint modulator comprises administering to a subject a therapeutically effective amount of a Notch pathway inhibitor in combination with a therapeutically effective amount of an immune checkpoint modulator. In some embodiments, a method to increase the efficacy of an immune checkpoint modulator comprises administering to a subject a therapeutically effective amount of a Notch pathway inhibitor and a therapeutically effective amount of an immune checkpoint modulator, wherein the Notch pathway inhibitor is a DLL4 antagonist. In some embodiments, a method to increase the efficacy of an immune checkpoint modulator comprises administering to a subject a therapeutically effective amount of a Notch pathway inhibitor and a therapeutically effective amount of an immune checkpoint modulator, wherein the Notch pathway inhibitor is a Notch receptor antagonist. In some embodiments, the immune checkpoint modulator is an immune checkpoint inhibitor. In some embodiments, the immune checkpoint modulator is an immune checkpoint enhancer or stimulator.

In another aspect, the invention provides a method of reducing or preventing metastasis in a subject. In some embodiments, a method of reducing or preventing metastasis in a subject comprises administering to the subject a therapeutically effective amount of a Notch pathway inhibitor and a therapeutically effective amount of a second agent, wherein the second agent is an immunotherapeutic agent. In some embodiments, a method of reducing or preventing metastasis in a subject comprises administering to the subject a therapeutically effective amount of a Notch pathway inhibitor and a therapeutically effective amount of an immunotherapeutic agent, wherein the Notch pathway inhibitor is a DLL4 antagonist. In some embodiments, a method of reducing or preventing metastasis in a subject comprises administering to the subject a therapeutically effective amount of a Notch pathway inhibitor and a therapeutically effective amount of an immunotherapeutic agent, wherein the Notch pathway inhibitor is a Notch receptor antagonist.

In another aspect, the invention provides a method of enhancing treatment for a subject who is being treated with an immune checkpoint inhibitor, the method comprising administering to the subject a therapeutically effective amount of a Notch pathway inhibitor. In some embodiments, the Notch pathway inhibitor is a DLL4 antagonist. In some embodiments, the Notch pathway inhibitor is a Notch receptor antagonist.

In another aspect, the invention provides a method of enhancing or inducing an anti-tumor immune response in a subject, the method comprising administering to the subject a therapeutically effective amount of a Notch pathway inhibitor. In some embodiments, the Notch pathway inhibitor is a DLL4 antagonist. In some embodiments, the Notch pathway inhibitor is a Notch receptor antagonist.

In another aspect, the invention provides a method of identifying a human tumor likely to be responsive to treatment with a Notch pathway inhibitor in combination with a second agent, wherein the second agent is an immunotherapeutic agent, the method comprising determining the expression level of PD-L1 in a sample obtained from the tumor. In some embodiments, a method of identifying a human tumor likely to be responsive to combination treatment with a Notch pathway inhibitor and an immunotherapeutic agent, comprises: a) obtaining a sample of the human tumor; b) measuring the expression level of PD-L1 in the sample; and c) identifying the tumor as likely to be responsive or non-responsive to combination treatment with a Notch pathway inhibitor and an immunotherapeutic agent based upon the expression level of PD-L1.

In another aspect, the invention provides a method of determining the responsiveness (or sensitivity) of a human tumor to treatment with a Notch pathway inhibitor in combination with a second agent, wherein the second agent is an immunotherapeutic agent, the method comprising: (a) obtaining a sample of the human tumor; (b) measuring the expression level of PD-L1 in the sample; and (c) determining the responsiveness of the tumor to treatment based upon the expression level of PD-L1. In some embodiments, the method comprises determining the responsiveness or sensitivity of a human tumor to treatment with a DLL4 antagonist in combination with at least one additional therapeutic agent. In some embodiments, the method comprises determining the responsiveness or sensitivity of a human tumor to treatment with a Notch receptor antagonist in combination with at least one additional therapeutic agent.

In another aspect, the invention provides a method of identifying a patient with cancer who is likely to respond to treatment with a Notch pathway inhibitor in combination with a second agent, wherein the second agent is an immunotherapeutic agent, the method comprising: (a) obtaining a sample from the patient; (b) measuring the expression level of PD-L1 in the sample; and (c) identifying the patient who is likely to respond to treatment based upon the expression level of PD-L1. In some embodiments, the sample is a tumor sample. In some embodiments, the sample is a blood or plasma sample. In some embodiments, the method comprises identifying a patient with cancer who is likely to respond to treatment with a Notch pathway inhibitor and an immunotherapeutic agent in combination with at least one additional therapeutic agent.

In another aspect, the invention provides a method of selecting a subject with a tumor for treatment with a Notch pathway inhibitor in combination with a second agent, wherein the second agent is an immunotherapeutic agent, the method comprising: a) determining the expression level of PD-L1 in a sample obtained from the subject; b) identifying the tumor as likely to be responsive or non-responsive to treatment with the Notch pathway inhibitor and the immunotherapeutic agent based upon the expression level of PD-L1; and c) selecting the subject for treatment if the tumor is identified as likely to be responsive to treatment. In some embodiments, the sample is a tumor sample. In some embodiments, the sample is a blood or plasma sample.

In another aspect, the invention provides a method of treating cancer in a patient, comprising: (a) identifying if the patient is likely to respond to treatment with a Notch pathway inhibitor in combination with a second agent, wherein the second agent is an immunotherapeutic agent, wherein the identification comprises: (i) obtaining a sample from the patient; (ii) measuring the expression level of PD-L1 in the sample; and (iii) identifying the patient who is likely to respond to treatment based upon the expression level of PD-L1; and (b) administering to the patient who is likely to response to treatment an effective amount of the Notch pathway inhibitor in combination with the immunotherapeutic agent. In some embodiments, the sample is a tumor sample. In some embodiments, the sample is a blood or plasma sample. In some embodiments, the method comprises identifying if the patient is likely to respond to treatment with a Notch pathway inhibitor in combination with a chemotherapeutic agent. In some embodiments, the method comprises administering to the patient the Notch pathway inhibitor and immunotherapeutic agent in combination with at least one additional therapeutic agent (e.g., a chemotherapeutic agent).

In another aspect, the invention provides a method of treating cancer in a patient, comprising: administering to the patient an effective amount of a Notch pathway inhibitor in combination with a second agent, wherein the second agent is an immunotherapeutic agent; wherein the patient is predicted to respond to treatment with a Notch pathway inhibitor and/or immunotherapeutic agent based upon the expression level of PD-L1 in a sample from the patient. In some embodiments, the sample is a tumor sample. In some embodiments, the sample is a blood or plasma sample. In some embodiments, the patient is predicted to respond to treatment with a Notch pathway inhibitor and immunotherapeutic agent in combination with a chemotherapeutic agent. In some embodiments, the method comprises administering to the patient the Notch pathway inhibitor and immunotherapeutic agent in combination with at least one additional therapeutic agent (e.g., a chemotherapeutic agent).

In another aspect, the invention provides a method for increasing the likelihood of effective treatment with a Notch pathway inhibitor in combination with a second agent, wherein the second agent is an immunotherapeutic agent, comprising: (a) identifying if a patient has a tumor that is likely to respond to treatment with a Notch pathway inhibitor and/or immunotherapeutic agent, wherein the identification comprises: (i) obtaining a sample from the patient; (ii) measuring the expression level of PD-L1 in the sample; and (iii) identifying the patient who is likely to respond to treatment based upon the expression level of the PD-L1; and (b) administering an effective amount of the Notch pathway inhibitor in combination with the immunotherapeutic agent to the patient. In some embodiments, the sample is a tumor sample. In some embodiments, the sample is a blood or plasma sample. In some embodiments, the method comprises identifying if a patient has a tumor that is likely to respond to treatment with a Notch pathway inhibitor in combination with a chemotherapeutic agent. In some embodiments, the method comprises administering to the patient the Notch pathway inhibitor and the immunotherapeutic agent in combination with at least one additional therapeutic agent (e.g., a chemotherapeutic agent).

In another aspect, the invention provides a method for increasing the likelihood of effective treatment with a Notch pathway inhibitor in combination with a second agent, wherein the second agent is an immunotherapeutic agent, comprising: administering an effective amount of a Notch pathway inhibitor and/or immunotherapeutic agent to a patient; wherein the patient is identified as likely to respond to treatment with the Notch pathway inhibitor and/or the immunotherapeutic agent based upon the expression level of PD-L1 in a sample. In some embodiments, the sample is a tumor sample. In some embodiments, the sample is a blood or plasma sample. In some embodiments, the patient is identified as likely to respond to treatment with a Notch pathway inhibitor in combination with a chemotherapeutic agent. In some embodiments, the method comprises administering to the patient the Notch pathway inhibitor and the immunotherapeutic agent in combination with at least one additional therapeutic agent (e.g., a chemotherapeutic agent).

In certain embodiments of each of the aforementioned aspects, as well as other aspects and embodiments described elsewhere herein, the Notch pathway inhibitor is a DLL4 antagonist. In some embodiments, the DLL4 antagonist is an antibody that specifically binds human DLL4. In some embodiments, the antibody specifically binds the extracellular domain of human DLL4. In some embodiments, the antibody specifically binds an epitope within amino acids 27-217 of the extracellular domain of human DLL4 (SEQ ID NO:17). In some embodiments, the DLL4 antagonist binds an epitope comprising amino acids 66-73 (QAVVSPGP, SEQ ID NO:18) of human DLL4. In some embodiments, the DLL4 antagonist binds an epitope comprising amino acids 139-146 (LISKIAIQ, SEQ ID NO:19) of human DLL4. In some embodiments, the DLL4 antagonist binds an epitope comprising amino acids 66-73 (QAVVSPGP, SEQ ID NO:18) and amino acids 139-146 (LISKIAIQ, SEQ ID NO:19) of human DLL4. In some embodiments, the DLL4 antagonist binds human DLL4 with a dissociation constant ($K_D$) of about 10 nM to about 0.1 nM.

In some embodiments, the DLL4 antagonist is an antibody which comprises a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5); and/or a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the DLL4 antagonist is an antibody which comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

In certain embodiments of each of the aforementioned aspects, as well as other aspects and embodiments described elsewhere herein, the DLL4 antagonist is an antibody comprising a heavy chain variable region having at least about 90%, at least about 95% or 100% sequence identity to SEQ ID NO:9, SEQ ID NO:10 or SEQ ID NO:11, and/or a light chain variable region having at least about 90%, at least about 95% or 100% sequence identity to SEQ ID NO:12. In some embodiments, the DLL4 antagonist is an antibody which comprises a heavy chain variable region comprising SEQ ID NO:10 and a light chain variable region comprising SEQ ID NO:12.

In some embodiments, the DLL4 antagonist is the antibody encoded by the plasmid having ATCC deposit no. PTA-8425 which was deposited with the American Type Culture Collection (ATCC), at 10801 University Boulevard, Manassas, Va., 20110, under the conditions of the Budapest Treaty on May 10, 2007. In some embodiments, the DLL4 antagonist is the antibody encoded by the plasmid DNA having ATCC deposit no. PTA-8427 which was deposited with the ATCC under the conditions of the Budapest Treaty on May 10, 2007. In some embodiments, the DLL4 antagonist is an antibody comprising the CDRs of the antibody produced by the hybridoma having ATCC deposit no. PTA-8670 which was deposited with the ATCC under the conditions of the Budapest Treaty on Sep. 28, 2007. In some embodiments, the anti-DLL4 antibody is demcizumab (OMP-h21M18).

In some embodiments, the DLL4 antagonist is a bispecific antibody which comprises a first antigen-binding site that specifically binds human VEGF, and a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYY-PLMDY (SEQ ID NO:22); wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the DLL4 antagonist is a bispecific antibody which comprises a first heavy chain variable region of SEQ ID NO:30; a second heavy chain variable region of SEQ ID NO:29; and a first and a second light chain variable region of SEQ ID NO:12. In some embodiments, the DLL4 antagonist is a bispecific antibody which comprises a first heavy chain of SEQ ID NO:32; a second heavy chain of SEQ ID NO:31; and a first and a second light chain of SEQ ID NO:33. In some embodiments, the DLL4 antagonist is OMP-305B83.

In certain embodiments of each of the aforementioned aspects, as well as other aspects and embodiments described elsewhere herein, the Notch pathway inhibitor is a Notch receptor antagonist. In some embodiments, the Notch receptor antagonist is an antibody that specifically binds human Notch2 and/or Notch3. In some embodiments, the antibody specifically binds the extracellular domain of human Notch2 and/or Notch3.

In some embodiments, the Notch receptor antagonist is an antibody that specifically binds the extracellular domain of human Notch2 and/or Notch3 and comprises a heavy chain CDR1 comprising SSSGMS (SEQ ID NO:34), a heavy chain CDR2 comprising VIASSGSNTYYADSVKG (SEQ ID NO:35), and a heavy chain CDR3 comprising SIFYTT (SEQ ID NO:36), and/or a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39). In some embodiments, the Notch2/3 antagonist is an antibody which comprises a heavy chain CDR1 comprising SSSGMS (SEQ ID NO:34), a heavy chain CDR2 comprising VIASSGSN-TYYADSVKG (SEQ ID NO:35), and a heavy chain CDR3 comprising SIFYTT (SEQ ID NO:36), and a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39).

In certain embodiments of each of the aforementioned aspects, as well as other aspects and embodiments described elsewhere herein, the Notch receptor antagonist is an antibody comprising a heavy chain variable region having at least about 90%, at least about 95% or 100% sequence identity to SEQ ID NO:40, and/or a light chain variable region having at least about 90%, at least about 95% or 100% sequence identity to SEQ ID NO:41. In some embodiments, the Notch receptor antagonist is an antibody which comprises a heavy chain variable region comprising SEQ ID NO:40 and a light chain variable region comprising SEQ ID NO:41.

In some embodiments, the Notch receptor antagonist is the antibody encoded by the plasmid DNA having ATCC deposit no. PTA-10170 which was deposited with the American Type Culture Collection (ATCC), at 10801 University Boulevard, Manassas, Va., 20110, under the conditions of the Budapest Treaty on Jul. 6, 2009. In some embodiments, the Notch receptor antagonist is the anti-Notch2/3 antibody tarextumab (OMP-59R5).

In some embodiments, the Notch receptor antagonist is an antibody that specifically binds human Notch1. In some embodiments, the antibody specifically binds a non-ligand binding membrane proximal region of the extracellular domain of Notch1. In some embodiments, the antibody that specifically binds Notch1 comprises a heavy chain CDR1 comprising RGYWIE (SEQ ID NO:46), a heavy chain CDR2 comprising QILPGTGRTNYNEKFKG (SEQ ID NO:47), and a heavy chain CDR3 comprising FDGNYGYYAMDY (SEQ ID NO:48), and/or a light chain CDR1 comprising RSSTGAVTTSNYAN (SEQ ID NO:49), a light chain CDR2 comprising GTNNRAP (SEQ ID NO:50), and a light chain CDR3 comprising ALWYSNHWVFGGGTKL (SEQ ID NO:51). In some embodiments, the Notch receptor antagonist is an antibody which comprises a heavy chain CDR1 comprising RGYWIE (SEQ ID NO:46), a heavy chain CDR2 comprising QIL-PGTGRTNYNEKFKG (SEQ ID NO:47), and a heavy chain CDR3 comprising FDGNYGYYAMDY (SEQ ID NO:48), and a light chain CDR1 comprising RSSTGAVTTSNYAN (SEQ ID NO:49), a light chain CDR2 comprising GTNN-RAP (SEQ ID NO:50), and a light chain CDR3 comprising ALWYSNHWVFGGGTKL (SEQ ID NO:51).

In certain embodiments of each of the aforementioned aspects, as well as other aspects and embodiments described elsewhere herein, the Notch receptor antagonist is an antibody comprising a heavy chain variable region having at least about 90%, at least about 95% or 100% sequence identity to SEQ ID NO:52, and/or a light chain variable region having at least about 90%, at least about 95% or 100% sequence identity to SEQ ID NO:53. In some embodiments, the Notch receptor antagonist is an antibody which comprises a heavy chain variable region comprising SEQ ID NO:52 and a light chain variable region comprising SEQ ID NO:53.

In some embodiments, the Notch receptor antagonist is the antibody encoded by the plasmid DNA having ATCC deposit no. PTA-9549 which was deposited with the American Type Culture Collection (ATCC), at 10801 University Boulevard, Manassas, Va., 20110, under the conditions of the Budapest Treaty on Oct. 15, 2008. In some embodiments, the Notch receptor antagonist is the anti-Notch1 antibody brontictuzumab (OMP-h52M51).

In certain embodiments of each of the aforementioned aspects, as well as other aspects and embodiments described elsewhere herein, the Notch pathway inhibitor is an antibody. In some embodiments, the Notch pathway inhibitor is an antibody that specifically binds human DLL4. In some embodiments, the Notch pathway inhibitor is an antibody that specifically binds human Notch2 and/or Notch3. In some embodiments, the Notch pathway inhibitor is an antibody that specifically binds human Notch1. In some embodiments, the antibody is a recombinant antibody. In some embodiments, the antibody is a monoclonal antibody, a chimeric antibody, a humanized antibody, or a human antibody. In some embodiments, the antibody is an antibody fragment comprising an antigen-binding site. In certain embodiments, the antibody or antibody fragment is monovalent, monospecific, bivalent, bispecific, or multispecific. In some embodiments, the antibody is an IgG1 antibody. In some embodiments, the antibody is an IgG2 antibody. In some embodiments, the antibody is an IgG4 antibody. In some embodiments, the antibody or antibody fragment is part of a bispecific agent. In some embodiments, the antibody or antibody fragment is part of a heterodimeric bispecific molecule. In some embodiments, the antibody or antibody fragment is part of a homodimeric bispecific molecule. In certain embodiments, the antibody or antibody fragment is isolated. In other embodiments, the antibody or antibody fragment is substantially pure.

In certain embodiments of each of the aforementioned aspects, as well as other aspects and embodiments described elsewhere herein, the immunotherapeutic agent is an agent that modulates immune responses. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity. In some embodiments, the immunotherapeutic agent is an agent that increases NK cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent that inhibits Treg activity. In some embodiments, the immunotherapeutic agent is an agent that inhibits MDSC activity. In some embodiments, the immunotherapeutic agent is an agent that inhibits the activity of inhibitory immune checkpoint receptors. In some embodiments, the immunotherapeutic agent is an agent that inhibits the activity of PD-1. In some embodiments, the immunotherapeutic agent is an agent that inhibits the activity of PD-L1 and/or PD-L2. In some embodiments, the immunotherapeutic agent is an agent that inhibits the activity of CTLA-4. In some embodiments, the immunotherapeutic agent is an agent that inhibits the activity of CD80 and/or CD86. In some embodiments, the immunotherapeutic agent is an agent that inhibits the activity of TIGIT. In some embodiments, the immunotherapeutic agent is an agent that inhibits the activity of KIR. In some embodiments, the immunotherapeutic agent is an agent that inhibits the activity of IDOL In some embodiments, the immunotherapeutic agent is an agent that enhances or stimulates the activity of activating immune checkpoint receptors. In some embodiments, the immunotherapeutic agent is an agent that enhances or stimulates the activity of GITR. In some embodiments, the immunotherapeutic agent is an agent that enhances or stimulates the activity of OX40. In some embodiments, the immunotherapeutic agent is an agent that enhances or stimulates the activity of CD40.

In some of the embodiments of the methods described herein, the immunotherapeutic agent is a PD-1 antagonist, a PD-L1 antagonist, a PD-L2 antagonist, a CTLA-4 antagonist, a CD80 antagonist, a CD86 antagonist, a TIGIT antagonist, a KIR antagonist, a Tim-3 antagonist, a LAG3 antagonist, a CD96 antagonist, a CD20 antagonist, or an IDO1 antagonist. In some embodiments, the PD-1 antagonist is an antibody that specifically binds PD-1. In some embodiments, the antibody that binds PD-1 is pembrolizumab (KEYTRUDA; MK-3475), pidilizumab (CT-011), or nivolumab (OPDIVO; BMS-936558). In some embodiments, the PD-L1 antagonist is an antibody that specifically binds PD-L1. In some embodiments, the antibody that binds PD-L1 is RG7446 (MPDL3280A), durvalumab (MEDI4736), or BMS-936559. In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the KIR antagonist is an antibody that specifically binds KIR. In some embodiments, the antibody that binds KIR is lirilumab.

In some of the embodiments of the methods described herein, the immunotherapeutic agent is a CD28 agonist, a 4-1BB agonist, an OX40 agonist, a CD27 agonist, a CD80 agonist, a CD86 agonist, a CD40 agonist, or a GITR agonist.

In some of the embodiments of the methods described herein, the immunotherapeutic agent is a cytokine. In some embodiments, the cytokine is a chemokine, an interferon, an interleukin, lymphokine, or a member of the tumor necrosis factor family. In some embodiments, the cytokine is IL-2, IL-15, or interferon-gamma.

In certain embodiments of each of the aforementioned aspects, as well as other aspects and embodiments described elsewhere herein, a method comprises administering at least one additional therapeutic agent. In some embodiments, the at least one additional therapeutic agent is a chemotherapeutic agent.

In certain embodiments of each of the aforementioned aspects, as well as other aspects and embodiments described elsewhere herein, a method comprises administering an antibody that specifically binds human DLL4 in combination with an antibody that specifically binds human PD-1. In some embodiments, a method comprises administering demcizumab in combination with pembrolizumab. In some embodiments, a method comprises administering demcizumab in combination with pembrolizumab and at least one chemotherapeutic agent. In some embodiments, a method comprises administering demcizumab in combination with pembrolizumab, carboplatin, and pemetrexed. In some embodiments, a method comprises administering a bispecific antibody that specifically binds human DLL4 and human VEGF in combination with an antibody that specifically binds human PD-1. In some embodiments, a method comprises administering OMP-305B83 in combination with pembrolizumab. In some embodiments, a method comprises administering OMP-305B83 in combination with pembrolizumab and at least one chemotherapeutic agent. In some embodiments, a method comprises administering OMP-305B83 in combination with pembrolizumab, carboplatin, and pemetrexed.

In certain embodiments of each of the aforementioned aspects, as well as other aspects and embodiments described elsewhere herein, the cancer is a cancer selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, glioblastoma multiforme, cervical cancer, stomach cancer, bladder cancer, head and neck cancer, and hepatoma. In some embodiments, the cancer is lung cancer. In some embodiments, a cancer or cancer cell expresses PD-L1. In some embodiments, a cancer or cancer cell over-expresses PD-L1. In some embodiments, a cancer or cancer cell expresses PD-L2. In some embodiments, a cancer or cancer cell over-expresses PD-L2. In some embodiments, a cancer or cancer cell has an increased level of PD-L1 expression as compared to a pre-determined level of PD-L1 expression.

In certain embodiments of each of the aforementioned aspects, as well as other aspects and embodiments described elsewhere herein, the tumor is a tumor selected from the group consisting of lung tumor, pancreatic tumor, breast tumor, colon tumor, colorectal tumor, melanoma, gastrointestinal tumor, gastric tumor, renal tumor, ovarian tumor, liver tumor, endometrial tumor, kidney tumor, prostate tumor, thyroid tumor, neuroblastoma, glioma, glioblastoma, glioblastoma multiforme, cervical tumor, stomach tumor, bladder tumor, head and neck tumor, and hepatoma. In some embodiments, the tumor is a lung tumor. In some embodiments, a tumor expresses PD-L1. In some embodiments, a tumor over-expresses PD-L1. In some embodiments, a tumor expresses PD-L2. In some embodiments, a tumor over-expresses PD-L2. In some embodiments, a tumor has an increased level of PD-L1 expression as compared to a pre-determined level of PD-L1 expression.

In certain embodiments of each of the aforementioned aspects, as well as other aspects and embodiments described elsewhere herein, the methods further comprise administering at least one additional therapeutic agent. In some embodiments, the additional therapeutic agent is a chemotherapeutic agent. In some embodiments, the additional therapeutic agent is an antibody.

In some of the aforementioned aspects and embodiments, a method comprises obtaining a sample from the subject or patient. In some embodiments, the sample is a biopsy sample. In some embodiments, the sample is from a tumor. In some embodiments, the sample comprises tumor cells, tumor infiltrating immune cells, stromal cells, and any combinations thereof. In some embodiments, the sample is a formalin-fixed paraffin embedded (FFPE) sample. In some embodiments, the sample is archival, fresh, or frozen tissue. In some embodiments, the sample is blood or plasma. In some embodiments, the expression level of PD-L1 in the sample is compared to a pre-determined expression level of PD-L1. In some embodiments, the pre-determined expression level of PD-L1 expression is an expression level of PD-L1 in a reference sample, a reference tumor sample, a reference normal tissue sample, a series of reference tumor samples, or a series of reference normal tissue samples. In some embodiments, the expression level of PD-L1 is determined using an immunohistochemistry (IHC) assay. In some embodiments, the expression level of PD-L1 is determined using an assay which comprises an H-score evaluation. In some embodiments, the expression level of PD-L1 is determined using an ELISA. In some embodiments, the expression level of PD-L1 is determined using an antibody that specifically binds PD-L1. In some embodiments, PD-L1 is detected on tumor cells. In some embodiments, PD-L1 is detected on tumor infiltrating immune cells. In some embodiments, the expression level of PD-L1 is determined using a PCR-based assay. In some embodiments, PD-L1 is detected in a cell lysate.

Also provided are pharmaceutical compositions which comprise a Notch pathway inhibitor (e.g., a DLL4 antagonist or a Notch receptor antagonist) described herein and a pharmaceutically acceptable vehicle used in combination with pharmaceutical compositions which comprise an immunotherapeutic agent described herein and a pharmaceutically acceptable vehicle.

Where aspects or embodiments of the invention are described in terms of a Markush group or other grouping alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE DRAWINGS

FIG. 1A. PD-1 level in tumor cell lysates from mice treated with anti-mDLL4 antibody 21R30, SIRPα-Fc protein, or control. FIG. 1B. A representative Western blot analysis from four individual tumors of each treatment group.

FIG. 2A and FIG. 2B. CT26.WT tumor cells were injected subcutaneously into Balb/C mice. Mice were treated with anti-mDLL4 antibody 21R30 (-■-), mIL-2-Fc (-▲-), a combination of anti-mDLL4 antibody 21R30 and mIL-2-Fc (—X—), or a control (-♦-). Data is shown as tumor volume (mm$^3$) over days post-treatment. FIG. 2C. KP_LUN01 tumor cells were injected subcutaneously into Balb/C mice. Mice were treated with anti-mDLL4 antibody 21R30 (-■-), mIL-2-Fc (-▲-), a combination of anti-mDLL4 antibody 21R30 and mIL-2-Fc (—X—), or a control (-♦-). Data is shown as tumor volume (mm$^3$) over days post-treatment.

FIG. 3A and FIG. 3B. Cells were harvested from the spleens of CT26.WT-tumor bearing mice treated with anti-mDLL4 antibody 21R30, mIL-2-Fc, a combination of anti-mDLL4 antibody 21R30 and mIL-2-Fc, or a control. Target cells (YAC-1 cells or CT26.WT cells) were labeled with 10 μM calcein AM and mixed with the splenocytes at an effector:target ratio of 25:1. Supernatants were harvested and calcein release was quantified on a fluorometer at an excitation of 485 nm and an emission of 535 nm. FIG. 3C. Cells were harvested from the spleens of KP_LUN01-tumor bearing mice treated with anti-mDLL4 antibody 21R30, mIL-2-Fc, a combination of anti-mDLL4 antibody 21R30 and mIL-2-Fc, or a control. Target cells (YAC-1 cells) were labeled with 10 μM calcein AM and mixed with the splenocytes at an effector:target ratio of 25:1. Supernatants were harvested and calcein release was quantified on a fluorometer at an excitation of 485 nm and an emission of 535 nm.

FIG. 4A. Cells were harvested from the spleens of CT26.WT-tumor bearing mice treated with anti-mDLL4 antibody 21R30, mIL-2-Fc, a combination of anti-mDLL4 antibody 21R30 and mIL-2-Fc, or a control. The splenocytes were stimulated with the AH-1 peptide. Target cells (CT26.WT cells) were labeled with 10 μM calcein AM and mixed with the stimulated splenocytes. Supernatants were harvested and calcein release was quantified on a fluorometer at an excitation of 485 nm and an emission of 535 nm. FIG. 4B. Cells were harvested from the spleens of KP_LUN01-tumor bearing mice treated with anti-mDLL4 antibody 21R30, mIL-2-Fc, a combination of anti-mDLL4 antibody 21R30 and mIL-2-Fc, or a control. The splenocytes were stimulated with mitomycin treated KP_LUN01 cells. Target cells (KP_LUN01 cells) were labeled with 10 µM calcein AM and mixed with the stimulated splenocytes. Supernatants were harvested and calcein release was quantified on a fluorometer at an excitation of 485 nm and an emission of 535 nm.

FIG. 7A. CT26.WT tumor cells were injected subcutaneously into Balb/C mice. Mice were treated with anti-mDLL4 antibody 21R30 (-▲-), an anti-PD-L1 antibody (—X—), an anti-CTLA-4 antibody (-■-), a combination of anti-mDLL4 antibody 21R30 and an anti-CTLA-4 antibody (—X—), a combination of anti-mDLL4 antibody 21R30 and an anti-PD-L1 antibody (-●-), or a control (-♦-). Data is shown as tumor volume (mm$^3$) over days post-treatment. FIGS. 7B and 7C. Results from individual mice from each treatment group.

FIG. 8A. CT26.WT tumor cells were injected subcutaneously into Balb/C mice. Mice were treated with anti-mDLL4 antibody 21R30 (-■-), an anti-PD-1 antibody (-▲-), a combination of anti-mDLL4 antibody 21R30 and an anti-PD-1 antibody (-●-), or a control (-♦-). Data is shown as tumor volume (mm$^3$) over days post-cell injection. FIG. 8B. Results from individual mice from each treatment group.

FIG. 10A. The number of cells producing IFN-gamma is shown. FIG. 10B. The number of cells producing IL-2 is shown. FIG. 10C. The number of cells producing IL-17 is shown. FIG. 10D. The amount of IL-6 produced is shown.

FIG. 15A. CT26.WT tumor cells were injected subcutaneously into Balb/C mice. Mice were treated with an anti-PD-1 antibody (-▲-), a combination of anti-mDLL4 antibody 21R30 and an anti-mVEGF antibody (-■-), a combination of anti-mDLL4 antibody 21R30, an anti-mVEGF antibody, and an anti-PD-1 antibody (—X—), or a control (-♦-). Data is shown as tumor volume (mm$^3$) over days post-cell injection. FIG. 15B. Renca tumor cells were injected subcutaneously into Balb/C mice. Mice were treated with an anti-PD-1 antibody (-■-), a combination of anti-mDLL4 antibody 21R50 and anti-mVEGF antibody B20 (—X—), a combination of anti-mDLL4 antibody 21R50, anti-mVEGF antibody B20, and an anti-PD-1 antibody (-●-), or a control (-♦-). Data is shown as tumor volume (mm$^3$) over days post-cell injection.

DETAILED DESCRIPTION OF THE INVENTION

Figure 1A:
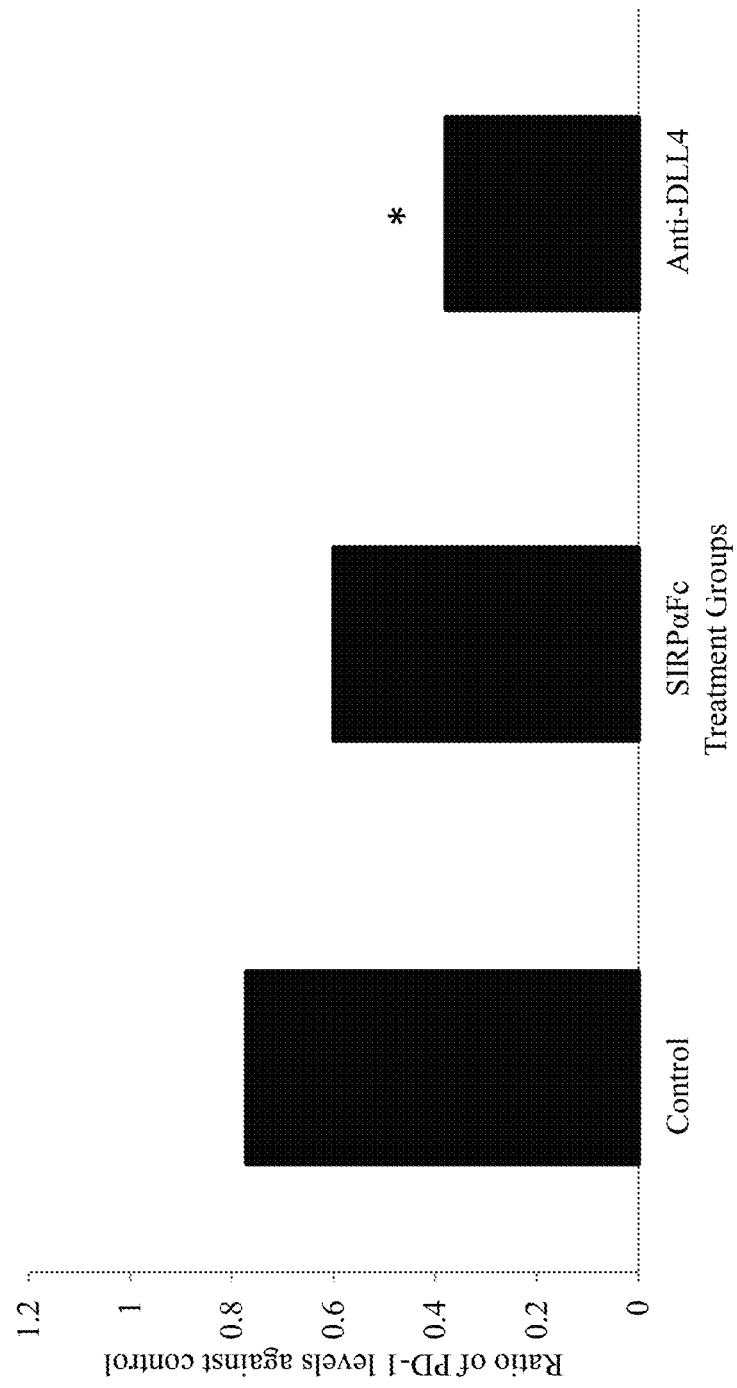
FIGS. 1A and 1B. Effect of anti-DLL4 antibody on PD-1 expression in cells from CT26.WT tumors.

The present invention provides methods of modulating immune responses, particularly anti-tumor immune responses, methods of inhibiting tumor growth, and methods of treating cancer. The methods provided herein comprise administering to a subject a therapeutically effective amount of a Notch pathway inhibitor in combination with a therapeutically effective amount of a second agent, wherein the second agent is an immunotherapeutic agent. In some embodiments, the Notch pathway inhibitor is a DLL4 antagonist. In some embodiments, the Notch pathway inhibitor is an antibody that specifically binds human DLL4. In some embodiments, the Notch pathway inhibitor is a Notch receptor antagonist. In some embodiments, the Notch pathway inhibitor is an antibody that specifically binds human Notch2 and/or Notch3. In some embodiments, the Notch pathway inhibitor is an antibody that specifically binds human Notch1. In some embodiments, the immunotherapeutic agent includes but is not limited to, a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide. The invention also provides methods of identifying a tumor likely to be responsive to treatment with a Notch pathway inhibitor in combination with an immunotherapeutic agent, the method comprising determining the expression level of PD-L1 in a sample obtained from the tumor. The invention provides methods of selecting a subject or patient for treatment with a Notch pathway inhibitor in combination with an immunotherapeutic agent, the method comprising determining the expression level of PD-L1 in a sample obtained from the subject.

I. Definitions

To facilitate an understanding of the present invention, a number of terms and phrases are defined below.

The terms "antagonist" and "antagonistic" as used herein refer to any molecule that partially or fully blocks, inhibits, reduces, or neutralizes a biological activity of a target and/or signaling pathway. The term "antagonist" is used herein to include any molecule that partially or fully blocks, inhibits, reduces, or neutralizes the activity of a protein. Suitable antagonist molecules include, but are not limited to, antagonist antibodies, antibody fragments, soluble receptors, and small molecules.

The terms "agonist" and "agonistic" as used herein refer to or describe an agent that is capable of, directly or indirectly, substantially inducing, activating, promoting, increasing, or enhancing the biological activity of a target and/or a signaling pathway. The term "agonist" is used herein to include any agent that partially or fully induces, activates, promotes, increases, or enhances the activity of a protein. Suitable agonists specifically include, but are not limited to, agonist antibodies or fragments thereof, soluble receptors, other fusion proteins, and small molecules.

The term "biomarker" as used herein may include but is not limited to, nucleic acids and proteins, and variants and fragments thereof. A biomarker may include DNA comprising the entire or partial nucleic acid sequence encoding the biomarker, or the complement of such a sequence. Biomarker nucleic acids useful in the invention are considered to include both DNA and RNA comprising the entire or partial sequence of any of the nucleic acid sequences of interest. Biomarker proteins are considered to comprise the entire or partial amino acid sequence of any of the biomarker proteins or polypeptides.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen-binding site within the variable region of the immunoglobulin molecule. As used herein, the term encompasses intact polyclonal antibodies, intact monoclonal antibodies, antibody fragments comprising an antigen-binding site (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-characterized subunit structures and three-dimensional configurations. Antibodies can be naked or conjugated to other molecules, including but not limited to, toxins and radioisotopes.

The term "antibody fragment" as used herein refers to a portion of an intact antibody and generally includes the antigenic determining variable region or antigen-binding site of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises at least one antigen-binding site or epitope-binding site.

The term "variable region" of an antibody as used herein refers to the variable region of the antibody light chain, or the variable region of the antibody heavy chain, either alone or in combination. The variable region of the heavy or light chain generally consists of four framework regions connected by three complementarity determining regions (CDRs), also known as "hypervariable regions". The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, *Sequences of Proteins of Immunological Interest*, 5th Edition, National Institutes of Health, Bethesda Md.), and (2) an approach based on crystallographic studies of antigen-antibody complexes (Al-Lazikani et al., 1997, *J. Mol. Biol.*, 273:927-948). Combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length antibodies as well as antibody fragments (e.g., Fab, Fab', F(ab')2, Fv), single chain (scFv) antibodies, fusion proteins comprising an antibody portion, and any other modified immunoglobulin molecule comprising at least one antigen-binding site. Furthermore, "monoclonal antibody" refers to such antibodies made by any number of techniques, including but not limited to, hybridoma production, phage selection, recombinant expression, and transgenic animals.

The term "humanized antibody" as used herein refers to antibodies that are specific immunoglobulin chains, chimeric immunoglobulins, or fragments thereof that contain minimal non-human sequences. Typically, humanized antibodies are human immunoglobulins in which amino acid residues of the CDRs are replaced by amino acid residues from the CDRs of a non-human species (e.g., mouse, rat, rabbit, or hamster) that have the desired specificity, affinity, and/or binding capability.

The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human).

The term "affinity-matured antibody" as used herein refers to an antibody with one or more alterations in one or more CDRs that result in an improvement in the affinity of the antibody for antigen, compared to a parent antibody that does not possess those alterations(s). In some instances, alterations are made in the framework regions. Preferred affinity-matured antibodies will have nanomolar or even picomolar affinities for the target antigen. Affinity-matured antibodies are produced by procedures known in the art including heavy chain and light chain variable region shuffling, random mutagenesis of CDR and/or framework residues, or site-directed mutagenesis of CDR and/or framework residues.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and non-contiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, or 8-10 amino acids in a unique spatial conformation.

The terms "selectively binds" or "specifically binds" as used herein mean that a binding agent or an antibody reacts or associates more frequently, more rapidly, with greater duration, with greater affinity, or with some combination of the above to the epitope, protein, or target molecule than with alternative substances, including unrelated or related proteins. In certain embodiments "specifically binds" means, for instance, that an antibody binds a target with a $K_D$ of about 0.1 mM or less, but more usually less than about 1 μM. In certain embodiments, "specifically binds" means that an antibody binds a target with a $K_D$ of at least about 0.1 μM or less, at least about 0.01 μM or less, or at least about 1 nM or less. Because of the sequence identity between homologous proteins in different species, specific binding can include an antibody that recognizes a protein in more than one species. Likewise, because of homology within certain regions of polypeptide sequences of different proteins, specific binding can include an antibody (or other polypeptide or binding agent) that recognizes more than one protein. It is understood that, in certain embodiments, an antibody or binding agent that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. Generally, but not necessarily, reference to binding means specific binding.

The term "soluble receptor" as used herein refers to an extracellular fragment (or a portion thereof) of a receptor protein preceding the first transmembrane domain of the receptor that can be secreted from a cell in soluble form.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The term "amino acid" as used herein refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. The phrase "amino acid analog" refers to compounds that have the same basic chemical structure as a naturally occurring amino acid, e.g., an alpha carbon that is bound to an hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. The phrase "amino acid mimetic" refers to chemical compounds that have a structure that is different from the general chemical structure of an amino acid, but that function similarly to a naturally occurring amino acid.

The terms "polynucleotide" and "nucleic acid" and "nucleotide sequence" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST and BLAST variations, ALIGN and ALIGN variations, Megalign, BestFit, GCG Wisconsin Package, etc. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60, at least about 60-80 nucleotides or amino acid residues in length or any integral value therebetween. In some embodiments, identity exists over a longer region than 60-80 nucleotides or amino acid residues, such as at least about 80-100 nucleotides or amino acid residues, and in some embodiments the sequences are substantially identical over the full length of the sequences being compared, such as the coding region of a nucleotide sequence.

The term "conservative amino acid substitution" as used herein refers to a substitution in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence to the antigen(s). Methods of identifying amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

As used herein, a polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells is characterized by unregulated cell growth. Examples of cancer include, but are not limited to, carcinoma, blastoma, sarcoma, and hematologic cancers such as lymphoma and leukemia.

The terms "proliferative disorder" and "proliferative disease" as used herein refer to disorders associated with abnormal cell proliferation such as cancer.

The terms "tumor" and "neoplasm" as used herein refer to any mass of tissue that results from excessive cell growth or proliferation, either benign (non-cancerous) or malignant (cancerous), including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is generally one that loses adhesive contacts with neighboring cells and migrates from the primary site of disease to invade neighboring tissue sites.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" as used herein refer to the total population of cells derived from a cancer or tumor or pre-cancerous lesion, including both non-tumorigenic cells, which comprise the bulk of the cancer cell population, and tumorigenic cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "subject" as used herein refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to an agent, compound, molecule, etc. approved or approvable by a regulatory agency of the Federal government, a state government, and/or listed in the U.S. Pharmacopeia or other generally recognized pharmacopeia for use in animals, including humans.

The phrases "pharmaceutically acceptable excipient, carrier or adjuvant" and "acceptable pharmaceutical carrier" refer to an excipient, carrier, or adjuvant that can be administered to a subject, together with a therapeutic agent, and which does not destroy the pharmacological activity thereof and is nontoxic when administered in doses sufficient to deliver a therapeutic effect. In general, those of skill in the art and the FDA consider a pharmaceutically acceptable excipient, carrier, or adjuvant to be an inactive ingredient of any formulation or pharmaceutical composition.

The terms "effective amount" and "therapeutically effective amount" and "therapeutic effect" as used herein refer to an amount of a binding agent, an antibody, a polypeptide, a polynucleotide, a small molecule, or other therapeutic agent effective to "treat" a disease or disorder in a subject or mammal. In the case of cancer, the therapeutically effective amount of an agent (e.g., an antibody) has a therapeutic effect and as such can boost the immune response, boost the anti-tumor response, increase cytolytic activity of immune cells, reduce the number of cancer cells; decrease tumorigenicity, tumorigenic frequency, or tumorigenic capacity; reduce the number or frequency of cancer stem cells; reduce tumor size; reduce the cancer cell population; inhibit and/or stop cancer cell infiltration into peripheral organs including, for example, the spread of cancer into soft tissue and bone; inhibit and stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent prevents growth and/or kills existing cancer cells, it can be referred to as cytostatic and/or cytotoxic.

The terms "treating" and "treatment" and "to treat" and "alleviating" and "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus, those in need of treatment include those who already have a disorder; those prone to have a disorder; and those in whom a disorder is to be prevented. In some embodiments, a subject is successfully "treated" according to the methods of the present invention if the patient shows one or more of the following: an increased immune response, an increased anti-tumor response, increased cytolytic activity of immune cells, increased killing of tumor cells by immune cells, a reduction in the number of or complete absence of cancer cells; a reduction in tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; inhibition or an absence of tumor growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Methods of Use and Pharmaceutical Compositions

A Notch pathway inhibitor described herein in combination with a second agent, wherein the second agent is an immunotherapeutic agent is useful in a variety of applications including, but not limited to, therapeutic treatment methods, such as immunotherapy for cancer. In certain embodiments, the combination of a Notch pathway inhibitor (e.g., a DLL4 antagonist or a Notch receptor antagonist) with a second agent, wherein the second agent is an immunotherapeutic agent, is useful for activating, promoting, increasing, and/or enhancing an immune response, inhibiting tumor growth, reducing tumor volume, increasing tumor cell apoptosis, and/or reducing the tumorigenicity of a tumor. The methods of use may be in vitro, ex vivo, or in vivo methods. In some embodiments, the combination of a Notch pathway inhibitor (e.g., a DLL4 antagonist or a Notch receptor antagonist) with an immunotherapeutic agent acts as an agonist of an immune response. In some embodiments, the combination of a Notch pathway inhibitor (e.g., a DLL4 antagonist or a Notch receptor antagonist) with an immunotherapeutic agent acts as an enhancer, activator, or stimulator of an immune response. In some embodiments, the combination of a Notch pathway inhibitor (e.g., a DLL4 antagonist or a Notch receptor antagonist) with an immunotherapeutic agent acts as an agonist of an anti-tumor immune response.

In some embodiments, the combination of a Notch pathway inhibitor (e.g., a DLL4 antagonist or Notch receptor antagonist) with an immunotherapeutic agent works as an antagonist of the PD-1/PD-L1 pathway. In some embodiments, the combination of a Notch pathway inhibitor (e.g., a DLL4 antagonist or a Notch receptor antagonist) with an immunotherapeutic agent works as an antagonist of PD-1 or PD-1 activity. In some embodiments, the combination of a Notch pathway inhibitor (e.g., a DLL4 antagonist or a Notch receptor antagonist) with an immunotherapeutic agent works as an antagonist of PD-L1 or PD-L1 activity. In some embodiments, the combination of a Notch pathway inhibitor (e.g., a DLL4 antagonist or a Notch receptor antagonist) with an immunotherapeutic agent works as an antagonist of the CTLA-4 pathway. In some embodiments, the combination of a Notch pathway inhibitor (e.g., a DLL4 antagonist or a Notch receptor antagonist) with an immunotherapeutic agent works as an antagonist of CTLA-4 or CTLA-4 activity. In some embodiments, the combination of a Notch pathway inhibitor (e.g., a DLL4 antagonist or a Notch receptor antagonist) with an immunotherapeutic agent works as an antagonist of Tim-3 or Tim-3 activity. In some embodiments, the combination of a Notch pathway inhibitor (e.g., a DLL4 antagonist or a Notch receptor antagonist) with an immunotherapeutic agent works as an antagonist of LAG3 or LAG3 activity. In some embodiments, the combination of a Notch pathway inhibitor (e.g., a DLL4 antagonist or a Notch receptor antagonist) with an immunotherapeutic agent works as an antagonist of TIGIT or TIGIT activity. In some embodiments, the combination of a Notch pathway inhibitor (e.g., a DLL4 antagonist or a Notch receptor antagonist) with an immunotherapeutic agent works as an antagonist of KIR or KIR activity.

In some embodiments, the combination of a Notch pathway inhibitor (e.g., a DLL4 antagonist or a Notch receptor antagonist) with an immunotherapeutic agent works as an agonist of the CTLA-4/CD28 pathway. In some embodiments, the combination of a Notch pathway inhibitor (e.g., a DLL4 antagonist or a Notch receptor antagonist) with an immunotherapeutic agent works as an agonist of CD28 or CD28 activity. In some embodiments, the combination of a Notch pathway inhibitor (e.g., a DLL4 antagonist or a Notch receptor antagonist) with an immunotherapeutic agent works as an agonist of 4-1BB or 4-1BB activity. In some embodiments, the combination of a Notch pathway inhibitor (e.g., a DLL4 antagonist or a Notch receptor antagonist) with an immunotherapeutic agent works as an agonist of OX40 or OX40 activity. In some embodiments, the combination of a Notch pathway inhibitor (e.g., a DLL4 antagonist or a Notch receptor antagonist) with an immunotherapeutic agent works as an agonist of GITR or GITR activity. In some embodiments, the combination of a Notch pathway inhibitor (e.g., a DLL4 antagonist or a Notch receptor antagonist) with an immunotherapeutic agent works as an agonist of CD40 or CD40 activity.

In certain embodiments of the methods described herein, a method of inhibiting tumor growth comprises contacting tumor cells with an effective amount of a Notch pathway inhibitor in combination with an effective amount of a second agent, wherein the second agent is an immunotherapeutic agent. The method may be in vivo or in vitro. In certain embodiments, the tumor is in a subject, and contacting tumor cells with the Notch pathway inhibitor and the immunotherapeutic agent comprises administering a therapeutically effective amount of each of the agents to the subject. In some embodiments, a method of inhibiting tumor growth comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting tumor growth comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, the Notch pathway inhibitor and the immunotherapeutic agent inhibit tumor growth by inhibiting or suppressing Treg activity. In some embodiments, the Notch pathway inhibitor and the immunotherapeutic agent inhibit tumor growth by inhibiting or suppressing MDSC activity. In some embodiments, the Notch pathway inhibitor and the immunotherapeutic agent inhibit tumor growth by increasing cytolytic cell activity. In some embodiments, the Notch pathway inhibitor and the immunotherapeutic agent inhibit tumor growth by increasing CD8+ cytolytic T-cell activity. In some embodiments, the Notch pathway inhibitor and the immunotherapeutic agent inhibit tumor growth by increasing NK cell activity. In some embodiments, the Notch pathway inhibitor and the immunotherapeutic agent inhibit tumor growth by decreasing PD-1 expression on T-cells. In some embodiments, the Notch pathway inhibitor and the immunotherapeutic agent inhibit tumor growth by decreasing the number or percentage of PD-1 expressing T-cells. In some embodiments, the Notch pathway inhibitor and the immunotherapeutic agent inhibit tumor growth by decreasing the number or percentage of MDSCs. In some embodiments, the Notch pathway inhibitor and the immunotherapeutic agent inhibit tumor growth by increasing the number or percentage of activated myeloid cells. In some embodiments, the Notch pathway inhibitor and the immunotherapeutic agent inhibit tumor growth by increasing the number or percentage of memory T-cells. In some embodiments, the Notch pathway inhibitor and the immunotherapeutic agent inhibit tumor growth by increasing or enhancing Th1-type immune responses. In some embodiments, the Notch pathway inhibitor and the immunotherapeutic agent inhibit tumor growth by increasing IFN-gamma production. In some embodiments, the Notch pathway inhibitor and the immunotherapeutic agent inhibit tumor growth by increasing IL-2 production. In some embodiments, the Notch pathway inhibitor and the immunotherapeutic agent inhibit tumor growth by decreasing or inhibiting Th17 immune responses. In some embodiments, the Notch pathway inhibitor and the immunotherapeutic agent inhibit tumor growth by decreasing IL-17 production. In some embodiments, the Notch pathway inhibitor and the immunotherapeutic agent inhibit tumor growth by decreasing or inhibiting Th2-type immune responses. In some embodiments, the Notch pathway inhibitor and the immunotherapeutic agent inhibit tumor growth by decreasing IL-6 production. In some embodiments, the Notch pathway inhibitor is a DLL4 antagonist. In some embodiments, a DLL4 antagonist is an anti-DLL4 antibody. In some embodiments, the Notch pathway inhibitor is a Notch receptor antagonist. In some embodiments, a Notch receptor antagonist is an anti-Notch2/3 antibody. In some embodiments, a Notch receptor antagonist is an anti-Notch1 antibody.

In certain embodiments of the methods described herein, a method of treating cancer comprises administering to a subject a therapeutically effective amount of a Notch pathway inhibitor in combination with a therapeutically effective amount of a second agent, wherein the second agent is an immunotherapeutic agent. In some embodiments, a method of treating cancer comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of treating cancer comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, the Notch pathway inhibitor and the immunotherapeutic agent treat cancer by inhibiting or suppressing Treg activity. In some embodiments, the Notch pathway inhibitor and the immunotherapeutic agent treat cancer by inhibiting or suppressing MDSC activity. In some embodiments, the Notch pathway inhibitor and the immunotherapeutic agent treat cancer by increasing cytolytic cell activity. In some embodiments, the Notch pathway inhibitor and the immunotherapeutic agent treat cancer by increasing NK cell activity. In some embodiments, the Notch pathway inhibitor and the immunotherapeutic agent treat cancer by increasing cytolytic T-cell activity. In some embodiments, the Notch pathway inhibitor and the immunotherapeutic agent treat cancer by increasing CD8+ cytolytic T-cell activity. In some embodiments, the Notch pathway inhibitor and the immunotherapeutic agent treat cancer by decreasing PD-1 expression on T-cells. In some embodiments, the Notch pathway inhibitor and the immunotherapeutic agent treat cancer by decreasing the number or percentage of PD-1 expressing T-cells. In some embodiments, the Notch pathway inhibitor and the immunotherapeutic agent treat cancer by decreasing the number or percentage of MDSCs. In some embodiments, the Notch pathway inhibitor and the immunotherapeutic agent treat cancer by increasing the number or percentage of activated myeloid cells. In some embodiments, the Notch pathway inhibitor and the immunotherapeutic agent treat cancer by increasing the number or percentage of memory T-cells. In some embodiments, the Notch pathway inhibitor and the immunotherapeutic agent treat cancer by increasing Th1-type immune responses. In some embodiments, the Notch pathway inhibitor and the immunotherapeutic agent treat cancer by increasing IFN-gamma production. In some embodiments, the Notch pathway inhibitor and the immunotherapeutic agent treat cancer by increasing IL-2 production. In some embodiments, the Notch pathway inhibitor and the immunotherapeutic agent treat cancer by decreasing IL-17 production. In some embodiments, the Notch pathway inhibitor and the immunotherapeutic agent treat cancer by decreasing IL-6 production. In some embodiments, the Notch pathway inhibitor is a DLL4 antagonist. In some embodiments, a DLL4 antagonist is an anti-DLL4 antibody. In some embodiments, the Notch pathway inhibitor is a Notch receptor antagonist. In some embodiments, a Notch receptor antagonist is an anti-Notch2/3 antibody. In some embodiments, a Notch receptor antagonist is an anti-Notch1 antibody.

In certain embodiments of the methods described herein, a method of cancer immunotherapy comprises administering to a subject a therapeutically effective amount of a Notch pathway inhibitor in combination with a therapeutically effective amount of a second agent, wherein the second agent is an immunotherapeutic agent, and wherein the combination results in enhanced therapeutic efficacy as compared to administration of either agent alone. In some embodiments, the Notch pathway inhibitor is a DLL4 antagonist. In some embodiments, the DLL4 antagonist is an anti-DLL4 antibody. In some embodiments, the Notch pathway inhibitor is a Notch receptor antagonist. In some embodiments, the Notch receptor antagonist is an anti-Notch2/3 antibody. In some embodiments, the Notch receptor antagonist is an anti-Notch1 antibody.

In certain embodiments of the methods described herein, a method of inhibiting the activity of Tregs comprises administering to a subject a therapeutically effective amount of a Notch pathway inhibitor in combination with a therapeutically effective amount of a second agent, wherein the second agent is an immunotherapeutic agent. In some embodiments, a method of inhibiting the activity of Tregs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the activity of Tregs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of inhibiting the suppression of immune responses by Tregs comprises administering to a subject a therapeutically effective amount of a Notch pathway inhibitor in combination with a therapeutically effective amount of a second agent, wherein the second agent is an immunotherapeutic agent. In some embodiments, a method of inhibiting the suppression of immune responses by Tregs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the suppression of immune responses by Tregs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of inhibiting the activity of MDSCs comprises administering to a subject a therapeutically effective amount of a Notch pathway inhibitor in combination with a therapeutically effective amount of a second agent, wherein the second agent is an immunotherapeutic agent. In some embodiments, a method of inhibiting the activity of MDSCs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the activity of MDSCs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of inhibiting the suppression of immune responses by MDSCs comprises administering to a subject a therapeutically effective amount of a Notch pathway inhibitor in combination with a therapeutically effective amount of a second agent, wherein the second agent is an immunotherapeutic agent. In some embodiments, a method of inhibiting the suppression of immune responses by MDSCs comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting the suppression of immune responses by MDSCs comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of enhancing the antigen-specific memory response to a tumor comprises administering to a subject a therapeutically effective amount of a Notch pathway inhibitor in combination with a therapeutically effective amount of a second agent, wherein the second agent is an immunotherapeutic agent. In some embodiments, a method of enhancing the antigen-specific memory response to a tumor comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of enhancing the antigen-specific memory response to a tumor comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch 1 antibody.

In certain embodiments of the methods described herein, a method of activating or enhancing a persistent or long-term immune response to a tumor comprises administering to a subject a therapeutically effective amount of a Notch pathway inhibitor in combination with a therapeutically effective amount of a second agent, wherein the second agent is an immunotherapeutic agent. In some embodiments, a method of activating or enhancing a persistent immune response to a tumor comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of activating or enhancing a persistent immune response to a tumor comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of inducing a persistent or long-term immunity which inhibits tumor relapse or tumor regrowth comprises administering to a subject a therapeutically effective amount of a Notch pathway inhibitor in combination with a therapeutically effective amount of a second agent, wherein the second agent is an immunotherapeutic agent. In some embodiments, a method of inducing a persistent immunity which inhibits tumor relapse or tumor regrowth comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inducing a persistent immunity which inhibits tumor relapse or tumor regrowth comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of inhibiting tumor relapse or tumor regrowth comprises administering to a subject a therapeutically effective amount of a Notch pathway inhibitor in combination with a therapeutically effective amount of a second agent, wherein the second agent is an immunotherapeutic agent. In some embodiments, a method of inhibiting tumor relapse or tumor regrowth comprises administering to a subject a therapeutically effective amount of a Notch pathway inhibitor and a therapeutically effective amount of a second agent, wherein the Notch pathway inhibitor is a DLL4 antagonist and the second agent is an immunotherapeutic agent. In some embodiments, a method of inhibiting tumor relapse or tumor regrowth comprises administering to a subject a therapeutically effective amount of a Notch pathway inhibitor and a therapeutically effective amount of a second agent, wherein the Notch pathway inhibitor is a Notch receptor antagonist and the second agent is an immunotherapeutic agent. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method to increase the efficacy of an immune checkpoint modulator comprises administering to a subject a therapeutically effective amount of a Notch pathway inhibitor in combination with a therapeutically effective amount of an immune checkpoint modulator. In some embodiments, a method to increase the efficacy of an immune checkpoint inhibitor comprises administering to a subject a therapeutically effective amount of a Notch pathway inhibitor and a therapeutically effective amount of an immune checkpoint modulator, wherein the Notch pathway inhibitor is a DLL4 antagonist. In some embodiments, a method to increase the efficacy of an immune checkpoint inhibitor comprises administering to a subject a therapeutically effective amount of a Notch pathway inhibitor and a therapeutically effective amount of an immune checkpoint modulator, wherein the Notch pathway inhibitor is a Notch receptor antagonist. In some embodiments, the immune checkpoint modulator is an immune checkpoint inhibitor. In some embodiments, the immune checkpoint modulator is an immune checkpoint enhancer or stimulator. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In certain embodiments of the methods described herein, a method of enhancing treatment for a subject who is being treated with an immune checkpoint modulator comprises administering to the subject a therapeutically effective amount of a Notch pathway inhibitor. In some embodiments, a method of enhancing treatment for a subject who is being treated with an immune checkpoint modulator comprises administering to the subject a therapeutically effective amount of a DLL4 antagonist. In certain embodiments, a method of enhancing treatment for a subject who is being treated with an immune checkpoint modulator comprises administering to the subject a therapeutically effective amount of a Notch receptor antagonist. In some embodiments, the immune checkpoint modulator is an immune checkpoint inhibitor. In some embodiments, the immune checkpoint inhibitor is a PD-1 antagonist. In some embodiments, the immune checkpoint inhibitor is an antibody that specifically binds PD-1. In some embodiments, the immune checkpoint inhibitor is a PD-L1 antagonist. In some embodiments, immune checkpoint inhibitor is an antibody that specifically binds PD-L1. In some embodiments, the immune checkpoint inhibitor is a CTLA-4 antagonist. In some embodiments, the immune checkpoint inhibitor is an antibody that specifically binds CTLA-4. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In some embodiments, the method of inhibiting tumor growth comprises contacting the tumor or tumor cells with a Notch pathway inhibitor (e.g., a DLL4 antagonist or a Notch receptor antagonist) and an immunotherapeutic agent in vivo. In certain embodiments, contacting a tumor or tumor cell with a Notch pathway inhibitor and an immunotherapeutic agent is undertaken in an animal model. For example, a Notch pathway inhibitor and an immunotherapeutic agent may be administered to mice which have tumors. In some embodiments, a Notch pathway inhibitor and an immunotherapeutic agent increases, promotes, and/or enhances the activity of immune cells in the mice. In some embodiments, a Notch pathway inhibitor and an immunotherapeutic agent are administered to an animal to inhibit growth of tumors. In some embodiments, a Notch pathway inhibitor and an immunotherapeutic agent are administered at the same time or shortly after introduction of tumor cells into the animal (preventative model). In some embodiments, a Notch pathway inhibitor and an immunotherapeutic agent are administered after the tumor cells have become established and grown to a tumor of specific size (therapeutic model).

In certain embodiments, a method of inhibiting growth of a tumor comprises administering to a subject a therapeutically effective amount of a Notch pathway inhibitor (e.g., a DLL4 antagonist or a Notch receptor antagonist) and a therapeutically effective amount of an immunotherapeutic agent. In certain embodiments, the subject is a human. In certain embodiments, the subject has a tumor or has had a tumor which was removed. In certain embodiments, the tumor comprises cancer stem cells. In certain embodiments, the frequency of cancer stem cells in the tumor is reduced by administration of the Notch pathway inhibitor.

The invention also provides a method of reducing or preventing metastasis in a subject comprising administering to the subject a therapeutically effective amount of a Notch pathway inhibitor and a therapeutically effective amount of an immunotherapeutic agent. In some embodiments, the Notch pathway inhibitor is a DLL4 antagonist. In some embodiments, the Notch pathway inhibitor is a Notch receptor antagonist. In some embodiments, the reduction or prevention of metastasis comprises inhibiting invasiveness of a tumor. In certain embodiments, the subject is a human. In certain embodiments, the subject has a tumor or has had a tumor removed. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

In addition, the invention provides a method of reducing the tumorigenicity of a tumor in a subject, comprising administering to a subject a therapeutically effective amount of a Notch pathway inhibitor and a therapeutically effective amount of an immunotherapeutic agent. In some embodiments, the Notch pathway inhibitor is a DLL4 antagonist. In some embodiments, the Notch pathway inhibitor is a Notch receptor antagonist. In certain embodiments, the tumor comprises cancer stem cells. In some embodiments, the tumorigenicity of a tumor is reduced by reducing the frequency of cancer stem cells in the tumor. In certain embodiments, the frequency of cancer stem cells in the tumor is reduced by administration of the Notch pathway inhibitor. In some embodiments, the tumorigenicity of the tumor is reduced by inducing apoptosis of the tumor cells. In some embodiments, the tumorigenicity of the tumor is reduced by increasing apoptosis of the tumor cells. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody.

The invention also provides a method of reducing cancer stem cell frequency in a tumor comprising cancer stem cells, the method comprising administering to a subject a therapeutically effective amount of a Notch pathway inhibitor and a therapeutically effective amount of an immunotherapeutic agent. In some embodiments, the Notch pathway inhibitor is a DLL4 antagonist. In some embodiments, the Notch pathway inhibitor is a Notch receptor antagonist. In some embodiments, a DLL4 antagonist is an anti-DLL4 antibody. In some embodiments, a Notch receptor antagonist is an anti-Notch2/3 antibody. In some embodiments, a Notch receptor antagonist is an anti-Notch1 antibody. In certain embodiments, the Notch pathway inhibitor in combination with an immunotherapeutic agent is capable of reducing the tumorigenicity of a tumor comprising cancer stem cells in an animal model, such as a mouse model. In certain embodiments, the number or frequency of cancer stem cells in a treated tumor is reduced by at least about two-fold, about three-fold, about five-fold, about ten-fold, about 50-fold, about 100-fold, or about 1000-fold as compared to the number or frequency of cancer stem cells in an untreated tumor. In certain embodiments, the reduction in the number or frequency of cancer stem cells is determined by limiting dilution assay using an animal model.

In some embodiments for the methods described herein, the Notch pathway inhibitor augments the activity of the immunotherapeutic agent. In some embodiments, the Notch pathway inhibitor augments the activity of the immunotherapeutic agent in a subject that has not been previously treated with the immunotherapeutic agent. In some embodiments, the Notch pathway inhibitor augments the activity of the immunotherapeutic agent in a subject that has been previously treated with the immunotherapeutic agent. In some embodiments, a DLL4 antagonist augments the activity of an anti-PD-1 antibody. In some embodiments, a DLL4 antagonist augments the activity of an anti-PD-L1 antibody. In some embodiments, a Notch receptor antagonist augments the activity of an anti-PD-1 antibody. In some embodiments, a Notch receptor antagonist augments the activity of an anti-PD-L1 antibody.

In some embodiments for the methods described herein, the Notch pathway inhibitor augments the activity of the immunotherapeutic agent in a subject that has been previously treated with the immunotherapeutic agent, wherein the subject has become insensitive or resistant to the immunotherapeutic agent. In some embodiments, the Notch pathway inhibitor restores a subject's sensitivity to the activity of the immunotherapeutic agent. In some embodiments, a DLL4 antagonist restores a subject's sensitivity to an anti-PD-1 antibody. In some embodiments, a DLL4 antagonist restores a subject's sensitivity to an anti-PD-L1 antibody. In some embodiments, a Notch receptor antagonist restores a subject's sensitivity to an anti-PD-1 antibody. In some embodiments, a Notch receptor restores a subject's sensitivity to an anti-PD-L1 antibody.

In some embodiments for the methods described herein, the Notch pathway inhibitor increases a subject's sensitivity to the activity of the immunotherapeutic agent. In some embodiments, the Notch pathway inhibitor increases a subject's sensitivity to the activity of the immunotherapeutic agent, wherein the subject has been found to be insensitive to the immunotherapeutic agent.

The invention also provides a method of identifying a human tumor likely to be responsive to treatment with a Notch pathway inhibitor in combination with a second agent, wherein the second agent is an immunotherapeutic agent, the method comprising determining the expression level of PD-L1 in a sample obtained from the tumor. In some embodiments, a method of identifying a human tumor likely to be responsive to combination treatment with a Notch pathway inhibitor and an immunotherapeutic agent, comprises: a) obtaining a sample of the human tumor; b) measuring the expression level of PD-L1 in the sample; and c) identifying the tumor as likely to be responsive or non-responsive to combination treatment with a Notch pathway inhibitor and an immunotherapeutic agent based upon the expression level of PD-L1 in the sample.

The invention also provides a method of determining the responsiveness (or sensitivity) of a human tumor to treatment with a Notch pathway inhibitor in combination with a second agent, wherein the second agent is an immunotherapeutic agent, the method comprising: (a) obtaining a sample of the human tumor; (b) measuring the expression level of PD-L1 in the sample; and (c) determining the responsiveness of the tumor to treatment based upon the expression level of PD-L1. In some embodiments, the method comprises determining the responsiveness or sensitivity of a human tumor to treatment with a DLL4 antagonist. In some embodiments, the method comprises determining the responsiveness or sensitivity of a human tumor to treatment with a DLL4 antagonist in combination with at least one additional therapeutic agent (e.g., a chemotherapeutic agent). In some embodiments, the method comprises determining the responsiveness or sensitivity of a human tumor to treatment with a Notch receptor antagonist. In some embodiments, the method comprises determining the responsiveness or sensitivity of a human tumor to treatment with a Notch receptor antagonist in combination with at least one additional therapeutic agent (e.g., a chemotherapeutic agent).

The invention also provides a method of identifying a patient with cancer who is likely to respond to treatment with a Notch pathway inhibitor in combination with a second agent, wherein the second agent is an immunotherapeutic agent, the method comprising: (a) obtaining a sample from the patient; (b) measuring the expression level of PD-L1 in the sample; and (c) identifying the patient who is likely to respond to treatment based upon the expression level of PD-L1. In some embodiments, the sample is a tumor sample. In some embodiments, the sample is a blood or plasma sample. In some embodiments, the method comprises identifying a patient with cancer who is likely to respond to treatment with a Notch pathway inhibitor and an immunotherapeutic agent in combination with at least one additional therapeutic agent.

The invention also provides a method of selecting a subject with a tumor for treatment with a Notch pathway inhibitor in combination with a second agent, wherein the second agent is an immunotherapeutic agent, the method comprising: a) determining the expression level of PD-L1 in a sample obtained from the subject; b) identifying the tumor as likely to be responsive or non-responsive to treatment with the Notch pathway inhibitor and the immunotherapeutic agent based upon the expression level of PD-L1 in the sample; and c) selecting the subject for treatment if the tumor is identified as likely to be responsive to treatment. In some embodiments, the sample is a tumor sample. In some embodiments, the sample is a blood or plasma sample. In some embodiments, the method further comprises administering an effective amount of a Notch pathway inhibitor in combination with an effective amount of an immunotherapeutic agent to the subject.

The invention also provides a method of treating cancer in a patient, comprising: (a) identifying if the patient is likely to respond to treatment with a Notch pathway inhibitor in combination with a second agent, wherein the second agent is an immunotherapeutic agent, wherein the identification comprises: (i) obtaining a sample from the patient; (ii) measuring the expression level of PD-L1 in the sample; and (iii) identifying the patient who is likely to respond to treatment based upon the expression level of PD-L1; and (b) administering to the patient who is likely to response to treatment an effective amount of the Notch pathway inhibitor in combination with the immunotherapeutic agent. In some embodiments, the sample is a tumor sample. In some embodiments, the sample is a blood or plasma sample. In some embodiments, the method comprises identifying if the patient is likely to respond to treatment with a Notch pathway inhibitor in combination with an additional therapeutic agent. In some embodiments, the method comprises administering to the patient the Notch pathway inhibitor and immunotherapeutic agent in combination with at least one additional therapeutic agent.

The invention also provides a method of treating cancer in a patient, comprising: administering an effective amount of a Notch pathway inhibitor in combination with a second agent, wherein the second agent is an immunotherapeutic agent to the patient; wherein the patient is predicted to respond to treatment with a Notch pathway inhibitor and/or immunotherapeutic agent based upon expression level of PD-L1 in a sample from the patient. In some embodiments, the sample is a tumor sample. In some embodiments, the sample is a blood or plasma sample. In some embodiments, the patient is predicted to respond to treatment with a Notch pathway inhibitor and immunotherapeutic agent in combination with a chemotherapeutic agent. In some embodiments, the method comprises administering to the patient the Notch pathway inhibitor and immunotherapeutic agent in combination with at least one additional therapeutic agent.

The invention also provides a method for increasing the likelihood of effective treatment with a Notch pathway inhibitor in combination with a second agent, wherein the second agent is an immunotherapeutic agent, comprising: (a) identifying if a patient has a tumor that is likely to respond to treatment with a Notch pathway inhibitor and/or immunotherapeutic agent, wherein the identification comprises: (i) obtaining a sample from the patient; (ii) measuring the expression level of PD-L1 in the sample; and (iii) identifying the patient who is likely to respond to treatment based upon the expression level of the PD-L1; and (b) administering an effective amount of the Notch pathway inhibitor in combination with the immunotherapeutic agent to the patient. In some embodiments, the sample is a tumor sample. In some embodiments, the sample is a blood or plasma sample. In some embodiments, the method comprises identifying if a patient has a tumor that is likely to respond to treatment with a Notch pathway inhibitor in combination with a chemotherapeutic agent. In some embodiments, the method comprises administering to the patient the Notch pathway inhibitor and the immunotherapeutic agent in combination with at least one additional therapeutic agent.

The invention also provides a method for increasing the likelihood of effective treatment with a Notch pathway inhibitor in combination with a second agent, wherein the second agent is an immunotherapeutic agent, comprising: administering an effective amount of a Notch pathway inhibitor and/or immunotherapeutic agent to a patient; wherein the patient is identified as likely to respond to treatment with the Notch pathway inhibitor and/or the immunotherapeutic agent based upon expression level of PD-L1 in a sample. In some embodiments, the sample is a tumor sample. In some embodiments, the sample is a blood or plasma sample. In some embodiments, the patient is identified as likely to respond to treatment with a Notch pathway inhibitor in combination with a chemotherapeutic agent. In some embodiments, the method comprises administering to the patient the Notch pathway inhibitor and the immunotherapeutic agent in combination with at least one additional therapeutic agent.

In some embodiments of the methods described herein, the sample is a biopsy sample. In some embodiments, the sample is a blood or plasma sample. In some embodiments, the sample is a tumor sample. In some embodiments, the sample comprises tumor cells, tumor infiltrating immune cells, stromal cells, and any combination thereof. In some embodiments, the sample is a formalin-fixed paraffin embedded (FFPE) sample. In some embodiments, the sample is archival, fresh, or frozen tissue. In some embodiments, the expression level of PD-L1 in the sample is compared to a pre-determined expression level of PD-L1. In some embodiments, the pre-determined expression level of PD-L1 expression is an expression level of PD-L1 in a reference tumor sample, a reference normal tissue sample, a series of reference tumor samples, or a series of reference normal tissue samples. In some embodiments, the expression level of PD-L1 is determined using an immunohistochemistry (IHC) assay. In some embodiments, the expression level of PD-L1 is determined using an assay which comprises an H-score evaluation. In some embodiments, the expression level of PD-L1 is determined using an ELISA. In some embodiments, the expression level of PD-L1 is determined using a PCR-based assay.

In some embodiments, the expression level of PD-L1 is determined using an antibody that specifically binds PD-L1. In some embodiments, the antibody that specifically binds human PD-L1 is a polyclonal antibody, a monoclonal antibody, a recombinant antibody, a chimeric antibody, a humanized antibody, a human antibody, a mouse antibody, a rabbit antibody, a rat antibody, or an antibody fragment comprising an antigen-binding site.

In some embodiments, PD-L1 is detected on tumor cells. In some embodiments, PD-L1 is detected on tumor infiltrating immune cells. In some embodiments, the tumor infiltrating immune cells are lymphocytes. In some embodiments, the tumor infiltrating immune cells are T-cells. In some embodiments, PD-L1 is detected on antigen-presenting cells (APCs). In some embodiments, PD-L1 is detected on macrophages and/or dendritic cells. In some embodiments, the APCs, macrophages, and/or dendritic cells are within the tumor microenvironment.

In some embodiments of the methods described herein, the tumor is a tumor selected from the group consisting of lung tumor, pancreatic tumor, breast tumor, colon tumor, colorectal tumor, melanoma, gastrointestinal tumor, gastric tumor, renal tumor, ovarian tumor, liver tumor, endometrial tumor, kidney tumor, prostate tumor, thyroid tumor, neuroblastoma, glioma, glioblastoma, glioblastoma multiforme, cervical tumor, stomach tumor, bladder tumor, head and neck tumor, and hepatoma. In certain embodiments, the tumor is a breast tumor. In certain embodiments, the tumor is a breast tumor is a triple negative breast tumor. In some embodiments, the tumor is an ovarian tumor. In certain embodiments, the tumor is a lung tumor. In certain embodiments, the lung tumor is a non-small cell lung tumor. In certain embodiments, the lung tumor is a small cell lung tumor. In certain embodiments, the tumor is a pancreatic tumor. In certain embodiments, the tumor is a kidney tumor. In some embodiments, the kidney tumor is a renal cell carcinoma. In some embodiments, the tumor expresses PD-L1. In some embodiments, the tumor over-expresses PD-L1. In some embodiments, the tumor expresses PD-L2. In some embodiments, the tumor over-expresses PD-L2. In some embodiments, the tumor has an increased level of PD-L1 expression as compared to a pre-determined level. In some embodiments, the "pre-determined level" of PD-L1 expression is the amount of PD-L1 expression in a normal immune cell. In some embodiments, the "pre-determined level" of PD-L1 expression is the amount of PD-L1 expression in a normal tissue. In some embodiments, the "pre-determined level" of PD-L1 expression is the amount of PD-L1 expression in a similar tumor type. In some embodiments, the "pre-determined level" of PD-L1 expression is the amount of PD-L1 expression in a mixture of tumor types.

In some embodiments of the methods described herein the cancer is a cancer selected from the group consisting of lung cancer, pancreatic cancer, breast cancer, colon cancer, colorectal cancer, melanoma, gastrointestinal cancer, gastric cancer, renal cancer, ovarian cancer, liver cancer, endometrial cancer, kidney cancer, prostate cancer, thyroid cancer, neuroblastoma, glioma, glioblastoma, glioblastoma multiforme, cervical cancer, stomach cancer, bladder cancer, head and neck cancer, and hepatoma. In some embodiments, the cancer is lung cancer. In some embodiments, the cancer is ovarian cancer.

In some embodiments, the Notch pathway inhibitor is an antibody. In some embodiments, the antibody is a monoclonal antibody. In some embodiments, the antibody is a humanized antibody. In some embodiments, the antibody is a recombinant antibody, a chimeric antibody, a human antibody, or an antibody fragment comprising an antigen-binding site. In some embodiments, the antibody is a monospecific antibody. In some embodiments, the antibody is a bispecific antibody. In some embodiments, the antibody is an IgG1 antibody. In some embodiments, the antibody is an IgG2 antibody. In some embodiments, the antibody is an IgG4 antibody.

In some embodiments of the methods described herein, the Notch pathway inhibitor is a DLL4 antagonist. In some embodiments, the Notch pathway inhibitor is an antibody that specifically binds human DLL4. In some embodiments, the Notch pathway inhibitor is an antibody that specifically binds the extracellular domain of human DLL4. In some embodiments, the Notch pathway inhibitor is an antibody that specifically binds an epitope within amino acids 27-217 of the extracellular domain of human DLL4 (SEQ ID NO:17). In some embodiments, the Notch pathway inhibitor is an antibody that specifically binds within the N-terminal region of human DLL4 (SEQ ID NO:14). In some embodiments, the Notch pathway inhibitor is an antibody that specifically binds an epitope comprising amino acids 66-73 (QAVVSPGP, SEQ ID NO:18) of human DLL4. In some embodiments, the Notch pathway inhibitor is an antibody that specifically binds an epitope comprising amino acids 139-146 (LISKIAIQ, SEQ ID NO:19) of human DLL4. In some embodiments, the Notch pathway inhibitor is an antibody that specifically binds an epitope comprising amino acids 66-73 (QAVVSPGP, SEQ ID NO:18) and amino acids 139-146 (LISKIAIQ, SEQ ID NO:19) of human DLL4. In some embodiments, the Notch pathway inhibitor is an antibody that binds human DLL4 with a dissociation constant ($K_D$) of about 10 nM to about 0.1 nM.

In some embodiments of the methods described herein, the Notch pathway inhibitor is an antibody that specifically binds human DLL4, wherein the antibody comprises a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5), and/or a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the Notch pathway inhibitor is an antibody that specifically binds human DLL4, wherein the antibody comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

In certain embodiments of the methods described herein, the Notch pathway inhibitor is an antibody that specifically binds human DLL4, wherein the antibody comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8) and is administered in combination with an immunotherapeutic agent. In some embodiments, the immunotherapeutic agent is an antibody that specifically binds PD-1. In some embodiments, the immunotherapeutic agent is an antibody that specifically binds PD-L1.

In certain embodiments of any of the methods described herein, the Notch pathway inhibitor is an antibody that specifically binds human DLL4, wherein the antibody comprises a heavy chain variable region having at least about 90%, at least about 95% or 100% sequence identity to SEQ ID NO:9, SEQ ID NO:10, or SEQ ID NO:11; and/or a light chain variable region having at least about 90%, at least about 95% or 100% sequence identity to SEQ ID NO:12. In some embodiments, the DLL4 antagonist is an antibody which comprises a heavy chain variable region having at least about 90%, at least about 95%, 96%, 97%, 98%, or 99% sequence identity to SEQ ID NO:10 and a light chain variable region having at least about 90%, at least about 95%, 96%, 97%, 98%, or 99% sequence identity to SEQ ID NO:12. In some embodiments, the DLL4 antagonist is an antibody which comprises a heavy chain variable region comprising SEQ ID NO:10 and a light chain variable region comprising SEQ ID NO:12.

In some embodiments of the methods described herein, the Notch pathway inhibitor is a bispecific antibody, wherein the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

In certain embodiments of the methods described herein, the Notch pathway inhibitor is a bispecific antibody, wherein the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8) and is administered in combination with an immunotherapeutic agent. In some embodiments, the immunotherapeutic agent is an antibody that specifically binds PD-1. In some embodiments, the immunotherapeutic agent is an antibody that specifically binds PD-L1.

In certain embodiments of any of the methods described herein, the Notch pathway inhibitor is a bispecific antibody, wherein the bispecific antibody comprises a first antigen-binding site that specifically binds human VEGF, and a second antigen-binding site that specifically binds human DLL4, wherein the first antigen-binding site comprises a first heavy chain variable region of SEQ ID NO:30, the second antigen-binding site comprises a second heavy chain variable region of SEQ ID NO:29; and wherein the first and the second antigen-binding site comprises a first and a second light chain variable region of SEQ ID NO:12.

In some embodiments, the Notch pathway inhibitor is bispecific antibody 305B83.

In certain embodiments of any of the methods described herein, the Notch pathway inhibitor is an antibody that specifically binds human DLL4 and the immunotherapeutic agent is a PD-1 antagonist. In some embodiments, the Notch pathway inhibitor is an antibody that specifically binds human DLL4 and the immunotherapeutic agent is a PD-L1 antagonist. In some embodiments, the Notch pathway inhibitor is an antibody that specifically binds human DLL4 and the immunotherapeutic agent is a PD-L2 antagonist. In some embodiments, the Notch pathway inhibitor is an antibody that specifically binds human DLL4 and the immunotherapeutic agent is a CTLA-4 antagonist. In some embodiments, the Notch pathway inhibitor is an antibody that specifically binds human DLL4 and the immunotherapeutic agent is a CD80 antagonist. In some embodiments, the Notch pathway inhibitor is an antibody that specifically binds human DLL4 and the immunotherapeutic agent is a CD86 antagonist. In some embodiments, the Notch pathway inhibitor is an antibody that specifically binds human DLL4 and the immunotherapeutic agent is a KIR antagonist. In some embodiments, the Notch pathway inhibitor is an antibody that specifically binds human DLL4 and the immunotherapeutic agent is a Tim-3 antagonist. In some embodiments, the Notch pathway inhibitor is an antibody that specifically binds human DLL4 and the immunotherapeutic agent is a LAG3 antagonist. In some embodiments, the Notch pathway inhibitor is an antibody that specifically binds human DLL4 and the immunotherapeutic agent is a TIGIT antagonist. In some embodiments, the Notch pathway inhibitor is an antibody that specifically binds human DLL4 and the immunotherapeutic agent is a CD96 antagonist. In some embodiments, the Notch pathway inhibitor is an antibody that specifically binds human DLL4 and the immunotherapeutic agent is an IDO1 antagonist. In some embodiments, the Notch pathway inhibitor is an antibody that specifically binds human DLL4 and the immunotherapeutic agent is a CD28 agonist. In some embodiments, the Notch pathway inhibitor is an antibody that specifically binds human DLL4 and the immunotherapeutic agent is a 4-1BB agonist. In some embodiments, the Notch pathway inhibitor is an antibody that specifically binds human DLL4 and the immunotherapeutic agent is an OX40 agonist. In some embodiments, the Notch pathway inhibitor is an antibody that specifically binds human DLL4 and the immunotherapeutic agent is a CD27 agonist. In some embodiments, the Notch pathway inhibitor is an antibody that specifically binds human DLL4 and the immunotherapeutic agent is a CD80 agonist. In some embodiments, the Notch pathway inhibitor is an antibody that specifically binds human DLL4 and the immunotherapeutic agent is a CD86 agonist. In some embodiments, the Notch pathway inhibitor is an antibody that specifically binds human DLL4 and the immunotherapeutic agent is a CD40 agonist. In some embodiments, the Notch pathway inhibitor is an antibody that specifically binds human DLL4 and the immunotherapeutic agent is a GITR agonist. In some embodiments, the Notch pathway inhibitor is an antibody that specifically binds human DLL4 and the immunotherapeutic agent is a cytokine. In some embodiments, the Notch pathway inhibitor is an antibody that specifically binds human DLL4 and the immunotherapeutic agent is an interferon. In some embodiments, the Notch pathway inhibitor is an antibody that specifically binds human DLL4 and the immunotherapeutic agent is a lymphokine.

In some embodiments of the methods described herein, the Notch pathway inhibitor is a Notch receptor antagonist. In some embodiments, the Notch receptor antagonist is an antibody that specifically binds human Notch1, Notch2, and/or Notch3. In some embodiments, the Notch receptor antagonist is an antibody that specifically binds human Notch1. In some embodiments, the Notch receptor antagonist is an antibody that specifically binds human Notch2 and/or Notch3. In some embodiments, the Notch receptor antagonist is an antibody that specifically binds human Notch2 and Notch3.

In some embodiments of the methods described herein, the Notch receptor antagonist is an antibody that specifically binds the extracellular domain of human Notch2 and/or Notch3, wherein the antibody comprises a heavy chain CDR1 comprising SSSGMS (SEQ ID NO:34), a heavy chain CDR2 comprising VIASSGSNTYYADSVKG (SEQ ID NO:35), and a heavy chain CDR3 comprising SIFYTT (SEQ ID NO:36), and/or a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39). In some embodiments, the antibody comprises a heavy chain CDR1 comprising SSSGMS (SEQ ID NO:34), a heavy chain CDR2 comprising VIASSGSNTYYADSVKG (SEQ ID NO:35), and a heavy chain CDR3 comprising SIFYTT (SEQ ID NO:36); and a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39).

In certain embodiments of the methods described herein, the Notch receptor antagonist is an antibody that specifically binds human Notch2 and/or Notch3, wherein the antibody comprises a heavy chain CDR1 comprising SSSGMS (SEQ ID NO:34), a heavy chain CDR2 comprising VIASSGSN-TYYADSVKG (SEQ ID NO:35), and a heavy chain CDR3 comprising SIFYTT (SEQ ID NO:36); and/or a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39) and is administered in combination with an immunotherapeutic agent. In some embodiments, the immunotherapeutic agent is an antibody that specifically binds PD-1. In some embodiments, the immunotherapeutic agent is an antibody that specifically binds PD-L1.

In certain embodiments of any of the methods described herein, the Notch receptor antagonist is an antibody that specifically binds human Notch2 and/or Notch3, wherein the antibody comprises a heavy chain variable region having at least about 90%, at least about 95% or 100% sequence identity to SEQ ID NO:40 and/or a light chain variable region having at least about 90%, at least about 95% or 100% sequence identity to SEQ ID NO:41. In some embodiments, the Notch receptor antagonist is an antibody which comprises a heavy chain variable region having at least about 90%, at least about 95%, 96%, 97%, 98%, or 99% sequence identity to SEQ ID NO:40 and a light chain variable region having at least about 90%, at least about 95%, 96%, 97%, 98%, or 99% sequence identity to SEQ ID NO:41. In some embodiments, the Notch receptor antagonist is an antibody which comprises a heavy chain variable region comprising SEQ ID NO:40 and a light chain variable region comprising SEQ ID NO:41.

In some embodiments, the Notch pathway inhibitor is antibody tarextumab (OMP-59R5).

In certain embodiments of any of the methods described herein, the Notch pathway inhibitor is an antibody that specifically binds human Notch2 and/or Notch3 and the immunotherapeutic agent is a PD-1 antagonist. In some embodiments, the Notch pathway inhibitor is an antibody that specifically binds human Notch2 and/or Notch3 and the immunotherapeutic agent is a PD-L1 antagonist. In some embodiments, the Notch pathway inhibitor is an antibody that specifically binds human Notch2 and/or Notch3 and the immunotherapeutic agent is a PD-L2 antagonist. In some embodiments, the Notch pathway inhibitor is an antibody that specifically binds human Notch2 and/or Notch3 and the immunotherapeutic agent is a CTLA-4 antagonist. In some embodiments, the Notch pathway inhibitor is an antibody that specifically binds human Notch2 and/or Notch3 and the immunotherapeutic agent is a CD80 antagonist. In some embodiments, the Notch pathway inhibitor is an antibody that specifically binds human Notch2 and/or Notch3 and the immunotherapeutic agent is a CD86 antagonist. In some embodiments, the Notch pathway inhibitor is an antibody that specifically binds human Notch2 and/or Notch3 and the immunotherapeutic agent is a KIR antagonist. In some embodiments, the Notch pathway inhibitor is an antibody that specifically binds human Notch2 and/or Notch3 and the immunotherapeutic agent is a Tim-3 antagonist. In some embodiments, the Notch pathway inhibitor is an antibody that specifically binds human Notch2 and/or Notch3 and the immunotherapeutic agent is a LAG3 antagonist. In some embodiments, the Notch pathway inhibitor is an antibody that specifically binds human Notch2 and/or Notch3 and the immunotherapeutic agent is a TIGIT antagonist. In some embodiments, the Notch pathway inhibitor is an antibody that specifically binds human Notch2 and/or Notch3 and the immunotherapeutic agent is a CD96 antagonist. In some embodiments, the Notch pathway inhibitor is an antibody that specifically binds human Notch2 and/or Notch3 and the immunotherapeutic agent is an IDO1 antagonist. In some embodiments, the Notch pathway inhibitor is an antibody that specifically binds human Notch2 and/or Notch3 and the immunotherapeutic agent is a CD28 agonist. In some embodiments, the Notch pathway inhibitor is an antibody that specifically binds human Notch2 and/or Notch3 and the immunotherapeutic agent is a 4-1BB agonist. In some embodiments, the Notch pathway inhibitor is an antibody that specifically binds human Notch2 and/or Notch3 and the immunotherapeutic agent is an OX40 agonist. In some embodiments, the Notch pathway inhibitor is an antibody that specifically binds human Notch2 and/or Notch3 and the immunotherapeutic agent is a CD27 agonist. In some embodiments, the Notch pathway inhibitor is an antibody that specifically binds human Notch2 and/or Notch3 and the immunotherapeutic agent is a CD80 agonist. In some embodiments, the Notch pathway inhibitor is an antibody that specifically binds human Notch2 and/or Notch3 and the immunotherapeutic agent is a CD86 agonist. In some embodiments, the Notch pathway inhibitor is an antibody that specifically binds human Notch2 and/or Notch3 and the immunotherapeutic agent is a CD40 agonist. In some embodiments, the Notch pathway inhibitor is an antibody that specifically binds human Notch2 and/or Notch3 and the immunotherapeutic agent is a GITR agonist. In some embodiments, the Notch pathway inhibitor is an antibody that specifically binds human Notch2 and/or Notch3 and the immunotherapeutic agent is a cytokine. In some embodiments, the Notch pathway inhibitor is an antibody that specifically binds human Notch2 and/or Notch3 and the immunotherapeutic agent is an interferon. In some embodiments, the Notch pathway inhibitor is an antibody that specifically binds human Notch2 and/or Notch3 and the immunotherapeutic agent is a lymphokine.

In some embodiments of the methods described herein, the Notch receptor antagonist is an antibody that specifically binds human Notch1, wherein the antibody comprises a heavy chain CDR1 comprising RGYWIE (SEQ ID NO:46), a heavy chain CDR2 comprising QILPGT-GRTNYNEKFKG (SEQ ID NO:47), and a heavy chain CDR3 comprising FDGNYGYYAMDY (SEQ ID NO:48), and/or a light chain CDR1 comprising RSST-GAVTTSNYAN (SEQ ID NO:49), a light chain CDR2 comprising GTNNRAP (SEQ ID NO:50), and a light chain CDR3 comprising ALWYSNHWVFGGGTKL (SEQ ID NO:51). In some embodiments, the antibody comprises a heavy chain CDR1 comprising RGYWIE (SEQ ID NO:46), a heavy chain CDR2 comprising QILPGT-GRTNYNEKFKG (SEQ ID NO:47), and a heavy chain CDR3 comprising FDGNYGYYAMDY (SEQ ID NO:48), and a light chain CDR1 comprising RSSTGAVTTSNYAN (SEQ ID NO:49), a light chain CDR2 comprising GTNN-RAP (SEQ ID NO:50), and a light chain CDR3 comprising ALWYSNHWVFGGGTKL (SEQ ID NO:51).

In certain embodiments of the methods described herein, the Notch receptor antagonist is an antibody that specifically binds human Notch1, wherein the antibody comprises a heavy chain CDR1 comprising RGYWIE (SEQ ID NO:46), a heavy chain CDR2 comprising QILPGT-GRTNYNEKFKG (SEQ ID NO:47), and a heavy chain CDR3 comprising FDGNYGYYAMDY (SEQ ID NO:48), and a light chain CDR1 comprising RSSTGAVTTSNYAN (SEQ ID NO:49), a light chain CDR2 comprising GTNN-RAP (SEQ ID NO:50), and a light chain CDR3 comprising ALWYSNHWVFGGGTKL (SEQ ID NO:51) and is administered in combination with an immunotherapeutic agent. In some embodiments, the immunotherapeutic agent is an antibody that specifically binds PD-1. In some embodiments, the immunotherapeutic agent is an antibody that specifically binds PD-L1.

In certain embodiments of any of the methods described herein, the Notch receptor antagonist is an antibody that specifically binds human Notch1, wherein the antibody comprises a heavy chain variable region having at least about 90%, at least about 95% or 100% sequence identity to SEQ ID NO:52 and/or a light chain variable region having at least about 90%, at least about 95% or 100% sequence identity to SEQ ID NO:53. In some embodiments, the Notch receptor antagonist is an antibody which comprises a heavy chain variable region having at least about 90%, at least about 95%, 96%, 97%, 98%, or 99% sequence identity to SEQ ID NO:52, and a light chain variable region having at least about 90%, at least about 95%, 96%, 97%, 98%, or 99% sequence identity to SEQ ID NO:53. In some embodiments, the Notch receptor antagonist is an antibody which comprises a heavy chain variable region comprising SEQ ID NO:52 and a light chain variable region comprising SEQ ID NO:53.

In some embodiments, the Notch pathway inhibitor is antibody brontictuzumab (OMP-52M51).

In certain embodiments of any of the methods described herein, the Notch pathway inhibitor is an antibody that specifically binds human Notch1 and the immunotherapeutic agent is a PD-1 antagonist. In some embodiments, the Notch pathway inhibitor is an antibody that specifically binds human Notch1 and the immunotherapeutic agent is a PD-L1 antagonist. In some embodiments, the Notch pathway inhibitor is an antibody that specifically binds human Notch1 and the immunotherapeutic agent is a PD-L2 antagonist. In some embodiments, the Notch pathway inhibitor is an antibody that specifically binds human Notch1 and the immunotherapeutic agent is a CTLA-4 antagonist. In some embodiments, the Notch pathway inhibitor is an antibody that specifically binds human Notch1 and the immunotherapeutic agent is a CD80 antagonist. In some embodiments, the Notch pathway inhibitor is an antibody that specifically binds human Notch1 and the immunotherapeutic agent is a CD86 antagonist. In some embodiments, the Notch pathway inhibitor is an antibody that specifically binds human Notch1 and the immunotherapeutic agent is a KIR antagonist. In some embodiments, the Notch pathway inhibitor is an antibody that specifically binds human Notch1 and the immunotherapeutic agent is a Tim-3 antagonist. In some embodiments, the Notch pathway inhibitor is an antibody that specifically binds human Notch2 and/or Notch3 and the immunotherapeutic agent is a LAG3 antagonist. In some embodiments, the Notch pathway inhibitor is an antibody that specifically binds human Notch1 and the immunotherapeutic agent is a TIGIT antagonist. In some embodiments, the Notch pathway inhibitor is an antibody that specifically binds human Notch1 and the immunotherapeutic agent is a CD96 antagonist. In some embodiments, the Notch pathway inhibitor is an antibody that specifically binds human Notch1 and the immunotherapeutic agent is an IDO1 antagonist. In some embodiments, the Notch pathway inhibitor is an antibody that specifically binds human Notch1 and the immunotherapeutic agent is a CD28 agonist. In some embodiments, the Notch pathway inhibitor is an antibody that specifically binds human Notch1 and the immunotherapeutic agent is a 4-1BB agonist. In some embodiments, the Notch pathway inhibitor is an antibody that specifically binds human Notch1 and the immunotherapeutic agent is an OX40 agonist. In some embodiments, the Notch pathway inhibitor is an antibody that specifically binds human Notch1 and the immunotherapeutic agent is a CD27 agonist. In some embodiments, the Notch pathway inhibitor is an antibody that specifically binds human Notch1 and the immunotherapeutic agent is a CD80 agonist. In some embodiments, the Notch pathway inhibitor is an antibody that specifically binds human Notch1 and the immunotherapeutic agent is a CD86 agonist. In some embodiments, the Notch pathway inhibitor is an antibody that specifically binds human Notch1 and the immunotherapeutic agent is a CD40 agonist. In some embodiments, the Notch pathway inhibitor is an antibody that specifically binds human Notch1 and the immunotherapeutic agent is a GITR agonist. In some embodiments, the Notch pathway inhibitor is an antibody that specifically binds human Notch1 and the immunotherapeutic agent is a cytokine. In some embodiments, the Notch pathway inhibitor is an antibody that specifically binds human Notch1 and the immunotherapeutic agent is an interferon. In some embodiments, the Notch pathway inhibitor is an antibody that specifically binds human Notch1 and the immunotherapeutic agent is a lymphokine.

The present invention further provides compositions comprising Notch pathway inhibitors and compositions comprising immunotherapeutic agents. In some embodiments, a composition comprises a DLL4 antagonist described herein. In some embodiments, a composition comprises an antibody that specifically binds DLL4 described herein. In some embodiments, a composition comprises a Notch receptor antagonist described herein. In some embodiments, a composition comprises an antibody that specifically binds Notch2 and/or Notch3 described herein. In some embodiments, a composition comprises an antibody that specifically binds Notch1 described herein. In some embodiments, a composition comprises an immunotherapeutic agent described herein.

In some embodiments, a composition is a pharmaceutical composition comprising a Notch pathway inhibitor and a pharmaceutically acceptable vehicle. In some embodiments, a composition is a pharmaceutical composition comprising an immunotherapeutic agent and a pharmaceutically acceptable vehicle. The pharmaceutical compositions find use in modulating immune responses in human patients, particularly immune responses to tumors. The pharmaceutical compositions find use in inhibiting tumor cell growth in human patients. The pharmaceutical compositions find use in treating cancer in human patients. The pharmaceutical compositions find use in any of the methods described herein. In some embodiments, a Notch pathway inhibitor described herein finds use in the manufacture of a medicament for the treatment of cancer in combination with at least one immunotherapeutic agent. In some embodiments, a DLL4 antagonist described herein finds use in the manufacture of a medicament for the treatment of cancer in combination with at least one immunotherapeutic agent. In some embodiments, a Notch receptor antagonist described herein finds use in the manufacture of a medicament for the treatment of cancer in combination with at least one immunotherapeutic agent.

Formulations and/or pharmaceutical compositions are prepared for storage and use by combining a therapeutic agent of the present invention with a pharmaceutically acceptable carrier, excipient, and/or stabilizer as a sterile lyophilized powder, aqueous solution, etc. (*Remington: The Science and Practice of Pharmacy*, 22$^{nd}$ Edition, 2012, Pharmaceutical Press, London). Those of skill in the art generally consider pharmaceutically acceptable carriers, excipients, and/or stabilizers to be inactive ingredients of a formulation or pharmaceutical composition.

Suitable carriers, excipients, or stabilizers comprise non-toxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (such as less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose, or sorbitol; salt-forming counter-ions such as sodium; metal complexes (e.g. Zn-protein complexes); and/or non-ionic surfactants such as polysorbate (TWEEN) or polyethylene glycol (PEG).

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. As described herein, pharmaceutical carriers are considered to be inactive ingredients of a formulation or composition. Conventional tableting ingredients include corn starch, lactose, sucrose, sorbitol, talc, stearic acid, magnesium stearate, dicalcium phosphate or gums, and other diluents (e.g. water) to form a solid pre-formulation composition containing a homogeneous mixture of a compound of the present invention, or a non-toxic pharmaceutically acceptable salt thereof. The solid pre-formulation composition is then subdivided into unit dosage forms of the type described above. The tablets, pills, etc., of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, including a number of polymeric acids and mixtures of polymeric acids with such materials as shellac, cetyl alcohol and cellulose acetate.

Pharmaceutical formulations may include the Notch pathway inhibitors and/or the immunotherapeutic agents of the present invention complexed with liposomes. Liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The Notch pathway inhibitors and/or immunotherapeutic agents can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, 22$^{nd}$ Edition, 2012, Pharmaceutical Press, London.

In addition, sustained-release preparations comprising Notch pathway inhibitors and/or immunotherapeutic agents can be prepared. Suitable examples of sustained-release preparations include semi-permeable matrices of solid hydrophobic polymers containing the agent, which matrices are in the form of shaped articles (e.g., films or microcapsules). Examples of sustained-release matrices include polyesters, hydrogels such as poly(2-hydroxyethyl-methacrylate) or poly(vinylalcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The Notch pathway inhibitors and immunotherapeutic agents are administered as appropriate pharmaceutical compositions to a human patient according to known methods. The pharmaceutical compositions can be administered in any number of ways for either local or systemic treatment. Suitable methods of administration include, but are not limited to, intravenous (administration as a bolus or by continuous infusion over a period of time), intraarterial, intramuscular (injection or infusion), intratumoral, intraperitoneal, intracerobrospinal, subcutaneous, intra-articular, intrasynovial, intracranial (e.g., intrathecal or intraventricular), or oral. In additional, administration can be topical, (e.g., transdermal patches, ointments, lotions, creams, gels, drops, suppositories, sprays, liquids and powders) or pulmonary (e.g., by inhalation or insufflation of powders or aerosols, including by nebulizer; intratracheal, intranasal, epidermal and transdermal).

For the treatment of a disease, the appropriate dosage(s) of a Notch pathway inhibitor in combination with an immunotherapeutic agent of the present invention depends on the type of disease to be treated, the severity and course of the disease, the responsiveness of the disease, whether the inhibitors are administered for therapeutic or preventative purposes, previous therapy, the patient's clinical history, and so on, all at the discretion of the treating physician. The Notch pathway inhibitor can be administered one time or as a series of treatments spread over several days to several months, or until a cure is effected or a diminution of the disease state is achieved (e.g., reduction in tumor size). The immunotherapeutic agent can be administered one time or as a series of treatments spread over several days to several months, or until a cure is effected or a diminution of the disease state is achieved (e.g., reduction in tumor size). Optimal dosing schedules for each agent can be calculated from measurements of drug accumulation in the body of the patient and will vary depending on the relative potency of an individual agent. The administering physician can determine optimum dosages, dosing methodologies, and repetition rates.

In some embodiments, combined administration includes co-administration in a single pharmaceutical formulation. In some embodiments, combined administration includes using separate formulations and consecutive administration in either order but generally within a time period such that all active agents can exert their biological activities simultaneously. In some embodiments, combined administration includes using separate formulations and a staggered dosing regimen. In some embodiments, combined administration includes using separate formulations and administration in a specific order. In some embodiments, combined administration includes using separate formulations and administration of the agents in a specific order and in a staggered dosing regimen.

In certain embodiments, dosage of a Notch pathway inhibitor is from about 0.01 µg to about 100 mg/kg of body weight, from about 0.1 µg to about 100 mg/kg of body weight, from about 1 µg to about 100 mg/kg of body weight, from about 1 µg to about 100 mg/kg of body weight, about 1 µg to about 80 mg/kg of body weight from about 10 mg to about 100 mg/kg of body weight, from about 10 mg to about 75 mg/kg of body weight, or from about 10 mg to about 50 mg/kg of body weight. In certain embodiments, the dosage of the Notch pathway inhibitor is from about 0.01 mg to about 10 mg/kg of body weight. In certain embodiments, the dosage of the Notch pathway inhibitor is from about 0.01 mg to about 5 mg/kg of body weight. In certain embodiments, the dosage of the Notch pathway inhibitor is from about 0.05 mg to about 5 mg/kg of body weight. In certain embodiments, the dosage of the Notch pathway inhibitor is from about 0.1 mg to about 20 mg/kg of body weight. In certain embodiments, the dosage of the Notch pathway inhibitor is from about 0.5 mg to about 10 mg/kg of body weight. In some embodiments, the Notch pathway inhibitor is administered to the subject at a dosage of about 2 mg/kg to about 15 mg/kg. In some embodiments, the Notch pathway inhibitor is administered to the subject at a dosage of about 5 mg/kg to about 15 mg/kg. In certain embodiments, the Notch pathway inhibitor is administered once or more daily, weekly, monthly, or yearly. In certain embodiments, the Notch pathway inhibitor is administered once every week. In certain embodiments, the Notch pathway inhibitor is administered once every two weeks. In certain embodiments, the Notch pathway inhibitor is administered once every three weeks. In certain embodiments, the Notch pathway inhibitor is administered once every four weeks.

In certain embodiments, dosage of an immunotherapeutic agent is from about 0.01 µg to about 100 mg/kg of body weight, from about 0.1 µg to about 100 mg/kg of body weight, from about 1 µg to about 100 mg/kg of body weight, from about 1 mg to about 100 mg/kg of body weight, about 1 mg to about 80 mg/kg of body weight from about 10 mg to about 100 mg/kg of body weight, from about 10 mg to about 75 mg/kg of body weight, or from about 10 mg to about 50 mg/kg of body weight. In certain embodiments, the dosage of an immunotherapeutic agent is from about 0.01 mg to about 10 mg/kg of body weight. In certain embodiments, the dosage of an immunotherapeutic agent is from about 0.01 mg to about 5 mg/kg of body weight. In certain embodiments, the dosage of an immunotherapeutic agent is from about 0.05 mg to about 10 mg/kg of body weight. In certain embodiments, the dosage of an immunotherapeutic agent is from about 0.1 mg to about 20 mg/kg of body weight. In some embodiments, an immunotherapeutic agent is administered to the subject at a dosage of about 2 mg/kg to about 15 mg/kg. In some embodiments, the Notch pathway inhibitor is administered to the subject at a dosage of about 5 mg/kg to about 15 mg/kg. In certain embodiments, an immunotherapeutic agent is administered once or more daily, weekly, monthly, or yearly. In certain embodiments, an immunotherapeutic agent is administered twice a week. In certain embodiments, an immunotherapeutic agent is administered once every week. In certain embodiments, an immunotherapeutic agent is administered once every two weeks. In certain embodiments, an immunotherapeutic agent is administered once every three weeks. In certain embodiments, an immunotherapeutic agent is administered once every four weeks.

In some embodiments, dosage of an immunotherapeutic agent is determined by what is considered "standard-of-care" for a particular agent by those of skill in the art (e.g., treating physicians).

In some embodiments, an inhibitor may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

The present invention provides methods of treating cancer in a subject comprising using a dosing strategy for administering two or more agents that may reduce side effects and/or toxicities associated with administration of a Notch pathway inhibitor and/or an immunotherapeutic agent. In some embodiments, a method for treating cancer in a human subject comprises administering to the subject a therapeutically effective dose of a Notch pathway inhibitor in combination with a therapeutically effective dose of an immunotherapeutic agent, wherein one or both of the inhibitors are administered according to an intermittent dosing strategy. In some embodiments, the intermittent dosing strategy comprises administering an initial dose of a Notch pathway inhibitor to the subject, and administering subsequent doses of the Notch pathway inhibitor about once every 2 weeks. In some embodiments, the intermittent dosing strategy comprises administering an initial dose of a Notch pathway inhibitor to the subject, and administering subsequent doses of the Notch pathway inhibitor about once every 3 weeks. In some embodiments, the intermittent dosing strategy comprises administering an initial dose of a Notch pathway inhibitor to the subject, and administering subsequent doses of the Notch pathway inhibitor about once every 4 weeks. In some embodiments, the Notch pathway inhibitor is administered using an intermittent dosing strategy and the immunotherapeutic agent is administered once a week, once every two weeks, or once every three weeks.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. Combination therapy comprising an immunotherapeutic agent may allow one agent to enhance the immune response to a tumor or tumor cells while the second agent may be effective at killing tumor cells more directly.

In some embodiments, the combination of a Notch pathway inhibitor and an immunotherapeutic agent results in additive or synergetic results. In some embodiments, the combination therapy results in an increase in the therapeutic index of the Notch pathway inhibitor. In some embodiments, the combination therapy results in an increase in the therapeutic index of the immunotherapeutic agent. In some embodiments, the combination therapy results in a decrease in the toxicity and/or side effects of the Notch pathway inhibitor. In some embodiments, the combination therapy results in a decrease in the toxicity and/or side effects of the immunotherapeutic agent.

The treating physician can estimate repetition rates for dosing based on measured residence times and concentrations of the drug in bodily fluids or tissues. The progress of therapy can be monitored by conventional techniques and assays.

In certain embodiments, in addition to administering a Notch pathway inhibitor in combination with an immunotherapeutic agent, treatment methods may further comprise administering at least one additional therapeutic agent prior to, concurrently with, and/or subsequently to administration of the Notch pathway inhibitor and/or the immunotherapeutic agent.

In some embodiments, the additional therapeutic agent(s) will be administered substantially simultaneously or concurrently with the Notch pathway inhibitor or the immunotherapeutic agent. For example, a subject may be given the Notch pathway inhibitor and the immunotherapeutic agent while undergoing a course of treatment with the additional therapeutic agent (e.g., a chemotherapeutic agent). In certain embodiments, the Notch pathway inhibitor and the immunotherapeutic agent will be administered within 1 year of the treatment with the additional therapeutic agent. In certain alternative embodiments, the Notch pathway inhibitor and the immunotherapeutic agent will be administered within 10, 8, 6, 4, or 2 months of any treatment with the additional therapeutic agent. In certain other embodiments, the Notch pathway inhibitor and the immunotherapeutic agent will be administered within 4, 3, 2, or 1 week of any treatment with the additional therapeutic agent. In some embodiments, the Notch pathway inhibitor and the immunotherapeutic agent will be administered within 5, 4, 3, 2, or 1 days of any treatment with the additional therapeutic agent. It will further be appreciated that the agents or treatment may be administered to the subject within a matter of hours or minutes (i.e., substantially simultaneously) with the Notch pathway inhibitor or the immunotherapeutic agent.

Therapeutic agents that may be administered in combination with a Notch pathway inhibitor and an immunotherapeutic agent include chemotherapeutic agents. Thus, in some embodiments, the method or treatment involves the administration of a Notch pathway inhibitor and immunotherapeutic agent of the present invention in combination with a chemotherapeutic agent or cocktail of multiple different chemotherapeutic agents. Treatment with a Notch pathway inhibitor and immunotherapeutic agent can occur prior to, concurrently with, or subsequent to administration of chemotherapies. Preparation and dosing schedules for such chemotherapeutic agents can be used according to manufacturers' instructions or as determined empirically by the skilled practitioner. Preparation and dosing schedules for such chemotherapy are also described in *Chemotherapy Service*, 1992, M. C. Perry, Editor, Williams & Wilkins, Baltimore, Md.

Chemotherapeutic agents useful in the instant invention include, but are not limited to, alkylating agents such as thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; platinum analogs or platinum complex such as cisplatin and carboplatin; platinum; etoposide (VP-16); ifosfamide; mitomycin C; mitoxantrone; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene; and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1.

In some embodiments, a DLL4 antagonist is administered in combination with an immune checkpoint inhibitor and at least one chemotherapeutic agent. In some embodiments, an anti-DLL4 antibody is administered in combination with an anti-PD-1 antibody and at least one chemotherapeutic agent. In some embodiments, demcizumab is administered in combination with pembrolizumab and at least one chemotherapeutic agent. In some embodiments, demcizumab is administered in combination with pembrolizumab, carboplatin, and pemetrexed. In some embodiments, demcizumab is administered in combination with pembrolizumab, carboplatin, and pemetrexed for the treatment of lung cancer. In some embodiments, demcizumab is administered in combination with pembrolizumab, carboplatin, and pemetrexed for the treatment of NSCLC. In some embodiments, demcizumab is administered in combination with nivolumab and at least one chemotherapeutic agent. In some embodiments, demcizumab is administered in combination with nivolumab, carboplatin, and pemetrexed. In some embodiments, demcizumab is administered in combination with nivolumab, carboplatin, and pemetrexed for the treatment of lung cancer. In some embodiments, demcizumab is administered in combination with nivolumab, carboplatin, and pemetrexed for the treatment of NSCLC.

In some embodiments, an additional therapeutic agent that may be administered in combination with a Notch pathway inhibitor and an immunotherapeutic agent is an agent such as a small molecule. For example, treatment can involve the combined administration of a Notch pathway inhibitor and an immunotherapeutic agent with a small molecule that acts as an inhibitor against tumor-associated proteins including, but not limited to, EGFR, HER2 (ErbB2), and/or VEGF. In some embodiments, a Notch pathway inhibitor and an immunotherapeutic agent are administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), mereletinib (AZD9291), and pazopanib (GW786034B). In some embodiments, an additional therapeutic agent comprises a mTOR inhibitor.

In some embodiments, an additional therapeutic agent comprises a biological molecule, such as an antibody. For example, treatment can involve the combined administration of a Notch pathway inhibitor and an immunotherapeutic agent with antibodies against tumor-associated proteins including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that inhibits a cancer stem cell pathway. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

Furthermore, treatment can involve the combined administration of a Notch pathway inhibitor and an immunotherapeutic agent with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician.

In some embodiments, treatment can involve the combined administration of a Notch pathway inhibitor and an immunotherapeutic agent with a growth factor selected from the group consisting of, but not limited to: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, IL-1, IL-2, IL-3, IL-4, IL-5, IL-6, IL-7, IL-12, IL-15, and IL-18.

In certain embodiments, treatment can involve the combined administration of a Notch pathway inhibitor and an immunotherapeutic agent with radiation therapy. Treatment with a Notch pathway inhibitor and an immunotherapeutic agent can occur prior to, concurrently with, or subsequent to administration of radiation therapy. Dosing schedules for such radiation therapy can be determined by the skilled medical practitioner.

III. Notch Pathway Inhibitors

The present invention provides Notch pathway inhibitors described herein for use in methods of modulating immune responses, in methods of inhibiting tumor growth, and/or in methods of treating cancer, in combination with a second agent, wherein the second agent is an immunotherapeutic agent.

In some embodiments of the methods described herein, the Notch pathway inhibitor is a DLL4 antagonist. The DLL4 antagonists can be referred to herein as "DLL4-binding agents". In certain embodiments, the DLL4-binding agent specifically binds human DLL4. In certain embodiments, in addition to specifically binding DLL4, the DLL4-binding agent specifically binds at least one additional target or antigen. In some embodiments, the DLL4-binding agent is a polypeptide. In some embodiments, the DLL4-binding agent is an antibody. In certain embodiments, the DLL4-binding agent is a bispecific antibody. In certain embodiments, the DLL4-binding agent is a heterodimeric bispecific molecule. In some embodiments, the DLL4-binding agent is a homodimeric bispecific molecule. In some embodiments, the DLL4-binding agent is a bifunctional molecule comprising a DLL4-binding agent and an immunotherapeutic agent.

In certain embodiments, the DLL4 antagonist specifically binds the extracellular domain of human DLL4. In some embodiments, the DLL4 antagonist is an antibody. In some embodiments, the DLL4 antagonist specifically binds an epitope within amino acids 27-217 of the extracellular domain of human DLL4 (SEQ ID NO:17). In some embodiments, the DLL4 antagonist specifically binds within the N-terminal region of human DLL4 (SEQ ID NO:14). In some embodiments, the DLL4 antagonist binds an epitope comprising amino acids 66-73 (QAVVSPGP; SEQ ID NO:18) of human DLL4. In some embodiments, the DLL4 antagonist binds an epitope comprising amino acids 139-146 (LISKIAIQ; SEQ ID NO:19) of human DLL4. In some embodiments, the DLL4 antagonist binds an epitope comprising amino acids 66-73 (QAVVSPGP; SEQ ID NO:18) and amino acids 139-146 (LISKIAIQ; SEQ ID NO:19) of human DLL4.

In certain embodiments, the DLL4 antagonist (e.g., an antibody) binds human DLL4 with a dissociation constant ($K_D$) of about 1 μM or less, about 100 nM or less, about 40 nM or less, about 20 nM or less, about 10 nM or less, or about 1 nM or less. In certain embodiments, the DLL4 antagonist binds human DLL4 with a $K_D$ of about 40 nM or less, about 20 nM or less, about 10 nM or less, or about 1 nM or less. In certain embodiments, the DLL4 antagonist binds human DLL4 with a $K_D$ of about 1 nM. In certain embodiments, the DLL4 antagonist binds human DLL4 with a $K_D$ of about 0.8 nM. In certain embodiments, the DLL4 antagonist binds human DLL4 with a $K_D$ of about 0.6 nM. In certain embodiments, the DLL4 antagonist binds human DLL4 with a $K_D$ of about 0.5 nM. In certain embodiments, the DLL4 antagonist binds human DLL4 with a $K_D$ of about 0.4 nM. In some embodiments, the $K_D$ is measured by surface plasmon resonance. In some embodiments, the dissociation constant of the antagonist to DLL4 is the dissociation constant determined using a DLL4 fusion protein comprising a DLL4 extracellular domain (e.g., a DLL4 ECD-Fc fusion protein) immobilized on a Biacore chip.

In certain embodiments, the DLL4 antagonist (e.g., an antibody) binds DLL4 with a half maximal effective concentration ($EC_{50}$) of about 1 μM or less, about 100 nM or less, about 40 nM or less, about 20 nM or less, about 10 nM or less, or about 1 nM or less. In certain embodiments, the DLL4 antagonist binds human DLL4 with an $EC_{50}$ of about 40 nM or less, about 20 nM or less, about 10 nM or less, or about 1 nM or less.

In some embodiments of the methods described herein, the Notch pathway inhibitor is a Notch receptor antagonist. The Notch receptor antagonists can be referred to herein as "Notch-binding agents". In certain embodiments, the Notch-binding agent specifically binds human Notch1, Notch2, and/or Notch3. In certain embodiments, in addition to specifically binding at least one Notch receptor, the Notch-binding agent specifically binds at least one additional target or antigen. In some embodiments, the Notch-binding agent is a polypeptide. In some embodiments, the Notch-binding agent is an antibody. In certain embodiments, the Notch-binding agent is a bispecific antibody. In certain embodiments, the Notch-binding agent is a heterodimeric bispecific molecule. In some embodiments, the Notch-binding agent is a homodimeric bispecific molecule. In some embodiments, the Notch-binding agent is a bifunctional molecule comprising a Notch-binding agent and an immunotherapeutic agent.

In certain embodiments, the Notch receptor antagonist specifically binds human Notch1, Notch2, and/or Notch3. In certain embodiments, the Notch receptor antagonist specifically binds human Notch1. In certain embodiments, the Notch receptor antagonist specifically binds human Notch2 and/or Notch3. In certain embodiments, the Notch receptor antagonist specifically binds human Notch2 and Notch3. In some embodiments, the Notch receptor antagonist is an antibody.

In certain embodiments, the Notch receptor antagonist (e.g., an antibody) binds one or more human Notch receptors with a dissociation constant ($K_D$) of about 1 µM or less, about 100 nM or less, about 40 nM or less, about 20 nM or less, about 10 nM or less, or about 1 nM or less. In certain embodiments, the Notch receptor antagonist binds one or more human Notch receptors with a $K_D$ of about 40 nM or less, about 20 nM or less, about 10 nM or less, or about 1 nM or less. In certain embodiments, the Notch receptor antagonist binds one or more human Notch receptors with a $K_D$ of about 1 nM. In certain embodiments, the Notch receptor antagonist binds one or more human Notch receptors with a $K_D$ of about 0.8 nM. In certain embodiments, the Notch receptor antagonist binds one or more human Notch receptors with a $K_D$ of about 0.6 nM. In certain embodiments, the Notch receptor antagonist binds one or more human Notch receptors with a $K_D$ of about 0.5 nM. In certain embodiments, the Notch receptor antagonist binds one or more human Notch receptors with a $K_D$ of about 0.4 nM. In some embodiments, the $K_D$ is measured by surface plasmon resonance. In some embodiments, the dissociation constant of the antagonist or antibody to one or more human Notch receptors is the dissociation constant determined using a Notch receptor fusion protein comprising a Notch receptor extracellular domain (e.g., a Notch2 ECD-Fc fusion protein) immobilized on a Biacore chip.

In certain embodiments, the Notch receptor antagonist (e.g., an antibody) binds one or more human Notch receptors with a half maximal effective concentration ($EC_{50}$) of about 1 µM or less, about 100 nM or less, about 40 nM or less, about 20 nM or less, about 10 nM or less, or about 1 nM or less. In certain embodiments, the Notch receptor antagonist binds one or more human Notch receptors with an $EC_{50}$ of about 40 nM or less, about 20 nM or less, about 10 nM or less, or about 1 nM or less.

In certain embodiments, the Notch pathway inhibitor is a polypeptide. In certain embodiments, the Notch pathway inhibitor is an antibody. In certain embodiments, the antibody is an IgG antibody. In some embodiments, the antibody is an IgG1 antibody. In certain embodiments, the antibody is an IgG2 antibody. In some embodiments, the antibody is an IgG4 antibody. In certain embodiments, the antibody is a monoclonal antibody. In some embodiments, the antibody is a bispecific antibody. In certain embodiments, the antibody is a humanized antibody. In certain embodiments, the antibody is a human antibody. In certain embodiments, the antibody is an antibody fragment comprising an antigen-binding site.

The Notch pathway inhibitors (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al., Editors, 1994-present, *Current Protocols in Molecular Biology*, John Wiley & Sons, Inc., New York, N.Y.).

In a non-limiting example, the specific binding of a DLL4 antagonist (e.g., an antibody) to human DLL4 may be determined using ELISA. An ELISA assay comprises preparing DLL4 antigen, coating wells of a 96 well microtiter plate with antigen, adding to the wells the DLL4 antagonist or antibody conjugated to a detectable compound such as an enzymatic substrate (e.g., horseradish peroxidase or alkaline phosphatase), incubating for a period of time and detecting the presence of the binding agent or antibody. In some embodiments, the DLL4 antagonist or antibody is not conjugated to a detectable compound, but instead a second conjugated antibody that recognizes the DLL4 antagonist or antibody is added to the well. In some embodiments, instead of coating the well with DLL4 antigen, the DLL4 antagonist or antibody can be coated on the well, antigen is added to the coated well and then a second antibody conjugated to a detectable compound is added. One of skill in the art would be knowledgeable as to the parameters that can be modified and/or optimized to increase the signal detected, as well as other variations of ELISAs that can be used (see, e.g., Ausubel et al., Editors, 1994-present, *Current Protocols in Molecular Biology*, John Wiley & Sons, Inc., New York, N.Y.).

In an alternative non-limiting example, the specific binding of a DLL4 antagonist (e.g., an antibody) to human DLL4 may be determined using FACS. A FACS screening assay may comprise generating a cDNA construct that expresses an antigen as a fusion protein, transfecting the construct into cells, expressing the antigen on the surface of the cells, mixing the DLL4 antagonist with the transfected cells, and incubating for a period of time. The cells bound by the DLL4 antagonist may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening.

The binding affinity of an antagonist (e.g., antibody) to its target (e.g., DLL4 or Notch receptor) and the on-off rate of a binding agent-antigen interaction can be determined by competitive binding assays. In some embodiments, a competitive binding assay is a radioimmunoassay comprising the incubation of labeled antigen (e.g., $^3H$ or $^{125}I$), or fragment or variant thereof, with the agent of interest in the presence of increasing amounts of unlabeled antigen followed by the detection of the agent bound to the labeled antigen. The affinity of the agent for the antigen and the on-off rates can be determined from the data by Scatchard plot analysis. In some embodiments, Biacore kinetic analysis is used to determine the binding affinities and on-off rates of antagonists or binding agents. Biacore kinetic analysis comprises analyzing the binding and dissociation of binding agents from antigens (e.g., DLL4 or Notch proteins) that have been immobilized on the surface of a Biacore chip. In some embodiments, Biacore kinetic analyses can be used to study binding of different binding agents in qualitative epitope competition binding assays.

In certain embodiments of the methods described herein, a method comprises a Notch pathway inhibitor that is a DLL4-binding agent. In some embodiments, the DLL4-binding agent is a DLL4 antagonist. In some embodiments, the DLL4 antagonist is an antibody that specifically binds human DLL4. In some embodiments, the DLL4 antagonist is an antibody that specifically binds the extracellular domain of human DLL4. In some embodiments, the antibody that specifically binds the extracellular domain of human DLL4 comprises a heavy chain CDR1 comprising TAYYIH (SEQ ID NO:1), a heavy chain CDR2 comprising YISCYNGATNYNQKFKG (SEQ ID NO:2), YISSYNGATNYNQKFKG (SEQ ID NO:3), or YISVYNGATNYNQKFKG (SEQ ID NO:4), and a heavy chain CDR3 comprising RDYDYDVGMDY (SEQ ID NO:5). In some embodiments, the antibody further comprises a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the antibody comprises a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the DLL4 antagonist is an antibody which comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

In certain embodiments of the methods described herein, a method comprises an antibody that specifically binds the extracellular domain of human DLL4, wherein the antibody comprises a heavy chain variable region having at least about 80% sequence identity to SEQ ID NO:9, SEQ ID NO:10, or SEQ ID NO:11, and/or a light chain variable region having at least 80% sequence identity to SEQ ID NO:12. In certain embodiments, the antibody comprises a heavy chain variable region having at least about 85%, at least about 90%, at least about 95%, 96%, 97%, 98%, or 99% sequence identity to SEQ ID NO:9, SEQ ID NO:10, or SEQ ID NO:11. In certain embodiments, the antibody comprises a light chain variable region having at least about 85%, at least about 90%, at least about 95%, 96%, 97%, 98%, or 99% sequence identity to SEQ ID NO:12. In certain embodiments, the antibody comprises a heavy chain variable region having at least about 95% sequence identity to SEQ ID NO:9 and/or a light chain variable region having at least about 95% sequence identity to SEQ ID NO:12. In certain embodiments, the antibody comprises a heavy chain variable region comprising SEQ ID NO:9, and/or a light chain variable region comprising SEQ ID NO:12. In certain embodiments, the antibody comprises a heavy chain variable region comprising SEQ ID NO:9 and a light chain variable region comprising SEQ ID NO:12. In certain embodiments, the antibody comprises a heavy chain variable region having at least about 95% sequence identity to SEQ ID NO:10 and/or a light chain variable region having at least about 95% sequence identity to SEQ ID NO:12. In certain embodiments, the antibody comprises a heavy chain variable region comprising SEQ ID NO:10 and/or a light chain variable region comprising SEQ ID NO:12. In certain embodiments, the antibody comprises a heavy chain variable region comprising SEQ ID NO:10 and a light chain variable region comprising SEQ ID NO:12. In certain embodiments, the antibody comprises a heavy chain variable region having at least about 95% sequence identity to SEQ ID NO:11 and/or a light chain variable region having at least about 95% sequence identity to SEQ ID NO:12. In certain embodiments, the antibody comprises a heavy chain variable region comprising SEQ ID NO:11 and/or a light chain variable region comprising SEQ ID NO:12. In certain embodiments, the antibody comprises a heavy chain variable region comprising SEQ ID NO:11 and a light chain variable region comprising SEQ ID NO:12.

In certain embodiments of the methods described herein, a method comprises the antibody produced by the hybridoma deposited with the American Type Culture Collection (ATCC), at 10801 University Boulevard, Manassas, Va., 20110, under the conditions of the Budapest Treaty on Sep. 28, 2007 and having ATCC deposit number PTA-8670, also known as murine 21M18. The murine 21M18 antibody is described in detail in U.S. Pat. No. 7,750,124, filed Sep. 28, 2007.

In certain embodiments of the methods described herein, a method comprises an antibody comprising the heavy chain CDRs and light chain CDRs of the antibody produced by the hybridoma deposited with ATCC on Sep. 28, 2007 and having ATCC deposit number PTA-8670.

In certain embodiments of the methods described herein, a method comprises an antibody comprising the heavy chain variable region and the light chain variable region encoded by the plasmid DNA deposited with ATCC at 10801 University Boulevard, Manassas, Va., 20110, under the conditions of the Budapest Treaty on May 10, 2007, and having ATCC deposit number PTA-8425.

In certain embodiments of the methods described herein, a method comprises the antibody encoded by the plasmid DNA deposited with ATCC on May 10, 2007, having ATCC deposit number PTA-8425, also known as 21M18 H7L2 and OMP-21M18. The OMP-21M18 antibody is described in detail in U.S. Pat. No. 7,750,124, filed Sep. 28, 2007. This antibody is also known as demcizumab.

In certain embodiments of the methods described herein, a Notch pathway inhibitor is a polypeptide. The polypeptides include, but are not limited to, antibodies that specifically bind human DLL4. In certain embodiments, a polypeptide comprises one, two, three, four, five, and/or six of the CDRs of demcizumab (OMP-21M18). In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, a Notch pathway inhibitor comprises a polypeptide comprising a sequence selected from the group consisting of: SEQ ID NO:9, SEQ ID NO:10, SEQ ID NO:11, and SEQ ID NO:12.

In certain embodiments, a Notch pathway inhibitor comprises the heavy chain variable region and light chain variable region of demcizumab. In certain embodiments, a Notch pathway inhibitor comprises the heavy chain and light chain of the demcizumab (with or without the leader sequence). In certain embodiments, a Notch pathway inhibitor comprises, consists essentially of, or consists of, demcizumab.

In certain embodiments of the methods described herein, a method comprises a DLL4 antagonist (e.g., antibody) that competes for specific binding to human DLL4 with an antibody that comprises a heavy chain variable region comprising SEQ ID NO:10 and a light chain variable region comprising SEQ ID NO:12. In certain embodiments, the DLL4 antagonist competes with demcizumab for specific binding to human DLL4. In some embodiments, the DLL4 antagonist (e.g., an antibody) competes with demcizumab for specific binding to human DLL4 in an in vitro competitive binding assay.

In certain embodiments of the methods described herein, a method comprises a DLL4 antagonist (e.g., an antibody) that binds the same epitope, or essentially the same epitope, on human DLL4 as an antibody of the invention. In another embodiment, a DLL4 antagonist is an antibody that binds an epitope on human DLL4 that overlaps with the epitope on DLL4 bound by an antibody of the invention. In certain embodiments, the DLL4 antagonist (e.g., an antibody) binds the same epitope or essentially the same epitope on human DLL4 as demcizumab. In another embodiment, the DLL4 antagonist is an antibody that binds an epitope on human DLL4 that overlaps with the epitope on DLL4 bound by demcizumab.

In certain embodiments of the methods described herein, a method comprises a Notch pathway inhibitor that is a Notch-binding agent. In some embodiments, the Notch-binding agent is a Notch receptor antagonist. In some embodiments, the Notch receptor antagonist is an antibody that specifically binds human Notch2 and/or Notch3. In some embodiments, the Notch receptor antagonist is an antibody that specifically binds the extracellular domain of human Notch2 and/or Notch3. In some embodiments, the antibody that specifically binds the extracellular domain of human Notch2 and/or Notch3 comprises a heavy chain CDR1 comprising SSSGMS (SEQ ID NO:34), a heavy chain CDR2 comprising VIASSGSNTYYADSVKG (SEQ ID NO:35), and a heavy chain CDR3 comprising SIFYTT (SEQ ID NO:36). In some embodiments, the antibody further comprises a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39). In some embodiments, the antibody comprises a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39). In some embodiments, the Notch receptor antagonist is an antibody which comprises a heavy chain CDR1 comprising SSSGMS (SEQ ID NO:34), a heavy chain CDR2 comprising VIASSGSNTYYADSVKG (SEQ ID NO:35), and a heavy chain CDR3 comprising SIFYTT (SEQ ID NO:36); and a light chain CDR1 comprising RASQSVRSNYLA (SEQ ID NO:37), a light chain CDR2 comprising GASSRAT (SEQ ID NO:38), and a light chain CDR3 comprising QQYSNFPI (SEQ ID NO:39).

In certain embodiments of the methods described herein, a method comprises an antibody that specifically binds the extracellular domain of human Notch2 and/or Notch3, wherein the antibody comprises a heavy chain variable region having at least about 80% sequence identity to SEQ ID NO:40 and/or a light chain variable region having at least 80% sequence identity to SEQ ID NO:41. In certain embodiments, the antibody comprises a heavy chain variable region having at least about 85%, at least about 90%, at least about 95%, 96%, 97%, 98%, or 99% sequence identity to SEQ ID NO:40. In certain embodiments, the antibody comprises a light chain variable region having at least about 85%, at least about 90%, at least about 95%, 96%, 97%, 98%, or 99% sequence identity to SEQ ID NO:41. In certain embodiments, the antibody comprises a heavy chain variable region having at least about 95% sequence identity to SEQ ID NO:40 and/or a light chain variable region having at least about 95% sequence identity to SEQ ID NO:41. In certain embodiments, the antibody comprises a heavy chain variable region comprising SEQ ID NO:40 and/or a light chain variable region comprising SEQ ID NO:41. In certain embodiments, the antibody comprises a heavy chain variable region comprising SEQ ID NO:40 and a light chain variable region comprising SEQ ID NO:41.

In certain embodiments of the methods described herein, a method comprises an antibody comprising the heavy chain variable region and the light chain variable region encoded by the plasmid DNA deposited with ATCC at 10801 University Boulevard, Manassas, Va., 20110, under the conditions of the Budapest Treaty on Jul. 6, 2009, and having ATCC deposit number PTA-10170, also known as 59R5 and OMP-59R5. The OMP-59R5 antibody is described in detail in U.S. Pat. No. 8,226,943, filed Jul. 8, 2009. This antibody is also known as tarextumab.

In certain embodiments of the methods described herein, the Notch receptor antagonist is an antibody that specifically binds human Notch1. In some embodiments, the Notch receptor antagonist is an antibody that specifically binds a non-ligand binding membrane proximal region of the extracellular domain of human Notch1. In some embodiments, the antibody that specifically binds human Notch1 comprises a heavy chain CDR1 comprising RGYWIE (SEQ ID NO:46), a heavy chain CDR2 comprising QILPGTGRTNYNEKFKG (SEQ ID NO:47), and a heavy chain CDR3 comprising FDGNYGYYAMDY (SEQ ID NO:48). In some embodiments, the antibody further comprises a light chain CDR1 comprising RSSTGAVTTSNYAN (SEQ ID NO:49), a light chain CDR2 comprising GTNNRAP (SEQ ID NO:50), and a light chain CDR3 comprising ALWYSNHWVFGGGTKL (SEQ ID NO:51). In some embodiments, the antibody comprises a light chain CDR1 comprising RSSTGAVTTSNYAN (SEQ ID NO:49), a light chain CDR2 comprising GTNNRAP (SEQ ID NO:50), and a light chain CDR3 comprising ALWYSNHWVFGGGTKL (SEQ ID NO:51). In some embodiments, the Notch receptor antagonist is an antibody which comprises a heavy chain CDR1 comprising RGYWIE (SEQ ID NO:46), a heavy chain CDR2 comprising QILPGTGRTNYNEKFKG (SEQ ID NO:47), and a heavy chain CDR3 comprising FDGNYGYYAMDY (SEQ ID NO:48); and a light chain CDR1 comprising RSSTGAVTTSNYAN (SEQ ID NO:49), a light chain CDR2 comprising GTNNRAP (SEQ ID NO:50), and a light chain CDR3 comprising ALWYSNHWVFGGGTKL (SEQ ID NO:51).

In certain embodiments of the methods described herein, a method comprises an antibody that specifically binds human Notch1, wherein the antibody comprises a heavy chain variable region having at least about 80% sequence identity to SEQ ID NO:52 and/or a light chain variable region having at least 80% sequence identity to SEQ ID NO:53. In certain embodiments, the antibody comprises a heavy chain variable region having at least about 85%, at least about 90%, at least about 95%, 96%, 97%, 98%, or 99% sequence identity to SEQ ID NO:52. In certain embodiments, the antibody comprises a light chain variable region having at least about 85%, at least about 90%, at least about 95%, 96%, 97%, 98%, or 99% sequence identity to SEQ ID NO:53. In certain embodiments, the antibody comprises a heavy chain variable region having at least about 95% sequence identity to SEQ ID NO:52 and/or a light chain variable region having at least about 95% sequence identity to SEQ ID NO:53. In certain embodiments, the antibody comprises a heavy chain variable region comprising SEQ ID NO:52 and/or a light chain variable region comprising SEQ ID NO:53. In certain embodiments, the antibody comprises a heavy chain variable region comprising SEQ ID NO:52 and a light chain variable region comprising SEQ ID NO:53.

In certain embodiments of the methods described herein, a method comprises an antibody comprising the heavy chain CDRs and light chain CDRs of the antibody produced by the hybridoma deposited with the American Type Culture Collection (ATCC), at 10801 University Boulevard, Manassas, Va., 20110, under the conditions of the Budapest Treaty on Aug. 7, 2008 and having ATCC deposit number PTA-9405, also known as murine 52M51. The murine 52M51 antibody is described in detail in U.S. Pat. No. 8,435,513, filed Jul. 8, 2009.

In certain embodiments of the methods described herein, a method comprises an antibody comprising the heavy chain variable region and the light chain variable region encoded by the plasmid DNA deposited with ATCC at 10801 University Boulevard, Manassas, Va., 20110, under the conditions of the Budapest Treaty on Oct. 15, 2008, and having ATCC deposit number PTA-9549, also known as 52M51-H4L3 and OMP-h52M51. The OMP-h52M51 antibody is described in detail in U.S. Pat. No. 8,435,513, filed Jul. 8, 2009. This antibody is also known as brontictuzumab.

In certain embodiments of the methods described herein, a Notch pathway inhibitor is a polypeptide. The polypeptides include, but are not limited to, antibodies that specifically bind human Notch2 and/or Notch3, and antibodies that specifically bind human Notch1. In certain embodiments, a polypeptide comprises one, two, three, four, five, and/or six of the CDRs of tarextumab (OMP-59R5). In certain embodiments, a polypeptide comprises one, two, three, four, five, and/or six of the CDRs of brontictuzumab (OMP-h52M51). In some embodiments, a polypeptide comprises CDRs with up to four (i.e., 0, 1, 2, 3, or 4) amino acid substitutions per CDR. In certain embodiments, the heavy chain CDR(s) are contained within a heavy chain variable region. In certain embodiments, the light chain CDR(s) are contained within a light chain variable region.

In some embodiments, a Notch pathway inhibitor comprises a polypeptide comprising a sequence of SEQ ID NO:40 and/or SEQ ID NO:41.

In certain embodiments, a Notch pathway inhibitor comprises the heavy chain variable region and light chain variable region of tarextumab. In certain embodiments, a Notch pathway inhibitor comprises the heavy chain and light chain of the tarextumab (with or without the leader sequence). In certain embodiments, a Notch pathway inhibitor comprises, consists essentially of, or consists of, tarextumab.

In certain embodiments of the methods described herein, a method comprises a Notch receptor antagonist (e.g., antibody) that competes for specific binding to human Notch2 and/or Notch3 with an antibody that comprises a heavy chain variable region comprising SEQ ID NO:40 and a light chain variable region comprising SEQ ID NO:41. In certain embodiments, the Notch receptor antagonist competes with tarextumab for specific binding to human Notch2 and/or Notch3. In some embodiments, the Notch receptor antagonist (e.g., an antibody) competes with tarextumab for specific binding to human Notch2 and/or Notch3 in an in vitro competitive binding assay.

In certain embodiments of the methods described herein, a method comprises a Notch receptor antagonist (e.g., an antibody) that binds the same epitope, or essentially the same epitope, on human Notch2 and/or Notch3 as an antibody of the invention. In another embodiment, a Notch receptor antagonist is an antibody that binds an epitope on human Notch2 and/or Notch3 that overlaps with the epitope on Notch2 and/or Notch3 bound by an antibody of the invention. In certain embodiments, the Notch receptor antagonist (e.g., an antibody) binds the same epitope or essentially the same epitope on human Notch2 and/or Notch3 as tarextumab. In another embodiment, the Notch receptor antagonist is an antibody that binds an epitope on human Notch2 and/or Notch3 that overlaps with the epitope on Notch2 and/or Notch3 bound by tarextumab.

In some embodiments, a Notch pathway inhibitor comprises a polypeptide comprising a sequence of SEQ ID NO:52 and/or SEQ ID NO:53.

In certain embodiments, a Notch pathway inhibitor comprises the heavy chain variable region and light chain variable region of brontictuzumab. In certain embodiments, a Notch pathway inhibitor comprises the heavy chain and light chain of the brontictuzumab (with or without the leader sequence). In certain embodiments, a Notch pathway inhibitor comprises, consists essentially of, or consists of, brontictuzumab.

In certain embodiments of the methods described herein, a method comprises a Notch receptor antagonist (e.g., antibody) that competes for specific binding to human Notch1 with an antibody that comprises a heavy chain variable region comprising SEQ ID NO:52 and a light chain variable region comprising SEQ ID NO:53. In certain embodiments, the Notch receptor antagonist competes with brontictuzumab for specific binding to human Notch1. In some embodiments, the Notch receptor antagonist (e.g., an antibody) competes with brontictuzumab for specific binding to human Notch1 in an in vitro competitive binding assay.

In certain embodiments of the methods described herein, a method comprises a Notch receptor antagonist (e.g., an antibody) that binds the same epitope, or essentially the same epitope, on human Notch1 as an antibody of the invention. In another embodiment, a Notch receptor antagonist is an antibody that binds an epitope on human Notch1 that overlaps with the epitope on Notch1 bound by an antibody of the invention. In certain embodiments, the Notch receptor antagonist (e.g., an antibody) binds the same epitope or essentially the same epitope on human Notch1 as brontictuzumab. In another embodiment, the Notch receptor antagonist is an antibody that binds an epitope on human Notch1 that overlaps with the epitope on Notch1 bound by brontictuzumab.

In some embodiments, the Notch pathway inhibitor is a polyclonal antibody. Polyclonal antibodies can be prepared by any known method. In some embodiments, polyclonal antibodies are raised by immunizing an animal (e.g., a rabbit, rat, mouse, goat, donkey) by multiple subcutaneous or intraperitoneal injections of the relevant antigen (e.g., a purified peptide fragment, full-length recombinant protein, or fusion protein). The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from blood and/or ascites of the immunized animal. The polyclonal antibodies can be purified from serum or ascites according to standard methods in the art including, but not limited to, affinity chromatography, ion-exchange chromatography, gel electrophoresis, and dialysis.

In some embodiments, the Notch pathway inhibitor is a monoclonal antibody. Monoclonal antibodies can be prepared using hybridoma methods known to one of skill in the art. In some embodiments, using the hybridoma method, a mouse, hamster, rat, or other appropriate host animal, is immunized as described above to elicit from lymphocytes the production of antibodies that will specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen may be identified by a variety of methods including, but not limited to, immunoprecipitation, immunoblotting, and in vitro binding assay (e.g., flow cytometry, FACS, ELISA, and radioimmunoassay). The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques known to one skilled in the art. The polynucleotides encoding a monoclonal antibody are isolated from mature B-cells or hybridoma cells, such as by RT-PCR using oligonucleotide primers that specifically amplify genes encoding the heavy and light chains of the antibody, and their sequence is determined using conventional techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins. In other embodiments, recombinant monoclonal antibodies, or fragments thereof, can be isolated from phage display libraries.

The polynucleotide(s) encoding a monoclonal antibody can be further modified in a number of different manners using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. In some embodiments, site-directed or high-density mutagenesis of the variable region can be used to optimize specificity, affinity, etc. of a monoclonal antibody.

In some embodiments, the Notch pathway inhibitor is a humanized antibody. Typically, humanized antibodies are human immunoglobulins in which amino acid residues within the CDRs are replaced by amino acid residues from CDRs of a non-human species (e.g., mouse, rat, rabbit, hamster, etc.) that have the desired specificity, affinity, and/or binding capability using methods known to one skilled in the art. In some embodiments, the framework region amino acid residues of a human immunoglobulin are replaced with corresponding amino acid residues in an antibody from a non-human species. In some embodiments, the humanized antibody can be further modified by the substitution of additional amino acid residues either in the framework region and/or within the replaced non-human residues to further refine and optimize antibody specificity, affinity, and/or capability. In general, the humanized antibody will comprise variable domain regions containing all, or substantially all, of the CDRs that correspond to the non-human immunoglobulin whereas all, or substantially all, of the framework regions are those of a human immunoglobulin sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject.

In certain embodiments, the Notch pathway inhibitor is a human antibody. Human antibodies can be directly prepared using various techniques known in the art. In some embodiments, immortalized human B lymphocytes immunized in vitro or isolated from an immunized individual that produces an antibody directed against a target antigen can be generated. In some embodiments, the human antibody can be selected from a phage library, where that phage library expresses human antibodies. Alternatively, phage display technology can be used to produce human antibodies and antibody fragments in vitro, from immunoglobulin variable domain gene repertoires from unimmunized donors. Techniques for the generation and use of antibody phage libraries are well-known in the art and antibody phage libraries are commercially available Affinity maturation strategies including, but not limited to, chain shuffling and site-directed mutagenesis, are known in the art and may be employed to generate high affinity human antibodies.

In some embodiments, human antibodies can be made in transgenic mice that contain human immunoglobulin loci. These mice are capable, upon immunization, of producing the full repertoire of human antibodies in the absence of endogenous immunoglobulin production.

This invention also encompasses bispecific antibodies. In some embodiments, a bispecific antibody specifically recognizes human DLL4 or a human Notch receptor. Bispecific antibodies are capable of specifically recognizing and binding at least two different epitopes. The different epitopes can either be within the same molecule (e.g., two different epitopes on human DLL4) or on different molecules (e.g., one epitope on DLL4 and a different epitope on a second protein). In some embodiments, the bispecific antibody is a monoclonal human or a humanized antibody. In some embodiments, the bispecific antibody comprises an intact antibody. In some embodiments, the bispecific antibody is an antibody fragment. In certain embodiments, the antibody is multispecific. In some embodiments, the antibody can specifically recognize and bind a first antigen target (e.g., DLL4 or a Notch receptor) as well as a second antigen target (e.g., CD2, CD3, CD28, CD80 or CD86) or a Fc receptor (e.g., CD64, CD32, or CD16). In some embodiments, the antibody can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA. Techniques for making bispecific or multispecific antibodies are known by those skilled in the art.

In certain embodiments, the methods of the invention comprise a DLL4 antagonist which is a bispecific antibody that specifically binds human DLL4 and human VEGF. In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YIX$_1$X$_2$YX$_3$X$_4$ATNYNQKFKG (SEQ ID NO:26), wherein X$_1$ is serine or alanine, X$_2$ is serine, asparagine, or glycine, X$_3$ is asparagine or lysine, and X$_4$ is glycine, arginine, or aspartic acid, and a heavy chain CDR3 comprising RDYDYDVGMDY (SEQ ID NO:5); and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YIANYNRATNYNQKFKG (SEQ ID NO:24), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the a bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YIAGYKDATNYNQKFKG (SEQ ID NO:23), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22); wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

In some embodiments, the methods of the invention comprise a bispecific antibody that comprises a first antigen-binding site that specifically binds human VEGF, and a second antigen-binding site that specifically binds human DLL4, wherein the first antigen-binding site comprises a first heavy chain variable region of SEQ ID NO:30, the second antigen-binding site comprises a second heavy chain variable region of SEQ ID NO:29; and wherein the first and the second antigen-binding site comprises a first and a second light chain variable region of SEQ ID NO:12.

In some embodiments, the methods of the invention comprise a bispecific antibody that specifically binds human VEGF and specifically binds human DLL4, wherein the antibody comprises a first heavy chain of SEQ ID NO:32 and a second heavy chain of SEQ ID NO:31; and a first and a second light chain of SEQ ID NO:33.

In certain embodiments, the bispecific antibody specifically binds DLL4, as well as VEGF. In some embodiments, the bispecific antibody is a bispecific antibody disclosed in U.S. patent application Ser. No. 13/625,417, filed on Sep. 24, 2012. In some embodiments, the anti-VEGF/DLL4 bispecific antibody is 219R45-MB-21M18, 219R45-MB-21R79, 219R45-MB-21R75, or 219R45-MB-21R83 (also referred to as 305B83 or OMP-305B83) as disclosed in U.S. patent application Ser. No. 13/625,417, filed on Sep. 24, 2012. In some embodiments, the bispecific antibody is OMP-305B83.

In some embodiments, the bispecific antibody specifically binds DLL4 and specifically binds PD-1. In some embodiments, the bispecific antibody specifically binds DLL4 and specifically binds PD-L1.

In certain embodiments, the antibodies (or other polypeptides) described herein may be monospecific. For example, in certain embodiments, each of the one or more antigen-binding sites that an antibody contains is capable of binding (or binds) a homologous epitope on different proteins.

In certain embodiments, the Notch pathway inhibitor is an antibody fragment comprising an antigen-binding site. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from E. coli or other host cells, allowing for the production of large amounts of these fragments. In some embodiments, antibody fragments are isolated from antibody phage libraries as discussed herein. For example, methods can be used for the construction of Fab expression libraries to allow rapid and effective identification of monoclonal Fab fragments with the desired specificity for DLL4 or a Notch receptor or derivatives, fragments, analogs or homologs thereof. In some embodiments, antibody fragments are linear antibody fragments. In certain embodiments, antibody fragments are monospecific or bispecific. In certain embodiments, the Notch pathway inhibitor is a scFv. Various techniques can be used for the production of single-chain antibodies specific to human DLL4 or to a human Notch receptor.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis). In some embodiments, an antibody is modified to decrease its serum half-life.

The invention also encompasses Notch pathway inhibitors that are bispecific and/or bifunctional molecules. In some embodiments, the bispecific and/or bifunctional molecules are heterodimeric molecules. In some embodiments, the bispecific and/or bifunctional molecules are homodimeric molecules. In some embodiments, the homodimeric molecules are polypeptides. In some embodiments, the heterodimeric molecules are polypeptides. Generally the homodimeric molecule comprises two identical polypeptides. Generally the heterodimeric molecule comprises two non-identical polypeptides. In some embodiments, a heterodimeric molecule is capable of binding at least two targets, e.g., a bispecific agent. The targets may be, for example, two different proteins on a single cell or two different proteins on two separate cells. The term "arm" may be used herein to describe the structure of a homodimeric molecule, a heterodimeric molecule, and/or a bispecific antibody. In some embodiments, one "arm" may comprise an antigen-binding site from an antibody. In some embodiments, one "arm" may comprise a binding portion of a receptor. In some embodiments, a homodimeric bispecific molecule comprises two identical arms. In some embodiments, a heterodimeric bispecific molecule comprises two different arms. As used herein, a heterodimeric bispecific molecule can be a bispecific antibody.

In some embodiments, a heterodimeric bispecific molecule comprises a first arm which binds DLL4 and a second arm that comprises an immunotherapeutic agent. In some embodiments, the immunotherapeutic agent is an agonist of a target. In some embodiments, the immunotherapeutic agent is an antagonist of a target. In some embodiments, the immunotherapeutic agent is a lymphokine or a cytokine. In some embodiments, the immunotherapeutic agent is an immunoadhesion. In some embodiments, the immunotherapeutic agent is selected from the group consisting of, but not limited to, granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, GITRL, OX40 ligand, CD40L, anti-CD3 antibody, anti-CTLA-4 antibody, anti-OX40 antibody, anti-GITR antibody, anti-TIGIT antibody, anti-PD1 antibody, anti-PD-L1 antibody, anti-LAG-3 antibody, and anti-TIM-3 antibody.

In some embodiments, the heterodimeric bispecific molecule comprises a first arm which binds DLL4 and a second arm which binds PD-1. In some embodiments, the heterodimeric bispecific molecule comprises a first arm which binds DLL4 and a second arm which binds PD-L1. In some embodiments, the heterodimeric bispecific molecule comprises a first arm which binds DLL4 and a second arm which binds CTLA-4. In some embodiments, the heterodimeric bispecific molecule comprises a first arm which binds DLL4 and a second arm which binds TIGIT. In some embodiments, the heterodimeric bispecific molecule comprises a first arm which binds DLL4 and a second arm which binds GITR. In some embodiments, the heterodimeric bispecific molecule comprises a first arm which binds DLL4 and a second arm which binds OX40. In some embodiments, the heterodimeric bispecific molecule comprises a first arm which binds DLL4 and a second arm which binds CD40. In some embodiments, the heterodimeric bispecific molecule comprises a first arm which binds DLL4 and a second arm binds LAG-3.

In some embodiments, a heterodimeric bispecific molecule comprises a first arm which binds a Notch receptor and a second arm that comprises an immunotherapeutic agent. In some embodiments, the immunotherapeutic agent is an agonist of a target. In some embodiments, the immunotherapeutic agent is an antagonist of a target. In some embodiments, the immunotherapeutic agent is a lymphokine or a cytokine. In some embodiments, the immunotherapeutic agent is an immunoadhesion. In some embodiments, the immunotherapeutic agent is selected from the group consisting of, but not limited to, granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, GITRL, OX40 ligand, CD40L, anti-CD3 antibody, anti-CTLA-4 antibody, anti-OX40 antibody, anti-GITR antibody, anti-TIGIT antibody, anti-PD1 antibody, anti-PD-L1 antibody, anti-LAG-3 antibody, and anti-TIM-3 antibody.

In some embodiments, the heterodimeric bispecific molecule comprises a first arm which binds a Notch receptor and a second arm which binds PD-1. In some embodiments, the heterodimeric bispecific molecule comprises a first arm which binds a Notch receptor and a second arm which binds PD-L1. In some embodiments, the heterodimeric bispecific molecule comprises a first arm which binds a Notch receptor and a second arm which binds CTLA-4. In some embodiments, the heterodimeric bispecific molecule comprises a first arm which binds a Notch receptor and a second arm which binds TIGIT. In some embodiments, the heterodimeric bispecific molecule comprises a first arm which binds a Notch receptor and a second arm which binds GITR. In some embodiments, the heterodimeric bispecific molecule comprises a first arm which binds a Notch receptor and a second arm which binds OX40. In some embodiments, the heterodimeric bispecific molecule comprises a first arm which binds a Notch receptor and a second arm which binds CD40. In some embodiments, the heterodimeric bispecific molecule comprises a first arm which binds a Notch receptor and a second arm binds LAG-3.

In some embodiments, the heterodimeric bispecific agent comprises two arms, wherein each arm comprises a human CH3 domain, wherein each CH3 domain is modified to promote formation of heterodimers. In some embodiments, the first and second CH3 domains are modified using a knobs-into-holes technique. In some embodiments, the first and second CD3 domains are modified based upon electrostatic effects.

Heteroconjugate antibodies are also within the scope of the present invention. Heteroconjugate antibodies are composed of two covalently joined antibodies. Such antibodies have, for example, been proposed to target immune cells to unwanted cells. It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., human DLL4 or a Notch receptor). In this regard, the variable region may comprise or be derived from any type of mammal that can be induced to mount a humoral response and generate immunoglobulins against the desired tumor-associated antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs will be derived preferably from an antibody from a different species. It may not be necessary to replace all of the CDRs with all of the CDRs from the donor variable region to transfer the antigen binding capacity of one variable domain to another. Rather, it may only be necessary to transfer those amino acid residues that are necessary to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization and/or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1 CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ACH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete the part of one or more constant region domains that control a specific effector function (e.g. complement C1q binding). Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells, release of inflammatory mediators, placental transfer, and control of immunoglobulin production.

In certain embodiments, the Notch pathway inhibitors are antibodies that provide for altered effector functions. These altered effector functions may affect the biological profile of the administered antibody. For example, in some embodiments, the deletion or inactivation (through point mutations or other means) of a constant region domain may reduce Fc receptor binding of the circulating modified antibody (e.g., anti-DLL4 antibody or anti-Notch receptor antibody) thereby increasing cancer cell localization and/or tumor penetration. In other embodiments, the constant region modifications increase or reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques well within the purview of the skilled artisan.

In certain embodiments, a Notch pathway inhibitor is an antibody that does not have one or more effector functions. For instance, in some embodiments, the antibody has no ADCC activity, and/or no CDC activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations.

In certain embodiments, the antibodies described herein are isolated. In certain embodiments, the antibodies described herein are substantially pure.

In some embodiments of the present invention, the Notch pathway inhibitors are polypeptides. The polypeptides can be recombinant polypeptides, natural polypeptides, or synthetic polypeptides comprising an antibody, or fragment thereof, that bind human DLL4 or bind one or more human Notch receptors. It will be recognized in the art that some amino acid sequences of the invention can be varied without significant effect on the structure or function of the protein. Thus, the invention further includes variations of the polypeptides which show substantial activity or which include regions of an antibody, or fragment thereof, against human DLL4 or one or more human Notch receptors. In some embodiments, amino acid sequence variations of DLL4-binding polypeptides or Notch-binding polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve the solubility, the biological half-life, and/or absorption of the polypeptide. The moieties can also reduce or eliminate any undesirable side effects of the polypeptides and variants. An overview for chemical moieties can be found in *Remington: The Science and Practice of Pharmacy*, $22^{nd}$ *Edition*, 2012, Pharmaceutical Press, London.

The isolated polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express polypeptides (e.g., antibodies), or fragments thereof, which bind human DLL4 or one or more human Notch receptors. For example, recombinant expression vectors can be replicable DNA constructs which have synthetic or cDNA-derived DNA fragments encoding a polypeptide chain of an anti-DLL4 antibody or fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host yeast cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a polypeptide include prokaryotes, yeast cells, insect cells, or higher eukaryotic cells. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are known to those skilled in the art.

Various mammalian cell culture systems are used to express recombinant polypeptides. Expression of recombinant proteins in mammalian cells can be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present invention provides cells comprising a Notch pathway inhibitor described herein. In some embodiments, the cells produce the Notch pathway inhibitors (e.g., antibodies) described herein. In certain embodiments, the cells produce an antibody. In certain embodiments, the cells produce demcizumab. In certain embodiments, the cells produce OMP-305B83. In certain embodiments, the cells produce tarextumab. In certain embodiments, the cells produce brontictuzumab.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a binding agent. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

In certain embodiments, the Notch pathway inhibitor is a small molecule.

In certain embodiments, the Notch pathway inhibitor can be used in any one of a number of conjugated (i.e. an immunoconjugate or radioconjugate) or non-conjugated forms. In certain embodiments, antibodies can be used in a non-conjugated form to harness the subject's natural defense mechanisms including complement-dependent cytotoxicity and antibody dependent cellular toxicity to eliminate the malignant or cancer cells.

In some embodiments, the Notch pathway inhibitor is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}Ho$, $^{177}Lu$, $^{186}Re$, $^{188}Re$ and $^{212}Bi$. In some embodiments, conjugates of an antibody and one or more small molecule toxins, such as a calicheamicin, maytansinoids, a trichothene, and CC1065, and the derivatives of these toxins that have toxin activity, can be produced. In certain embodiments, conjugates of an antibody and a cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In certain embodiments, the Notch pathway inhibitor (e.g., antibody) is an antagonist of DLL4. In certain embodiments, the Notch pathway inhibitor inhibits activity of DLL4. In certain embodiments, the Notch pathway inhibitor inhibits at least about 10%, at least about 20%, at least about 30%, at least about 50%, at least about 75%, at least about 90%, or about 100% of the activity of DLL4.

In certain embodiments, the Notch pathway inhibitor (e.g., antibody) inhibits binding of DLL4 to an appropriate receptor. In certain embodiments, the Notch pathway inhibitor inhibits binding of DLL4 to one or more human Notch proteins. In some embodiments, the one or more human Notch proteins are selected from the group consisting of: Notch1, Notch2, Notch3, and Notch4. In certain embodiments, the inhibition of binding of DLL4 to a Notch protein by a Notch pathway inhibitor is at least about 10%, at least about 25%, at least about 50%, at least about 75%, at least about 90%, or at least about 95%. In certain embodiments, a Notch pathway inhibitor that inhibits binding of DLL4 to a Notch protein also inhibits Notch pathway signaling. In certain embodiments, a Notch pathway inhibitor that inhibits human Notch pathway signaling is demcizumab.

In certain embodiments, the Notch pathway inhibitor (e.g., antibody) is an antagonist of one or more Notch receptors. In certain embodiments, the Notch pathway inhibitor inhibits activity of Notch1, Notch2, and/or Notch3. In certain embodiments, the Notch pathway inhibitor inhibits at least about 10%, at least about 20%, at least about 30%, at least about 50%, at least about 75%, at least about 90%, or about 100% of the activity of Notch1, Notch2, and/or Notch3.

In certain embodiments, the Notch pathway inhibitor (e.g., antibody) inhibits binding of a Notch receptor to an appropriate ligand. In certain embodiments, the Notch pathway inhibitor inhibits binding of a Notch receptor to one or more human Notch ligands. In some embodiments, the one or more human Notch ligands are selected from the group consisting of: DLL1, DLL3, DLL4, JAG1, and JAG2. In certain embodiments, the inhibition of binding of a Notch receptor to a Notch ligand by a Notch pathway inhibitor is at least about 10%, at least about 25%, at least about 50%, at least about 75%, at least about 90%, or at least about 95%. In certain embodiments, a Notch pathway inhibitor that inhibits binding of a Notch receptor to a Notch ligand also inhibits Notch pathway signaling. In certain embodiments, a Notch pathway inhibitor that inhibits human Notch pathway signaling is tarextumab. In certain embodiments, a Notch pathway inhibitor that inhibits human Notch pathway signaling is brontictuzumab.

In certain embodiments, a Notch pathway inhibitor has one or more of the following effects: inhibit proliferation of tumor cells, inhibit tumor growth, reduce the frequency of cancer stem cells in a tumor, reduce the tumorigenicity of a tumor, reduce the tumorigenicity of a tumor by reducing the frequency of cancer stem cells in the tumor, trigger cell death of tumor cells, induce cells in a tumor to differentiate, differentiate tumorigenic cells to a non-tumorigenic state, induce expression of differentiation markers in the tumor cells, prevent metastasis of tumor cells, decrease survival of tumor cells, or modulate an immune response.

In certain embodiments, a Notch pathway inhibitor is capable of reducing the tumorigenicity of a tumor. In certain embodiments, a Notch pathway inhibitor is capable of reducing the tumorigenicity of a tumor comprising cancer stem cells in an animal model, such as a mouse model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236, and U.S. Patent Publication Nos. 2008/0064049, and 2008/0178305.

In certain embodiments, the Notch pathway inhibitors described herein are active in vivo for at least 1 hour, at least about 2 hours, at least about 5 hours, at least about 10 hours, at least about 24 hours, at least about 2 days, at least about 3 days, at least about 1 week, or at least about 2 weeks. In certain embodiments, the Notch pathway inhibitor is an IgG (e.g., IgG1 or IgG2) antibody that is active in vivo for at least 1 hour, at least about 2 hours, at least about 5 hours, at least about 10 hours, at least about 24 hours, at least about 2 days, at least about 3 days, at least about 1 week, or at least about 2 weeks. In certain embodiments, the Notch pathway inhibitor is a fusion protein that is active in vivo for at least 1 hour, at least about 2 hours, at least about 5 hours, at least about 10 hours, at least about 24 hours, at least about 2 days, at least about 3 days, at least about 1 week, or at least about 2 weeks.

In certain embodiments, the Notch pathway inhibitors described herein have a circulating half-life in mice, cynomolgus monkeys, or humans of at least about 5 hours, at least about 10 hours, at least about 24 hours, at least about 2 days, at least about 3 days, at least about 1 week, or at least about 2 weeks. In certain embodiments, the Notch pathway inhibitor is an IgG (e.g., IgG1, IgG2, or IgG4) antibody that has a circulating half-life in mice, cynomolgus monkeys, or humans of at least about 5 hours, at least about 10 hours, at least about 24 hours, at least about 2 days, at least about 3 days, at least about 1 week, or at least about 2 weeks. In certain embodiments, the Notch pathway inhibitor is a fusion protein that has a circulating half-life in mice, cynomolgus monkeys, or humans of at least about 5 hours, at least about 10 hours, at least about 24 hours, at least about 2 days, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn). Known methods of increasing the circulating half-life of antibody fragments lacking the Fc region include such techniques as PEGylation.

IV. Immunotherapeutic Agents

The present invention provides Notch pathway inhibitors for use in combination therapy with immunotherapeutic agents for modulating immune responses, inhibiting tumor growth, and/or for the treatment of cancer. In some embodiments of the methods described herein, a immunotherapeutic agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments, an immunotherapeutic agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, an IDO1 antagonist, and/or a KIR antagonist.

In some embodiments, an immunotherapeutic agent is selected from the group consisting of: a CD28 agonist, a 4-1BB agonist, an OX40 agonist, a CD27 agonist, a CD80 agonist, a CD86 agonist, a CD40 agonist, and a GITR agonist.

In some embodiments, an immunotherapeutic agent includes, but is not limited to, cytokines such as chemokines, interferons, interleukins, lymphokines, and members of the tumor necrosis factor (TNF) family. In some embodiments, an immunotherapeutic agent includes immunostimulatory oligonucleotides, such as CpG dinucleotides.

In some embodiments, a immunotherapeutic agent includes, but is not limited to, anti-PD-1 antibodies, anti-PD-L1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, and anti-IDO1 antibodies.

In some embodiments, a PD-1 antagonist is an antibody that specifically binds PD-1. In some embodiments, the antibody that binds PD-1 is pembrolizumab (KEYTRUDA, MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody comprising the CDR regions of any of these antibodies. In other embodiments, a PD-1 antagonist is a fusion protein that comprises the extracellular domain of PD-L1 or PD-L2, for example, AMP-224. In other embodiments, a PD-1 antagonist is a peptide inhibitor, for example, AUNP-12.

In some embodiments, a PD-L1 antagonist is an antibody that specifically binds PD-L1. In some embodiments, the antibody that binds PD-L1 is atezolizumab (RG7446, MPDL3280A), durvalumab (MEDI4736), BMS-936559 (MDX-1105), avelumab (MSB-0010718C), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that comprises the CDR regions of any of these antibodies.

In some embodiments, a CTLA-4 antagonist is an antibody that specifically binds CTLA-4. In some embodiments, the antibody that binds CTLA-4 is ipilimumab (YERVOY) or tremelimumab (CP-675,206). In some embodiments, a CTLA-4 antagonist is a CTLA-4 fusion protein or a soluble CTLA-4 receptor, for example, KAHR-102.

In some embodiments, a KIR antagonist is an antibody that specifically binds KIR. In some embodiments, the antibody that binds KIR is lirilumab.

In some embodiments, a LAG3 antagonist is an antibody that specifically binds LAG3. In some embodiments, the antibody that binds LAG3 is IMP701, IMP731, BMS-986016, LAG525, and GSK2831781. In some embodiments, a LAG3 antagonist is a LAG3 fusion protein or a soluble LAG3 receptor, for example, IMP321.

In some embodiments, an IDO1 antagonist is indoximad (NLG-9189), epacadostat (INCB024360), or NLG0919.

In some embodiments, an immunotherapeutic agent is a CD28 agonist, a 4-1BB agonist, an OX40 agonist, a CD27 agonist, a CD80 agonist, a CD86 agonist, a CD40 agonist, or a GITR agonist.

In some embodiments, an OX40 agonist comprises an OX40 ligand, or an OX40-binding portion thereof. In some embodiments, an OX40 agonist is MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the antibody that binds OX40 is described in PCT Publication WO 2012/027328, for example, antibody mouse 119-122, Ch119-122, Hu199-122, or 106-222, or an antibody that comprises the CDR regions of any of these antibodies. In some embodiments, an OX40 agonist is a vector (e.g., an expression vector or virus, such as an adenovirus) capable of expressing OX40 ligand. In some embodiments, the OX40L-expressing vector is Delta-24-RGDOX or DNX2401.

In some embodiments, a 4-1BB (CD137) agonist is a binding molecule, such as an anticalin. In some embodiments, the anticalin is PRS-343. In some embodiments, a 4-1BB agonist is an antibody that specifically binds 4-1BB. In some embodiments, antibody that binds 4-1BB is PF-2566 (PF-05082566) or urelumab (BMS-663513).

In some embodiments, a CD27 agonist is an antibody that specifically binds CD27. In some embodiments, the antibody that binds CD27 is varlilumab (CDX-1127).

In some embodiments, a GITR agonist comprises a GITR ligand or a GITR-binding portion thereof. In some embodiments, a GITR agonist is an antibody that specifically binds GITR. In some embodiments, the antibody that binds GITR is TRX518, MK-4166, or INBRX-110.

EXAMPLES

Example 1

Effect of Anti-DLL4 Antibody on PD-1 Expression in Cells from CT26.WT Tumors

The murine colon carcinoma CT26.WT was obtained from ATCC. CT26.WT cells were injected subcutaneously into the rear flanks of 6-8 week old Balb/C mice. Tumors were allowed to grow until they reached an average size of 200 mm$^3$. The mice were randomized into groups (n=10) and treated with anti-mouse DLL4 (mDLL4) antibody 21R30 (10 mg/kg, weekly), SIRPα-Fc protein (10 mg/kg, biweekly), or a control Fc protein (10 mg/kg, weekly). The agents were administered by injection into the intraperitoneal cavity. Fourteen days after the initial dose, the tumors were harvested and total protein was isolated from individual mice using tissue extraction buffer (Life Technologies). Proteins (20 µg) were resolved by SDS-PAGE gel electrophoresis, and Western blot analysis was performed using an anti-PD-1 antibody.

Figure 1B:
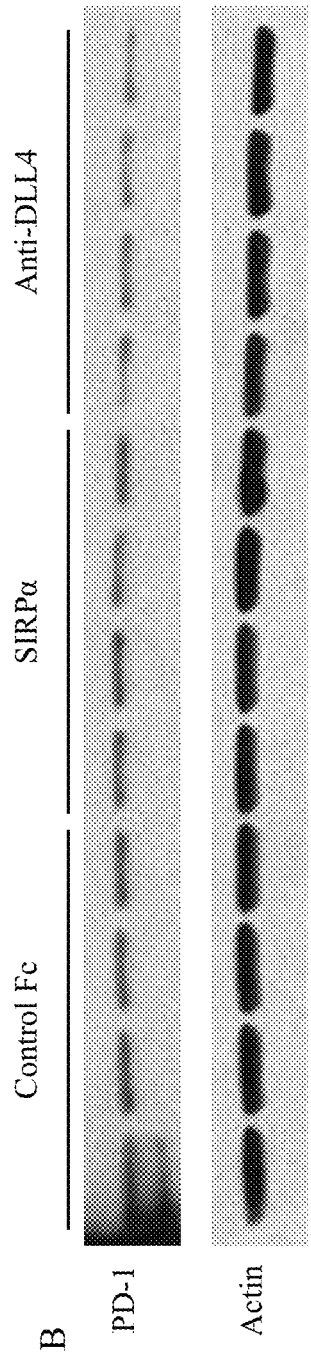

As shown in FIG. 1A, PD-1 expression in tumor cell lysates from mice treated with anti-mDLL4 antibody 21R30 was significantly decreased (p<0.05) relative to PD-1 expression in tumor cell lysates from mice treated with the control. This decrease was greater than the decrease in tumor cell lysates from mice treated with a SIRPα-Fc protein. FIG. 1B shows a representative Western blot analysis from four individual tumors of each treatment group.

PD-1 (programmed cell death protein 1) is expressed on the surface of activated T-cells, B-cells, NK cells, and macrophages and has been shown to negatively regulate immune responses, including anti-tumor responses. Since PD-1 is not expressed on the surface of tumor cells, these results suggest that treatment with anti-DLL4 antibodies may be directly or indirectly affecting the expression of PD-1 on tumor-associated immune cells. This suggests that anti-DLL4 antibodies or other DLL4 antagonists could potentially inhibit or block the suppressive activity of PD-1-expressing cells and enhance anti-tumor immune responses.

Example 2

Effect of Mouse IL-2-Fc and Anti-mDLL4 Antibody on Tumor Growth

Murine colon carcinoma CT26.WT cells were injected subcutaneously into the flanks of 6-8 week old Balb/C mice. Tumors were allowed to grow to an average tumor volume of 100 mm$^3$. The mice were randomized into groups (n=10) and treated with anti-mDLL4 antibody 21R30 (30 mg/kg, weekly), mIL-2-Fc protein (1 mg/kg, 5 days each week), or a combination of anti-mDLL4 antibody and mIL-2-Fc. An anti-GFP antibody and a murine Fc protein were used as controls for 21R30 and mIL-2-Fc, respectively. Agents were administered by intraperitoneal injection. Tumor growth was monitored and tumor volumes measured using electronic calipers at the indicated time points. The data are expressed as average tumor volume±SEM.

Figure 2A:
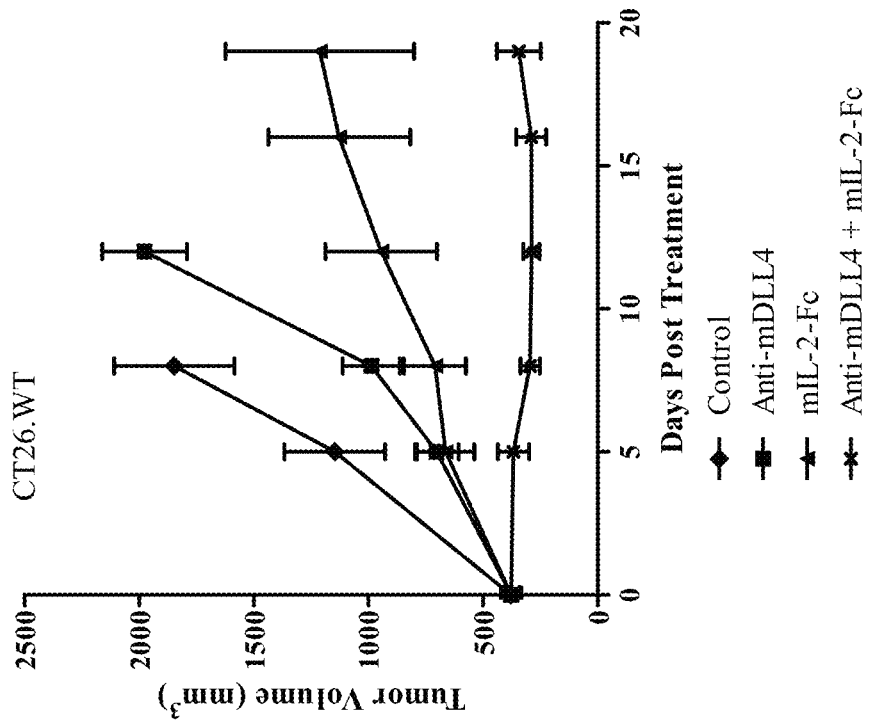
FIGS. 2A, 2B, and 2C. Inhibition of tumor growth.

As shown in FIG. 2A, anti-mDLL4 antibody 21R30 and mIL-2-Fc both inhibited CT26.WT tumor growth as single agents as compared to control. Furthermore, a combination of the anti-mDLL4 antibody and mIL-2-Fc inhibited tumor growth to a greater extent than either agent alone.

This experiment was repeated to assess the agents' effect on larger established tumors. As described above, CT26.WT cells were injected subcutaneously into the rear flanks of 6-8 week old Balb/C mice, but tumors were allowed to grow to an average tumor volume of 400 mm$^3$. The mice were randomized into groups (n=6) and treated with a control anti-GFP antibody (30 mg/kg, weekly), anti-mDLL4 antibody 21R30 (30 mg/kg, weekly), mIL-2-Fc protein (1 mg/kg, 5 days each week), or a combination of anti-mDLL4 antibody and mIL-2-Fc. Agents were administered by intraperitoneal injection. Tumor growth was monitored and tumor volumes measured using electronic calipers at the indicated time points. The data are expressed as average tumor volume±SEM.

Figure 2B:
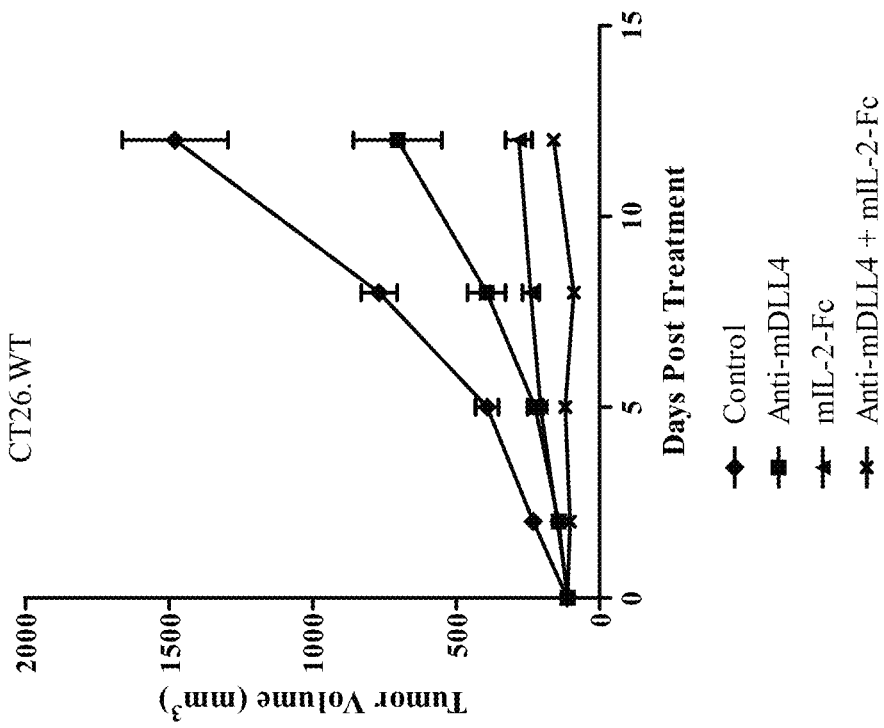

As shown in FIG. 2B, when the tumors are larger and more established the combination of anti-mDLL4 antibody 21R30 and mIL-2-Fc had a much greater effect on inhibiting the growth of CT26.WT tumors than either agent alone or the control.

A similar experiment was conducted with a murine lung tumor. A mouse model of non-small cell lung cancer (NSCLC) was established at OncoMed and herein is referred to as KP_LUN01. This tumor line was observed to have a poorly differentiated morphology, have a very short tumor latency in vivo, and to be highly metastatic.

Murine lung tumor KP_LUN01 cells (50,000 cells) were injected subcutaneously into the flanks of 6-8 week old C57BL/6J mice (Day 0). Tumors were allowed to grow for 8 days to an average tumor volume of 100 mm$^3$. The mice were randomized into groups (n=10) and treated with a control anti-GFP antibody (20 mg/kg), anti-mDLL4 antibody 21R30 (20 mg/kg, on Days 8, 15 and 19), mIL-2-Fc protein (1 mg/kg, on Days 11, 12, 13, 14, 15, and 19), or a combination of anti-mDLL4 antibody and mIL2-Fc (same doses and administration as single agents). Agents were administered by intraperitoneal injection. Tumor growth was monitored and tumor volumes measured using electronic calipers at the indicated time points. The data are expressed as average tumor volume±SEM.

Figure 2C:
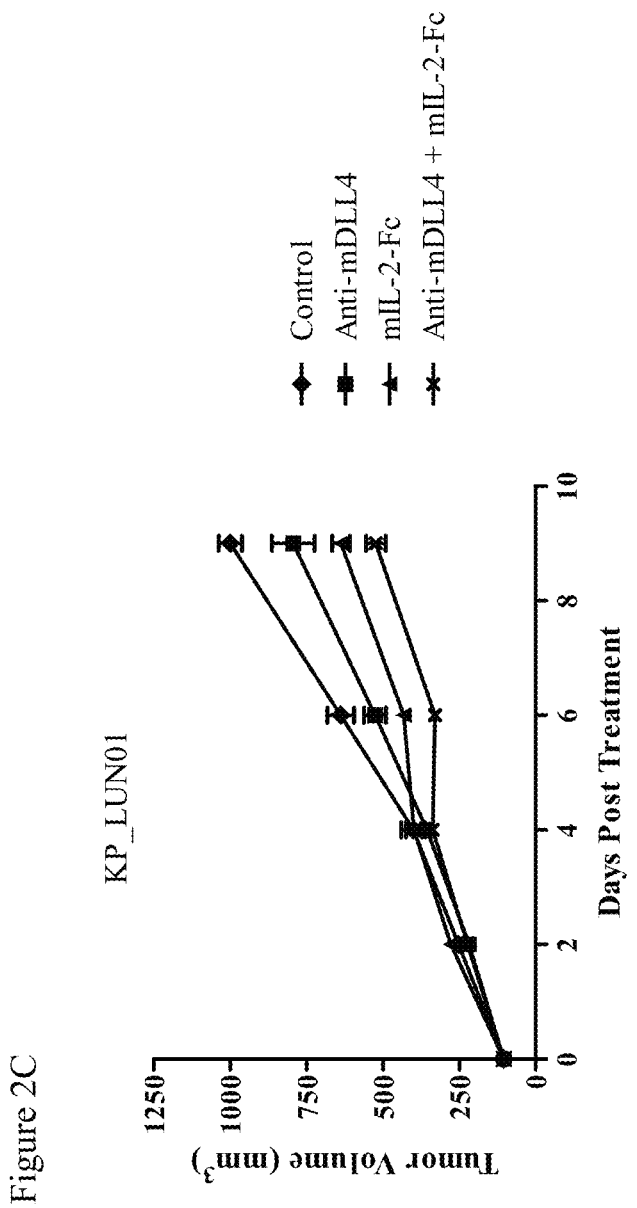

As shown in FIG. 2C, anti-mDLL4 antibody 21R30 and mIL-2-Fc inhibited the growth of the KP_LUN01 tumors as single agents as compared to control. In addition, the combination of anti-mDLL4 antibody 21R30 and mIL2-Fc had a greater effect on inhibiting the growth of KP_LUN01 tumors than either agent alone or the control.

These results suggest that a combination of an anti-DLL4 antagonist in combination with an immunotherapeutic agent could be a potential anti-tumor therapy.

Example 3

Cell Cytotoxicity Assays

For natural killer (NK) cytotoxicity assays, the mouse lymphoblast cell line YAC-1 and the mouse colon carcinoma cell line CT26.WT were cultured in RPMI 1640 culture medium (Gibco/Life Technologies, Grand Island, N.Y.) supplemented with 10% (v/v) fetal bovine serum (FBS), 2 mM L-glutamine, 100 U/ml penicillin, and 100 µg/ml streptomycin (Gibco) at 37° C. in a humidified atmosphere of 5% CO2. YAC-1 cells are known to be sensitive to NK cell activity and are a good target for NK cell assays.

Cells were harvested from the spleens of the CT26.WT tumor-bearing mice described above in Example 2. Cells were plated in 96-well V-bottom plates in RPMI 1640 culture medium (Gibco/Life Technologies, Grand Island, N.Y.) supplemented with 10% (v/v) fetal bovine serum (FBS), 2 mM L-glutamine, 100 U/ml penicillin, and 100 µg/ml streptomycin (Gibco). Target cells (YAC-1 or CT26.WT) were labeled with 10 µM calcein AM (Life Technologies) for 1 hour at 37° C. and then combined with the splenocytes at an effector:target ratio of 25:1. Following a 4 hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

Figure 3A:
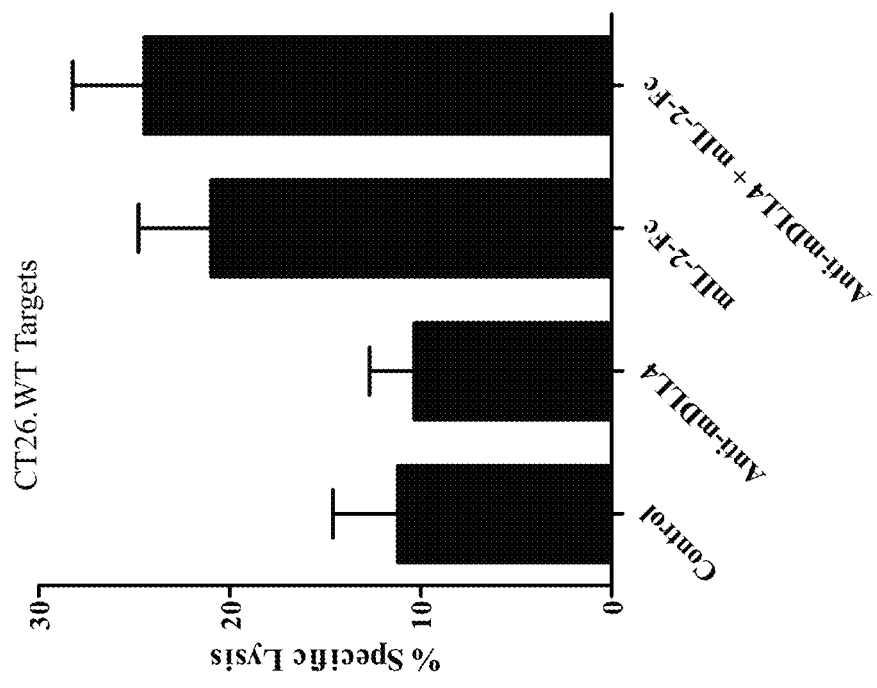
FIGS. 3A, 3B, and 3C. NK cell cytotoxicity assays.
Figure 3B:
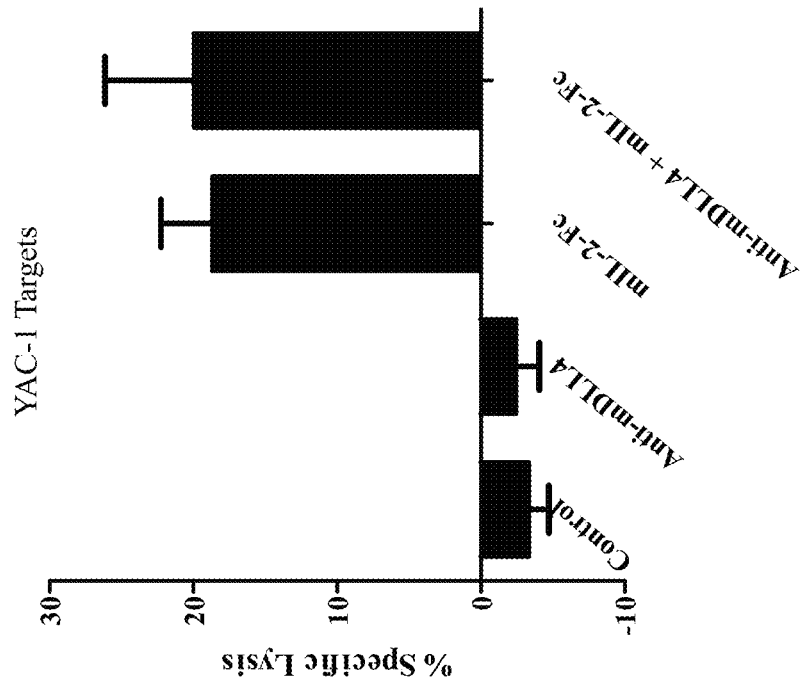

NK cells from CT26.WT tumor-bearing mice demonstrated an increased ability to kill YAC-1 and CT26.WT target cells when the mice had been treated with mIL-2-Fc. Treatment with anti-mDLL4 antibody appeared to have no effect on NK cytotoxicity in this experiment, either alone or in combination with mIL-2 (FIGS. 3A and 3B).

Figure 3C:
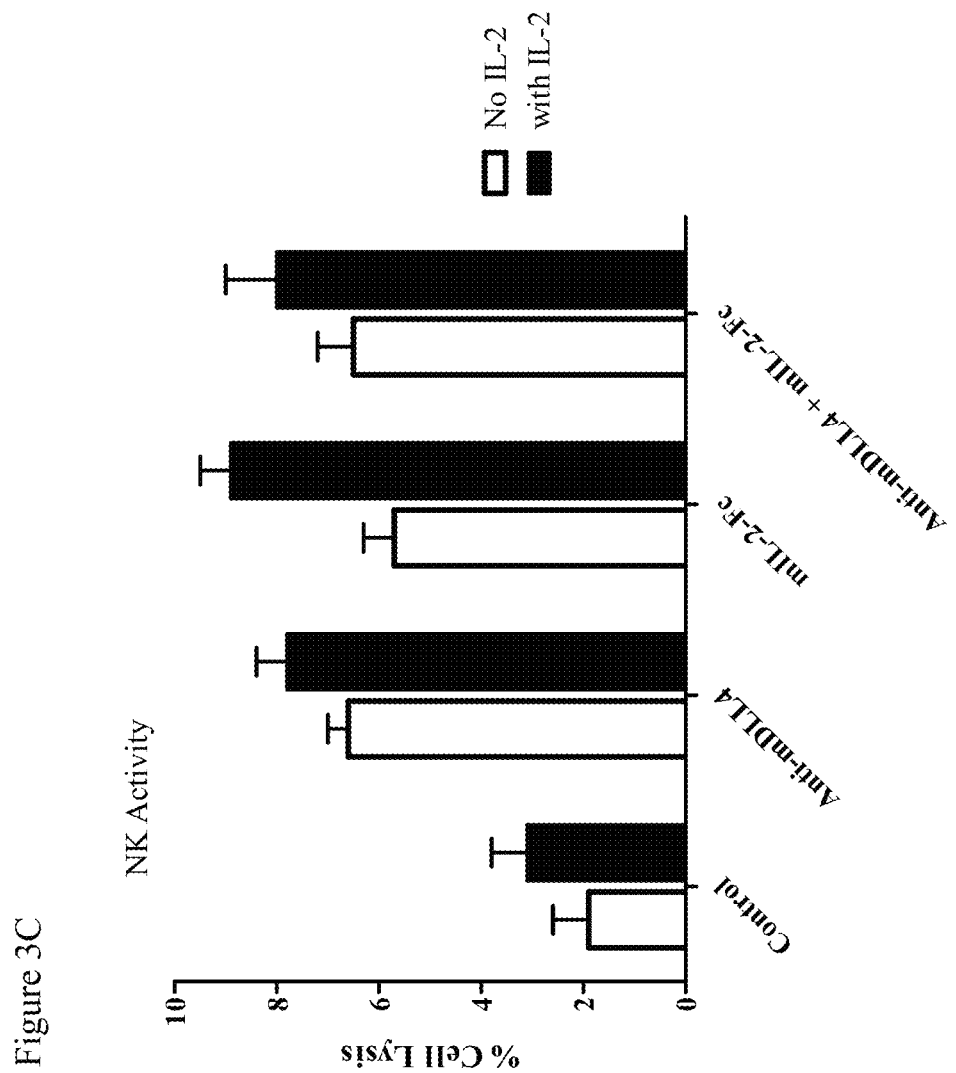

A similar experiment was conducted with cells harvested from the spleens of the KP_LUN01 tumor-bearing mice described above in Example 2. The cells were isolated after treatment and the assays were run using YAC-1 cells as targets. NK cells from KP_LUN01 tumor-bearing mice demonstrated an increased ability to kill YAC-1 target cells when the mice had been treated with anti-mDLL4 antibody 21R30 or mIL-2-Fc as single agents. There was no increase in NK activity when the agents were combined (FIG. 3C).

For T-cell cytotoxicity assays, cells were harvested from the spleens of CT26.WT tumor-bearing mice after treatment and cultured in media supplemented with 30 IU/mL recombinant murine IL-2 (Peprotech, Rocky Hill, N.J.) and 0.1 µg/ml AH-1 peptide (Anaspec, Fremont, Calif.). The sequence of this peptide (SPSYVYHQF) is the $H2-L^d$-restricted epitope (amino acids 6-14) of the gp70 envelope protein of an ecotropic murine leukemia provirus endogenous to the CT26.WT cell line. The splenocytes were cultured for 5 days at 37° C., harvested, counted, and used in cytotoxicity assays as described above, with CT26.WT tumor cells as targets. The effector $CD8^+$ phenotype of the cells was confirmed by FACS analysis after peptide/IL-2 stimulation (data not shown).

Figure 4A:
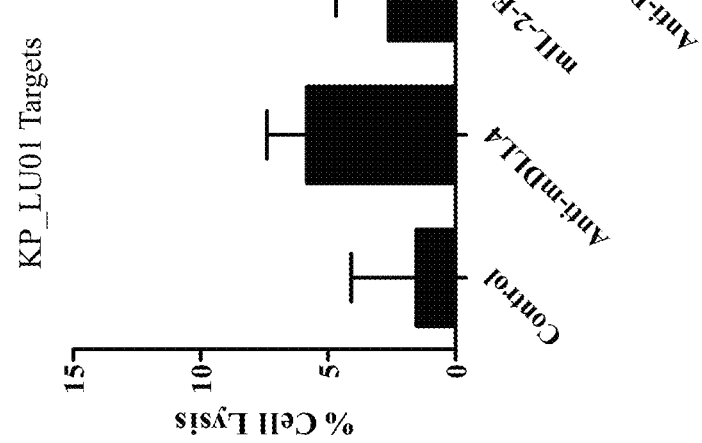
FIGS. 4A and 4B. T-cell cytotoxicity assays.

As shown in FIG. 4A, $CD8^+$ cytotoxic cells from CT26.WT tumor-bearing mice demonstrated an increased ability to kill CT26.WT target cells when the mice had been treated with anti-mDLL4 antibody as compared to cells from mice treated with control. $CD8^+$ cells from tumor-bearing mice treated with mIL-2-Fc also showed an increased ability to kill target cells as compared to control, although the effect was not as strong as with the anti-mDLL4 antibody. Furthermore, cells from mice treated with a combination of an anti-mDLL4 antibody and mIL-2-Fc had a greater ability to kill target cells than either treatment alone.

A similar experiment was conducted with cells harvested from the spleens of the KP_LUN01 tumor-bearing mice described above in Example 2. A $CD8^+$ T-cell specific MHC class I tumor peptide sequence is not known for the KP_LUN01 tumor line, therefore the KP_LUN01 tumor cells were used as stimulators. KP_LUN01 cells were treated with 25 µg/ml mitomycin C (Sigma-Aldrich) for 30 minutes at 37° C., washed, and resuspended at $10^7$ cells/ml in RPMI-1640 media containing 10% FCS, 2 mM L-glutamine, and antibiotics. Splenocytes were co-cultured with the mitomycin-treated KP_LUN01 cells at a ratio of 20:1, incubated for 7 days at 37° C., harvested, counted, and used in cytotoxicity assays as described above. Calcein AM-labeled KP_LUN01 tumor cells were used as targets at an effector:target ratio of 12.5:1. Calcein release was determined after 4 hours and specific lysis was calculated as described above.

Figure 4B:
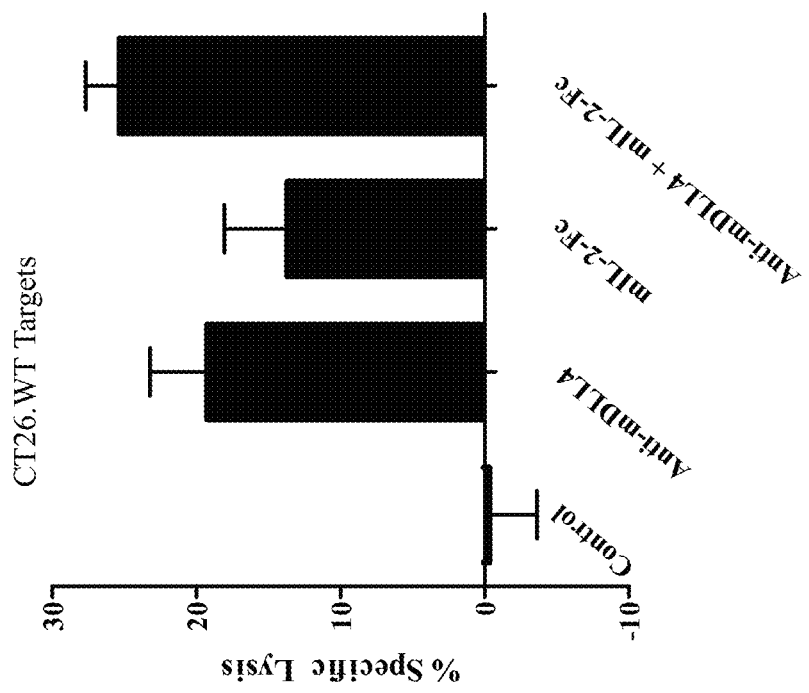

As shown in FIG. 4B, $CD8^+$ cytotoxic T-cells from KP_LUN01 tumor-bearing mice demonstrated an increased ability to kill KP_LUN01 target cells when the mice had been treated with anti-mDLL4 antibody. $CD8^+$ T-cells from tumor-bearing mice treated with mIL-2-Fc showed only a slight increase in cytolytic activity as compared to cells from mice treated with the control. Cells from mice treated with a combination of an anti-mDLL4 antibody and mIL-2-Fc had a significantly greater ability to kill target cells than either treatment alone.

These results demonstrate that treatment with a DLL4 antagonist may increase the cytotoxic activity of NK cells and tumor-specific $CD8^+$ T-cells. Furthermore, combination treatment with a DLL4 antagonist and an immunotherapeutic agent such as IL-2 may further enhance the cytolytic activity of NK cells and CTLs, and therefore prompt a stronger anti-tumor response.

Example 4

ELISpot Assay for IFN-Gamma

ELISpot is a highly sensitive immunoassay for the detection of cytokine-secreting cells. Briefly, an ELISpot assay employs a capture antibody specific for a desired cytokine, pre-coated onto the wells of a microplate. Stimulated cells are aliquoted into the wells and the immobilized antibody in the immediate vicinity of any cytokine-secreting cell binds the secreted cytokine. Standard wash steps and incubation with appropriate detection reagents follow. For example, a biotinylated detection antibody followed by streptavidin conjugated to alkaline-phosphatase and a colored substrate solution is commonly used. A colored precipitate forms at the sites of cytokine localization and appears as a spot, with each individual spot representing an individual cytokine-secreting cell. The spots may be counted with an automated reader system or manually using a microscope.

Interferon (IFN)-gamma secreting cells were detected using a mouse IFN-gamma ELISpot kit (mouse IFN-gamma ELISpot PLUS kit, Mabtech, Cincinnati, Ohio). Cells were isolated from the spleens of CT26.WT tumor-bearing mice treated with anti-mDLL4 antibody 21R30 and/or mIL-2-Fc, as described above in Example 2. Splenocytes from each mouse ($2\times10^5$ cells/well) were plated onto the provided plates, which were pre-coated with a capture antibody specific for murine IFN-gamma. The cells were cultured in the presence or the absence of a tumor specific $CD8^+$ T-cell peptide (AH-1) and incubated for 48 hours. Cells secreting IFN-gamma were detected following the manufacturer's instructions. Spots were counted using a 6000 F-z Bioreader (Biosys, Miami, Fla.). Data are expressed as the mean±S.E.M spots/well or total optical density.

Figure 5:
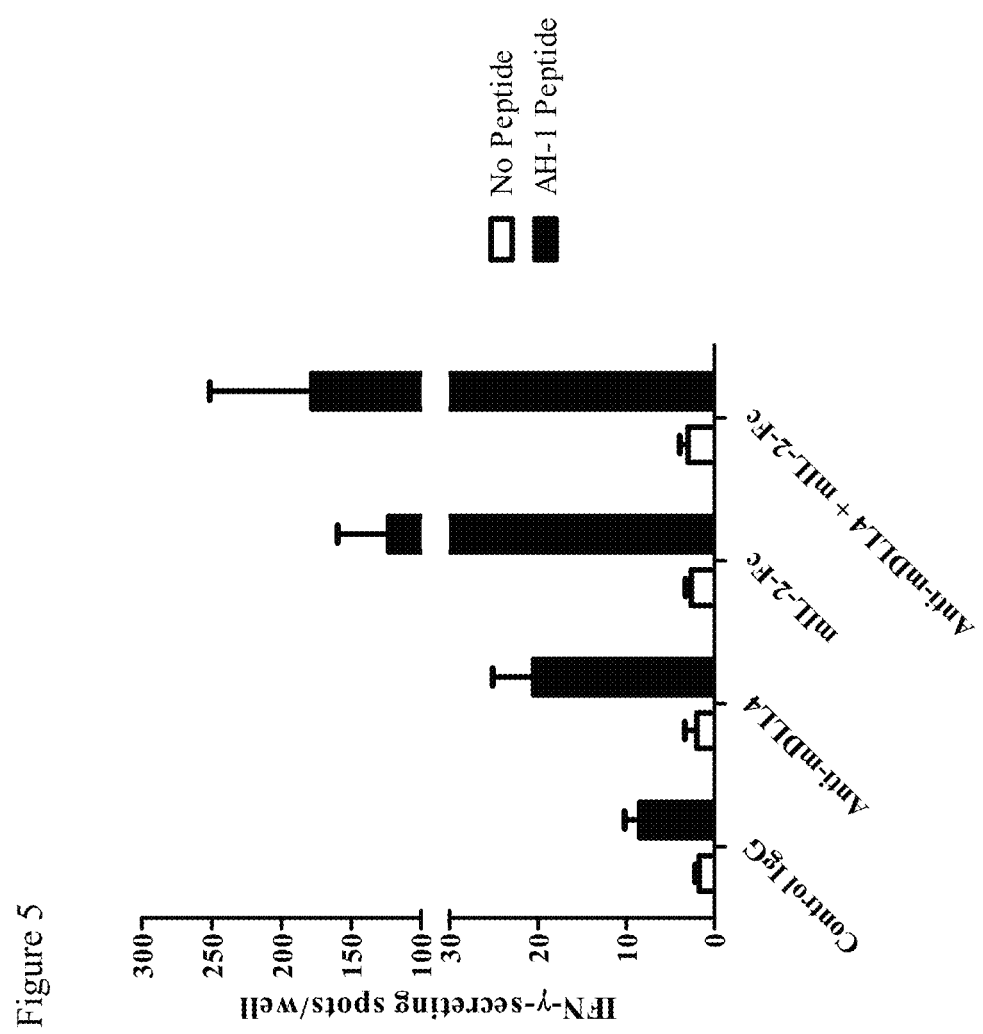
FIG. 5. ELISpot assay for IFN-gamma. Cells were harvested from the spleens of CT26.WT-tumor bearing mice treated with anti-mDLL4 antibody 21R30, mIL-2-Fc, a combination of anti-mDLL4 antibody 21R30 and mIL-2-Fc, or a control. The number of cells producing IFN-gamma is shown.

As shown in FIG. 5, tumor-specific IFN-gamma-secreting $CD8^+$ T-cells were increased in mice treated with mIL-2-Fc as a single agent. A modest but detectable increase in IFN-gamma-producing CD8$^+$ T-cells was also observed in mice treated with anti-mDLL4 antibody 21R30. Furthermore, tumor-specific IFN-gamma-secreting CD8$^+$ T-cells from mice treated with a combination of anti-mDLL4 antibody and mIL-2-Fc were increased to a greater extent than with either agent alone.

These data suggest that a DLL4 antagonist can induce tumor-specific CD8$^+$ T-cell activity and strengthens the hypothesis that a combination of a DLL4 antagonist and a T cell-targeting immunotherapeutic would be a good anti-tumor therapy.

Example 5

CD45$^+$PD-1$^+$ Cells in CT26.WT Tumors

Based on the results from Examples 1-4, the inventors further investigated the effect that treatment by a DLL4 antagonist either as a single agent or in combination with an immunotherapeutic agent had on immune checkpoint receptors, such as PD-1, on immune cells.

CT26.WT cells were injected subcutaneously into the flanks of 6-8 week old Balb/C mice. Tumors were allowed to grow until they reached an average size of 100 mm$^3$. The mice were randomized into groups (n=7) and treated with anti-mDLL4 antibody 21830, mIL-2-Fc, a combination of anti-mDLL4 antibody and mIL-2-Fc, or a control protein. The anti-mDLL4 antibody was dosed weekly at 30 mg/kg and the mIL-2-Fc was dosed for 5 days each week at 1 mg/kg. Administration was by injection into the intraperitoneal cavity. Twenty-one days after tumor cell injection and 15 days after the initial treatment, tumors were harvested and single cell suspensions were prepared. Cells were stained for CD45 using an anti-CD45 antibody conjugated to FITC and for PD-1 using an anti-PD-1 antibody conjugated to allophycocyanin (APC). Fluorescent activated cell sorting analysis (FACS) was performed using a FACSCanto II instrument (BD Biosciences, San Jose, Calif.) and the data was processed using Diva software.

CD45 is exclusively expressed on hematolymphoid cells and has been referred to as a "common leukocyte antigen". It is expressed at high levels on the cell surface of all nucleated hematopoietic cells and their precursors, therefore this protein can be used to detected tumor-associated immune cells. As described above, PD-1 is a protein on the cell surface of immune cells generally involved in suppressing immune responses.

Figure 6:
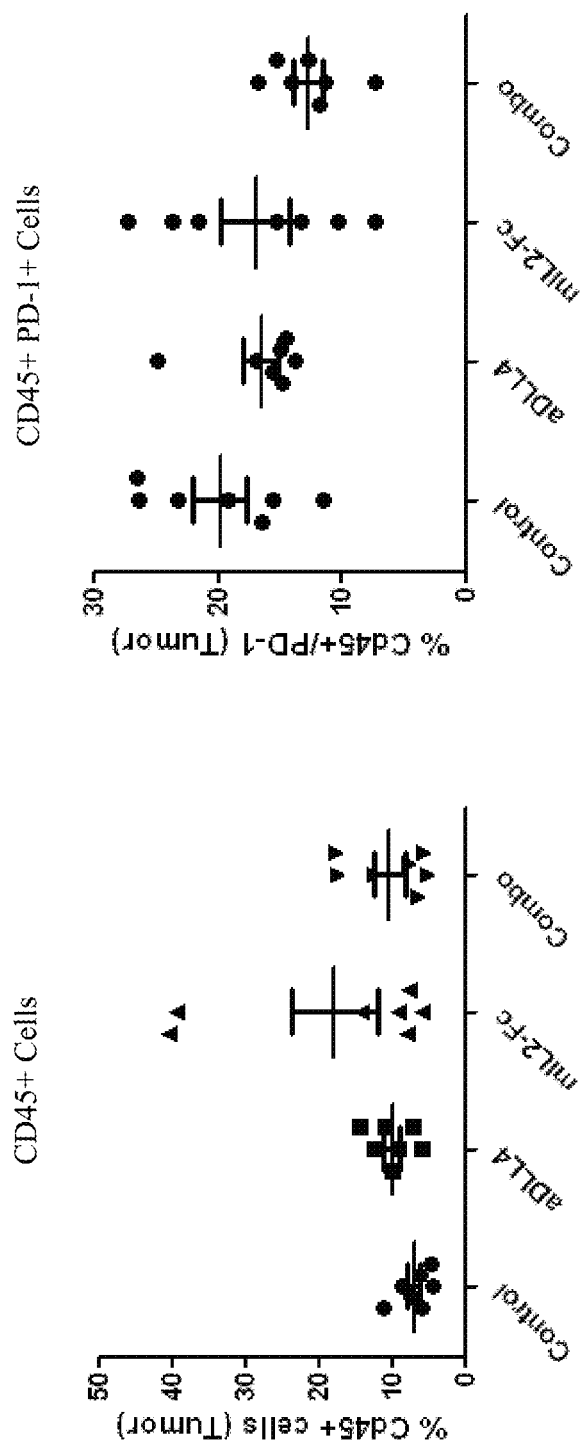
FIG. 6. CD45$^+$PD-1$^+$ cells in CT26.WT tumors. Tumors were harvested from mice treated with anti-mDLL4 antibody 21R30, mIL-2-Fc, a combination of anti-mDLL4 antibody 21R30 and mIL-2-Fc, or a control and single cell suspensions were prepared. Cells were analyzed for CD45 expression and PD-1 expression by FACS analysis.

The percentage of CD45$^+$ cells and CD45$^+$PD-1$^+$ cells in tumors from treated mice is shown in FIG. 6. The percentage of CD45$^+$ cells was increased in tumors from mice treated with mIL-2-Fc, although there was a high level of variability between individual mice. Interestingly, the percentage of CD45$^+$PD-1$^+$ cells was reduced in tumors from mice treated with anti-mDLL4 antibody and from mice treated with mIL-2-Fc. These results are consistent with the data from Western blot analyses described in Example 1. The percentage of CD45$^+$PD-1$^+$ cells was further decreased in tumors from mice treated with a combination of anti-mDLL4 antibody and mIL-2-Fc.

These results suggest that a combination of a DLL4 antagonist and an immunotherapeutic agent such as IL2 could be used to decrease the number of tumor-associated PD-1$^+$ immune cells and therefore inhibit the suppressive effects of those cells.

Example 6

Effect of Anti-DLL4 Antibody, Anti-CTLA-4 Antibody, and Anti-PD-L1 Antibody on Growth of CT26.WT Tumors CT26.WT cells were injected subcutaneously into the flanks of 6-8 week old Balb/C mice. Tumors were allowed to grow to an average tumor volume of 100 mm$^3$. The mice were randomized into groups (n=9) and treated with a control antibody (30 mg/kg, weekly), anti-mDLL4 antibody 21R30 (30 mg/kg, weekly), anti-mPD-L1 antibody (10 mg/kg, 3 times each week), anti-mCTLA-4 antibody (10 mg/kg, 3 times each week), a combination of anti-mDLL4 antibody and anti-mPD-L1, or a combination of anti-mDLL4 antibody and anti-mCTLA-4. Agents were administered by intraperitoneal injection. Tumor growth was monitored and tumor volumes measured using electronic calipers at the indicated time points. The data are expressed as average tumor volume±SEM.

Figure 7A:
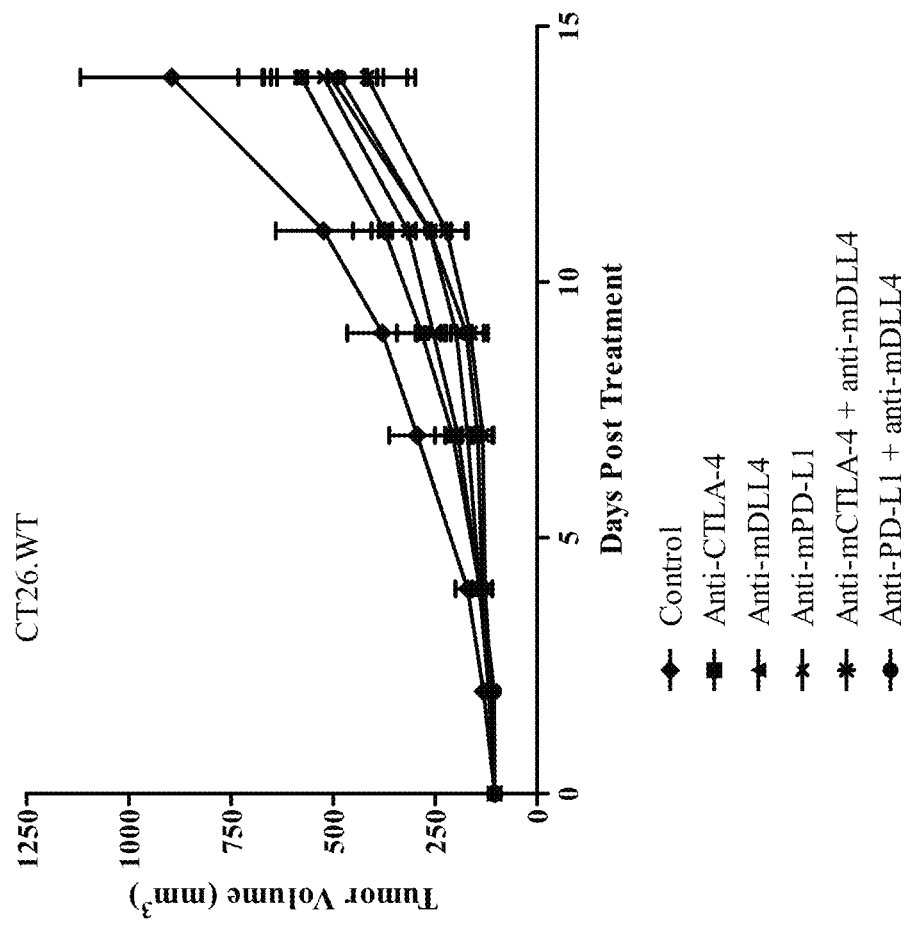
FIGS. 7A, 7B and 7C. Inhibition of CT26.WT tumor growth.
Figure 7B:
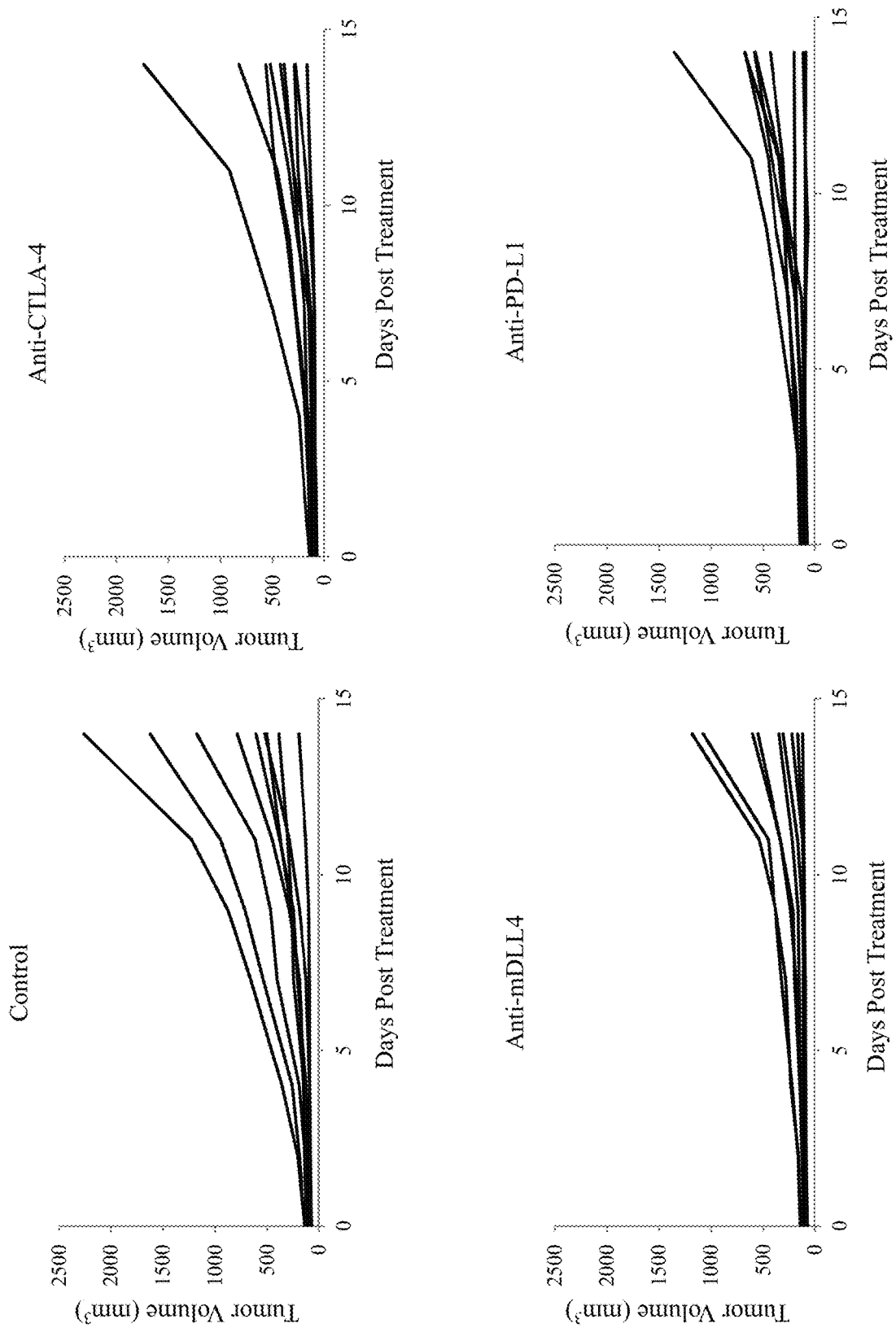
Figure 7C:
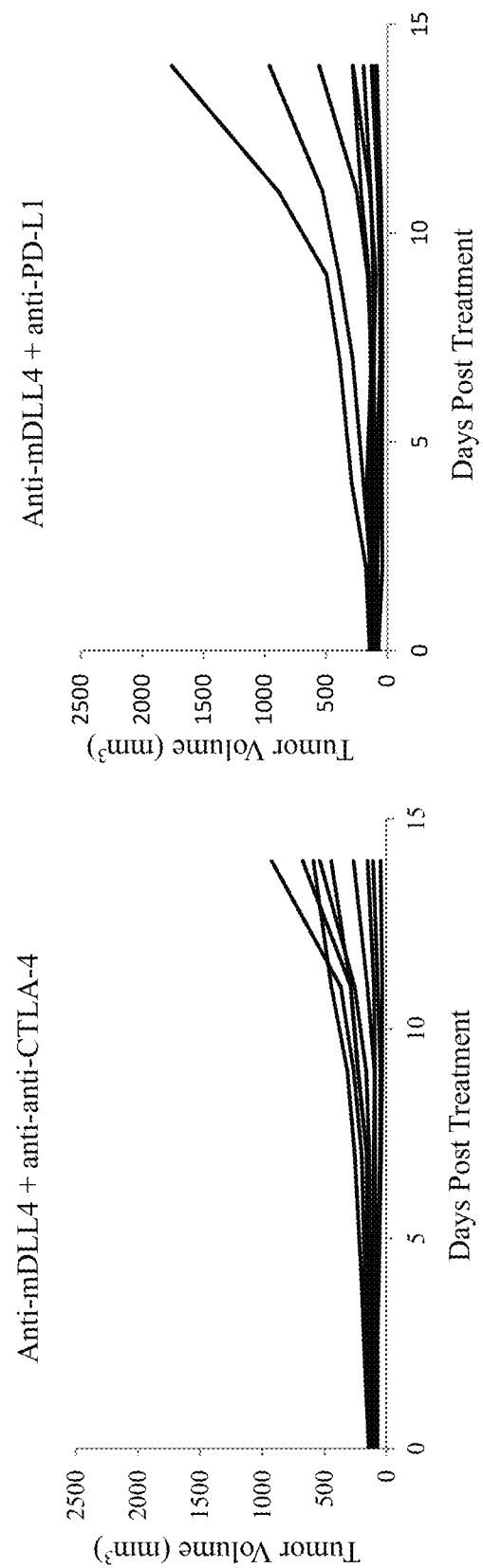

As shown in FIG. 7A, as a single agent anti-mDLL4 antibody inhibited CT26.WT tumor growth to a similar extent as anti-mPD-L1 or anti-mCTLA-4 antibodies. When viewed as average tumor volume the combination therapies were not detectably better than the single agents. However, when the inhibition of tumor growth was assessed on a mouse by mouse basis, the combination of anti-mDLL4 antibody 21R30 in combination with either anti-mCLTA-4 antibody or anti-mPD-L1 antibody appeared to have a greater inhibitory effect on tumor growth in more individual mice than when the antibodies were used as single agents (FIGS. 7B and 7C).

These results suggest that a DLL4 antagonist can enhance, and may synergize with, immune checkpoint inhibitors, such as anti-CTLA-4 and anti-PD-L1 antibodies to further inhibit tumor growth.

Example 7

Inhibition of CT26.WT Colon Tumor Growth In Vivo

Single cell suspensions of CT26.WT tumor cells (20,000 cells) were injected subcutaneously into the flanks of 6-8 week old Balb/C mice. One week following tumor cell injection, mice with palpable tumors were treated with an anti-mPD-1 antibody (250 µg/mouse), anti-mDLL4 antibody 21R30 (20 mg/kg), a combination of anti-mPD-1 antibody and anti-mDLL4 antibody 21R30, or the same amount of an isotype control antibody. Mice were administered the antibodies twice a week for 3 weeks by intraperitoneal injection. Tumor growth was monitored and tumor volumes were measured with electronic calipers at the indicated time points. Data are expressed as mean±S.E.M.

Figure 8A:
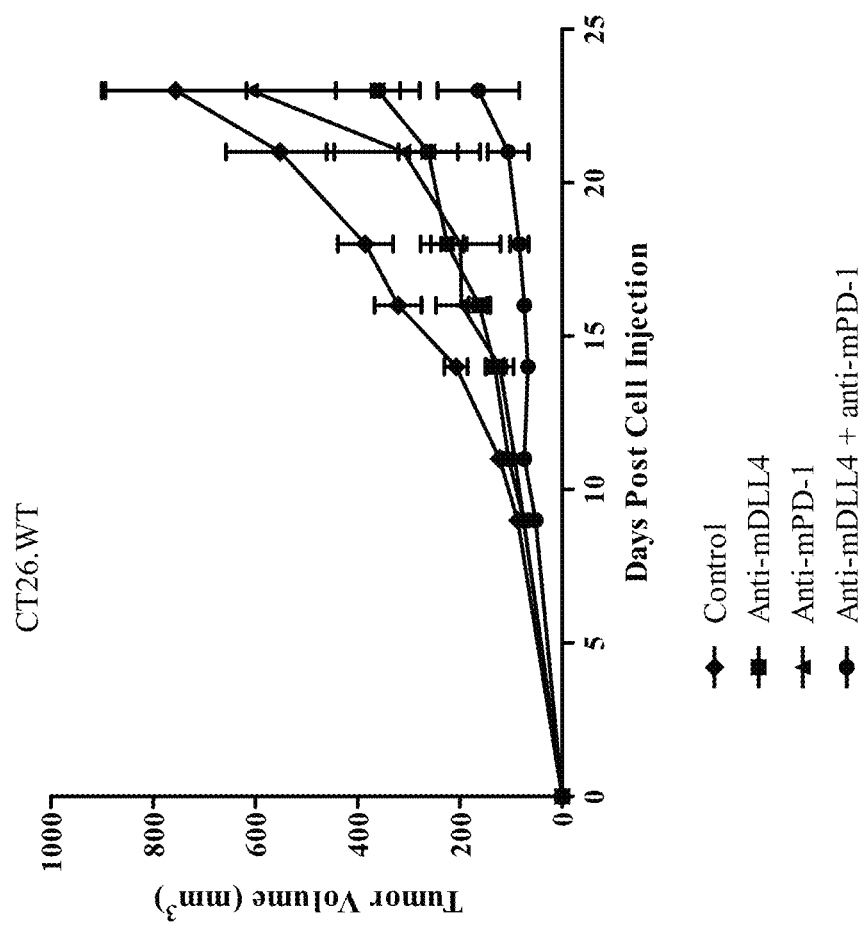
FIGS. 8A and 8B. Inhibition of CT26.WT tumor growth.
Figure 8B:
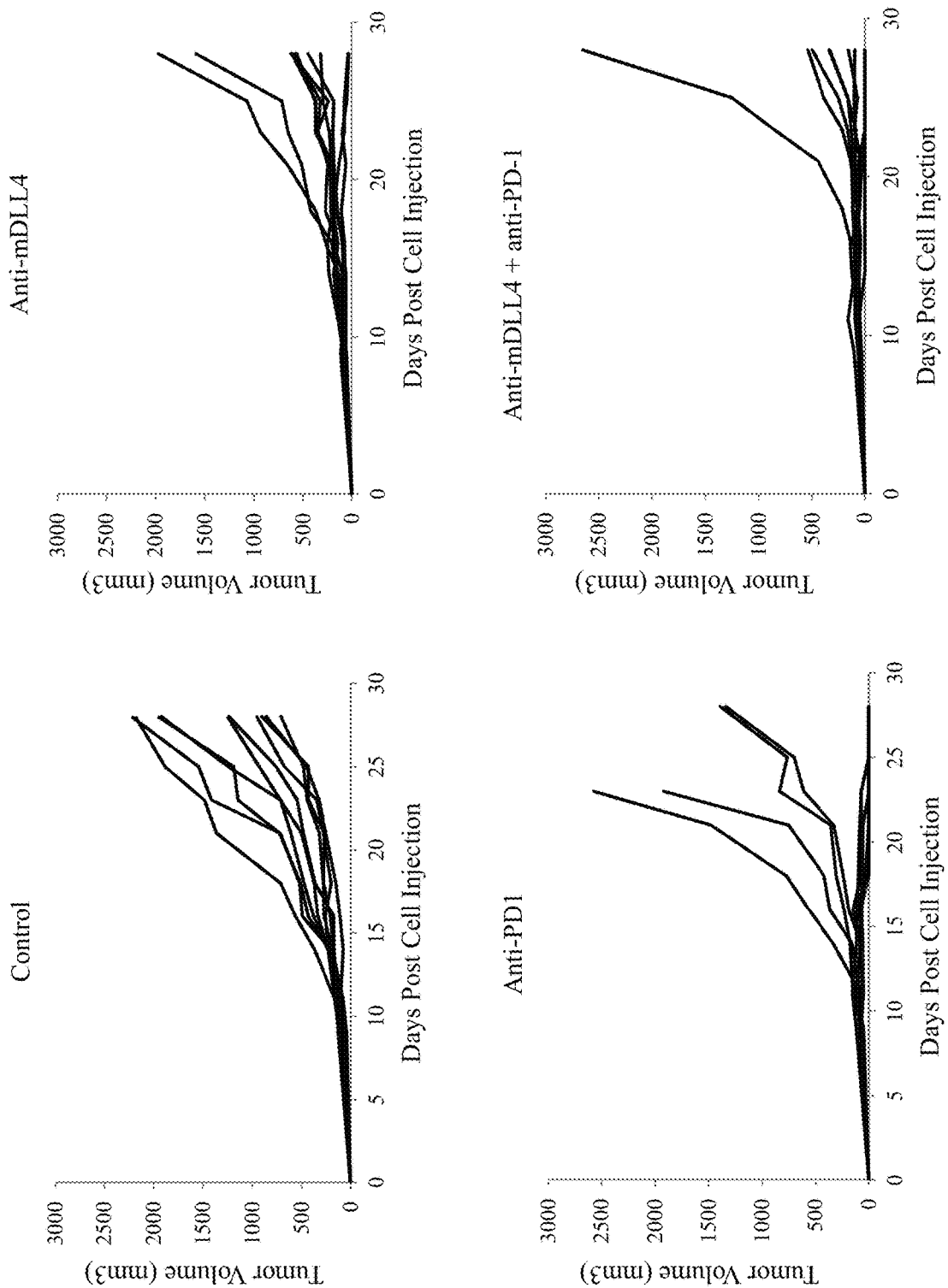

As shown in FIG. 8A, treatment with the combination of anti-mDLL4 antibody 21R30 and anti-mPD-1 antibody significantly reduced CT26.WT tumor growth as compared to treatment with the control antibody. Tumor growth was inhibited 78% as compared to control on Day 23, p=0.0016. Evaluation of individual mice at Day 28 showed no detectable tumors in 3 of 10 mice (FIG. 8B). In a second experiment 14 of 20 mice treated with a combination of anti-mDLL4 antibody 21R30 and anti-mPD-1 antibody showed no detectable tumors.

One method of evaluating the presence and/or functionally of an anti-tumor memory cell population is to re-challenge previously treated mice with fresh tumor cells. Mice previously treated with anti-mPD-1 antibody (n=11) or a combination of anti-mPD-1 antibody and anti-mDLL4 antibody 21R30 (n=14) from the studies described above were used for a re-challenge study. Mice whose tumors had regressed completely and were undetectable at least 85 days after the first tumor injection were rechallenged with CT26.WT tumor cells (20,000 cells). The mice subjected to tumor re-challenge had received a last treatment dose 66 days prior to re-challenge. Naive Balb/C mice (n=10) were injected with CT26.WT tumor cells (20,000 cells) as a control group. Tumor growth was monitored and tumor volumes were measured with electronic calipers at the indicated time points. Data are expressed as mean±S.E.M.

Figure 9:
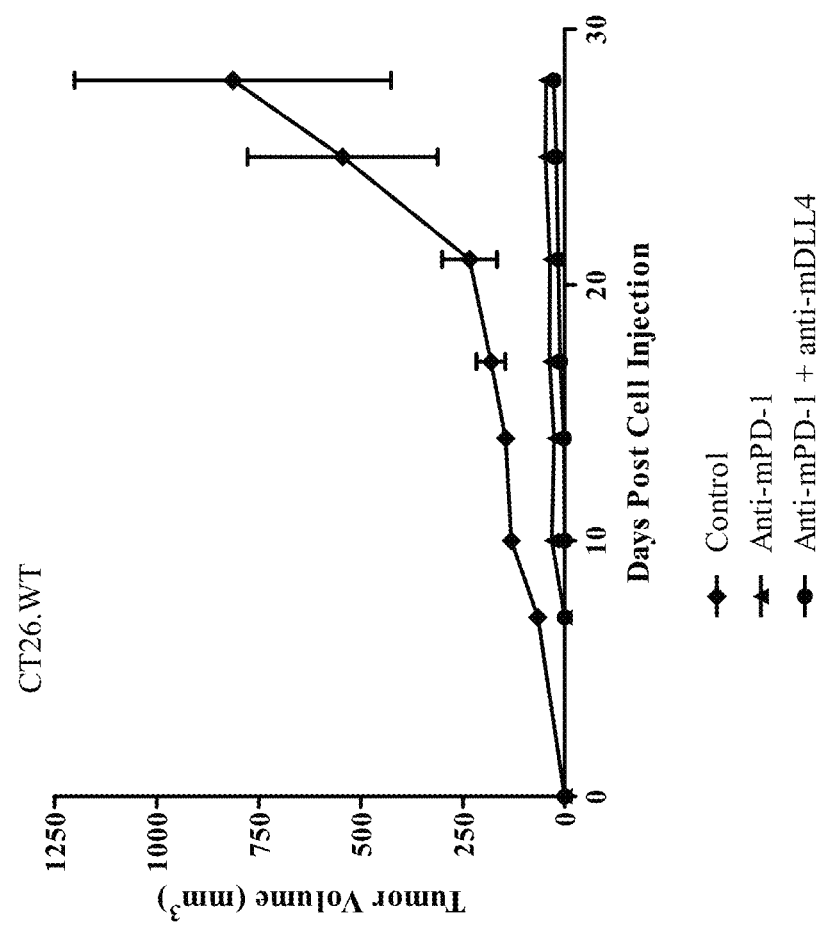
FIG. 9. CT26.WT tumor growth in treated mice after rechallenge with tumor. Mice previously treated with anti-PD-1 antibody (-▲-) or a combination of anti-mDLL4 antibody 21R30 and an anti-PD-1 antibody (-●-) whose tumors had regressed to undetectable levels were rechallenged with CT26.WT tumor cells. Data is shown as tumor volume (mm$^3$) over days post-rechallenge.

As shown in FIG. 9, the average tumor volume of CT26.WT tumors in naive mice grew steadily up to Day 28, where upon the mice were euthanized. In contrast, the average tumor volume of CT26.WT tumors in mice which had previously been treated with anti-PD-1 antibody or a combination of anti-PD-1 antibody and anti-mDLL4 antibody 21R30 was very small (46 mm$^3$ and 27 mm$^3$, respectively). Evaluation of individual mice showed that 5 of 11 (46%) mice originally treated with anti-mPD-1 antibody appeared to be completely protected (no detectable tumors) and 11/14 (79%) mice originally treated with a combination of anti-mPD-1 and anti-mDLL4 were completely protected.

Five mice from each group which had developed no tumors upon first re-challenge were rechallenged for a second time with 50,000 CT26.WT cells (2.5 times the number of cells of initial dose). Again as a control, 5 naïve mice were injected with CT26.WT cells with the same number of CT26.WT cells (50,000 cells/mouse). As in the earlier experiment, all 5 mice in the control group developed large tumors and were euthanized at Day 21. Small tumors (average 56 mm$^3$) grew in 3 of the 5 mice that had been originally treated with anti-mPD-1 antibody. No tumors grew in the mice that had been originally treated with a combination of anti-DLL4 antibody and anti-mPD-1 antibody. These results are summarized in Table 1 and presented as the percentage of tumor-free mice in each group.

TABLE 1

|  | Initial Challenge 20,000 cells | 1$^{st}$ Re-challenge 20,000 cells | 2$^{nd}$ Re-challenge 50,000 cells |
|---|---|---|---|
| Control Mice | 0% (0/10) | 0% (0/10) | 0% (0/5) |
| Mice treated with anti-mPD-1 Ab$^1$ | 55% (11/20) | 46% (5/11) | 40% (2/5) |
| Mice treated with anti-mPD-1 Ab and anti-mDLL4 Ab$^1$ | 70% (14/20) | 79% (11/14) | 100 (5/5) |

$^1$Mice treated with antibody only after initial tumor challenge

These mice appeared to be strongly protected from re-challenge with the CT26.WT tumor cells. These results suggest the existence of immunogenic memory after treatment with a combination of anti-mDLL4 and anti-mPD-1 antibodies.

Example 8

ELISpot Assays for IFN-Gamma, IL-2 and IL-17 and ELISA for IL-6

IFN-gamma secreting cells were detected using a mouse IFN-gamma ELISpot kit (MabTech). Cells were isolated from the spleens of tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5). Splenocytes (5×10$^5$/well) from each mouse in each treatment group were dispensed into a 96 well plate coated with an antibody specific for mouse IFN-gamma. The cells were cultured in the presence or the absence of a tumor specific CD8$^+$ T-cell peptide (AH-1) and incubated for 48 hours. Cells secreting IFN-gamma were detected following the manufacturer's instructions. Spots were counted using a Bioreader 6000 F-z instrument (BioSys). Data are expressed as mean±S.E.M.

Figure 10A:
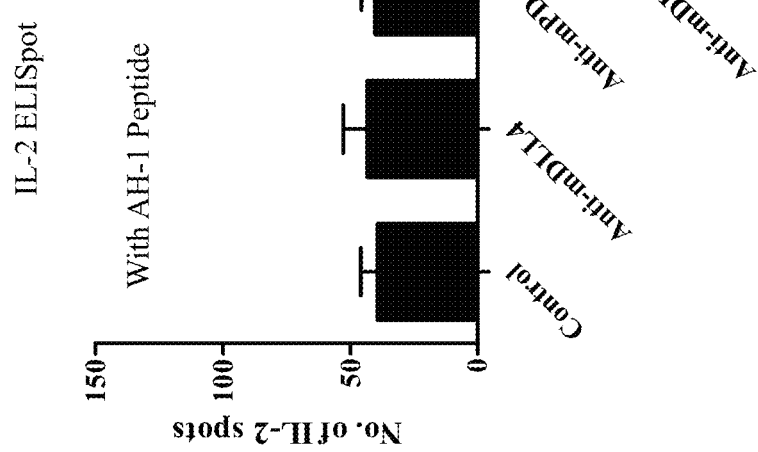
FIGS. 10A, 10B, 10C, and 10D. ELISpot and ELISA assays. Cells were harvested from the spleens of CT26.WT-tumor bearing mice treated with anti-mDLL4 antibody 21R30, an anti-PD-1 antibody, a combination of anti-mDLL4 antibody 21R30 and an anti-PD-1 antibody, or a control antibody.

As shown in FIG. 10A, tumor-specific IFN-gamma secreting CD8$^+$ T-cells were increased in mice treated with anti-mPD-1 antibody and in mice treated with a combination of anti-mDLL4 antibody 21R30 and anti-PD-1 antibody.

IL-2 secreting cells were detected using a mouse IL-2 ELISpot kit (MabTech). Cells were isolated from the spleens of tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5). Splenocytes (5×10$^5$/well) from each mouse in each treatment group were dispensed into a 96 well plate coated with an antibody specific for mouse IL-2. The cells were incubated in the presence of the AH-1 peptide for 48 hours. Cells secreting IL-2 were detected following the manufacturer's instructions. Spots were counted using Bioreader 6000 F-z instrument (BioSys). Data are expressed as mean±S.E.M.

Figure 10B:
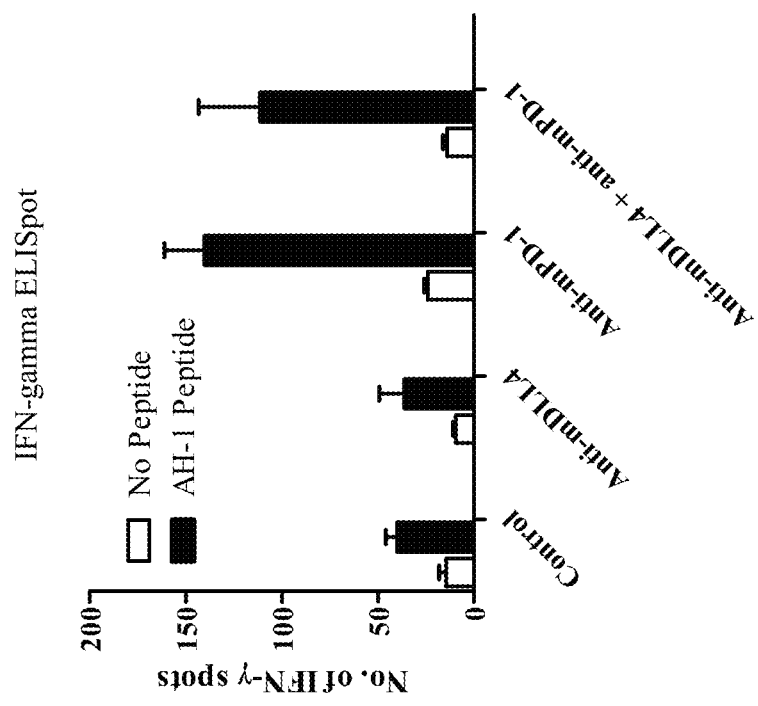

As shown in FIG. 10B, IL-2 secreting cells were increased only in mice treated with a combination of anti-mDLL4 antibody 21R30 and anti-PD1 antibody.

IL-17 secreting cells were detected using a mouse IL-17 ELISPOT kit (MabTech). Cells were isolated from the spleens of tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5). Splenocytes (5×10$^5$/well) from each mouse within each treatment group were dispensed into a 96 well plate coated with an antibody specific for mouse IL-17. The cells were incubated for 48 hours. Cells secreting IL-17 were detected following the manufacturer's instructions. Spots were counted using a Bioreader 6000 F-z instrument (BioSys). Data are expressed as mean±S.E.M.

Figure 10D:
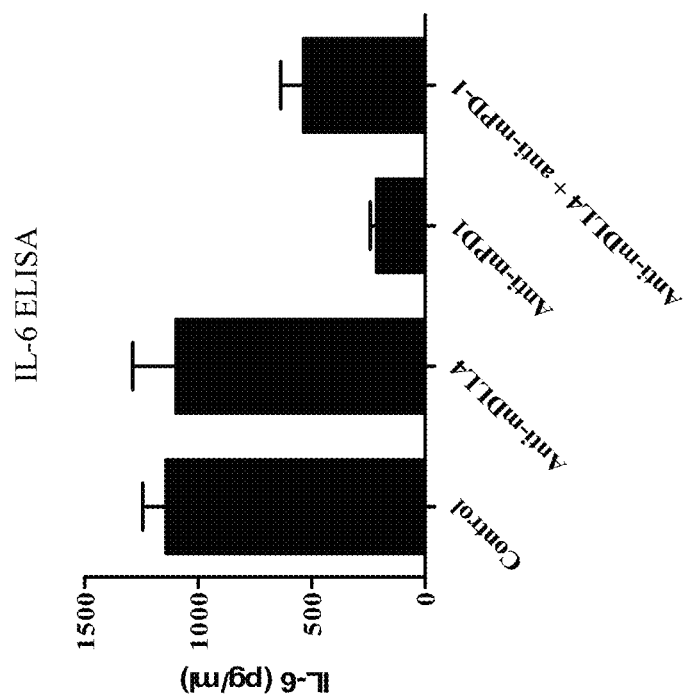
Figure 10C:
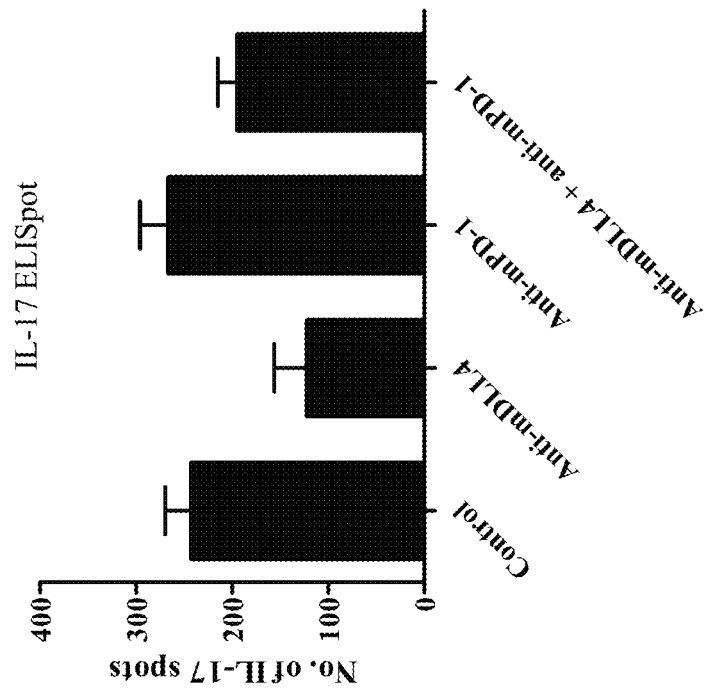

As shown in FIG. 10C, IL-17 secreting cells were decreased in mice treated with anti-mDLL4 antibody 21R30 and in mice treated with a combination of anti-mDLL4 antibody 21R30 and anti-mPD-1 antibody. In subsequent experiments, it was shown that anti-mPD-1 antibody as a single agent, a combination of anti-mDLL4 antibody and anti-mVEGF antibody, and a triple combination of anti-mDLL4 antibody, anti-mVEGF antibody, and anti-mPD-1 antibody did not reduce the number of IL-17-secreting cells in spleens from treated mice (data not shown). This suggests that blocking DLL4 alone may have a different mechanism regulating immune responses as compared to the mechanism of blocking DLL4 in combination with VEGF or blocking DLL4 in combination with VEGF and PD-1.

IL-6 production was detected using a mouse IL-6 ELISA kit (eBioscience). Cells were isolated from the spleens of tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5). Splenocytes (5×10$^5$/well) from each mouse within each treatment group were dispensed into a 96 well plate. The cells were cultured in the presence or the absence of a tumor specific CD8$^+$ T-cell peptide (AH-1) and incubated for 48 hours. The level of IL-6 was detected in each cell supernatant following the manufacturer's instructions. The plate was read using a SpectraMax Plus instrument (Molecular Devices). Data are expressed as mean±S.E.M.

IL-6 production was the same in supernatants from cells incubated in the presence or the absence of the AH-1 peptide. As shown in FIG. 10D, the level of IL-6 produced by splenocytes from mice treated with anti-mPD-1 antibody and in mice treated with a combination of anti-mDLL4 antibody 21R30 and anti-mPD1 antibody was greatly reduced as compared to IL-6 produced by splenocytes from mice treated with only anti-mDLL4 antibody 21R30 or the control antibody.

IFN-gamma is generally produced by NK cells, Th1 $CD4^+$ T-cells, $CD8^+$ T-cells, antigen presenting cells, and B-cells. Studies have suggested a role for IFN-gamma in tumor immunity and that it may be a regulator of anti-tumor activity mediated by other cytokines, in particular IL-12 and IL-2. The predominant source of IL-2 is the Th1 $CD4^+$ T-cell and its major role is to promote the activation and proliferation of T-cells and NK cells in an autocrine and paracrine manner. In particular, exposure of NK cells to IL-2 results in proliferation and enhanced cytolytic activity. In addition, IL-2 is required for the maintenance and survival of memory T-cells. Thus, treatment with a DLL4 antagonist and/or an anti-mPD-1 antibody that results in an increase in IFN-gamma and/or IL-2 should enhance anti-tumor immunity. IL-17 is produced by $T_H17$ cells, a subset of helper T-cells believed to have a pro-inflammatory role in autoimmune disease. IL-17 contributes to the recruitment of myeloid cells of the monocyte and granulocyte lineages through local induction of chemokines and stimulation of G-CSF and GM-CSF production. A factor of ineffective or absent immune responses against tumors can be the presence of MDSCs derived from both the monocytic and granulocytic lineages. Tumor-specific $T_H17$ cells may play a role in promoting the attraction of myeloid cells to the tumor and thus the promotion of an immune suppressive environment. The ability of a DLL4 antagonist to reduce the frequency of tumor-specific $T_H17$ cells and the production of IL-17 may therefore reduce the generation of MDSC and promote anti-tumor immunity. IL-6 is generally produced by macrophages, endothelial cells, and some activated T-cells. In contrast to IFN-gamma and IL-2, over-expression of IL-6 appears to play a role in the pathogenesis of many cancers. Thus, treatment with a DLL4 antagonist and/or an anti-PD-1 antibody that results in a decrease in IL-6 production should enhance anti-tumor immunity.

Example 9

FACS Analysis of Myeloid-Derived Suppressor Cells and Activated Myeloid Cells

Studies have identified myeloid origin cells that are potent suppressors of tumor immunity and therefore a significant impediment to cancer immunotherapy (see, e.g., Ostrand-Rosenberg et al., 2009, 1 *Immunol.*, 182:4499-4506). MDSCs accumulate in the blood, lymph nodes, bone marrow, and at tumor sites in most patients and experimental animals with cancer. MDSCs have been shown to inhibit both adaptive and innate immunity.

It is believed that MDSCs facilitate cancer progression by inhibiting anti-tumor immune responses, promoting angiogenesis, and creating a pre-metastatic environment. MDSCs suppress the proliferation and activation of $CD4^+$ T-cells and $CD8^+$ T-cells, thereby inhibiting anti-tumor immunity. Importantly, MDSCs facilitate the generation of Treg cells.

MDSCs are a heterogeneous family of myeloid cells. In mice, MDSCs are characterized by the cell surface expression of the myeloid lineage differentiation antigens Gr1 and CD11b. MDSCs can be divided into two subpopulations: granulocytic MDSCs (G-MDSC) and monocytic MDSCs (M-MDSC). G-MDSCs typically have multilobed nuclei and a $CD11b^+Ly6G^+Ly6C^{low}$ phenotype, whereas M-MDSCs have a monocytic morphology and a $CD11b^+Ly6G^{+/-}Ly6C^{high}$ phenotype. Both populations of MDSCs have been shown to suppress T-cell responses by multiple mechanisms including increased production of arginase, inducible nitric oxide synthase (iNOS), nitric oxide, and reactive oxygen species. Thus, MDSCs contribute to an immunosuppressive tumor microenvironment and may limit the effects of anti-tumor immune responses.

The number of MDSCs in mice treated with a DLL4 antagonist and/or an anti-PD1 antibody was evaluated. Cells were isolated from the spleens of CT26.WT tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5).

The freshly prepared single cell suspensions were blocked using a blocking solution for 10 minutes and then stained with anti-mouse Gr1 (clone RB6-8C5, BioLegend) and anti-mouse CD11b (clone M1/70, BioLegend) in FACS buffer (HBSS plus 2% FCS) for 20 minutes on ice. The activated myeloid cell population was analyzed by staining spleen cells with anti-mouse CD11b and anti-mouse MHC class II antibody. The cells are washed, labeled with fixable cell viability dye (eBiosciences), and fixed in 2% paraformaldehyde for analysis. Cells were analyzed using a FACSCanto II instrument (BD Sciences) and using Diva software. Dead cells were excluded using the viability dye and cell doublets and clumps were excluded using doublet discrimination gating. Cells were analyzed for M-MDSC and activated myeloid populations.

Figure 11:
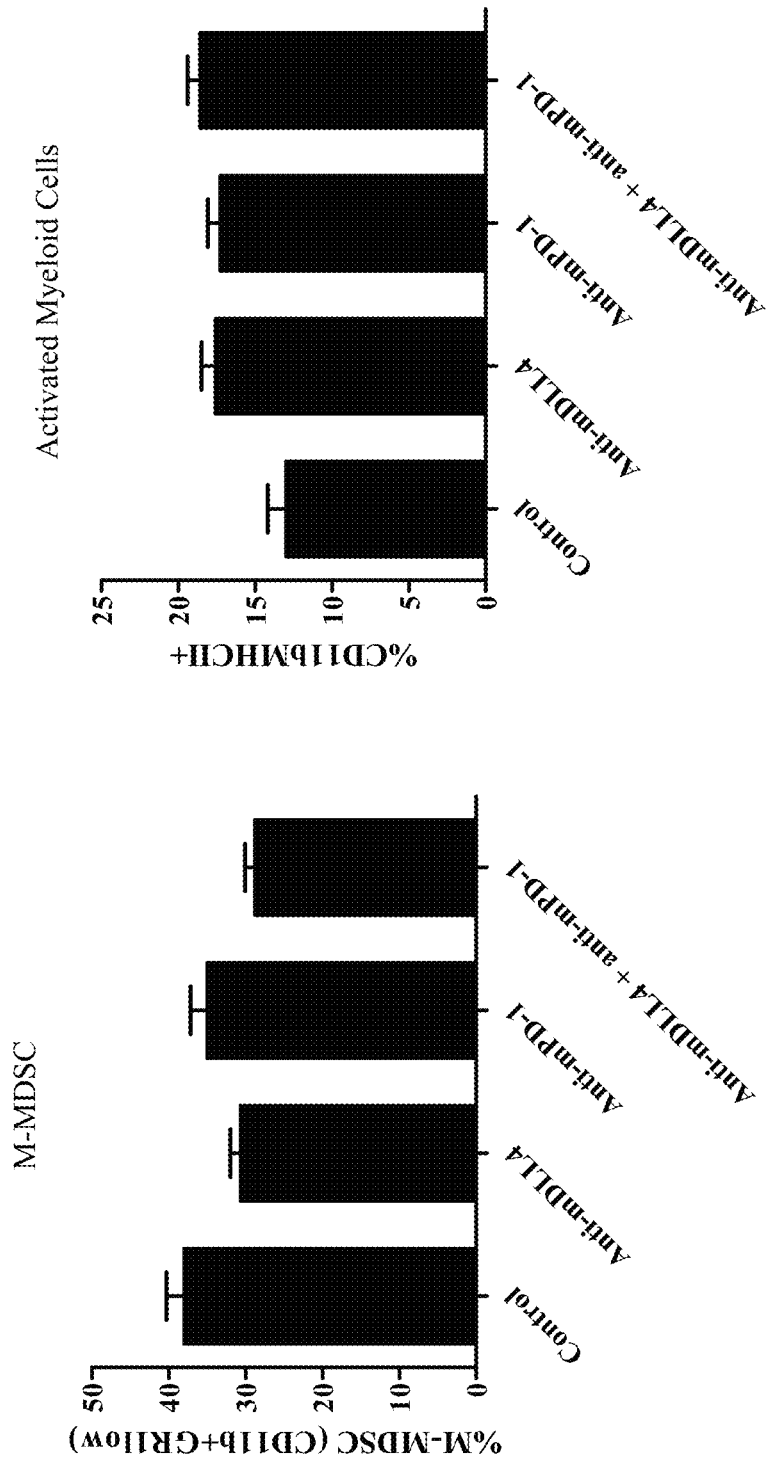
FIG. 11. FACS analysis of myeloid-derived suppressor cells and activated myeloid cells.

As shown in FIG. 11, treatment with anti-mDLL4 antibody 21R30 alone or antibody 21R30 in combination with anti-mPD-1 antibody reduced the percentage of M-MDSCs in spleens from tumor-bearing mice as compared to treatment with anti-mPD-1 antibody alone or with a control antibody. In contrast, treatment with anti-mDLL4 antibody 21R30 alone, anti-mPD-1 antibody alone, or a combination of anti-mDLL4 antibody 21R30 and anti-mPD-1 antibody increased the percentage of activated myeloid cells as compared to treatment with control antibody.

These data suggest that targeting DLL4 may contribute to inhibiting the suppressive activity of MDSCs by reducing the percentage and/or number of these immunosuppressive cells. This result is consistent with our hypothesis that DLL4 antagonist treatment may reduce the generation of MDSC and promote a productive anti-tumor immunity by reducing the frequency of tumor-specific $T_H17$ cells. The reduction on MDSC number and/or the activation of myeloid cells may be even greater within the tumor microenvironment, but this has not been assessed at this point in time due to the small tumor size after treatment.

Example 10

FACS Analysis of Memory T-Cells

Memory T-cells are a heterogeneous T-cell population and are separated into two distinct subsets (central memory T-cells and effector memory T-cells) based upon phenotype and function. In mice, central and effector memory $CD8^+$ T cells can be separated into two distinct populations according to their respective CD44 and CD62L expression levels. A $CD44^{high}$ $CD62L^{low}$ $CD8^+$ T-cell population rapidly acquires effector functions which constitute the effector memory, whereas $CD8^+$ T-cells expressing a $CD44^{high}CD62L^{high}$ population acquire profound proliferative capacities upon antigen recognition, and constitute the central memory T cells.

The number of central memory cells or effector memory CD8+ T-cells in mice treated with anti-PD1 and/or anti-mDLL4 antibodies was evaluated. Cells were isolated from the spleens of CT26.WT tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5).

FACS staining was done as described above using anti-mouse CD8b (clone 53-5.8, BioLegend), anti-mouse CD4 (clone GK1.5, BioLegend, Clone), anti-mouse CD62L (clone MEL-14, BioLegend) and anti-mouse CD44 (clone 1M7, BioLegend). Cells were analyzed for $CD44^{high}CD62L^{high}$ expression (central memory) and $CD44^{high}$ $CD62L^{low}$ CD8+ expression (effector memory).

Figure 12:
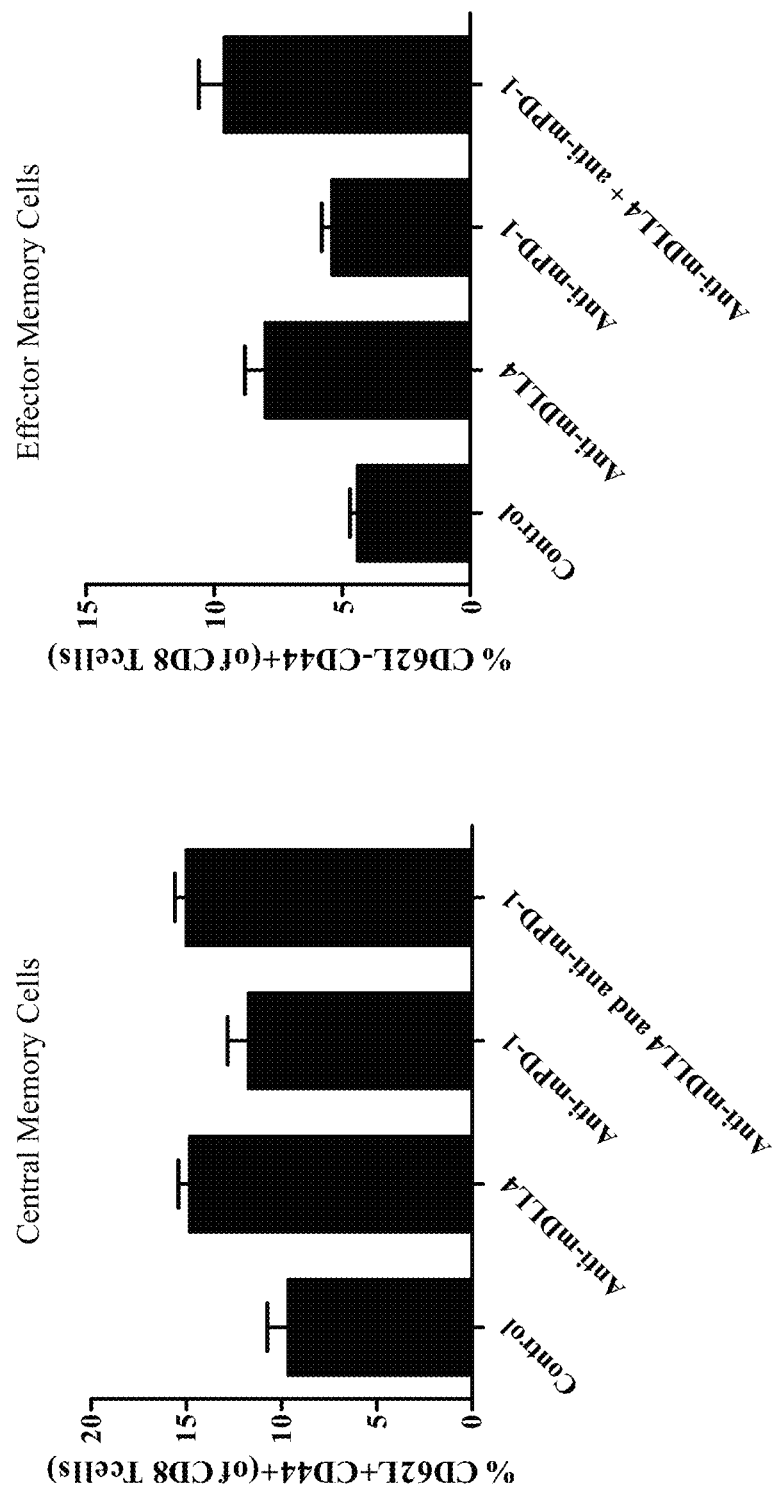
FIG. 12. FACS analysis of memory T-cells.

As shown in FIG. 12, treatment with anti-mDLL4 antibody 21R30 alone or anti-mDLL4 antibody 21R30 in combination with anti-mPD-1 antibody increased the percentage of central memory and effector memory CD8+ T-cells in spleens as compared to treatment with anti-mPD-1 antibody alone or with a control antibody.

These results suggest that the combination of a DLL4 antagonist and an anti-PD-1 antibody facilitates the generation of central and effector memory CD8+ T-cells. These memory T-cells may provide long-term immune memory function and work to provide an immune response against reoccurrence of tumors and/or metastases. These results are also consistent with our hypothesis that by reducing the frequency of tumor-specific $T_H17$ cells, DLL4 antagonist treatment reduces the generation of MDSC and thereby enables T cells to mount a more productive and substantial anti-tumor immune response. The distinct mechanism of DLL4 antagonist is able to complement and promote the anti-tumor response promoted by an immune checkpoint inhibitor such as an anti-PD-1 antibody.

Example 11

Regulatory T-Cell (Treg) Assay

Tregs are an immune T-cell population that suppresses the proliferative responses of CD4+ and CD8+ T cells. The functionality of Tregs in mice treated with a DLL4 antagonist and/or a PD-1 antibody was evaluated by determining the effect the Tregs had on proliferation of naïve CD4+ or CD8+ T-cells.

Naive T-cells were purified from the spleens of untreated mice using a mouse CD3+ T-cell enrichment column (R&D Systems). Purified T-cells were labeled with 5 µM violet tracking dye (VTD) (Life Technologies). $2 \times 10^5$ VTD-labeled T-cells were stimulated with anti-CD3 and anti-CD28 antibody-coated beads to stimulate T-cell proliferation. Tregs were isolated from the spleens of CT26.WT tumor-bearing mice treated with anti-mDLL4 antibody 21R30 (n=6), anti-PD-1 antibody (n=6), a combination of anti-mDLL4 antibody 21R30 and anti-PD-1 antibody (n=5), or a control antibody (n=5) using a Treg isolation kit (Miltenyi Biotec). To determine the impact of Tregs on T-cell proliferation, the VTD-labeled naïve T-cells were co-cultured with isolated splenic Tregs from the mice treated with anti-mDLL4 antibody, the mice treated with anti-mPD-1 antibody, the mice treated with a combination of anti-mDLL4 antibody and anti-mPD-1 antibody, and the mice treated with the control antibody. The stimulated VTD-labeled cells (effectors) were co-cultured with Treg cells (effector:Treg of 1:0.5 or 1:0.25). On day 4, cells were washed, and stained with anti-mCD4 and anti-mCD8 antibodies. Changes in VTD concentration were evaluated by FACS analysis and the results were used to calculate T-cell proliferation.

Figure 13:
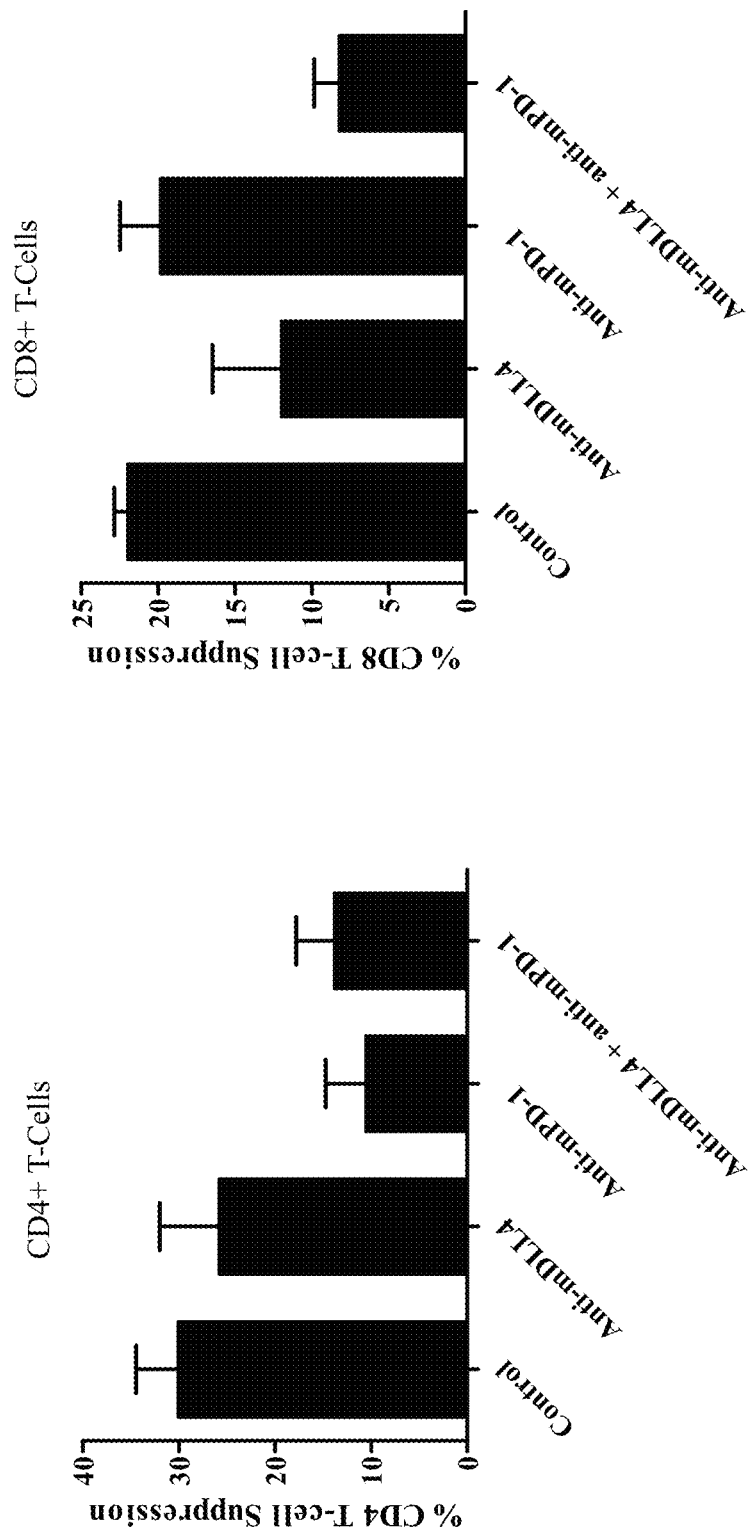
FIG. 13. Regulatory T-cell (Treg) assay.

As shown in FIG. 13, treatment with anti-mPD-1 antibody reduced the suppressive function of Treg on CD4+ T-cell proliferation. Treatment with a combination of anti-mDLL4 antibody 21R30 and anti-mPD-1 antibody also reduced the suppressive function of Treg on the CD4+ T-cell proliferation, but to a lesser extent. In contrast, treatment with anti-DLL4 antibody 21R30 had a greater effect than anti-mPD-1 antibody on reducing the suppressive function of Treg on the CD8+ T-cell proliferation. And interestingly, treatment with a combination of anti-mDLL4 antibody 21R30 and anti-mPD-1 antibody had a significantly greater effect on reducing the suppressive function of Treg on the CD8+ T-cell proliferation than either antibody alone.

These results suggest that a combination of a DLL4 antagonist and an anti-PD-1 antibody can lead to reduced Treg function. A suppression of Treg function could enhance total anti-tumor immune responses. These results are consistent with our hypothesis that by reducing the frequency of tumor-specific $T_H17$ cells, DLL4 antagonist treatment reduces the generation of MDSC and thereby promotes a more robust immune response. MDSC contribute to the maintenance and expansion of Tregs though several mechanisms including PD-L1/B7-H1 and arginase. The distinct mechanism of DLL4 antagonist both promotes anti-tumor immunity as a single agent and also compliments the action of checkpoint inhibitors such as anti-PD-1.

Example 12

T-Cell Cytotoxicity Assay

The functionality of CD8+ cytotoxic T-cells in mice treated with a DLL4 antagonist and/or anti-PD-1 antibody was evaluated. Cells were harvested from the spleens of CT26.WT tumor-bearing mice treated with anti-mDLL4 antibody 21R30 (n=6), anti-mPD-1 antibody (n=6), a combination of anti-mDLL4 antibody 21R30 and anti-mPD-1 antibody (n=5), or a control antibody (n=5). The splenocytes were cultured in media supplemented with 30 IU/ml recombinant murine IL-2 (Peprotech, Rocky Hill, N.J.) and 1 µg/ml CD8+ T-cell peptide AH-1 peptide. The splenocytes were incubated for 7 days at 37° C., harvested, counted, and used in cytotoxicity assays with CT26.WT tumor cells as targets. The CT26.WT target cells were labeled with 10 µM calcein AM (Life Technologies) for 1 hour at 37° C. and then combined with the splenocytes at an effector:target ratio of 50:1. Following a four hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

Figure 14:
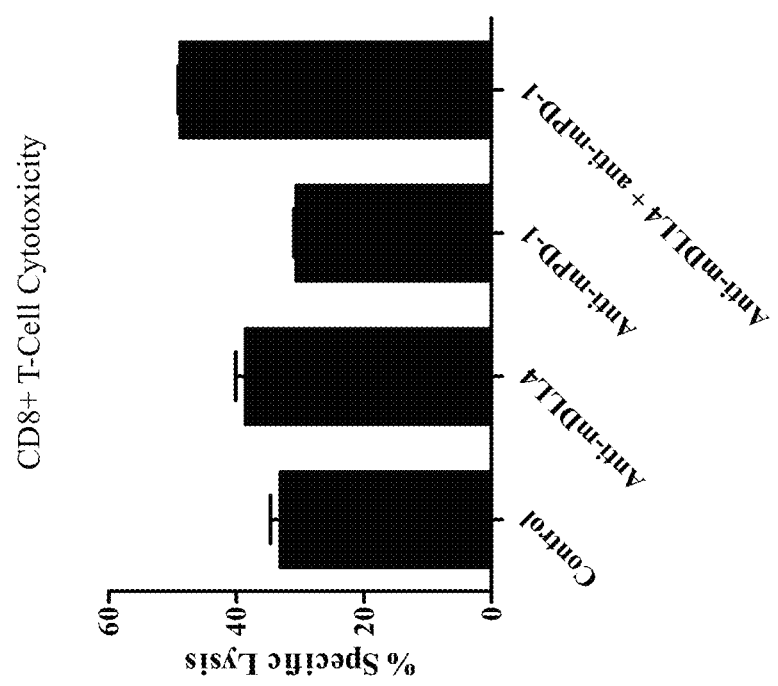
FIG. 14. CD8$^+$ T-cell cytotoxicity assay.

As shown in FIG. 14, tumor-specific CD8+ T-cells from mice treated with either anti-mDLL4 antibody 21R30 or combination of anti-mDLL4 antibody 21R30 and an anti-mPD-1 antibody had an increased level of cytolytic activity against parental tumor cells as compared to control, and the combination of anti-mDLL4 antibody and anti-mPD-1 antibody further increased CD8+ T-cell activity relative to single agents.

These results suggest that a combination of a DLL4 antagonist and an anti-PD-1 antibody increases cytolytic CD8+ T-cell function. This increased cytolytic T-cell function could enhance total anti-tumor immune responses. These results are also consistent with our hypothesis that by reducing the frequency of tumor-specific $T_H17$ cells, DLL4 antagonist treatment reduces the generation of MDSC and thereby promotes increased cytolytic T-cell function and an a more robust total anti-tumor immune response.

Example 13

PD-L1 Protein Expression Assessed by IHC

A PD-L1 immunohistochemistry (IHC) assay is used to determine the expression level of PD-L1 in samples. FFPE sections are cut and mounted on coated glass slides. Tissues are deparaffinized and rehydrated by successively incubating them in xylene, 100% ethanol, 95% ethanol, 70% ethanol, and distilled water for antigen retrieval. Slides are placed into retrieval solution and placed in a decloaker for antigen retrieval. To block endogenous peroxidase activity slides are incubated in 6% hydrogen peroxide for 5 minutes and washed in PBS. To block non-specific background staining slides are incubated in CAS-Block (Life Technologies) for 30 minutes at room temperature. Slides are incubated with an anti-PD-L1 antibody. The anti-PD-L1 antibody is detected using a secondary antibody labeled with horseradish peroxidase. The antibody complex is visualized with a hydrogen peroxide substrate and a 3,3'-diaminobenzidine tetrahydrochloride (DAB) chromogen which produces a brown precipitate.

The slides are analyzed either manually or using an automated instrument. The staining intensity of each tumor cell (0: no expression, 1: weak expression, 2: moderate expression, 3: strong expression) is measured and cells of each staining level are counted and a percentage for each type was calculated. The data is combined into a weighted H-score for each tissue section: H-score=[3×(% 3+ cells)]+[2×(% 2+ cells)]+[1×(% 1+ cells)]. This calculation allows for a top H-score of 300. Positive and negative controls may include human tissue sections purchased from a commercial supplier as well as patient-derived xenograft samples from the OncoMed tumor bank with known expression levels of PD-L1.

Example 14

Phase 1 Study of Demcizumab (OMP-h21M18) in Combination with Pembrolizumab (Anti-PD-1; KEYTRUDA) with or without Chemotherapy in Subjects with Solid Tumors The study is an open-label Phase 1b dose-escalation and expansion study of demcizumab (OMP-21M18) in combination with pembrolizumab (anti-PD-1; KEYTRUDA) with or without chemotherapy in subjects with advanced or metastatic solid tumors. The primary objective of the study is to identify dose-limiting toxicities (DLTs) and estimate the maximum tolerated dose (MTD) of demcizumab with pembrolizumab and to identify DLTs and estimate the MTD of demcizumab with pembrolizumab administered with pemetrexed and carboplatin. The secondary objectives are to determine the safety, the incidence of immunogenicity, the pharmacokinetics of demcizumab and pembrolizumab as compared to the respective single agent drug exposure, the preliminary response rate as assessed by immune-based criteria, and the preliminary efficacy.

Approximately 6-12 patients will be enrolled in the dose-escalation stage of demcizumab in combination with pembrolizumab. Dose escalation will be conducted to determine the MTD of demcizumab when given with pembrolizumab. Approximately two cohorts per demcizumab dose level will be tested. The dose levels of demcizumab will be 2.5 and 5 mg/kg administered IV once every 3 weeks through Day 63. In the absence of disease progression, a second course of study drug (demcizumab at 1, 2.5 or 5 mg/kg) will be administered once every 3 weeks for 4 doses starting at Day 168 if the subject fulfills study criteria. No dose escalation or reduction will be allowed within a dose cohort and intermediate dosing cohorts may be added. If two or more patients in a single cohort experience Grade ≥2 adverse events attributed to demcizumab or pembrolizumab or one or more DLTs are observed, there will be additional cohorts at smaller incremental doses.

Three patients will be initially treated at the 2.5 mg/kg demcizumab and 2 mg/kg pembrolizumab dose level. If 1 of 3 subjects experiences a DLT, that dose level will be expanded to 6 subjects. If 2 or more patients experience a DLT, no further patients will be dosed at that level and 3 additional patients will be tested at 1 mg/kg demcizumab and 2 mg/kg pembrolizumab dose level. Patients will be assessed for DLTs from the time of the first dose through Day 21. Dose escalation, if appropriate, will occur after all patients in a cohort have completed their Day 21 DLT assessment. The maximum dose of demcizumab to be tested is 5 mg/kg. Once the MTD of demcizumab with pembrolizumab has been established, patients will be enrolled into the cohort expansion stage.

Approximately 30 patients will be enrolled in the indication specific expansion stage. This stage includes multiple cohorts to better characterize the safety, tolerability, PK variability, biomarkers of anti-tumor activity, and preliminary efficacy of demcizumab in combination with pembrolizumab in different cancer types. The planned expansion cohorts will include, but may not be limited to, patients with non-squamous stage IIIB/IV NSCLC treated with up to 2 prior lines of chemotherapy, patients with any solid tumor that has progressed on prior treatment with an anti-PD1 or anti PDL-1 inhibitor, patients with castrate-resistant prostate cancer that has progressed on prior therapy, patients with colorectal cancer treated with up to 3 prior lines of chemotherapy, and patients with pancreatic cancer treated with up to 2 prior lines of chemotherapy.

In the expansion cohort comprising NSCLC patients, dose escalation with the addition of carboplatin and pemetrexed will be initiated at one dose level lower of the demcizumab MTD in combination with 2 mg/kg pembrolizumab. Three patients will be initially treated at the −1 dose level of demcizumab and 2 mg/kg pembrolizumab dose level in combination with pemetrexed and carboplatin. Demcizumab will be administered by IV infusion once every 3 weeks up to Day 63. In the absence of disease progression, a second course of study drug (demcizumab at 1, 2.5 or 5 mg/kg) will be administered once every 3 weeks for 4 doses starting at Day 168 if the subject's Day 168 BNP is ≤100 pg/mL, peak tricuspid velocity is ≤3.0 m/s and LVEF is ≥50%, and the subject fulfills study criteria. Pembrolizumab will be administered IV at a dose of 2 mg/kg over 30 minutes every 3 weeks. Pemetrexed at 500 mg/m² will be administered as an intravenous infusion over 10 minutes once every 21 days. Carboplatin at 6 mg/ml×min will be administered as an intravenous infusion over 15 to 60 minutes once every 21 days for 4 cycles (or less than 4 full cycles if disease progression or toxicity warrants treatment interruption or termination). If 1 of 3 subjects experiences a DLT, that dose level will be expanded to 6 subjects. If 2 or more patients experience a DLT, no further patients will be dosed at that level and 3 additional patients will be tested at 1 mg/kg demcizumab and 2 mg/kg pembrolizumab dose level. Patients will be assessed for DLTs from the time of the first dose through Day 21. Dose escalation, if appropriate, will occur after all patients in a cohort have completed their Day 21 DLT assessment. The maximum dose of demcizumab to be tested is 5 mg/kg. Once the MTD of demcizumab with pembrolizumab has been established, approximately 10 patients with previously untreated stage IIIB/IV non-squamous NSCLC will be enrolled into the cohort expansion stage. This stage is designed to further characterize the safety and tolerability of the demcizumab, pembrolizumab, pemetrexed, and carboplatin combination and to assess preliminary efficacy. For other indications, the chemotherapy will generally comprise standard-of-care combinations.

Example 15

Inhibition of Tumor Growth In Vivo with Combination of Anti-DLL4, Anti-VEGF, and Anti-PD-1 Antibodies Single cell suspensions of CT26.WT tumor cells (30,000 cells) were injected subcutaneously into the flanks of 6-8 week old Balb/C mice. Ten days following tumor inoculation, mice with palpable tumors (approximately 125-130 $mm^3$) were treated with an anti-mPD-1 antibody (250 µg/mouse, twice a week), a combination of anti-mDLL4 antibody 21R50 (5 mg/kg, once a week) and anti-mVEGF antibody (2.5 mg/kg, once a week), a combination of anti-mPD-1 antibody, anti-mDLL4 antibody 21R50, and anti-mVEGF antibody, or a control antibody (20 mg/kg, twice a week). Mice were administered the antibodies for 3 weeks by intraperitoneal injection. Tumor growth was monitored and tumor volumes were measured with electronic calipers at the indicated time points. Data are expressed as mean±S.E.M.

Figure 15B:
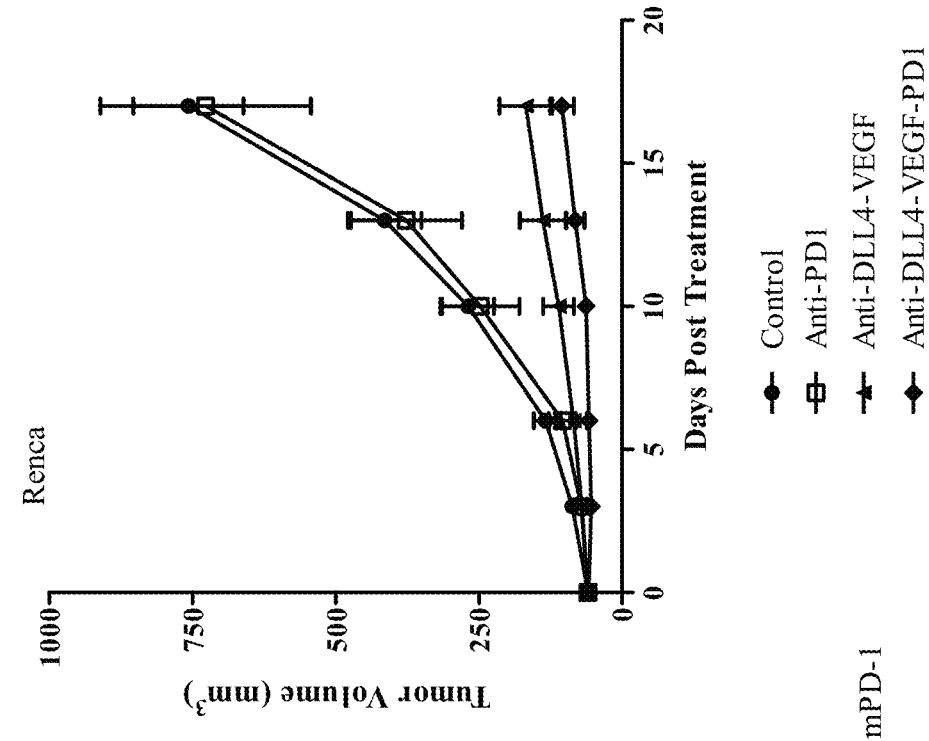
FIGS. 15A and 15B. Inhibition of CT26.WT tumor growth and inhibition of Renca tumor growth.
Figure 15A:
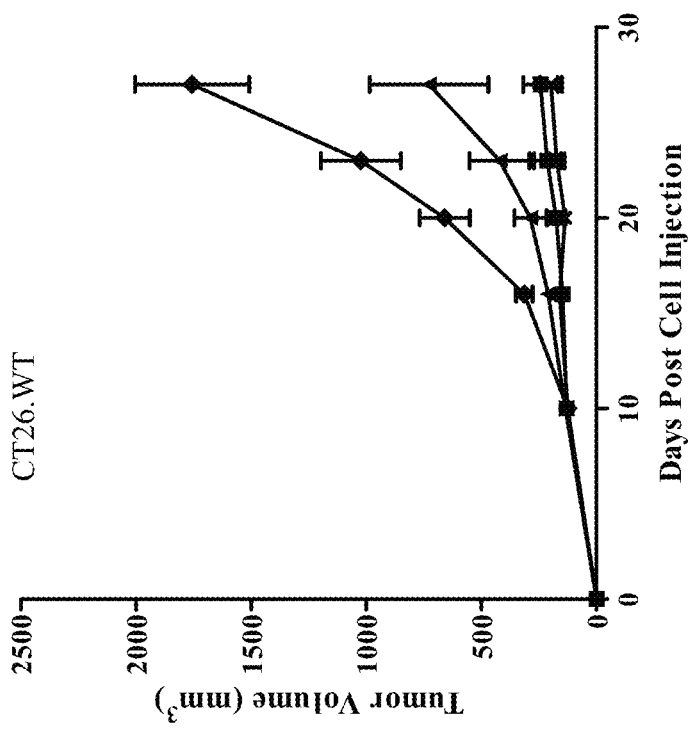

As shown in FIG. 15A, treatment with the combination of anti-mDLL4 antibody 21R50, anti-mVEGF antibody, and anti-mPD-1 antibody significantly reduced CT26.WT tumor growth as compared to treatment with the control antibody. On Day 27 average tumor growth in the treated mice was inhibited 89% as compared to mice treated with control antibody. Treatment with the combination of anti-mDLL4 antibody 21R50 and anti-mVEGF antibody significantly reduced CT26.WT tumor growth as compared to treatment with the control antibody. On Day 27 average tumor growth in the treated mice was inhibited 86% as compared to mice treated with control antibody. Anti-mPD-1 antibody as a single agent was not as effective and inhibited tumor growth only 59% as compared to mice treated with control antibody.

On Day 27 evaluation of individual mice treated with the combination of anti-mDLL4 antibody 21R50, anti-mVEGF antibody, and anti-mPD-1 antibody showed 10 of 20 mice (50%) had tumors that were the same size or had regressed to a smaller size than the size of the tumor prior to treatment. Evaluation of individual mice treated with the combination of anti-mDLL4 antibody 21R50 and anti-mVEGF antibody showed 5 of 10 mice (50%) had tumors that were the same size or had regressed to a smaller size than the size of the tumor prior to treatment and evaluation of mice treated with just anti-mPD-1 antibody showed 6 of 15 mice (40%) had tumors that were the same size or had regressed to a size smaller than the size of the tumor prior to treatment.

These results suggest that a blockade of DLL4, VEGF, and PD-1 in CT26.WT tumor cells has anti-tumor efficacy and that the efficacy may be better than PD-1 blockade alone.

A similar experiment was conducted with the murine renal adenocarcinoma, Renca. Single cell suspensions of Renca tumor cells ($5\times10^5$ cells) were injected subcutaneously into the flanks of 6-8 week old Balb/C mice. Eight days following tumor inoculation, mice with palpable tumors (approximately 60 $mm^3$) were treated with an anti-mPD-1 antibody (10 mg/kg, twice a week), anti-mDLL4 21R50 (10 mg/kg, once a week), a combination of anti-mDLL4 antibody 21R50 (10 mg/kg, once a week) and anti-mVEGF antibody (10 mg/kg, once a week), a combination of anti-mDLL4 antibody 21R50 (10 mg/kg, once a week) and anti-mPD-1 antibody (10 mg/kg, twice a week), a combination of anti-mPD-1 antibody, anti-mDLL4 antibody 21R50, and anti-mVEGF antibody, or a control antibody (20 mg/kg, twice a week). Mice were administered the antibodies for 3 weeks by intraperitoneal injection. Tumor growth was monitored and tumor volumes were measured with electronic calipers at the indicated time points. Data are expressed as mean±S.E.M.

As shown in FIG. 15B, treatment with the combination of anti-mDLL4 antibody 21R50, anti-mVEGF antibody, and anti-mPD-1 antibody significantly reduced Renca tumor growth as compared to treatment with the control antibody. On Day 17 average tumor growth in the treated mice was inhibited 86% as compared to mice treated with control antibody. Treatment with the combination of anti-mDLL4 antibody 21R50 and anti-mVEGF antibody also reduced Renca tumor growth as compared to treatment with the control antibody (78%). In contrast, treatment with an anti-PD-1 antibody as a single agent did not inhibit tumor growth.

Similar to what was seen in CT26.WT cells, these results suggest that a blockade of DLL4, VEGF, and PD-1 in tumor cells has anti-tumor efficacy.

Example 16

FACS Analysis of Central Memory T-Cells

Cells were harvested from the spleens of the CT26.WT tumor-bearing mice described above (Example 15). At Day 30 post-cell injection splenocytes were isolated. Splenocytes ($1\times10^6$) were incubated for 10 minutes with a recombinant Fc protein to block non-specific binding, and then incubated with fluorochrome-conjugated antibodies in 100 µl FACS staining buffer (HBSS plus 2% heat inactivated calf serum) for 20 min on ice. Unbound antibodies were removed by washing and dead cells were labeled with a fixable viability dye. Cells were fixed in 2% paraformaldehyde for 20 min at room temperature and analyzed using a FACSCanto II instrument and FACSDiva Software v6.1.3 (BD Biosciences).

Total T-cells were identified using an anti-mouse CD3e antibody, CD4+ T-cells using an anti-mouse CD4 antibody, and CD8+ T-cells using an anti-mouse CD8 antibody. Central memory cells were identified using an anti-mouse/human CD44 antibody and an anti-human CD62L antibody. FACS staining was done as described above using anti-mouse CD8b antibody (clone 53-5.8, BioLegend), anti-mouse CD4 antibody (clone GK1.5, BioLegend), anti-mouse CD62L antibody (clone MEL-14, BioLegend), and anti-mouse CD44 antibody (clone 1M7, BioLegend). Cells were analyzed for $CD44^{high}CD62L^{high}$ expression, indicating central memory cells (gated on CD8+ T-cells).

Figure 16:
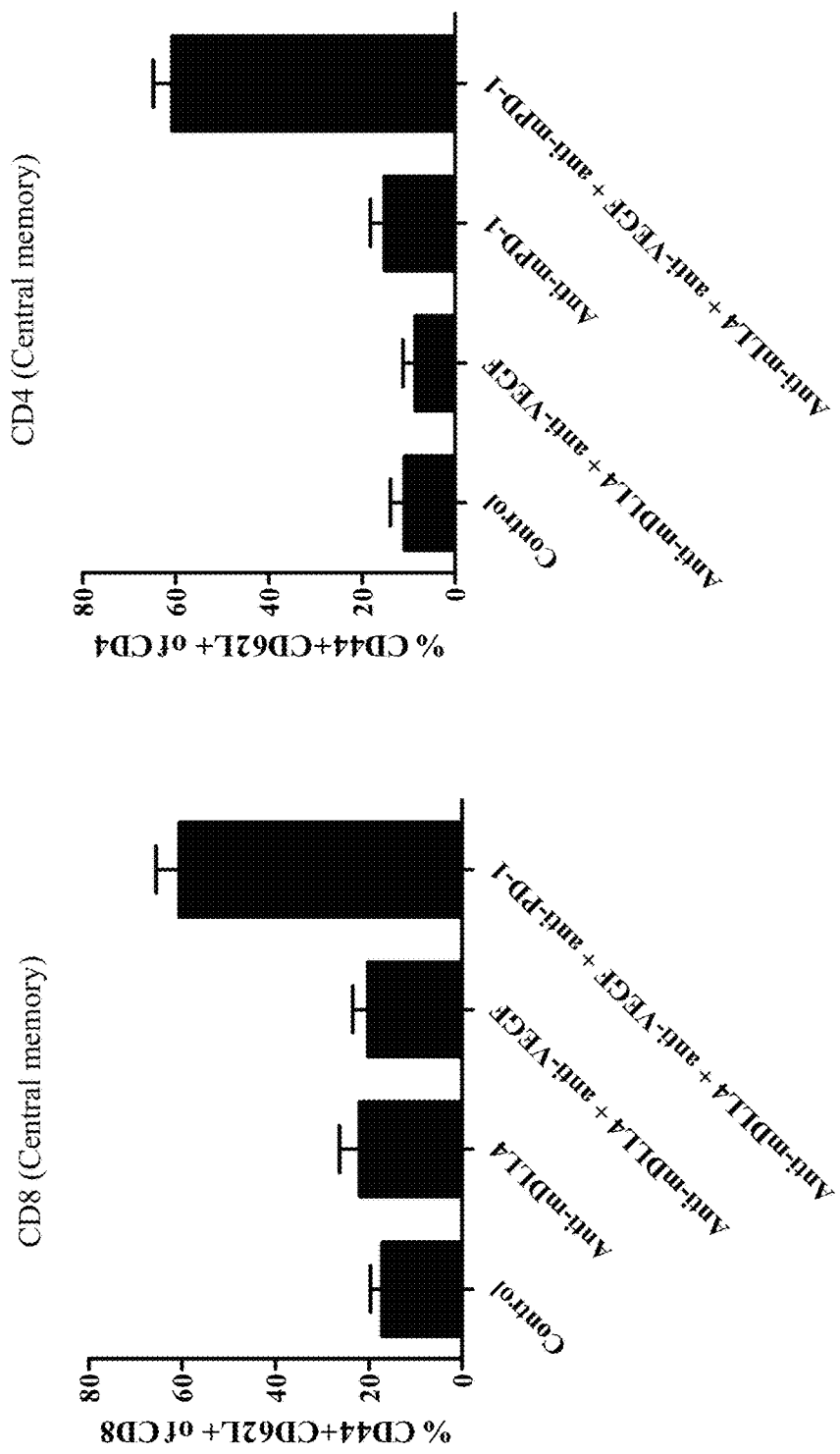
FIG. 16. FACS analysis of central memory CD4+ and CD8+ T-cells.

FACS analysis indicated that CT26.WT tumor-bearing mice treated with a combination of anti-mDLL4 antibody, anti-mVEGF antibody, and anti-mPD-1 antibody had an increased percentage of central memory cells within the CD4+ T-cell population and within the CD8+ T-cell population as compared to mice treated with a control antibody (FIG. 16). In contrast, mice treated with a combination of anti-mDLL4 and anti-mVEGF or mice treated with anti-mPD1 antibody as a single agent did not have a noticeable change in the percentage of central memory cells.

Example 17

Cytokine Expression in Tumor Samples

Tumor samples were taken from the CT26.WT tumor-bearing mice described above in Example 15. For immune response gene expression, quantitative real-time RT-PCR was performed on total RNA obtained from the tumor samples. The tumor samples are expected to contain tumor cells, immune cells associated with the tumor, and any stromal cells attached to the tumor sample. Tumor specimens were harvested and immediately snap frozen and stored at −80° C. prior to RNA isolation. Total RNA was extracted using the RNeasy Fibrous Mini Kit (Qiagen, Valencia Calif., PN #74704) with TissueLyzer homogenization and DNase I treatment according to the manufacturer's protocol. RNAs were visualized on a Bioanalyzer 2100 (Agilent, Santa Clara, Calif.) and verified to be intact with RIN values >6.0. All RNAs had A260/A280 ratios >1.8.

cDNA was synthesized from total RNA using random hexamers. The cDNA and PCR Master Mix were added to a TaqMan Array Immune Response Plate (Applied Biosystems/Life Technologies) and reactions were run on a real-time PCR instrument according to the manufacturer's protocol.

Figure 17A:
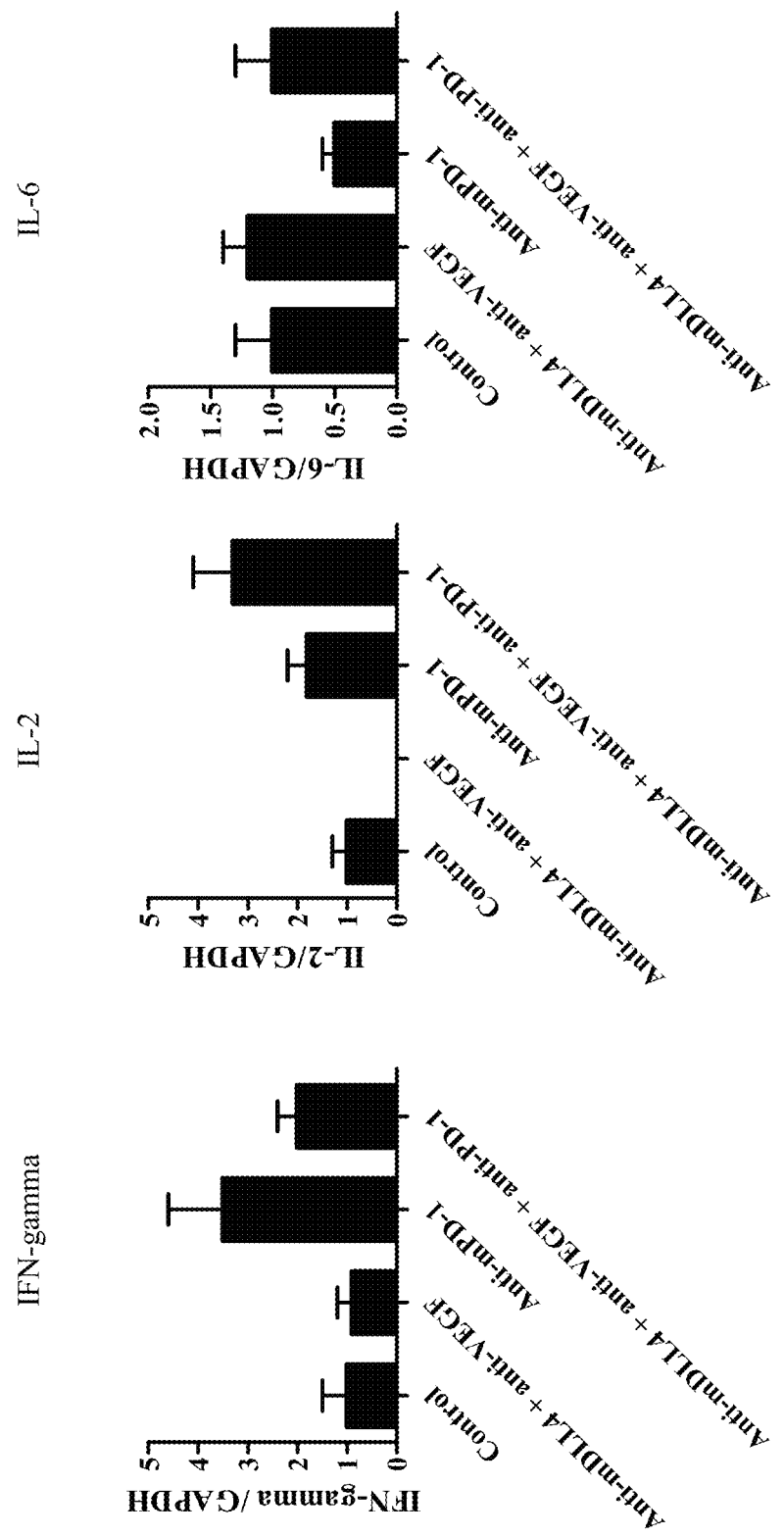
FIGS. 17A and 17B. Cytokine expression at tumor site.
Figure 17B:
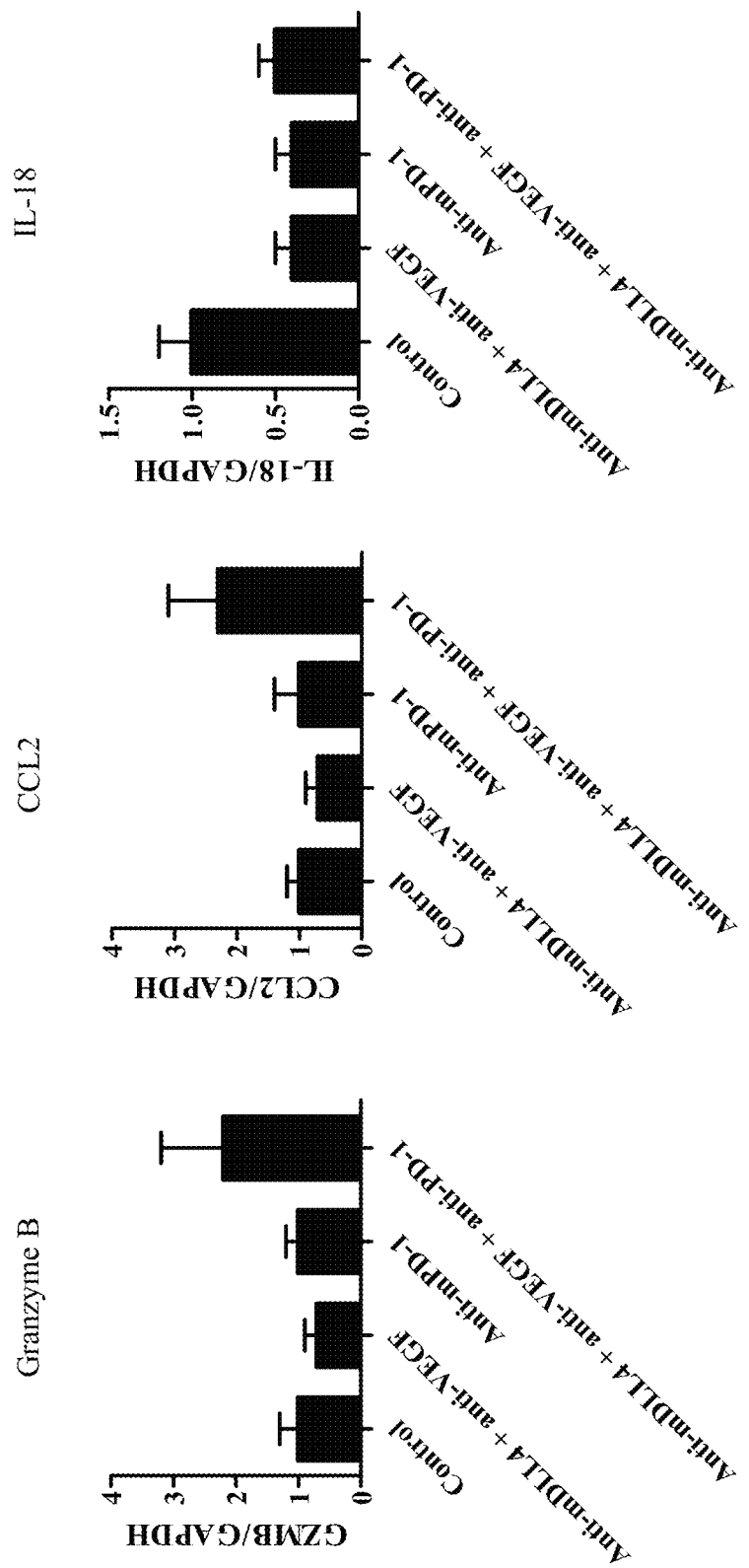

As shown in FIGS. 17A and 17B, treatment with a combination of anti-mDLL4, anti-mVEGF, and anti-mPD-1 increased gene expression of IL-2, granzyme B, and CCL2 in the tumor sample. Treatment with anti-mPD-1 as a single agent increased gene expression of IFN-gamma and decreased gene expression of IL-6 at the tumor site. In addition, all treatments decreased gene expression of IL-18.

IL-18 has been shown to have pleiotropic functions and appears to play a dual role in cancer (see, e.g., Palma et al., 2013, *Biochimica et Biophysica Acta*, 1836:296-303). IL-18 is generally considered to be part of a Th1-type response and one might have expected to see increased levels of IL-18 expression. These results will be evaluated further. IL-2 is required for secondary population expansion of CD8+ memory T-cells, therefore these results suggest that the triple blockade of DLL4, VEGF, and PD-1 may increase T-cell activation, maintenance of T-cells, and memory T-cell function. CCL2 (C—C motif ligand 2) is a chemokine which is also referred to as monocyte chemotactic protein 1 (MCP1) and small inducible cytokine A2. Chemokines have been shown to recruit monocytes, memory T cells, and dendritic cells to the sites of inflammation and tumors. The recruitment of immune cells may enhance an anti-tumor response. However, in some studies, chemokines have been found to promote tumorigenesis, therefore this result will need to be studied further. Granzyme B is a serine protease found in the granules of CTLs and NK cells. It is secreted by these cells along with the pore forming protein perforin to mediate apoptosis in target cells. The increased expression of granzyme B suggests the presence of active tumor-killing cells at the tumor site in mice treated with anti-mDLL4, anti-mVEGF, and anti-mPD-1.

Example 18

Inhibition of CT26.WT Colon Tumor Growth In Vivo

Single cell suspensions of CT26.WT tumor cells (30,000 cells) were injected subcutaneously into the flanks of 6-8 week old Balb/C mice. On Day 6 following tumor injection, mice with tumors of average size of approximately 43 mm$^3$ were randomized into groups (n=10) and treated with an anti-mPD-1 antibody (10 mg/kg), anti-Notch2/3 antibody 59R5 (40 mg/kg), a combination of anti-mPD-1 antibody and anti-Notch2/3 antibody 59R5, or an isotype control antibody. Mice were administered the anti-PD-1 antibody twice a week for 3 weeks and the anti-Notch2/3 antibody once a week for 3 weeks by intraperitoneal injection. Tumor growth was monitored and tumor volumes were measured with electronic calipers at the indicated time points. Data are expressed as mean±S.E.M.

Figure 18:
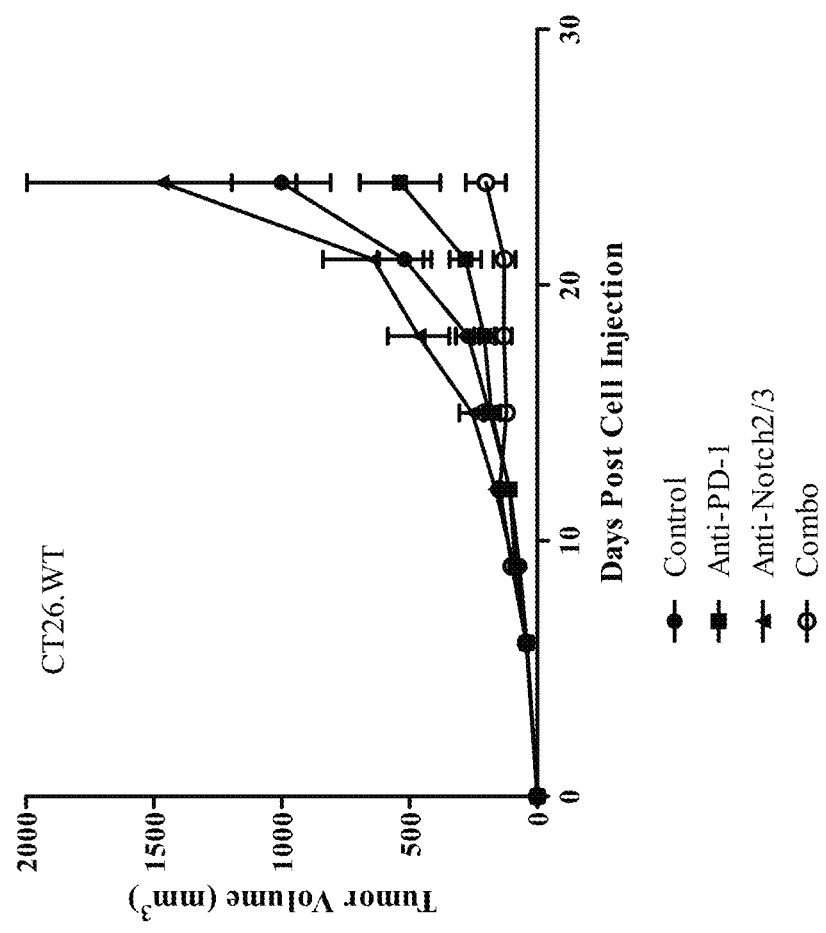
FIG. 18. Inhibition of CT26.WT tumor growth. CT26.WT tumor cells were injected subcutaneously into Balb/C mice. Mice were treated with anti-Notch2/3 antibody 59R5 (-▲-), an anti-PD-1 antibody (-■-), a combination of anti-Notch2/3 antibody 59R5 and an anti-PD-1 antibody (-○-), or a control (-●-). Data is shown as tumor volume (mm$^3$) over days post-cell injection.

As shown in FIG. 18, treatment with the combination of anti-Notch2/3 antibody 59R5 and an anti-mPD-1 antibody significantly reduced CT26.WT tumor growth as compared to treatment with the control antibody. Tumor growth was inhibited 80% as compared to control on Day 24. In contrast, an anti-PD-1 antibody as a single agent inhibited tumor growth by only 46% as compared to control and treatment with anti-Notch2/3 antibody 59R5 was observed to increase tumor growth as compared to control. In this experiment, tumors regressed to undetectable levels in 3 of the 10 mice treated with the combination of anti-Notch2/3 antibody and anti-PD-1 antibody and were still undetectable at Day 90. In contrast, tumor regression was observed in only one mouse treated with anti-PD-1 antibody as a single agent.

These results suggest that treatment with Notch pathway inhibitors, including Notch receptor antagonists as well as DLL4 antagonists, in combination with immunotherapeutic agents is efficacious for inhibiting tumor growth. Furthermore, in some subjects the treatment is successful as regressing tumors to undetectable levels with no relapse.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The sequences disclosed in the application are:

21M18 Heavy chain CDR1
(SEQ ID NO: 1)
TAYYIH

21M18 - H2 Heavy chain CDR2
(SEQ ID NO: 2)
YISCYNGATNYNQKFKG

-continued

21M18 - H7 Heavy chain CDR2
(SEQ ID NO: 3)
YISSYNGATNYNQKFKG

21M18 - H9 Heavy chain CDR2
(SEQ ID NO: 4)
YISVYNGATNYNQKFKG

21M18 Heavy chain CDR3
(SEQ ID NO: 5)
RDYDYDVGMDY

21M18 Light chain CDR1
(SEQ ID NO: 6)
RASESVDNYGISFMK

21M18 Light chain CDR2
(SEQ ID NO: 7)
AASNQGS

21M18 Light chain CDR3
(SEQ ID NO: 8)
QQSKEVPWTFGG

21M18 - H2 Heavy chain variable region
(SEQ ID NO: 9)
QVQLVQSGAEVKKPGASVKISCKASGYSFTAYYIHWVKQAPGQGLEWIGY
ISCYNGATNYNQKFKGRVTFTTDTSTSTAYMELRSLRSDDTAVYYCARDY
DYDVGMDYWGQGTLVTVSS 21M18 - H7 Heavy chain variable region
(SEQ ID NO: 10)
QVQLVQSGAEVKKPGASVKISCKASGYSFTAYYIHWVKQAPGQGLEWIGY
ISSYNGATNYNQKFKGRVTFTTDTSTSTAYMELRSLRSDDTAVYYCARDY
DYDVGMDYWGQGTLVTVSS 21M18 - H9 Heavy chain variable region
(SEQ ID NO: 11)
QVQLVQSGAEVKKPGASVKISCKASGYSFTAYYIHWVKQAPGQGLEWIGY
ISVYNGATNYNQKFKGRVTFTTDTSTSTAYMELRSLRSDDTAVYYCARDY
DYDVGMDYWGQGTLVTVSS 21M18 Light chain variable region
(SEQ ID NO: 12)
DIVMTQSPDSLAVSLGERATISCRASESVDNYGISFMKWFQQKPGQPPKL
LIYAASNQGSGVPDRFSGSGSGTDFTLTISSLQAEDVAVYYCQQSKEVPW
TFGGGTKVEIK Human DLL4 extracellular domain with predicted signal sequence underlined
(SEQ ID NO: 13)
MAAASRSASGWALLLLVALWQQRAAGSGVFQLQLQEFINERGVLASGRPC
EPGCRTFFRVCLKHFQAVVSPGPCTFGTVSTPVLGTNSFAVRDDSSGGGR
NPLQLPFNFTWPGTFSLIIEAWHAPGDDLRPEALPPDALISKIAIQGSLA
VGQNWLLDEQTSILTRLRYSYRVICSDNYYGDNCSRLCKKRNDHFGHYVC
QPDGNLSCLPGWTGEYCQQPICLSGCHEQNGYCSKPAECLCRPGWQGRLC
NECIPHNGCRHGTCSTPWQCTCDEGWGGLFCDQDLNYCTHHSPCKNGATC
SNSGQRSYTCTCRPGYTGVDCELELSECDSNPCRNGGSCKDQEDGYHCLC
PPGYYGLHCEHSTLSCADSPCFNGGSCRERNQGANYACECPPNFTGSNCE
KKVDRCTSNPCANGGQCLNRGPSRMCRCRPGFTGTYCELHVSDCARNPCA
HGGTCHDLENGLMCTCPAGFSGRRCEVRTSIDACASSPCFNRATCYTDLS
TDTFVCNCPYGFVGSRCEFPVG Human DLL4 N-terminal region with predicted signal sequence underlined
(SEQ ID NO: 14)
MAAASRSASGWALLLLVALWQQRAAGSGVFQLQLQEFINERGVLASGRPC
EPGCRTFFRVCLKHFQAVVSPGPCTFGTVSTPVLGTNSFAVRDDSSGGGR
NPLQLPFNFTWPGTFSLIIEAWHAPGDDLRPEALPPDALISKIAIQGSLA
VGQN Human DLL4 DSL Region
(SEQ ID NO: 15)
WLLDEQTSTLTRLRYSYRVICSDNYYGDNCSRLCKKRNDHFGHYVCQPDG
NLSCLPGWTGEYC Human DLL4 amino acids 1-217 with predicted signal sequence underlined
(SEQ ID NO: 16)
MAAASRSASGWALLLLVALWQQRAAGSGVFQLQLQEFINERGVLASGRPC
EPGCRTFFRVCLKHFQAVVSPGPCTFGTVSTPVLGTNSFAVRDDSSGGGR
NPLQLPFNFTWPGTFSLIIEAWHAPGDDLRPEALPPDALISKIAIQGSLA
VGQNWLLDEQTSTLTRLRYSYRVICSDNYYGDNCSRLCKKRNDHFGHYVC
QPDGNLSCLPGWTGEYC Human DLL4 amino acids 27-217
(SEQ ID NO: 17)
SGVFQLQLQEFINERGVLASGRPCEPGCRTFFRVCLKHFQAVVSPGPCTF
GTVSTPVLGTNSFAVRDDSSGGGRNPLQLPFNFTWPGTFSLIIEAWHAPG
DDLRPEALPPDALISKIAIQGSLAVGQNWLLDEQTSTLTRLRYSYRVICS
DNYYGDNCSRLCKKRNDHFGHYVCQPDGNLSCLPGWTGEYC Human DLL4 amino acids 66-73
(SEQ ID NO: 18)
QAVVSPGP Human DLL4 amino acids 139-146
(SEQ ID NO: 19)
LISKIAIQ 219R45 Heavy chain CDR1
(SEQ ID NO: 20)
NYWMH 219R45 Heavy chain CDR2
(SEQ ID NO: 21)
DINPSNGRTSYKEKFKR 219R45 Heavy chain CDR3
(SEQ ID NO: 22)
HYDDKYYPLMDY 21R75 Heavy chain CDR2
(SEQ ID NO: 23)
YIAGYKDATNYNQKFKG 21R79 Heavy chain CDR2
(SEQ ID NO: 24)
YIANYNRATNYNQKFKG 21R83 Heavy chain CDR2
(SEQ ID NO: 25)
YISNYNRATNYNQKFKG Anti-DLL4 heavy chain CDR2 consensus sequence
(SEQ ID NO: 26)
YIX$_1$X$_2$YX$_3$X$_4$ATNYNQKFKG, where X$_1$ is serine or alanine, X$_2$ is serine, asparagine, or glycine, X$_3$ is asparagine or lysine, and X$_4$ is glycine, -continued arginine, or aspartic acid 21R75 Heavy chain variable region
(SEQ ID NO: 27)
QVQLVQSGAEVKKPGASVKISCKASGYSFTAYYIHWVKQAPGQGLEWIGY

IAGYKDATNYNQKFKGRVTFTTDTSTSTAYMELRSLRSDDTAVYYCARDY

DYDVGMDYWGQGTLVTVSS

21R79 Heavy chain variable region
(SEQ ID NO: 28)
QVQLVQSGAEVKKPGASVKISCKASGYSFTAYYIHWVKQAPGQGLEWIGY

IANYNRATNYNQKFKGRVTFTTDTSTSTAYMELRSLRSDDTAVYYCARDY

DYDVGMDYWGQGTLVTVSS

21R83 Heavy chain variable region
(SEQ ID NO: 29)
QVQLVQSGAEVKKPGASVKISCKASGYSFTAYYIHWVKQAPGQGLEWIGY

ISNYNRATNYNQKFKGRVTFTTDTSTSTAYMELRSLRSDDTAVYYCARDY

DYDVGMDYWGQGTLVTVSS

219R45 Heavy chain variable region
(SEQ ID NO: 30)
QVQLVQSGAEVKKPGASVKVSCKASGYTFTNYWMHWVRQAPGQGLEWMGD

INPSNGRTSYKEKFKRRVTLSVDKSSSTAYMELSSLRSEDTAVYFCTIHY

DDKYYPLMDYWGQGTLVTVSS

21R83 Heavy chain (heterodimer variant) without
predicted signal sequence
(SEQ ID NO: 31)
QVQLVQSGAEVKKPGASVKISCKASGYSFTAYYIHWVKQAPGQGLEWIGY

ISNYNRATNYNQKFKGRVTFTTDTSTSTAYMELRSLRSDDTAVYYCARDY

DYDVGMDYWGQGTLVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVEGFYPSDIAVEWESNGQPENNYKTTPPMLDSDG

SFFLYSELTVDKSRWQQGNVFSCSVMHEALHNHYTQKSLSLSPGK

219R45 Heavy chain (heterodimer variant) without
predicted signal sequence
(SEQ ID NO: 32)
QVQLVQSGAEVKKPGASVKVSCKASGYTFTNYWMHWVRQAPGQGLEWMGD

INPSNGRTSYKEKFKRRVTLSVDKSSSTAYMELSSLRSEDTAVYFCTIHY

DDKYYPLMDYWGQGTLVTVSSASTKGPSVFPLAPCSRSTSESTAALGCLV

KDYFPEPVTVSWNSGALTSGVHTFPAVLQSSGLYSLSSVVTVPSSNFGTQ

TYTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYT

LPPSREKMTKNQVSLTCLVKGFYPSDIAVEWESNGQPENNYKTTPPMLKS

DGSFFLYSKLTVDKSRWQQGNVFSCSVMHEALHNHYTQKSLSLSPGK

Light chain without predicted signal sequence
(SEQ ID NO: 33)
DIVMTQSPDSLAVSLGERATISCRASESVDNYGISFMKWFQQKPGQPPKL

LIYAASNQGSGVPDRFSGSGSGTDFTLTISSLQAEDVAVYYCQQSKEVPW

TFGGGTKVEIKRTVAAPSVIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC

59R5 Heavy chain CDR1
(SEQ ID NO: 34)
SSSGMS

59R5 Heavy chain CDR2
(SEQ ID NO: 35)
VIASSGSNTYYADSVKG

59R5 Heavy chain CDR3
(SEQ ID NO: 36)
SIFYTT

59R5 Light chain CDR1
(SEQ ID NO: 37)
RASQSVRSNYLA

59R5 Light chain CDR2
(SEQ ID NO: 38)
GASSRAT

59R5 Light chain CDR3
(SEQ ID NO: 39)
QQYSNFPI

59R5 Heavy chain variable region
(SEQ ID NO: 40)
EVQLVESGGGLVQPGGSLRLSCAASGFTFSSSGMSWVRQAPGKGLEWVSV

IASSGSNTYYADSVKGRFTISRDNSKNTLYLQMNSLRAEDTAVYYCARSI

FYTTWGQGTLVTVSSAST

59R5 Light chain variable region
(SEQ ID NO: 41)
DIVLTQSPATLSLSPGERATLSCRASQSVRSNYLAWYQQKPGQAPRLLIY

GASSRATGVPARFSGSGSGTDFTLTISSLEPEDFAVYYCQQYSNFPITFG

QGTKVEIKR

59R5 Heavy chain with predicted signal sequence
underlined
(SEQ ID NO: 42)
<u>MKHLWFFLLLVAAPRWVLS</u>EVQLVESGGGLVQPGGSLRLSCAASGFTFSS

SGMSWVRQAPGKGLEWVSVIASSGSNTYYADSVKGRFTISRDNSKNTLYL

QMNSLRAEDTAVYYCARSIFYTTWGQGTLVTVSSASTKGPSVFPLAPCSR

STSESTAALGCLVKDYFPEPVTVSWNSGALTSGVHTFPAVLQSSGLYSLS

SVVTVPSSNFGTQTYTCNVDHKPSNTKVDKTVERKCCVECPPCPAPPVAG

PSVFLFPPKPKDTLMISRTPEVTCVVVDVSHEDPEVQFNWYVDGVEVHNA

KTKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQP

ENNYKTTPPMLDSDGSFFLYSKLTVDKSRWQQGNVFSCSVMHEALHNHYT

QKSLSLSPGK

59R5 Heavy chain without predicted signal sequence
(SEQ ID NO: 43)
EVQLVESGGGLVQPGGSLRLSCAASGFTFSSSGMSWVRQAPGKGLEWVSV

IASSGSNTYYADSVKGRFTISRDNSKNTLYLQMNSLRAEDTAVYYCARSI

FYTTWGQGTLVTVSSASTKGPSVFPLAPCSRSTSESTAALGCLVKDYFPE

PVTVSWNSGALTSGVHTFPAVLQSSGLYSLSSVVTVPSSNFGTQTYTCNV

DHKPSNTKVDKTVERKCCVECPPCPAPPVAGPSVFLFPPKPKDTLMISRT

-continued

PEVTCVVVDVSHEDPEVQFNWYVDGVEVHNAKTKPREEQFNSTFRVVSVL

TVVHQDWLNGKEYKCKVSNKGLPAPIEKTISKTKGQPREPQVYTLPPSRE

EMTKNQVSLTCLVKGFYPSDIAVEWESNGQPENNYKTTPPMLDSDGSFFL

YSKLTVDKSRWQQGNVFSCSVMHEALHNHYTQKSLSLSPGK

59R5 Light chain with predicted signal sequence
underlined
(SEQ ID NO: 44)
<u>MVLQTQVFISLLLWISGAYG</u>DIVLTQSPATLSLSPGERATLSCRASQSVR

SNYLAWYQQKPGQAPRLLIYGASSRATGVPARFSGSGSGTDFTLTISSLE

PEDFAVYYCQQYSNFPITFGQGTKVEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

59R5 Light chain without predicted signal sequence
(SEQ ID NO: 45)
DIVLTQSPATLSLSPGERATLSCRASQSVRSNYLAWYQQKPGQAPRLLIY

GASSRATGVPARFSGSGSGTDFTLTISSLEPEDFAVYYCQQYSNFPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

52M51 Heavy chain CDR1
(SEQ ID NO: 46)
RGYWIE

52M51 Heavy chain CDR2
(SEQ ID NO: 47)
QILPGTGRTNYNEKFKG

52M51 Heavy chain CDR3
(SEQ ID NO: 48)
FDGNYGYYAMDY

52M51 Light chain CDR1
(SEQ ID NO: 49)
RSSTGAVTTSNYAN

52M51 Light chain CDR2
(SEQ ID NO: 50)
GTNNRAP

52M51 Light chain CDR3
(SEQ ID NO: 51)
ALWYSNHWVFGGGTKL h52M51 Heavy chain variable region
(SEQ ID NO: 52)
QVQLVQSGAEVKKPGASVKISCKVSGYTLRGYWIEWVRQAPGKGLEWIGQ

ILPGTGRTNYNEKFKGRVTMTADTSTDTAYMELSSLRSEDTAVYYCARFD

GNYGYYAMDYWGQGTTVTVSSA h52M51-L3 Light chain variable region
(SEQ ID NO: 53)
SGVDSQAVVTQEPSLTVSPGGTVTLTCRSSTGAVTTSNYANWFQQKPGQA

PRTLIGGTNNRAPGVPARFSGSLLGGKAALTLSGAQPEDEAEYYCALWYS

NHWVFGGGTKLTVLG h52M51 Heavy chain amino acid sequence with
predicted signal sequence underlined
(SEQ ID NO: 54)
<u>MDWTWRVFCLLAVAPGVLS</u>QVQLVQSGAEVKKPGASVKISCKVSGYTLRG

YWIEWVRQAPGKGLEWIGQILPGTGRTNYNEKFKGRVTMTADTSTDTAYM

ELSSLRSEDTAVYYCARFDGNYGYYAMDYWGQGTTVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK h52M51 Heavy chain amino acid sequence without
predicted signal sequence
(SEQ ID NO: 55)
QVQLVQSGAEVKKPGASVKISCKVSGYTLRGYWIEWVRQAPGKGLEWIGQ

ILPGTGRTNYNEKFKGRVTMTADTSTDTAYMELSSLRSEDTAVYYCARFD

GNYGYYAMDYWGQGTTVTVSSASTKGPSVFPLAPCSRSTSESTAALGCLV

KDYFPEPVTVSWNSGALTSGVHTFPAVLQSSGLYSLSSVVTVPSSNFGTQ

TYTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK h52M51 Light chain amino acid sequence with
predicted signal sequence underlined
(SEQ ID NO: 56)
<u>MSVPTMAWMMLLLGLLAYG</u>SGVDSQAVVTQEPSLTVSPGGTVTLTCRSST

GAVTTSNYANWFQQKPGQAPRTLIGGTNNRAPGVPARFSGSLLGGKAALT

LSGAQPEDEAEYYCALWYSNHWVFGGGTKLTVLGQPKAAPSVTLFPPSSE

ELQANKATLVCLVSDFYPGAVTVAWKADGSPVKVGVETTKPSKQSNNKYA

ASSYLSLTPEQWKSHRSYSCRVTHEGSTVEKTVAPAECS h52M51 Light chain amino acid sequence without
predicted signal sequence
(SEQ ID NO: 57)
SGVDSQAVVTQEPSLTVSPGGTVTLTCRSSTGAVTTSNYANWFQQKPGQA

PRTLIGGTNNRAPGVPARFSGSLLGGKAALTLSGAQPEDEAEYYCALWYS

NHWVFGGGTKLTVLGQPKAAPSVTLFPPSSEELQANKATLVCLVSDFYPG

AVTVAWKADGSPVKVGVETTKPSKQSNNKYAASSYLSLTPEQWKSHRSYS

CRVTHEGSTVEKTVAPAECS

What is claimed is:

1. A method for inhibiting regulatory T-cell (Treg) activity in a subject, comprising administering to the subject a therapeutically effective amount of a delta-like ligand 4 (DLL4) antagonist and a therapeutically effective amount of a programmed cell death protein 1 (PD-1) antagonist.

2. The method of claim 1, wherein the DLL4 antagonist is an antibody that specifically binds the extracellular domain of human DLL4.

3. The method of claim 1, wherein the DLL4 antagonist is an antibody which comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

4. The method of claim 3, wherein the DLL4 antagonist is an antibody which comprises a heavy chain variable region having at least about 90% identity to SEQ ID NO:10 and a light chain variable region having at least about 90% identity to SEQ ID NO:12.

5. The method of claim 3, wherein the antibody is a monoclonal antibody, a recombinant antibody, a chimeric antibody, a humanized antibody, a human antibody, an antibody fragment comprising an antigen-binding site, a modified immunoglobulin molecule comprising an antigen-binding site, a bispecific antibody, an IgG1 antibody, an IgG2 antibody, or an IgG4 antibody.

6. The method of claim 1, wherein the PD-1 antagonist is an antibody that specifically binds PD-1.

7. The method of claim 1, wherein the DLL4 antagonist is an antibody that specifically binds the extracellular domain of human DLL4 and the PD-1 antagonist is an antibody that specifically binds human PD-1.

8. The method of claim 1, wherein the DLL4 antagonist is an antibody that specifically binds the extracellular domain of human DLL4 and the PD-1 antagonist is an antibody that specifically binds human programmed cell death ligand 1 (PD-L1).

9. The method of claim 1, wherein the DLL4 antagonist is a bispecific antibody which comprises:
   a) a first antigen-binding site that specifically binds human VEGF, and
   b) a second antigen-binding site that specifically binds human DLL4,
   wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22);
   wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and
   wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

10. A method for activating CD8+ or CD4+ T cells in a subject, comprising administering to the subject a therapeutically effective amount of a DLL4 antagonist and a therapeutically effective amount of a PD-1 antagonist.

11. The method of claim 10, wherein the DLL4 antagonist is an antibody that specifically binds the extracellular domain of human DLL4.

12. The method of claim 10, wherein the DLL4 antagonist is an antibody which comprises a heavy chain CDR1 comprising TAYYIH (SEQ ID NO:1), a heavy chain CDR2 comprising YISSYNGATNYNQKFKG (SEQ ID NO:3), and a heavy chain CDR3 comprising RDYDYDVGMDY (SEQ ID NO:5), and a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

13. The method of claim 12, wherein the DLL4 antagonist is an antibody which comprises a heavy chain variable region having at least about 90% identity to SEQ ID NO:10 and a light chain variable region having at least about 90% identity to SEQ ID NO:12.

14. The method of claim 12, wherein the antibody is a monoclonal antibody, a recombinant antibody, a chimeric antibody, a humanized antibody, a human antibody, an antibody fragment comprising an antigen-binding site, a modified immunoglobulin molecule comprising an antigen-binding site, a bispecific antibody, an IgG1 antibody, an IgG2 antibody, or an IgG4 antibody.

15. The method of claim 10, wherein the PD-1 antagonist is an antibody that specifically binds PD-1.

16. The method of claim 10, wherein the DLL4 antagonist is an antibody that specifically binds the extracellular domain of human DLL4 and the PD-1 antagonist is an antibody that specifically binds human PD-1.

17. The method of claim 10, wherein the DLL4 antagonist is an antibody that specifically binds the extracellular domain of human DLL4 and the PD-1 antagonist is an antibody that specifically binds human PD-L1.

18. The method of claim 10, wherein the DLL4 antagonist is a bispecific antibody which comprises:
   a) a first antigen-binding site that specifically binds human VEGF, and
   b) a second antigen-binding site that specifically binds human DLL4,
   wherein the first antigen-binding site comprises a heavy chain CDR1 comprising NYWMH (SEQ ID NO:20), a heavy chain CDR2 comprising DINPSNGRTSYKEKFKR (SEQ ID NO:21), and a heavy chain CDR3 comprising HYDDKYYPLMDY (SEQ ID NO:22);
   wherein the second antigen-binding site comprises a heavy chain CDR1 comprising TAYYIH (SEQ ID NO:1), a heavy chain CDR2 comprising YISNYNRATNYNQKFKG (SEQ ID NO:25), and a heavy chain CDR3 comprising RDYDYDVGMDY (SEQ ID NO:5); and
   wherein both the first and second antigen-binding sites comprise a light chain CDR1 comprising RASESVDNYGISFMK (SEQ ID NO:6), a light chain CDR2 comprising AASNQGS (SEQ ID NO:7), and a light chain CDR3 comprising QQSKEVPWTFGG (SEQ ID NO:8).

19. The method of claim 10, wherein CD8+ and CD4+ T cells are activated in the subject.

* * * * *

SEQUENCE LISTING

<160> NUMBER OF SEQ ID NOS: 57

<210> SEQ ID NO 1
<211> LENGTH: 6
<212> TYPE: PRT
<213> ORGANISM: Artificial Sequence
<220> FEATURE:
<223> OTHER INFORMATION: 21M18 Heavy chain CDR1

<400> SEQUENCE: 1

Thr Ala Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: 21M18 - H2 Heavy chain CDR2

<400> SEQUENCE: 2

Tyr Ile Ser Cys Tyr Asn Gly Ala Thr Asn Tyr Asn Gln Lys Phe Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: 21M18 - H7 Heavy chain CDR2

<400> SEQUENCE: 3

Tyr Ile Ser Ser Tyr Asn Gly Ala Thr Asn Tyr Asn Gln Lys Phe Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: 21M18 - H9 Heavy chain CDR2

<400> SEQUENCE: 4

Tyr Ile Ser Val Tyr Asn Gly Ala Thr Asn Tyr Asn Gln Lys Phe Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: 21M18 Heavy chain CDR3

<400> SEQUENCE: 5

Arg Asp Tyr Asp Tyr Asp Val Gly Met Asp Tyr
1               5                   10

<210> SEQ ID NO 6
<211> LENGTH: 15
<212> TYPE: PRT
<213> ORGANISM: Artificial Sequence
<220> FEATURE:

<223> OTHER INFORMATION: 21M18 Light chain CDR1

<400> SEQUENCE: 6

Arg Ala Ser Glu Ser Val Asp Asn Tyr Gly Ile Ser Phe Met Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: 21M18 Light chain CDR2

<400> SEQUENCE: 7

Ala Ala Ser Asn Gln Gly Ser
1               5

<210> SEQ ID NO 8
<211> LENGTH: 12
<212> TYPE: PRT
<213> ORGANISM: Artificial Sequence
<220> FEATURE:
<223> OTHER INFORMATION: 21M18 Light chain CDR3

<400> SEQUENCE: 8

Gln Gln Ser Lys Glu Val Pro Trp Thr Phe Gly Gly
1               5                   10

<210> SEQ ID NO 9
<211> LENGTH: 119
<212> TYPE: PRT
<213> ORGANISM: Artificial Sequence
<220> FEATURE:
<223> OTHER INFORMATION: 21M18 - H2 Heavy chain variable region

<400> SEQUENCE: 9

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Cys Tyr Asn Gly Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: 21M18 - H7 Heavy chain variable region

<400> SEQUENCE: 10

Gln Val Gln Leu Val Gln Ser Gly Ala Glu Val Lys Lys Pro Gly Ala
1               5                   10                  15

```
Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: 21M18 - H9 Heavy chain variable region

<400> SEQUENCE: 11

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Val Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 12
<211> LENGTH: 111
<212> TYPE: PRT
<213> ORGANISM: Artificial Sequence
<220> FEATURE:
<223> OTHER INFORMATION: 21M18 Light chain variable region

<400> SEQUENCE: 12

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
```

```
                    65                  70                  75                  80
Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
                100                 105                 110

<210> SEQ ID NO 13
<211> LENGTH: 522
<212> TYPE: PRT
<213> ORGANISM: Artificial Sequence
<220> FEATURE:
<223> OTHER INFORMATION: Human DLL4 extracellular domain
<220> FEATURE:
<221> NAME/KEY: SIGNAL
<222> LOCATION: (1)..(26)
<223> OTHER INFORMATION: predicted signal sequence

<400> SEQUENCE: 13

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
            115                 120                 125

Leu Arg Pro Glu Ala Leu Pro Pro Asp Ala Leu Ile Ser Lys Ile Ala
        130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
        210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
        290                 295                 300
```

-continued

```
Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly
        515                 520

<210> SEQ ID NO 14
<211> LENGTH: 154
<212> TYPE: PRT
<213> ORGANISM: Artificial Sequence
<220> FEATURE:
<223> OTHER INFORMATION: Human DLL4 N-terminal region
<220> FEATURE:
<221> NAME/KEY: SIGNAL
<222> LOCATION: (1)..(26)
<223> OTHER INFORMATION: predicted signal sequence

<400> SEQUENCE: 14

Met Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125
```

Leu Arg Pro Glu Ala Leu Pro Pro Asp Ala Leu Ile Ser Lys Ile Ala
            130                 135                 140

Ile Gln Gly Ser Leu Ala Val Gly Gln Asn
145                 150

<210> SEQ ID NO 15
<211> LENGTH: 63
<212> TYPE: PRT
<213> ORGANISM: Artificial Sequence
<220> FEATURE:
<223> OTHER INFORMATION: Human DLL4 DSL Region

<400> SEQUENCE: 15

Trp Leu Leu Asp Glu Gln Thr Ser Thr Leu Thr Arg Leu Arg Tyr Ser
1               5                   10                  15

Tyr Arg Val Ile Cys Ser Asp Asn Tyr Tyr Gly Asp Asn Cys Ser Arg
                20                  25                  30

Leu Cys Lys Lys Arg Asn Asp His Phe Gly His Tyr Val Cys Gln Pro
            35                  40                  45

Asp Gly Asn Leu Ser Cys Leu Pro Gly Trp Thr Gly Glu Tyr Cys
        50                  55                  60

<210> SEQ ID NO 16
<211> LENGTH: 217
<212> TYPE: PRT
<213> ORGANISM: Artificial Sequence
<220> FEATURE:
<223> OTHER INFORMATION: Human DLL4 amino acids 1-217
<220> FEATURE:
<221> NAME/KEY: SIGNAL
<222> LOCATION: (1)..(26)
<223> OTHER INFORMATION: predicted signal sequence

<400> SEQUENCE: 16

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
            130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

```
Asp His Phe Gly His Tyr Val Cys Gln Pro Asp Gly Asn Leu Ser Cys
            195                 200                 205

Leu Pro Gly Trp Thr Gly Glu Tyr Cys
    210                 215

<210> SEQ ID NO 17
<211> LENGTH: 191
<212> TYPE: PRT
<213> ORGANISM: Artificial Sequence
<220> FEATURE:
<223> OTHER INFORMATION: Human DLL4 amino acids 27-217

<400> SEQUENCE: 17

Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys
            180                 185                 190

<210> SEQ ID NO 18
<211> LENGTH: 8
<212> TYPE: PRT
<213> ORGANISM: Artificial Sequence
<220> FEATURE:
<223> OTHER INFORMATION: Human DLL4 amino acids 66-73

<400> SEQUENCE: 18

Gln Ala Val Val Ser Pro Gly Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Human DLL4 amino acids 139-146

<400> SEQUENCE: 19

Leu Ile Ser Lys Ile Ala Ile Gln
1               5
```

```
<210> SEQ ID NO 20
<211> LENGTH: 5
<212> TYPE: PRT
<213> ORGANISM: Artificial Sequence
<220> FEATURE:
<223> OTHER INFORMATION: 219R45 Heavy chain CDR1

<400> SEQUENCE: 20

Asn Tyr Trp Met His
1               5

<210> SEQ ID NO 21
<211> LENGTH: 17
<212> TYPE: PRT
<213> ORGANISM: Artificial Sequence
<220> FEATURE:
<223> OTHER INFORMATION: 219R45 Heavy chain CDR2

<400> SEQUENCE: 21

Asp Ile Asn Pro Ser Asn Gly Arg Thr Ser Tyr Lys Glu Lys Phe Lys
1               5                   10                  15

Arg

<210> SEQ ID NO 22
<211> LENGTH: 12
<212> TYPE: PRT
<213> ORGANISM: Artificial Sequence
<220> FEATURE:
<223> OTHER INFORMATION: 219R45 Heavy chain CDR3

<400> SEQUENCE: 22

His Tyr Asp Asp Lys Tyr Tyr Pro Leu Met Asp Tyr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: 21R75 Heavy chain CDR2

<400> SEQUENCE: 23

Tyr Ile Ala Gly Tyr Lys Asp Ala Thr Asn Tyr Asn Gln Lys Phe Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: 21R79 Heavy chain CDR2

<400> SEQUENCE: 24

Tyr Ile Ala Asn Tyr Asn Arg Ala Thr Asn Tyr Asn Gln Lys Phe Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: 21R83 Heavy chain CDR2

<400> SEQUENCE: 25
```

```
Tyr Ile Ser Asn Tyr Asn Arg Ala Thr Asn Tyr Asn Gln Lys Phe Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Anti-DLL4 heavy chain CDR2 consensus sequence
<220> FEATURE:
<221> NAME/KEY: MISC_FEATURE
<222> LOCATION: (3)..(3)
<223> OTHER INFORMATION: where Xaa is serine or alanine
<220> FEATURE:
<221> NAME/KEY: MISC_FEATURE
<222> LOCATION: (4)..(4)
<223> OTHER INFORMATION: where Xaa is serine, asparagine, or glycine
<220> FEATURE:
<221> NAME/KEY: MISC_FEATURE
<222> LOCATION: (6)..(6)
<223> OTHER INFORMATION: where Xaa is asparagine or lysine
<220> FEATURE:
<221> NAME/KEY: MISC_FEATURE
<222> LOCATION: (7)..(7)
<223> OTHER INFORMATION: where Xaa is glycine, arginine, or aspartic
      acid

<400> SEQUENCE: 26

Tyr Ile Xaa Xaa Tyr Xaa Xaa Ala Thr Asn Tyr Asn Gln Lys Phe Lys
1               5                   10                  15

Gly

<210> SEQ ID NO 27
<211> LENGTH: 119
<212> TYPE: PRT
<213> ORGANISM: Artificial Sequence
<220> FEATURE:
<223> OTHER INFORMATION: 21R75 Heavy chain variable region

<400> SEQUENCE: 27

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ala Gly Tyr Lys Asp Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser
        115

<210> SEQ ID NO 28
<211> LENGTH: 119
<212> TYPE: PRT
<213> ORGANISM: Artificial Sequence
<220> FEATURE:
<223> OTHER INFORMATION: 21R79 Heavy chain variable region
```

<400> SEQUENCE: 28

```
Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Ser Phe Thr Ala Tyr
            20                  25                  30
Tyr Ile His Trp Val Lys Gln Ala Pro Gly Gln Gly Leu Glu Trp Ile
        35                  40                  45
Gly Tyr Ile Ala Asn Tyr Asn Arg Ala Thr Asn Tyr Asn Gln Lys Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Asp Tyr Asp Val Gly Met Asp Tyr Trp Gly Gln Gly
            100                 105                 110
Thr Leu Val Thr Val Ser Ser
        115
```

<210> SEQ ID NO 29
<211> LENGTH: 119
<212> TYPE: PRT
<213> ORGANISM: Artificial Sequence
<220> FEATURE:
<223> OTHER INFORMATION: 21R83 Heavy chain variable region

<400> SEQUENCE: 29

```
Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Ser Phe Thr Ala Tyr
            20                  25                  30
Tyr Ile His Trp Val Lys Gln Ala Pro Gly Gln Gly Leu Glu Trp Ile
        35                  40                  45
Gly Tyr Ile Ser Asn Tyr Asn Arg Ala Thr Asn Tyr Asn Gln Lys Phe
    50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Asp Tyr Asp Val Gly Met Asp Tyr Trp Gly Gln Gly
            100                 105                 110
Thr Leu Val Thr Val Ser Ser
        115
```

<210> SEQ ID NO 30
<211> LENGTH: 121
<212> TYPE: PRT
<213> ORGANISM: Artificial Sequence
<220> FEATURE:
<223> OTHER INFORMATION: 219R45 Heavy chain variable region

<400> SEQUENCE: 30

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met His Trp Val Arg Gln Ala Pro Gly Gln Gly Leu Glu Trp Met
        35                  40                  45
```

Gly Asp Ile Asn Pro Ser Asn Gly Arg Thr Ser Tyr Lys Glu Lys Phe
            50                  55                  60

Lys Arg Arg Val Thr Leu Ser Val Asp Lys Ser Ser Thr Ala Tyr
65                  70                  75                  80

Met Glu Leu Ser Ser Leu Arg Ser Glu Asp Thr Ala Val Tyr Phe Cys
                    85                  90                  95

Thr Ile His Tyr Asp Asp Lys Tyr Tyr Pro Leu Met Asp Tyr Trp Gly
                100                 105                 110

Gln Gly Thr Leu Val Thr Val Ser Ser
            115                 120

<210> SEQ ID NO 31
<211> LENGTH: 445
<212> TYPE: PRT
<213> ORGANISM: Artificial Sequence
<220> FEATURE:
<223> OTHER INFORMATION: 21R83 Heavy chain (heterodimer variant)

<400> SEQUENCE: 31

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Asn Tyr Asn Arg Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

```
Pro Arg Glu Glu Gln Phe Asn Ser Thr Phe Arg Val Val Ser Val Leu
    290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Glu
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Glu Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 32
<211> LENGTH: 447
<212> TYPE: PRT
<213> ORGANISM: Artificial Sequence
<220> FEATURE:
<223> OTHER INFORMATION: 219R45 Heavy chain (heterodimer variant)

<400> SEQUENCE: 32

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Trp Met His Trp Val Arg Gln Ala Pro Gly Gln Gly Leu Glu Trp Met
            35                  40                  45
Gly Asp Ile Asn Pro Ser Asn Gly Arg Thr Ser Tyr Lys Glu Lys Phe
    50                  55                  60
Lys Arg Arg Val Thr Leu Ser Val Asp Lys Ser Ser Ser Thr Ala Tyr
65                  70                  75                  80
Met Glu Leu Ser Ser Leu Arg Ser Glu Asp Thr Ala Val Tyr Phe Cys
                85                  90                  95
Thr Ile His Tyr Asp Asp Lys Tyr Tyr Pro Leu Met Asp Tyr Trp Gly
            100                 105                 110
Gln Gly Thr Leu Val Thr Val Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
```

Lys Pro Ser Asn Thr Lys Val Asp Lys Thr Val Glu Arg Lys Cys Cys
            210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Lys Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Lys Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 33
<211> LENGTH: 217
<212> TYPE: PRT
<213> ORGANISM: Artificial Sequence
<220> FEATURE:
<223> OTHER INFORMATION: Light chain

<400> SEQUENCE: 33

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys Arg
            100                 105                 110

Thr Val Ala Ala Pro Ser Val Ile Phe Pro Pro Ser Asp Glu Gln Leu
        115                 120                 125

```
Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 34
<211> LENGTH: 6
<212> TYPE: PRT
<213> ORGANISM: Artificial Sequence
<220> FEATURE:
<223> OTHER INFORMATION: 59R5 Heavy chain CDR1

<400> SEQUENCE: 34

Ser Ser Ser Gly Met Ser
1               5

<210> SEQ ID NO 35
<211> LENGTH: 17
<212> TYPE: PRT
<213> ORGANISM: Artificial Sequence
<220> FEATURE:
<223> OTHER INFORMATION: 59R5 Heavy chain CDR2

<400> SEQUENCE: 35

Val Ile Ala Ser Ser Gly Ser Asn Thr Tyr Tyr Ala Asp Ser Val Lys
1               5                   10                  15

Gly

<210> SEQ ID NO 36
<211> LENGTH: 6
<212> TYPE: PRT
<213> ORGANISM: Artificial Sequence
<220> FEATURE:
<223> OTHER INFORMATION: 59R5 Heavy chain CDR3

<400> SEQUENCE: 36

Ser Ile Phe Tyr Thr Thr
1               5

<210> SEQ ID NO 37
<211> LENGTH: 12
<212> TYPE: PRT
<213> ORGANISM: Artificial Sequence
<220> FEATURE:
<223> OTHER INFORMATION: 59R5 Light chain CDR1

<400> SEQUENCE: 37

Arg Ala Ser Gln Ser Val Arg Ser Asn Tyr Leu Ala
1               5                   10

<210> SEQ ID NO 38
<211> LENGTH: 7
<212> TYPE: PRT
<213> ORGANISM: Artificial Sequence
<220> FEATURE:
```

<223> OTHER INFORMATION: 59R5 Light chain CDR2

<400> SEQUENCE: 38

Gly Ala Ser Ser Arg Ala Thr
1               5

<210> SEQ ID NO 39
<211> LENGTH: 8
<212> TYPE: PRT
<213> ORGANISM: Artificial Sequence
<220> FEATURE:
<223> OTHER INFORMATION: 59R5 Light chain CDR3

<400> SEQUENCE: 39

Gln Gln Tyr Ser Asn Phe Pro Ile
1               5

<210> SEQ ID NO 40
<211> LENGTH: 118
<212> TYPE: PRT
<213> ORGANISM: Artificial Sequence
<220> FEATURE:
<223> OTHER INFORMATION: 59R5 Heavy chain variable region

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Phe Tyr Thr Thr Trp Gly Gln Gly Thr Leu Val Thr
            100                 105                 110

Val Ser Ser Ala Ser Thr
        115

<210> SEQ ID NO 41
<211> LENGTH: 109
<212> TYPE: PRT
<213> ORGANISM: Artificial Sequence
<220> FEATURE:
<223> OTHER INFORMATION: 59R5 Light chain variable region

<400> SEQUENCE: 41

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

-continued

```
Pro Glu Asp Phe Ala Val Tyr Tyr Cys Gln Gln Tyr Ser Asn Phe Pro
                85                  90                  95
Ile Thr Phe Gly Gln Gly Thr Lys Val Glu Ile Lys Arg
            100                 105

<210> SEQ ID NO 42
<211> LENGTH: 460
<212> TYPE: PRT
<213> ORGANISM: Artificial Sequence
<220> FEATURE:
<223> OTHER INFORMATION: 59R5 Heavy chain
<220> FEATURE:
<221> NAME/KEY: SIGNAL
<222> LOCATION: (1)..(19)
<223> OTHER INFORMATION: predicted signal sequence

<400> SEQUENCE: 42

Met Lys His Leu Trp Phe Phe Leu Leu Leu Val Ala Ala Pro Arg Trp
1               5                   10                  15
Val Leu Ser Glu Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Ser Ser Gly Met Ser Trp Val Arg Gln Ala Pro Gly Lys Gly Leu
    50                  55                  60
Glu Trp Val Ser Val Ile Ala Ser Ser Gly Ser Asn Thr Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Ser Ile Phe Tyr Thr Thr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Asn Phe Gly Thr Gln Thr Tyr Thr Cys Asn Val Asp His Lys Pro Ser
    210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
            260                 265                 270
Thr Cys Val Val Val Asp Val Ser His Glu Asp Pro Glu Val Gln Phe
        275                 280                 285
Asn Trp Tyr Val Asp Gly Val Glu Val His Asn Ala Lys Thr Lys Pro
    290                 295                 300
Arg Glu Glu Gln Phe Asn Ser Thr Phe Arg Val Val Ser Val Leu Thr
305                 310                 315                 320
```

```
Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 43
<211> LENGTH: 441
<212> TYPE: PRT
<213> ORGANISM: Artificial Sequence
<220> FEATURE:
<223> OTHER INFORMATION: 59R5 Heavy chain

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Gly Met Ser Trp Val Arg Gln Ala Pro Gly Lys Gly Leu Glu Trp Val
        35                  40                  45

Ser Val Ile Ala Ser Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Phe Tyr Thr Thr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220
```

```
Pro Ala Pro Val Ala Gly Pro Ser Val Phe Leu Phe Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Phe Arg Val Val Ser Val Leu Thr Val Val His
        290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 44
<211> LENGTH: 235
<212> TYPE: PRT
<213> ORGANISM: Artificial Sequence
<220> FEATURE:
<223> OTHER INFORMATION: 59R5 Light chain
<220> FEATURE:
<221> NAME/KEY: SIGNAL
<222> LOCATION: (1)..(20)
<223> OTHER INFORMATION: predicted signal sequence

<400> SEQUENCE: 44

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Arg Ser Asn Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Val Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Tyr
            100                 105                 110

Ser Asn Phe Pro Ile Thr Phe Gly Gln Gly Thr Lys Val Glu Ile Lys
```

```
                 115                 120                 125
Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 45
<211> LENGTH: 215
<212> TYPE: PRT
<213> ORGANISM: Artificial Sequence
<220> FEATURE:
<223> OTHER INFORMATION: 59R5 Light chain

<400> SEQUENCE: 45

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ser Asn Phe Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 46
<211> LENGTH: 6
<212> TYPE: PRT
```

<213> ORGANISM: Artificial Sequence
<220> FEATURE:
<223> OTHER INFORMATION: 52M51 Heavy chain CDR1

<400> SEQUENCE: 46

Arg Gly Tyr Trp Ile Glu
1               5

<210> SEQ ID NO 47
<211> LENGTH: 17
<212> TYPE: PRT
<213> ORGANISM: Artificial Sequence
<220> FEATURE:
<223> OTHER INFORMATION: 52M51 Heavy chain CDR2

<400> SEQUENCE: 47

Gln Ile Leu Pro Gly Thr Gly Arg Thr Asn Tyr Asn Glu Lys Phe Lys
1               5                   10                  15

Gly

<210> SEQ ID NO 48
<211> LENGTH: 12
<212> TYPE: PRT
<213> ORGANISM: Artificial Sequence
<220> FEATURE:
<223> OTHER INFORMATION: 52M51 Heavy chain CDR3

<400> SEQUENCE: 48

Phe Asp Gly Asn Tyr Gly Tyr Tyr Ala Met Asp Tyr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: 52M51 Light chain CDR1

<400> SEQUENCE: 49

Arg Ser Ser Thr Gly Ala Val Thr Thr Ser Asn Tyr Ala Asn
1               5                   10

<210> SEQ ID NO 50
<211> LENGTH: 7
<212> TYPE: PRT
<213> ORGANISM: Artificial Sequence
<220> FEATURE:
<223> OTHER INFORMATION: 52M51 Light chain CDR2

<400> SEQUENCE: 50

Gly Thr Asn Asn Arg Ala Pro
1               5

<210> SEQ ID NO 51
<211> LENGTH: 16
<212> TYPE: PRT
<213> ORGANISM: Artificial Sequence
<220> FEATURE:
<223> OTHER INFORMATION: 52M51 Light chain CDR3

<400> SEQUENCE: 51

Ala Leu Trp Tyr Ser Asn His Trp Val Phe Gly Gly Gly Thr Lys Leu
1               5                   10                  15

<210> SEQ ID NO 52
<211> LENGTH: 122

```
<212> TYPE: PRT
<213> ORGANISM: Artificial Sequence
<220> FEATURE:
<223> OTHER INFORMATION: h52M51 Heavy chain variable region

<400> SEQUENCE: 52

Gln Val Gln Leu Val Gln Ser Gly Ala Glu Val Lys Lys Pro Gly Ala
1               5                   10                  15

Ser Val Lys Ile Ser Cys Lys Val Ser Gly Tyr Thr Leu Arg Gly Tyr
            20                  25                  30

Trp Ile Glu Trp Val Arg Gln Ala Pro Gly Lys Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Asp Gly Asn Tyr Gly Tyr Tyr Ala Met Asp Tyr Trp Gly
            100                 105                 110

Gln Gly Thr Thr Val Thr Val Ser Ser Ala
        115                 120

<210> SEQ ID NO 53
<211> LENGTH: 115
<212> TYPE: PRT
<213> ORGANISM: Artificial Sequence
<220> FEATURE:
<223> OTHER INFORMATION: h52M51-L3 Light chain variable region

<400> SEQUENCE: 53

Ser Gly Val Asp Ser Gln Ala Val Val Thr Gln Glu Pro Ser Leu Thr
1               5                   10                  15

Val Ser Pro Gly Gly Thr Val Thr Leu Thr Cys Arg Ser Ser Thr Gly
            20                  25                  30

Ala Val Thr Thr Ser Asn Tyr Ala Asn Trp Phe Gln Gln Lys Pro Gly
        35                  40                  45

Gln Ala Pro Arg Thr Leu Ile Gly Gly Thr Asn Asn Arg Ala Pro Gly
    50                  55                  60

Val Pro Ala Arg Phe Ser Gly Ser Leu Leu Gly Gly Lys Ala Ala Leu
65                  70                  75                  80

Thr Leu Ser Gly Ala Gln Pro Glu Asp Glu Ala Glu Tyr Tyr Cys Ala
                85                  90                  95

Leu Trp Tyr Ser Asn His Trp Val Phe Gly Gly Gly Thr Lys Leu Thr
            100                 105                 110

Val Leu Gly
        115

<210> SEQ ID NO 54
<211> LENGTH: 466
<212> TYPE: PRT
<213> ORGANISM: Artificial Sequence
<220> FEATURE:
<223> OTHER INFORMATION: h52M51 Heavy chain amino acid sequence
<220> FEATURE:
<221> NAME/KEY: SIGNAL
<222> LOCATION: (1)..(19)
<223> OTHER INFORMATION: predicted signal sequence

<400> SEQUENCE: 54
```

```
Met Asp Trp Thr Trp Arg Val Phe Cys Leu Ala Val Ala Pro Gly
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Val Ser Gly Tyr Thr Leu
                35                  40                  45

Arg Gly Tyr Trp Ile Glu Trp Val Arg Gln Ala Pro Gly Lys Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Arg Val Thr Met Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Phe Asp Gly Asn Tyr Gly Tyr Ala Met Asp
        115                 120                 125

Tyr Trp Gly Gln Gly Thr Thr Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
```

```
              420                 425                 430
Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 55
<211> LENGTH: 447
<212> TYPE: PRT
<213> ORGANISM: Artificial Sequence
<220> FEATURE:
<223> OTHER INFORMATION: h52M51 Heavy chain amino acid sequence

<400> SEQUENCE: 55

Gln Val Gln Leu Val Gln Ser Gly Ala Glu Val Lys Lys Pro Gly Ala
1               5                   10                  15

Ser Val Lys Ile Ser Cys Lys Val Ser Gly Tyr Thr Leu Arg Gly Tyr
            20                  25                  30

Trp Ile Glu Trp Val Arg Gln Ala Pro Gly Lys Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Asp Gly Asn Tyr Gly Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
```

```
305                 310                 315                 320
Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 56
<211> LENGTH: 239
<212> TYPE: PRT
<213> ORGANISM: Artificial Sequence
<220> FEATURE:
<223> OTHER INFORMATION: h52M51 Light chain amino acid sequence
<220> FEATURE:
<221> NAME/KEY: SIGNAL
<222> LOCATION: (1)..(19)
<223> OTHER INFORMATION: predicted signal sequence

<400> SEQUENCE: 56

Met Ser Val Pro Thr Met Ala Trp Met Met Leu Leu Leu Gly Leu Leu
1               5                   10                  15

Ala Tyr Gly Ser Gly Val Asp Ser Gln Ala Val Val Thr Gln Glu Pro
                20                  25                  30

Ser Leu Thr Val Ser Pro Gly Gly Thr Val Thr Leu Thr Cys Arg Ser
                35                  40                  45

Ser Thr Gly Ala Val Thr Thr Ser Asn Tyr Ala Asn Trp Phe Gln Gln
            50                  55                  60

Lys Pro Gly Gln Ala Pro Arg Thr Leu Ile Gly Gly Thr Asn Asn Arg
65                  70                  75                  80

Ala Pro Gly Val Pro Ala Arg Phe Ser Gly Ser Leu Leu Gly Gly Lys
                85                  90                  95

Ala Ala Leu Thr Leu Ser Gly Ala Gln Pro Glu Asp Glu Ala Glu Tyr
                100                 105                 110

Tyr Cys Ala Leu Trp Tyr Ser Asn His Trp Val Phe Gly Gly Gly Thr
            115                 120                 125

Lys Leu Thr Val Leu Gly Gln Pro Lys Ala Ala Pro Ser Val Thr Leu
130                 135                 140

Phe Pro Pro Ser Ser Glu Glu Leu Gln Ala Asn Lys Ala Thr Leu Val
145                 150                 155                 160

Cys Leu Val Ser Asp Phe Tyr Pro Gly Ala Val Thr Val Ala Trp Lys
                165                 170                 175

Ala Asp Gly Ser Pro Val Lys Val Gly Val Glu Thr Thr Lys Pro Ser
            180                 185                 190

Lys Gln Ser Asn Asn Lys Tyr Ala Ala Ser Ser Tyr Leu Ser Leu Thr
                195                 200                 205
```

```
Pro Gln Trp Lys Ser His Arg Ser Tyr Ser Cys Arg Val Thr His
    210             215                 220

Glu Gly Ser Thr Val Glu Lys Thr Val Ala Pro Ala Glu Cys Ser
225             230                 235

<210> SEQ ID NO 57
<211> LENGTH: 220
<212> TYPE: PRT
<213> ORGANISM: Artificial Sequence
<220> FEATURE:
<223> OTHER INFORMATION: h52M51 Light chain amino acid sequence

<400> SEQUENCE: 57

Ser Gly Val Asp Ser Gln Ala Val Val Thr Gln Glu Pro Ser Leu Thr
1               5                   10                  15

Val Ser Pro Gly Gly Thr Val Thr Leu Thr Cys Arg Ser Ser Thr Gly
            20                  25                  30

Ala Val Thr Thr Ser Asn Tyr Ala Asn Trp Phe Gln Gln Lys Pro Gly
                35                  40                  45

Gln Ala Pro Arg Thr Leu Ile Gly Gly Thr Asn Asn Arg Ala Pro Gly
    50                  55                  60

Val Pro Ala Arg Phe Ser Gly Ser Leu Leu Gly Gly Lys Ala Ala Leu
65                  70                  75                  80

Thr Leu Ser Gly Ala Gln Pro Glu Asp Glu Ala Glu Tyr Tyr Cys Ala
                85                  90                  95

Leu Trp Tyr Ser Asn His Trp Val Phe Gly Gly Gly Thr Lys Leu Thr
                100                 105                 110

Val Leu Gly Gln Pro Lys Ala Ala Pro Ser Val Thr Leu Phe Pro Pro
            115                 120                 125

Ser Ser Glu Glu Leu Gln Ala Asn Lys Ala Thr Leu Val Cys Leu Val
    130                 135                 140

Ser Asp Phe Tyr Pro Gly Ala Val Thr Val Ala Trp Lys Ala Asp Gly
145                 150                 155                 160

Ser Pro Val Lys Val Gly Val Glu Thr Thr Lys Pro Ser Lys Gln Ser
                165                 170                 175

Asn Asn Lys Tyr Ala Ala Ser Ser Tyr Leu Ser Leu Thr Pro Glu Gln
            180                 185                 190

Trp Lys Ser His Arg Ser Tyr Ser Cys Arg Val Thr His Glu Gly Ser
        195                 200                 205

Thr Val Glu Lys Thr Val Ala Pro Ala Glu Cys Ser
    210                 215                 220
```